US010888594B2

(12) United States Patent
Nakao et al.

(10) Patent No.: US 10,888,594 B2
(45) Date of Patent: Jan. 12, 2021

(54) GENETICALLY ENGINEERED VACCINIA VIRUSES

(71) Applicants: Astellas Pharma Inc., Chuo-ku, Tokyo (JP); National University Corporation Tottori University, Tottori-shi, Tottori (JP)

(72) Inventors: Shinsuke Nakao, Tokyo (JP); Tatsuya Kawase, Tokyo (JP); Takafumi Nakamura, Yonago (JP)

(73) Assignees: National University Corporation Tottori University, Tottori (JP); Astellas Pharma Inc., Tokyo (JP)

( * ) Notice: Subject to any disclaimer, the term of this patent is extended or adjusted under 35 U.S.C. 154(b) by 0 days.

(21) Appl. No.: 15/664,125

(22) Filed: Jul. 31, 2017

(65) Prior Publication Data

US 2017/0340687 A1 Nov. 30, 2017

Related U.S. Application Data

(63) Continuation of application No. PCT/JP2017/019921, filed on May 29, 2017.

(30) Foreign Application Priority Data

May 30, 2016 (JP) ................................ 2016-107481

(51) Int. Cl.

| | |
|---|---|
| ***C12N 15/863*** | (2006.01) |
| ***A61K 48/00*** | (2006.01) |
| ***A61K 35/76*** | (2015.01) |
| ***C12N 7/01*** | (2006.01) |
| ***C07K 14/54*** | (2006.01) |
| ***A61K 35/768*** | (2015.01) |
| ***C12N 7/00*** | (2006.01) |
| ***A61K 38/20*** | (2006.01) |
| ***C12N 15/86*** | (2006.01) |

(52) U.S. Cl.

CPC .......... *A61K 35/768* (2013.01); *A61K 38/208* (2013.01); *A61K 38/2046* (2013.01); *A61K 48/005* (2013.01); *C07K 14/5418* (2013.01); *C07K 14/5434* (2013.01); *C12N 7/00* (2013.01); *C12N 15/86* (2013.01); *C12N 2710/24132* (2013.01); *C12N 2710/24143* (2013.01); *C12N 2710/24162* (2013.01); *C12N 2710/24171* (2013.01)

(58) Field of Classification Search

None

See application file for complete search history.

(56) References Cited

U.S. PATENT DOCUMENTS

| | | | | |
|---|---|---|---|---|
| 6,379,674 | B1 | 4/2002 | Rabkin et al. | |
| 2002/0018767 | A1 | 2/2002 | Lee et al. | |
| 2007/0077231 | A1 | 4/2007 | Contag et al. | |
| 2007/0264235 | A1 * | 11/2007 | Erbs | C12N 9/78 424/93.2 |
| 2007/0298054 | A1 | 12/2007 | Shida et al. | |
| 2010/0297072 | A1 | 11/2010 | DePinho | |
| 2013/0071430 | A1 | 3/2013 | Nakamura et al. | |
| 2013/0195800 | A1 | 8/2013 | Roeth et al. | |
| 2013/0302367 | A1 * | 11/2013 | Shida | A61K 39/21 424/199.1 |
| 2015/0004188 | A1 | 1/2015 | Weiner et al. | |
| 2016/0281066 | A1 | 9/2016 | Nakamura | |

FOREIGN PATENT DOCUMENTS

| | | | |
|---|---|---|---|
| CA | 2387855 | A1 | 4/2001 |
| CA | 2931294 | A1 | 5/2015 |
| JP | 2001-513508 | A | 9/2001 |
| JP | 2003-512335 | A1 | 4/2003 |
| JP | 2012-527465 | A | 11/2012 |
| JP | 2013-527753 | A | 7/2013 |
| WO | WO 01/28583 | A2 | 4/2001 |
| WO | WO-2005/054451 | A1 | 6/2005 |
| WO | WO 2008/134879 | A1 | 11/2008 |
| WO | WO 2011/125469 | A1 | 10/2011 |
| WO | WO 2012/151272 | A2 | 11/2012 |
| WO | WO 2015/076422 | A1 | 5/2015 |
| WO | WO 2015124297 | * | 8/2015 |
| WO | WO 2015/150809 | A1 | 10/2015 |
| WO | WO 2017/079746 | A2 | 5/2017 |
| WO | WO 2017/118866 | A1 | 7/2017 |
| WO | WO 2017/147554 | A2 | 8/2017 |

OTHER PUBLICATIONS

Schilbach et al, Cancer-targeted IL-12 controls human rhabdomyosarcoma by senescence induction and myogenic differentiation, OncoImmunology, 2015, pp. 1-14.*
Weiss et al, Immunotherapy of Cancer by IL-12-based Cytokine Combinations, Expert Opin Biol Ther. Nov. 2007 ; 7(11): 1705-1721.*
Hill and Carlisle, Achieving systemic delivery of oncolytic viruses, Expert Opinion on Drig Delivery, 2019, pp. 1-15.*
Zheng et al, Oncolytic Viruses for Cancer Therapy: Barriers and Recent Advances, Molecular Therapy: Oncolytics, 2019, pp. 234-247.*
Fumoto et al, Targeted Gene Delivery: Importance of Administration Routes, Chapter 1, 2013, pp. 1-30.*
Guse et al., "Oncolytic vaccinia virus for the treatment of cancer," Expert Opin. Biol. Ther., Feb. 22, 2011, 11(5):595-608.
Leong et al., "Interleukin-7 Enhances Cell-Mediated Immune Responses in vivo in an Interleukin-2-Dependent Manner," Viral Immunology, 1997, 10(1):1-9.

(Continued)

*Primary Examiner* — Maria Marvich
(74) *Attorney, Agent, or Firm* — Foley & Lardner LLP

(57) ABSTRACT

The present invention provides a genetically recombinant vaccinia virus effective in preventing or treating cancer. Specifically, the present invention provides a vaccinia virus comprising two polynucleotides, a polynucleotide encoding IL-7 and a polynucleotide encoding IL-12; a combination kit of two vaccinia viruses, a vaccinia virus comprising a polynucleotide encoding IL-7 and a vaccinia virus comprising a polynucleotide encoding IL-12; and use of the two vaccinia viruses in combination.

25 Claims, 8 Drawing Sheets

Specification includes a Sequence Listing.

(56) References Cited

OTHER PUBLICATIONS

Mehrotra et al., "Synergistic Effects of IL-7 and IL-12 on Human T Cell Activation," The Journal of Immunology, May 1, 1995, 154:5093-5102.
Schilbach et al., "Cancer-targeted IL-12 controls human rhabdomyosarcoma by senescence induction and myogenic differentiation," OncoImmunology, Jul. 2015, 4(7):e1014760, 1-14.
Shen et al., "Fighting Cancer with Vaccinia Virus: Teaching New Tricks to an Old Dog," Molecular Therapy, Feb. 2005, 11(2):180-195.
Weiss et al., "Immunotherapy of cancer by IL-12-based cytokine combinations," Expert Opin. Biol. Ther., Nov. 1, 2007, 7(11):1705-1721.
Chen et al., "Elements of cancer immunity and the cancer-immune set point," Nature, Jan. 19, 2017, 541:321-330.
Ortiz-Sanchez et al., "Antibody-cytokine fusion proteins: applications in cancer therapy," Expert Opin. Biol. Ther., May 2008, 8(5):609-632.
Postow et al., "Immune-Related Adverse Events Associated with Immune Checkpoint Blockade," N. Eng. J. Med., Jan. 11, 2018, 378(2):158-168.
Chen et al., "Low-Dose Vaccinia Virus-Mediated Cytokine Gene Therapy of Glioma," Journal of Immunotherapy, 2001, 24(1):46-57.
Hikichi et al., "MicroRNA Regulation of Glycoprotein B5R in Oncolytic Vaccinia Virus Reduces Viral Pathogenicity Without Impairing Its Antitumor Efficacy," Molecular Therapy, Jun. 2011, 19(6):1107-1115.
Shida et al., "Effects and Virulences of Recombinant Vaccinia Viruses Derived from Attenuated Strains That Express the Human T-Cell Leukemia Virus Type I Envelope Gene," Journal of Virology, Dec. 1988, 62(12):4474-4480.
Chalikonda et al., "Oncolytic virotherapy for ovarian carcinomatosis using a replication-selective vaccinia virus armed with a yeast cytosine deaminase gene,"Cancer Gene Ther., Feb. 2008 (Epub Dec. 14, 2007), 15(2):115-125, Abstract.
Yakubitskyi et al., "Highly Immunogenic Variant of attenuated Vaccinia Virus,"Biochemistry, Biophysics and Molecular Biology, 2016, 466:35-38.

* cited by examiner

LC16mO ΔSCR
VGF-SP-IL12/O1L-SP-IL7

SEQUENCE LISTING

```
<160> NUMBER OF SEQ ID NOS: 23

<210> SEQ ID NO 1
<211> LENGTH: 37
<212> TYPE: DNA
<213> ORGANISM: Artificial Sequence
```

<220> FEATURE:
<223> OTHER INFORMATION: pTagBFP-N vector forward primer

<400> SEQUENCE: 1
atggccggac cggccaccgg tcgccaccat gagcgag 37

<210> SEQ ID NO 2
<211> LENGTH: 41
<212> TYPE: DNA
<213> ORGANISM: Artificial Sequence
<220> FEATURE:
<223> OTHER INFORMATION: pTagBFP-N vector reverse primer

<400> SEQUENCE: 2
tcgaattcgc tagcggccgc ttaattaagc ttgtgcccca g 41

<210> SEQ ID NO 3
<211> LENGTH: 18
<212> TYPE: DNA
<213> ORGANISM: Artificial Sequence
<220> FEATURE:
<223> OTHER INFORMATION: B4R forward primer

<400> SEQUENCE: 3
cagtcacgac gttgtaaa 18

<210> SEQ ID NO 4
<211> LENGTH: 73
<212> TYPE: DNA
<213> ORGANISM: Artificial Sequence
<220> FEATURE:
<223> OTHER INFORMATION: B4R reverse primer

<400> SEQUENCE: 4
catgcgcacc ttgaagcgca tgaactcctt gatgacgtcc tcggaggagg ccatttttat 60
ttatgagcgt taa 73

<210> SEQ ID NO 5
<211> LENGTH: 20
<212> TYPE: DNA
<213> ORGANISM: Artificial Sequence
<220> FEATURE:
<223> OTHER INFORMATION: DsRed forward primer

<400> SEQUENCE: 5
gagttcatgc gcttcaaggt 20

<210> SEQ ID NO 6
<211> LENGTH: 99
<212> TYPE: DNA
<213> ORGANISM: Artificial Sequence
<220> FEATURE:
<223> OTHER INFORMATION: DsRed reverse primer

<400> SEQUENCE: 6
ctcaattgat tctagctata agtctttaat cttttgatac ttgttcgtta ttaattatta 60
attattttaa cggatttata tctacaggaa caggtggtg 99

<210> SEQ ID NO 7
<211> LENGTH: 2379
<212> TYPE: DNA
<213> ORGANISM: Artificial Sequence
<220> FEATURE:
<223> OTHER INFORMATION: polynucleotide comprising human IL-12

<400> SEQUENCE: 7

```
accggtcgcc accatgtgtc atcagcaact tgtcatcagc tggttttcac tcgtgtttct      60
tgccagccct ttggtagcga tttgggaact caagaaagac gtgtatgtcg ttgagctgga     120
ttggtatcct gatgcccctg gagagatggt ggtgctgacc tgtgatactc ccgaagagga     180
tgggataacc tggacccttg accagtcctc tgaagtcctg ggagtggca aaactctgac     240
gattcaggtg aaagagtttg gcgacgctgg ccagtacacc tgtcataagg gtggcgaagt     300
actgtctcat tcccttctgc tgctgcacaa gaaagaggac gggatttggt caacagacat     360
tctgaaagac cagaaggaac cgaagaacaa aacgttcctc cgctgtgagg cgaagaacta     420
ctcaggcaga ttcacatgct ggtggctgac tacaatcagc actgatctga cgttctccgt     480
caagagttct cgaggaagct ctgatccgca aggagtcaca tgcggtgcag ccactctgag     540
cgctgagagg gtgagaggag acaacaaaga gtacgagtat tccgtggagt gccaggaaga     600
ttccgcctgt ccagccgcag aagaaagctt gcctatcgag gtgatggttg atgctgttca     660
caaactcaag tacgagaatt acacctccag cttctttatc cgggacatca tcaaacccga     720
tccacccaag aatctgcagt tgaaacccct caagaactca cgtcaggttg aggtgtcttg     780
ggagtatccc gatacatggt caacaccaca cagttatttc agcctgacct tttgcgtcca     840
ggtgcaaggg aagagcaagc gcgaaaagaa agacagggtg ttcaccgaca agactagtgc     900
taccgtgatt tgccggaaga atgccagcat atctgttaga gcacaggaca ggtactactc     960
ctcctcttgg agtgaatggg catcagtacc atgcagctga tgcatctagg gcggccaatt    1020
ccgcccctct ccctcccccc cccctaacgt tactggccga agccgcttgg aataaggccg    1080
gtgtgcgttt gtctatatgt gattttccac catattgccg tcttttggca atgtgagggc    1140
ccggaaacct ggccctgtct tcttgacgag cattcctagg ggtctttccc ctctcgccaa    1200
aggaatgcaa ggtctgttga atgtcgtgaa ggaagcagtt cctctggaag cttcttgaag    1260
acaaacaacg tctgtagcga ccctttgcag gcagcggaac cccccacctg gcgacaggtg    1320
cctctgcggc caaaagccac gtgtataaga tacacctgca aaggcggcac aaccccagtg    1380
ccacgttgtg agttggatag ttgtggaaag agtcaaatgg ctctcctcaa gcgtattcaa    1440
caaggggctg aaggatgccc agaaggtacc ccattgtatg ggatctgatc tggggcctcg    1500
gtgcacatgc tttacatgtg tttagtcgag gttaaaaaaa cgtctaggcc ccccgaacca    1560
cggggacgtg gttttccttt gaaaaacacg atgataagct tgccaatgtg gcctcctggt    1620
agtgcgtcac agccaccacc cagtcccgca gcagctactg gattgcatcc agctgctaga    1680
cctgtctctc tgcaatgtag gctgagcatg tgtccagcta ggagcttgct gcttgttgcc    1740
acgcttgtgc tcctggacca cctgtcattg gcacgcaatc tgcccgttgc cactcccgat    1800
ccaggcatgt ttccgtgcct ccatcactct cagaacctcc tgcgggcagt cagcaatatg    1860
ctgcagaaag cgaggcaaac actggagttt tacccgtgta ccagcgaaga gatagatcac    1920
gaggacatta ccaaggacaa gacgtcaaca gtggaagctt gtctgcctct ggagctcaca    1980
aagaatgagt cctgcctgaa tagccgtgaa accagtttca tcaccaatgg gtcttgcttg    2040
gctagtcgca aaacatcctt catgatggca ttgtgccttt cctccatcta tgaggatctc    2100
aagatgtatc aggtggagtt caaaaccatg aacgccaaac tgctgatgga tcccaaacga    2160
cagatctttc tcgatcagaa catgcttgcc gtaatcgacg aactgatgca agccctgaac    2220
ttcaacagcg aaactgtgcc tcagaagtct agccttgaag agcccgactt ctacaaaacc    2280
aagatcaagc tgtgcatact cctgcatgcc tttcggatta gagccgtgac tattgacaga    2340
```

-continued gtcatgtcct acctgaacgc ctcatgagct agcgaattc 2379

<210> SEQ ID NO 8
<211> LENGTH: 559
<212> TYPE: DNA
<213> ORGANISM: Artificial Sequence
<220> FEATURE:
<223> OTHER INFORMATION: polynucleotide comprising human IL-7

<400> SEQUENCE: 8
accggtcgcc accatgtttc atgtctcttt tcggtacatc tttggacttc cacccctgat 60
actggtgttg ctgcctgtag cctcatcaga ctgtgacatt gaaggcaaag acggcaaaca 120
gtatgagagc gttctcatgg tgagcatcga tcagctcctt gactccatga aggaaattgg 180
ctccaattgc ctcaataacg agttcaactt cttcaaacgt cacatttgcg atgccaacaa 240
agaggggatg ttcctgttta gagccgctcg aaagctcagg cagttcctga agatgaactc 300
tactggggat ttcgatctgc atctgctgaa agtgagtgaa gggactacga tactgctgaa 360
ttgtaccgga caagtcaaag gaagaaagcc cgcagctttg ggtgaagcgc aaccgacaaa 420
gagtctggag gagaataaga gcctgaaaga acagaagaag ctcaatgacc tttgctttct 480
gaaacgcctt ttgcaggaga tcaagacctg ttggaacaag atcctgatgg gtacaaagga 540
gcactgagct agcgaattc 559

<210> SEQ ID NO 9
<211> LENGTH: 3082
<212> TYPE: DNA
<213> ORGANISM: Artificial Sequence
<220> FEATURE:
<223> OTHER INFORMATION: Codon optimized LacZ

<400> SEQUENCE: 9
accggtcgcc accatggacc cggtggtgct gcagaggcgg gattgggaga atcctggggt 60
gacgcagctg aatcggctgg ctgctcaccc accatttgca tcatggagaa attccgaaga 120
ggcccggacc gaccgcccct ctcagcagct cagaagtctt aatggagaat ggcgcttcgc 180
atggtttcct gctcccgagg ctgtaccgga aagttggctc gagtgcgatt tgcccgaggc 240
agataccgtc gtggttccct ccaactggca gatgcacggc tatgatgccc ctatctacac 300
caatgtcact taccctataa cagtgaaccc accctttgtg cctaccgaga atcccaccgg 360
atgctacagt ctgacattta acgtggacga gtcttggctg caggaaggcc agactagaat 420
catcttcgat ggtgtcaaca gcgcttttca tctgtggtgc aacgggcgtt gggtgggtta 480
cggccaagac agtaggctcc cttctgaatt cgatctctct gccttcctgc gggccggtga 540
gaatagactt gccgttatgg ttctgcgttg gagcgacggt tcctacctgg aggaccagga 600
tatgtggagg atgtctggca ttttccgaga tgtgagcctc cttcacaaac ctaccactca 660
aatctccgac tttcatgttg ccacaaggtt caacgacgac ttttcacgcg ctgttctgga 720
ggccgaggtc caaatgtgcg gcgaactgcg cgattatctg cgcgtgactg tgagcctttg 780
gcaaggagag acacaggtgg catcaggcac cgcacccttc ggcggagaaa tcatcgacga 840
acggggagga tatgctgata gggttactct taggctgaat gtagaaaacc ccaagctctg 900
gtctgcagaa atacctaacc tctatcgcgc agttgtggaa ctgcacacgg cagacgggac 960
cctgattgaa gccgaagcct gtgacgtcgg cttccgtgaa gtgcgcatcg agaatgggct 1020
gctccttctt aacggtaagc cactgttgat cagaggcgtg aataggcatg agcatcatcc 1080

-continued

```
gctccacgga caggtgatgg atgagcagac aatggttcag gacatactct tgatgaaaca   1140
gaacaacttc aatgccgtgc gctgtagcca ctaccctaat cacccactgt ggtataccct   1200
gtgtgacagg tacggcctgt atgtcgtgga tgaggcaaac attgaaactc atggcatggt   1260
gccaatgaat cggctgacag atgaccccag atggctgccc gccatgtcag agcgtgtgac   1320
caggatggta cagcgggaca gaaatcaccc cagtgtcata atctggtccc ttgggaacga   1380
atcagggcat ggtgcaaacc acgatgctct gtaccgctgg attaagagcg ttgaccctag   1440
tcggccagtg cagtatgaag gtggaggcgc cgataccact gcaactgaca ttatttgccc   1500
aatgtacgct cgggtcgacg aggatcaacc gttccctgcg gtcccaaagt ggagcattaa   1560
gaaatggctg tctttgcctg gagaaacacg cccgctgatt ctgtgcgaat atgcccacgc   1620
aatggggaac tccctgggcg ggtttgcaaa gtattggcag gcttttcgcc agtatccacg   1680
actgcaggga ggctttgtgt gggactgggt agatcagagc ctgatcaaat acgacgaaaa   1740
tggcaatcca tggtccgcct atggaggtga ctttggtgat acccctaatg acaggcagtt   1800
ttgcatgaac ggactcgtct ttgcagatcg aactccacat ccggccctga ctgaggccaa   1860
gcatcagcag caattcttcc agtttcggct gtctgggcag accattgagg tgacttccga   1920
gtacttgttt cgacacagcg acaatgagct gctgcactgg atggtggccc tcgatggcaa   1980
accactggcc tcaggagagg tgcccctgga tgtagcgccc caggggaaac agcttatcga   2040
gttgcccgaa ctgccccaac ccgagtctgc tgggcaactc tggcttaccg tgcgagtcgt   2100
tcagccaaat gccactgcct ggtccgaggc tggccacatt agcgcatggc agcagtggag   2160
actggctgag aacctcagcg ttacccttcc cgcagcctct cacgccatcc ctcacttgac   2220
cactagtgag atggacttct gtatcgagct gggcaacaaa cgctggcagt ttaacagaca   2280
gtcaggcttc ttgtcccaga tgtggattgg cgacaagaag cagctgttga ccccttttgcg  2340
ggatcagttc acaagggcgc ctctggacaa tgacatcgga gtgagcgagg ctacacgaat   2400
agatccaaac gcgtgggtcg agaggtggaa ggcggctggg cactaccaag ctgaagcggc   2460
cctgttgcaa tgtaccgccg atacgctcgc cgatgccgtc ctcattacga cagcccacgc   2520
ttggcagcac cagggcaaaa cactgtttat ctcccgtaag acatacagaa tcgatggcag   2580
cggtcaaatg gccattacgg tagacgtgga agttgcgtca gatacacccc atcccgcgag   2640
gatcggactg aactgtcaat tggcccaagt cgcagagaga gtgaactggc tgggactcgg   2700
gcctcaggag aattatccag accggctcac agccgcttgc ttcgataggt gggaccttcc   2760
actctctgat atgtacaccc catacgtgtt cccctcagag aatggcctgc ggtgtgggac   2820
acgagaactg aactacggac cgcatcagtg gagaggggac ttccagttca acatcagccg   2880
gtatagtcag cagcagctga tggaaacgtc ccatagacat ctgctgcacg ctgaggaagg   2940
gacatggctg aacattgacg ggttccacat gggaataggt ggcgatgaca gctggtcccc   3000
tagcgtaagc gccgagtttc aactgagtgc tgggagatat cattaccaac tggtctggtg   3060
ccagaaatga gctagcgaat tc                                             3082
```

```
<210> SEQ ID NO 10
<211> LENGTH: 20
<212> TYPE: DNA
<213> ORGANISM: Artificial Sequence
<220> FEATURE:
<223> OTHER INFORMATION: VGF forward primer

<400> SEQUENCE: 10

ggtaacgcta tcgaaacgac                                                 20
```

<210> SEQ ID NO 11
<211> LENGTH: 20
<212> TYPE: DNA
<213> ORGANISM: Artificial Sequence
<220> FEATURE:
<223> OTHER INFORMATION: VGF reverse primer

<400> SEQUENCE: 11
ttagttcgtc gagtgaacct 20

<210> SEQ ID NO 12
<211> LENGTH: 20
<212> TYPE: DNA
<213> ORGANISM: Artificial Sequence
<220> FEATURE:
<223> OTHER INFORMATION: O1L forward primer

<400> SEQUENCE: 12
acagggatta agacggaaag 20

<210> SEQ ID NO 13
<211> LENGTH: 20
<212> TYPE: DNA
<213> ORGANISM: Artificial Sequence
<220> FEATURE:
<223> OTHER INFORMATION: O1L reverse primer

<400> SEQUENCE: 13
gtcaacaagc atcttccaac 20

<210> SEQ ID NO 14
<211> LENGTH: 20
<212> TYPE: DNA
<213> ORGANISM: Artificial Sequence
<220> FEATURE:
<223> OTHER INFORMATION: B5R forward primer-for PCR

<400> SEQUENCE: 14
cgtataatac gttggtctat 20

<210> SEQ ID NO 15
<211> LENGTH: 20
<212> TYPE: DNA
<213> ORGANISM: Artificial Sequence
<220> FEATURE:
<223> OTHER INFORMATION: B5R reverse primer-for PCR

<400> SEQUENCE: 15
gatcgtgcca atagtagtta 20

<210> SEQ ID NO 16
<211> LENGTH: 13
<212> TYPE: DNA
<213> ORGANISM: Artificial Sequence
<220> FEATURE:
<223> OTHER INFORMATION: 5' restriction enzyme site in SEQ ID NOS: 7 to 9

<400> SEQUENCE: 16
accggtcgcc acc 13

<210> SEQ ID NO 17
<211> LENGTH: 12
<212> TYPE: DNA
<213> ORGANISM: Artificial Sequence
<220> FEATURE:
<223> OTHER INFORMATION: 3' restriction enzyme site in SEQ ID NOS: 7 to 9

<400> SEQUENCE: 17
gctagcgaat tc 12

<210> SEQ ID NO 18
<211> LENGTH: 101
<212> TYPE: PRT
<213> ORGANISM: Artificial Sequence
<220> FEATURE:
<223> OTHER INFORMATION: 4 SCR domains deleted B5R protein

<400> SEQUENCE: 18

Met Lys Thr Ile Ser Val Val Thr Leu Leu Cys Val Leu Pro Ala Val
1 5 10 15

Val Tyr Ser Thr Cys Val Arg Ser Asn Glu Lys Phe Asp Pro Val Asp
20 25 30

Asp Gly Pro Asp Asp Glu Thr Asp Leu Ser Lys Leu Ser Lys Asp Val
35 40 45

Val Gln Tyr Glu Gln Glu Ile Glu Ser Leu Glu Ala Thr Tyr His Ile
50 55 60

Ile Ile Val Ala Leu Thr Ile Met Gly Val Ile Phe Leu Ile Ser Val
65 70 75 80

Ile Val Leu Val Cys Ser Cys Asp Lys Asn Asn Asp Gln Tyr Lys Phe
85 90 95

His Lys Leu Leu Pro
100

<210> SEQ ID NO 19
<211> LENGTH: 104
<212> TYPE: DNA
<213> ORGANISM: Artificial Sequence
<220> FEATURE:
<223> OTHER INFORMATION: Partial genome sequence of Vaccinia virus

<400> SEQUENCE: 19
tagtaaaatt aaattaatta taaaattata tatataattt actaacttta gttagataaa 60
ttaataatat ataagtttta gtacattaat attatatttt aaat 104

<210> SEQ ID NO 20
<211> LENGTH: 104
<212> TYPE: DNA
<213> ORGANISM: Artificial Sequence
<220> FEATURE:
<223> OTHER INFORMATION: Partial genome sequence of Vaccinia virus

<400> SEQUENCE: 20
atttaaaata taatattaat gtactaaaac ttatatatta ttaatttatc taactaaagt 60
tagtaaatta tatatataat tttataatta atttaatttt acta 104

<210> SEQ ID NO 21
<211> LENGTH: 202489
<212> TYPE: DNA
<213> ORGANISM: Artificial Sequence
<220> FEATURE:
<223> OTHER INFORMATION: Partial genome sequence of modified vaccinia virus

<400> SEQUENCE: 21
attttattta gtgtctagaa aaaaatgtgt gacccatgac tgtaggaaac tctagagtgt 60

-continued

```
aagaaagatc gatcgcttta tagagaccat cagaaagagg tttaatattt ttgtgagacc    120
atcgaagaga gaaagagata aaactttttt acgactccat cagaaagagg tttaatattt    180
ttgtgagacc atcgaagaga gaaagagata aaactttttt acgactccat cagaaagagg    240
tttaatattt ttgtgagacc atcgaaggag aaagagataa aacttttta cgactccatc    300
agaaagaggt ttaatatttt tgtgagacca tcgaagagag aaagagataa aacttttta    360
cgactccatc agaaagaggt ttaatatttt tgtgagacca tcgaagagag aaagagataa    420
aacttttta cgactccatc agaaagaggt ttaatatttt tgtgagacca tcgaagagag    480
aaagagataa aacttttta cgactccatc agaaagaggt ttaatatttt tgtgagacca    540
tcgaagagag aaagagataa aacttttta cgactccatc agaaagaggt ttaatatttt    600
tgtgagacca tcgaagagag aaagagataa aacttttta cgactccatc agaaagaggt    660
ttaatatttt tgtgagacca tcgaagagag aaagagataa aacttttta cgactccatc    720
agaaagaggt ttaatatttt tgtgagacca tcgaagagag aaagagataa aacttttta    780
cgactccatc agaaagaggt ttaatatttt tgtgagacca tcgaagagag aaagagataa    840
aacttttta cgactccatc agaaagaggt ttaatatttt tgtgagacca tcgaagagag    900
aaagagataa aacttttta cgactccatc agaaagaggt ttaatatttt tgtgagacca    960
tcgaagagag aaagagataa aacttttta cgactccatc agaaagaggt ttaatatttt   1020
tgtgagacca tcgaagagag aaagagataa aacttttta cgactccatc agaaagaggt   1080
ttaatatttt tgtgagacca tcgaagagag aaagagataa aacttttta cgactccatc   1140
agaaagaggt ttaatatttt tgtgagacca tcgaagagag aaagagataa aacttttta   1200
cgactccatc agaaagaggt ttaatatttt tgtgagacca tcgaagagag aaagagataa   1260
aacttttta cgactccatc agaaagaggt ttaatatttt tgtgagacca tcgaagagag   1320
aaagagataa aacttttta cgactccatc agaaagaggt ttaatatttt tgtgagacca   1380
tcgaagagag aaagagataa aacttttta cgactccatc agaaagaggt ttaatatttt   1440
tgtgagacca tcgaagagag aaagagataa aacttttta cgactccatc agaaagaggt   1500
ttaatatttt tgtgagacca tcgaagagag aaagagaaag agatagttag tctagatatt   1560
tttcttagta caaaagtcaa tgttttaaaa tatatggaca agaatttgtc tgtataaaaa   1620
cttgtgtgaa attttgtacc aaagaaaaaa tgtgagcagt atcccctaca tggattttac   1680
tagatcattt atataccaaa aaatattata cgatctacgt tttattatat gattttaacg   1740
tgtaaattat aaacattatt ttatgatata caattgtctg gtaacctaga tgggcatagg   1800
ggatgttgat aagctcgacg agtatatgtt gttggacgtt attgtttaag aaatagttga   1860
tgcatcagaa agagaataaa aaatatttta gtgagaccat cgaagagaga aagagataaa   1920
actttttac gactccatca gaaagaggtt taatattttt gtgagaccat cgaagagaga   1980
aagagaataa aaatatttta tgactccatt gaagagagaa agagaaaatg agaatgagaa   2040
taaaaatatt ttagtgacac catcagaaag aggtttaata tttttgtgag accatcgaag   2100
agagaaagag aataaaaata ttttatgact ccattgaaga gagaaagaga aaatgagaat   2160
gagaataaaa atattttagt gacaccatca gaaagaggtt taatattttt tatgagacca   2220
tcaaagagag aaagaaaata aaaatatttt tgtaaaactt tttttatgag accatcaaag   2280
agagaaagag aataaaaata tttttgtaaa actttttta tgagaccatc aaagagagaa   2340
agagaataaa aatattttg taaaactttt tttatgagac catcaaagag agaaagagaa   2400
```

-continued

```
taaaaatatt tttgtaaaac tttttttatg agaccatcaa agagagaaag agaataaaaa   2460
tatttttgta aaactttttt tatgagacca tcaaagagag aaagagaata aaaatatttt   2520
tgtaaaactt tttttatgag accatcaaag agagaaagag aataaaaata tttttgtaaa   2580
acttttttta tgagaccatc aaagagagaa agagaataaa aatatttttg taaaactttt   2640
tttatgagac catcaaagag agaaagagaa taaaaatatt tttgtaaaac tttttttatg   2700
agaccatcaa agagagaaag agaataaaaa tatttttgta aaactttttt tatgagacca   2760
tcaaagagag aaagagaata aaaatatttt tgtaaaactt tttttatgag accatcaaag   2820
agagaaagag aataaaaata tttttgtaaa acttttttta tgagaccatc aaagagagaa   2880
agagaataaa aatatttttg taaaactttt tttatgagac catcaaagag agaaagagaa   2940
taaaaatatt tttgtaaaac tttttttatg agaccatcaa agagagaaag agaataaaaa   3000
tatttttgta aaactttttt tatgagacca tcaaagagag aaagagaata aaaatatttt   3060
tgtaaaactt tttttatgag accatcaaag agagaaagag aataaaaata tttttgtaaa   3120
acttttttta tgagaccatc aaagagagaa agagaataaa aatatttttg taaaactttt   3180
tttatgagac catcaaagag agaaagagaa taaaaatatt tttgtaaaac tttttttatg   3240
agaccatcaa agagagaaag agaataaaaa tatttttgta aaactttttt tatgagacca   3300
tcaaagagag aaagagaata aaaatatttt tgtaaaactt tttttatgag accatcaaag   3360
agagaaagag aataaaaata tttttgtaaa acttttttta tgataccatc aaagagagaa   3420
agagaataaa aatatttttg taaaactttt tttatgagac catcaaagag agaaagagaa   3480
taaaaatatt tttgtaaaac tttttttatg agaccatcaa agagagaaag agaataaaaa   3540
tatttttgta aaactttttt tatgagacca tcaaagagag aaagagaata aaaatatttt   3600
tgtaaaactt tttttatgag accatcaaag agagaaagag aataaaaata tttttgtaaa   3660
acttttttta tgagaccatc aaagagagaa agagaataaa aatatttttg taaaactttt   3720
tttatgagac catcaaagag agaaagagaa taaaaatatt tttgtaaaac tttttttatg   3780
agaccatcaa agagagaaag agaataaaaa tatttttgta aaactttttt tatgagacca   3840
tcaaagagag aaagagaata aaaatatttt tgtaaaactt tttttatgag accatcaaag   3900
agagaaagag aataaaaata tttttgtaaa acttttttta tgagaccatc aaagagagaa   3960
agagaataaa aatatttttg taaaactttt tttatgagac catcaaagag agaaagagaa   4020
taaaaatatt tttgtaaaac tttttttatg agaccatcaa agagagaaag agaataaaaa   4080
tatttttgta aaactttttt tatgagacca tcaaagagag aaagagaata aaaatatttt   4140
tgtaaaactt tttttatgag accatcaaag agagaaagag aataaaaata tttttgtaaa   4200
acttttttta tgagaccatc aaagagagaa agagaataaa aatatttttg taaaactttt   4260
tttatgagac catcaaagag agaaagagaa taaaaatatt tttgtaaaac tttttttatg   4320
agaccatcaa agagagaaag agaataaaaa tatttttgta aaactttttt tatgagacca   4380
tcaaagagag aaagagaata aaaatatttt tgtaaaactt tttttatgag accatcaaag   4440
agagaaagag aataaaaata tttttgtaaa acttttttta tgagaccatc aaagagagaa   4500
agagaataaa aatatttttg taaaactttt tttatgagac catcaaagag agaaagagaa   4560
taaaaatatt tttgtaaaac tttttttatg agaccatcaa agagagaaag agaataaaaa   4620
tatttttgta aaactttttt tatgagacca tcaaagagag aaagagaata aaaatatttt   4680
tgtaaaactt tttttatgag accatcaaag agagaaagag aataaaaata tttttgtaaa   4740
acttttttta tgagaccatc agaaagaggt ttaatatttt tgtgataccc tgaaaggaaa   4800
```

-continued

```
taggaatagg aataggaata ggaatagtgt cataatcgta tcacactatt gagacagaaa   4860
aagaagaagt cgcgagaggt aactttttgt gaatgtagtt aagaacattt ttgttttgca   4920
aaccggaata tagtgtccgg tacacttttt taattcgtgg tgtgcctgaa tcgttcgatt   4980
aaccctactc atccaatttc agatgaatag agttatcgat tcagacacac gctttgagtt   5040
ttgttgaatc gatgagtgaa gtatcatcgg ttgcaccttc agatgccgat ccgtcgacat   5100
acttgaatcc atccttgacc tcaagttcag atgattcctt gcacatgtct ccgatacgaa   5160
cgctaaactc tagattcttg acacattttg tatcgacgat cgttgaaccg atgatatctt   5220
cgtaactcac tttcttatga gagatgttag acccgagtac tggatgggtc ttgatgtcgc   5280
tgtctttctc ttcttcgcta catctgatgt cgatagacac ctcacagtct ttgatcatag   5340
caagagcttc ttcatgagtg atcgcgggag agtccttacc ttgtcctggg gacacgctgg   5400
acaatctagc attcactgtg tttccatcag cggattctga gatggattta atctgaggac   5460
atttggtgaa tccaaagttc attctcagac ctccaccgat gatggagtaa taagtggtag   5520
gaggatctac atcctcgact gatgtggaat catcttctga ttccacctcg ggatctggat   5580
ctgactcgga ctctgtaatt tccgttacgg attggcaaat cttatcattg gtcggtgttt   5640
ggtcttgctt tgtgactttg ataataacat cgattcccat atgatgtttg ttttcttctt   5700
ccgtacacga ggaggaggat gaggatgatt gctgaagact ggcaggcata gcagctgccg   5760
ccaggcacat gcatgccagt acgatatatt gtttcataat tgctattgat tgagtactgt   5820
tctttatgat tctacttcct taccgtgcaa taaattagaa tatattttct acttttacga   5880
gaaattaatt attgtattta ttatttatgg gtgaaaaact tactataaaa agtgggtggg   5940
tttggaatta gtgatcagtt tatgtatatc gcaactaccg ggcatatggc tatcgacatc   6000
gagaacatta cccacatgat aagagattgt atcagtttcg tagtcttgag tattggtatt   6060
actatatagt atatagatgt cgcccactag agttactgtc tccgaatgcg gcatgatagt   6120
atcattcttt gctttcgtta actgtttgga ggaagaatct ttgttattgc atttaatctc   6180
gaaattcaga gtgcacacct ttctcctgta aagaaacctg aagtcgctac cttattaagg   6240
acggagaagt atccatcacg aaagacggga tcgcagtctt tatgattcat agtaatagtt   6300
agttccgacg ttgagatgga ttcgctgaga ccggtagtgg tcgtccgagt acacgacgtg   6360
tcgttaactg gatacagatt aatttccaca tcgatatagt taaaggtatt actgggtacg   6420
ggttcgcatt tatctgcgga agagacggtg tgagaatatg ttccgagacc acacggagaa   6480
cagatgacgt ctccggatac tccgtatcct attccacatt ttgtttggga aacacatgcc   6540
ttgcatccgg atgatccttt gagaagacaa taatatccgg gagagcattc acagattcta   6600
ttgtgagtcg tgttacacga tcgcgtcttc cgttacaact tagacaagcg ggtaaatgat   6660
tattgcgaga tgtgaaggta cccgaaccac acggcgtaca ttgtgtgtta gtcttgctat   6720
cgcataatct ggaagcgtat gttcccggac acaaattatg gcgtttgtat tcgttgtctt   6780
tacactttcc atcggatggt gcatgcggtg ctatatctct tccgtttatt attatacatg   6840
agagaaacaa tatatacgag tataatacgg acttcatgat ttaataatgt agtaatcgtc   6900
gtcttgttcc tgtttcctac ttctccaatc atatagatat tttctttcta tcatggataa   6960
tatttgtaat ggttctttcc gtacaacata ctgtttagat gatattgcgc ataatttccg   7020
gaggcaaata cgatagtcta gattgaccga tggtagactc taatttattg agtgctttgt   7080
cgacgagttt acttttacgc tccatcgata gatggcactg ttctatgaga tcgtcgtaca   7140
```

-continued

```
tgggaaatga aatgtgactg tctgaatgta tggctttaag atagctgtga taccgtatac   7200
aggtcggtgt cggagattcg aatctcttta aggcgactta tgtcacgatg atggaatcta   7260
tcttatcgaa tgatatattt ttcataaata cacttttata gtcctcgttt aaacagaatt   7320
tactatgtag ttccgcgaat gactcgtccc ttaataggca gtaggctagt atcttttta    7380
cgtagtaatc gtcgtaggga gagacatctt gtagaacaac gatttaatca taggtagaga   7440
tactttcagt ctgtggtgga tgatgtcatt cacaacatcc gccttgtata tgatgtttct   7500
gttttcaaac accaagtcga ataccgtctt tagtcggaag gttgatgtcg tatccgatgt   7560
atgaggcaac attgttgtta caattttgaa aggcggtatt atagtattcg tctttctgaa   7620
tgtcgaacct atctaataga taccgtagta tattgagagt gtatccttga ttatgtttta   7680
tgaatagata aagtagatgt tgtccttctt ccttttgttc gtgccaattg agtaacatta   7740
tgagaatatg acctgttgca caatcgttcc atgatgggtg tacaatcaag attattacgt   7800
atcctcgaga taaaagagca tacaccacac gaggactatg tttggtatac tgttgaaggt   7860
aagtgtgtaa ccgcgttaat gtttgctcca taatctatta tcgcgtagat gaatcgcttc   7920
tcggctcgca tcttagtgtg acttgacttg taataattgc tttcgtagaa cgtggatatg   7980
tgtttacagt agtaatgaag agaagtgagt tcatcctcgt cggcgcaatt agggtcggat   8040
cctttgtaca gaacgtaata gtttaagctc ccattgaatt tatatctaag ataacacagc   8100
aatagatcgg atgatttact aaagtcatca atggtgtccg ttagtatatc aaagatcttg   8160
ttatcgattg atagtggtca tccttgctat caaagttacg catgccgtgg tgtaacaata   8220
tctttaatac agatggatta aatcgtgtat tcatcgtata gcaatgtaat ggagagttac   8280
ctcgtttatt cagatcgcag tgtttaataa ctagcttaaa cagatgagac gatgtattca   8340
catcaaagaa cgtgaaatac atatgacaga cattgttgac agaaacgtga ccttcattct   8400
taccgtcgtc cataaatacg ttaggtatgt accacatact gtcgcgaacg atgcgtacaa   8460
tctcgtccat ctcataatga tttacttttt cataattaaa gatgtgaaag aaaaacagaa   8520
caatatattt ttttagtaat gtttatgcga gacatataaa ataaactccg tgtttatgat   8580
gccggtaaat gtttttatca tcttggacgg aatcgatttt gtaatatgtc atggaaacaa   8640
atgaaacagg acattatcgc tccatgataa attatttaat ggagtaataa agtatctcca   8700
tgggtaattt cgaaatcaag ttatcgtctg tattaatgtt gtccactatg gagtcgatcc   8760
tctcattgtt ctttacagtt tctgtaatga tggacgttag ttcttttttg taccatttga   8820
tgtcggattc tttgcgtatc tcagtctgtg gcgtttgctt tgtttaaata atatatcaaa   8880
catggagacg cctgatatgt aggcattctt cattctatta atgtctgctc tatagcgctt   8940
tagttcctta tgacgaccgg cgatatcata ctttacttta gaaggaaaat catcatctat   9000
gattaaggcg tatctgatac aggcgaataa tggttcagga tatagatagc gtatatctct   9060
attaaatgcg tcaatcatag tctctagagt gggatggtag ctaagtaata aatcaactat   9120
cctcgttttg ttttctcttt ggtaactgct tttctggatg gccgtattga ttatcgagcg   9180
tgatgttgta acactcgctc catattccaa taaccgcttt gcaaattgta tattattgac   9240
atcgaccgcg taatatagta gagttatcga tcatatctat atcatccatg tacttgctta   9300
gtatatcaaa tacatctatt agtatggttt cataacagtg atacccgcaa ttattaaatc   9360
tcgataatat cagaccgtac atacatagac ggccattgtt cgatacgtga tttacagccg   9420
cgtgtccata ttttccacga taaaccttac gacgtttaca tcgacgagat tattattaac   9480
aaagtagtcg tgtagaggat agttgttgtc cgtcgtctta tccatggttg ctccgttatc   9540
```

-continued

```
caacatgcat tgaatgatag gtatacttac catatcgccg taatgtaagt agtttatcaa   9600
catggcttgt acatcctgtt gtctaaatct ctttagaatg ttatcgatga tgtagtggtt   9660
atattctctg gaatcgtacg aagtaatact acgcattacg tcgacaagag tatgacgtct   9720
ctcaataaga agattaacga tttccatgtc tacattatat ggggttactc taaatcgctt   9780
gtttagataa tacgcctcta atatagggct gacgtcgtat actctacacg tgtccacatc   9840
ctttattaat aataatttaa caatctctat atctatggtt gagcaagacc agtagtattg   9900
gatgggtaaa gatcctcctt cgtctctgcc atggatggaa acattgttat cgatcaaaca   9960
tttaattaca tccttggata gagattgaga ttctctatga gacgatatat agtaatgaag  10020
agagttctta cacatatcac tgtcgtacat acaggtacga aatacgtaac cggtgctgta  10080
acattctgat ttaagaagcc atagcaatac ttctggtctc ggattaggcg tcgttacgta  10140
tatatccacc aatccgagac cattgattgc ataattcgta ttcttggacg gacgtatccg  10200
tttatccaca attaggtatt ttagcagacg taagtcgata ttatccgaat acagatcgaa  10260
atcatttata ttcgacttga gttcgttaga ggaatttgaa tagctggata tcagtagatg  10320
cacaatctga gattttacgt atctatgctt actgtatact cctagcggag ttaatccttc  10380
gttgtttcta caaagtctct cgactccgcg agagagtaac agccgaacaa tcttaatgtc  10440
tgtatcgcat ttattggaga cgtaacaatg tagcgcattg tttcctcgtc tatctatatg  10500
ttttgataag ttgtgacacg tttcaatttc tagttttatt tttttgtacg tcacatcttc  10560
atccagtaga cgacatagaa tagtgcactc tctaccacaa taatccatag ctattctggt  10620
gctaattatt cctatttcac gaaaaatgat aaaggcaatc attcctcata agatgataaa  10680
aagtgtagtg agagagcatg aaggagattt agtatttagc agtgcggata tgatccaaga  10740
gggtgagata gtcgttctcg ttcagaatct ttcgcagcat aagtagtatg tcgatatact  10800
tatcgttgaa gactcttcca gagacgatag ctgattgagt acaaagtcca atgattgcac  10860
gaagttcttc ggcggttttc atggagtcat ttctgatgaa acatttaatg atctccacgc  10920
aattgtccca cggaagtgaa tccttcaact caccaccaaa gagctccgtt gcatcagttc  10980
tgaaagagat gagaagcctg tagagagacc ctgcgctttc tctatgggtc catctatgag  11040
aaacccacag gatgtattca gtcagacaat gtctgacgtc ggccacggta ttcagggagt  11100
ccttagtagc gtggcaatga cagggtctga actgggcaca aggaaaggcc attgtgaagg  11160
tagacgaagg ttaacctgat ggtagacctg tagccgtcta tgctaataga gggctttaat  11220
ttccattttt taatggggtt gtggatgagg aatgagagtg atatcatatt gagatacgta  11280
gttatgtaga ggtgtatttc ctatattatt tactttcggt ttcatatttt accaactctt  11340
taataaattt cttttcacga tgcatcttat taaatgacgt tttctcataa gtggacatat  11400
agatgcagaa gtaatgaaga aaagtattac ctctatcatc tacataatta gggtctgctc  11460
cttttttaa caacttatac agtacgtagt agtagtttat cggttttaaa tcaagtctag  11520
aatatatagt ggattaatat atttttatat tcgctaaagc tatctatact atcagaaagc  11580
atatcattct caacttcatc atgagttaaa tatttgtgta atggaatgtg accatcactg  11640
tcatgacata ctcctttaat aggtttttta aaacagatga ttcaaatcct tcattcatta  11700
gataacagtg taacggagtc gtaccttcta ctagtttgtt tatatcacag cattctacaa  11760
acagtctaaa caatagagaa gacggacaga ctttaacgta taaatgacac atgttatcga  11820
tattcgttga tgaattatta ttaaacgtag ttatgataaa tgattctaac gacatttctc  11880
```

-continued

```
gctagagata aaatctagta tcgtatcata ctcgcatagc atagtttttc ataattaata  11940
caatatttaa aagacttatt cggaaagtat tttaatacat gtatcatcga tggagatcca  12000
tatgaggagt cacttgtagt tcttcagtag taataacagt gctatcatcg atagtataat  12060
tatatgttgt tgtaattgga gtaactgttg gtagttcttc cgtggaatca ataattatac  12120
taacagcaat agtataatta tataaatatg ttccgttgat atcacatatt ttaatgaact  12180
catttctaac accctcagct atatctgtcc aattaaatgt agccaacaat ctactacgtt  12240
ctctttgatt gactacttgt acggtagcga cgctacacta tctttattgt cttctacatg  12300
ctccaattga atgtcatgat acaacgcagt ttttcttatg catgtttcat aacaccacga  12360
acatgtcgca gtaagataat ttttgtaaat tcatgattgc cggtcataaa caagcccgtc  12420
aataattgtg gctatatatt cagtttatag agcaaaataa ttaagcacaa tagcgcttaa  12480
tctcaaaata tgttatgttt atttttttca tattaaacat actggttaaa atcctctaaa  12540
ggctgatctt catctataaa tcaagatcat aattacattt agacagtggt ttcatgttta  12600
taaaaatgtt ctttttgtgt gaataaggaa tatactaatc aataatcaac catcgacccc  12660
attacgatag tatgcaggca accccccatt agagaggtac gtgtaatcag tctctccagt  12720
tttagtattt ttataagtca ttgttacata aacggctttt aaacagtctc ctcgataata  12780
agccatatct ggaaatttat taaatactcg agtcatttta cgcacggtca aaaaagtaag  12840
taatgtcgac gacttcttac attctataga aacacctaga atactcattt tcttttggaa  12900
aatatcctca gactctgatt tgaacaatgc acgacctata gtaaaccgtg accaataagt  12960
tatattagtc aatggtatat ccaaaccatc aagtgtggat agtacgccga tagtccagtc  13020
tttggtatcg atagtgtagt tattgaactg agaagttacc gtatagtctt tttggtcatc  13080
tctaaacaag gaaactaata cctctacact attgaacgat ttatcttccg taatgggtgg  13140
aataacggga atataaagtg gactagcgat ggatgaagtc acgaatataa gacacgctat  13200
taatccgtat atcatcattt tgatattact tataataacg atttgtttaa tttttagttt  13260
atactattaa ttgtaaatga tattattatt ttttttaagt attatcagct ttagtttata  13320
ctattactat ttgtaatatt tagacataga taaacgtgat aaaagtctat ttgtttatat  13380
ttattgcgga tagcagtatt tccctataaa aagtatacgt cctgtgttgt ctttaatcat  13440
gtacatgaat ggatggttta tgtagacctt cgtacgatat accatcgaaa agttagtcat  13500
aaatactcct gtaacggccg atgcttctgt atactcctca ttaacatcta taaacgtcgt  13560
atgtagaaat ttttctacag tgatagtttc attacacatc ttgctaaaat ctgcataata  13620
tccgaatata ttagtaagtc ctaaattttc taaaatcggt accagattat acggttctgt  13680
catttccact ttaaactttg gcatatacaa gtctatactt ttagtagata acataccaca  13740
ccattttttta aatttttcat ctgttatatt tttttctatg ttatatatac cttctatgtc  13800
gtccggtagt ataattacca tactagagtt tccctcgtat ggaatatcga taatagagaa  13860
tcctccgaat aattcattaa tatgtacata ttgcaagtta ttctcggtac ccaccatcat  13920
atcaacgctg gtaactatat tcttagaaat ataaaacttg tctgtatatg taagatgttt  13980
agaaaatgga tatttccaca ttgctttaaa atggacggcg ctaacaactg tcatacgagt  14040
attaatggat agcggactag tcaataagga attaatttta ccatttgtca ttgtcttaac  14100
ccattcgttg attagttcct ttgtttggtt agcattatta aagtttacag tttgaaaatc  14160
gtcttttatt ttttgtagga aggaggcatg gaactcgata ctatcgctac cgtatatttt  14220
atttgcggta gctagtgtcg cacaatacgg aatatctacg tccatgtcat tattgtcatc  14280
```

-continued

```
gggtgtattc tcattcatat tctctatata ttttgatagt tgttcagctg tagaaccagc  14340
tgctccatga tttagaatag ataaagtaga taaaatagaa actggagaaa tcaaaacatt  14400
ttcatccgtg tgttttaaga ttagttcttt aaagatatcc atggtataga ccaaacaata  14460
acgataacga tatatatcat aaataaataa tgttaaattt tagtttatgt ttgtaccccg  14520
tattcatact taacaaattg gtattgcgta cacaatcaat catattacat accattaata  14580
atgcaagcat aaaaaatcgt tagtagatgt ttctaaatat aggttccgta agcaaagaat  14640
ataagaatga agcggtaatg ataaaatcaa ttgttatcta aaatgatcat actcatttat  14700
tttattctat tatattaaca catacatttt taacagcaac acattcaata ttgtattgtt  14760
atttttatat tatttacaca attaacaata tattattagt ttatattact gaattaataa  14820
tataaaattc ccaatcttgt cataaacaca cactgagaaa cagcataaac acaaaatcca  14880
tcaaaaatgt tgataaatta tctgatgttg ttgttcgctg ctatgataat cagatcattc  14940
gccgatagtg gtaacgctat cgaaacgaca ttgccagaaa ttacaaacgc tacaacagat  15000
attccagcta tcagattatg cggtccagag ggagatggat attgtttaca cggtgactgt  15060
atccacgcta gagatattga cggtatgtat tgtagatgct ctcatggtta tacaggcatt  15120
agatgtcagc atgtagtatt agtagaattc ttacttgtac agctcgtcca tgccgagagt  15180
gatcccggcg gcggtcacga actccagcag gaccatgtga tcgcgcttct cgttggggtc  15240
tttgctcagg gcggactggg tgctcaggta gtggttgtcg ggcagcagca cggggccgtc  15300
gccgatgggg gtgttctgct ggtagtggtc ggcgagctgc acgctgccgt cctcgatgtt  15360
gtggcggatc ttgaagttca ccttgatgcc gttcttctgc ttgtcggcca tgatatagac  15420
gttgtggctg ttgtagttgt actccagctt gtgccccagg atgttgccgt cctccttgaa  15480
gtcgatgccc ttcagctcga tgcggttcac cagggtgtcg ccctcgaact tcacctcggc  15540
gcgggtcttg tagttgccgt cgtccttgaa gaagatggtg cgctcctgga cgtagccttc  15600
gggcatggcg gacttgaaga agtcgtgctg cttcatgtgg tcggggtagc ggctgaagca  15660
ctgcacgccg taggtcaggg tggtcacgag ggtgggccag ggcacgggca gcttgccggt  15720
ggtgcagatg aacttcaggg tcagcttgcc gtaggtggca tcgccctcgc cctcgccgga  15780
cacgctgaac ttgtggccgt ttacgtcgcc gtccagctcg accaggatgg gcaccacccc  15840
ggtgaacagc tcctcgccct tgctcaccat ggtggctgcg gccgccacgg cgatcttgcc  15900
gcccttcttg gccttaatga gaatctcgcg gatcttgcgg gcgtccaact tgccggtcag  15960
tcctttaggc acctcgtcca cgaacacaac accaccgcgc agcttcttgg cggttgtaac  16020
ctggctggcc acatagtcca cgatctcctt ctcggtcatg gttttaccgt gttccagcac  16080
gacgactgcg gcgggcagct cgccggcatc gtcgtcgggc aggccggcga ccccggcgtc  16140
gaagatgttg gggtgttgca gcaggatgct ctccagttcg gctggggcta cctggtagcc  16200
cttgtatttg atcaggctct tcagccggtc cacgatgaag aagtgctcgt cctcgtccca  16260
gtaggcgatg tcgccgctgt gcagccagcc gtccttgtcg atgagagcgt ttgtagcctc  16320
ggggttgtta acgtagccgc tcatgatcat ggggccacgg acgcacagct cgccgcgctg  16380
gttcacaccc agtgtcttac cggtgtccaa gtccaccacc ttagcctcga agaagggcac  16440
caccttgcct actgcgccag gcttgtcgtc cccttcgggg gtgatcagaa tggcgctggt  16500
tgtttctgtc aggccgtagc cctggcggat gcctggtagg tggaagcgtt tggccacggc  16560
ctcacctacc tccttgctga gcggcgcccc gccgctggcg atctcgtgca agttgcttag  16620
```

-continued

```
gtcgtacttg tcgatgagag tgctcttagc gaagaagcta aatagtgtgg gcaccagcag  16680
ggcagattga atcttatagt cttgcaagct gcgcaagaat agctcctcct cgaagcggta  16740
catgagcacg acccgaaagc cgcagatcaa gtagcccagc gtggtgaaca tgccgaagcc  16800
gtggtgaaat ggcaccacgc tgaggatagc ggtgtcgggg atgatctggt tgccgaagat  16860
ggggtcgcgg gcatgactga atcggacaca agcggtgcgg tgcggtaggg ctacgcccctt  16920
gggcaatccg gtactgccac tactgttcat gatcagggcg atggttttgt cccggtcgaa  16980
gctctcgggc acgaagtcgt actcgttgaa gccgggtggc aaatgggaag tcacgaaggt  17040
gtacatgctt tggaagccct ggtagtcggt cttgctatcc atgatgatga tcttttgtat  17100
gatcggtagc ttcttttgca cgttgaggat cttttgcagc cctttcttgc tcacgaatac  17160
gacggtgggc tggctgatgc ccatgctgtt cagcagctcg cgctcgttgt agatgtcgtt  17220
agctggggcc acagccacac cgatgaacag ggcacccaac acgggcatga agaactgcaa  17280
gctattctcg ctgcacacca cgatccgatg gtttgtattc agcccatagc gcttcatagc  17340
ttctgccagc cgaacgctca tctcgaagta ctcggcgtag gtaatgtcca cctcgatatg  17400
tgcgtcggta aaggcgatgg tgccgggcac cagggcgtag cgcttcatgg ctttgtgcag  17460
ctgctcgccg gcggtcccgt cttcgagtgg gtagaatggc gctgggccct tcttaatgtt  17520
tttggcatct tccatggccc cggccgtgca ataaattaga atagtttttc aatttttggt  17580
acctcgacct tatttatatg ccaaaaaaaa aaaaaaaaaa gctgatccaa tttcgacgag  17640
actatcaacg ttcagaaaac ccaaacacta caacgtcata tatcccatct cccggtatta  17700
tgcttgtatt agtaggcatt attattatta cgtgttgtct attatctgtt tataggttca  17760
ctcgacgaac taaactactt atacaagata tggttgtgcc ataattttta taaatttttt  17820
ttatgagtat ttttacaaaa atgtataaag tgtatgtctt atgtatattt ataaaaatgc  17880
taaatatgcg atgtatctat gttatttgta tttatctaaa caatacctct acctctagat  17940
attatacaaa aatttttat ttcagcatat taaagtaaaa tctagttacc ttgaaaatga  18000
atacagtggg tggttccgta tcaccagtaa gaacataata gtcgaataca gtatccgatt  18060
gagattttgc atacaatact agtctagaaa gaaatttgta atcattttct gtgacgggag  18120
tccatatatc tgtatcatcg tctagtttat cagtgtccca tgctatattc ctgttatcat  18180
cattagttaa tgaaaataac tctcgtgctt cagaaaagtc aaatattgta tccatacata  18240
catctccaaa actatcgctt atacgtttat ctttaacgat acctatacct agatggttat  18300
ttactaacag acattttcca gatctattga ctataactcc tatagtttcc acatcaacca  18360
agtaatgatc atctattgtt atataacaat aacataactc ttttccattt ttatcagtat  18420
gtatatctat atcaacgtcg tcgttgtagt gaatagtagt cattgatcta ttatatgaaa  18480
cggatatgtc tagaacggca attgttttac gtccagttaa cactttcttt gatttaaagt  18540
ctagagtctt tgcaaacata atatccttat ccgactttat atttcctgta gggtggtata  18600
attttatttt gcctccacat atcggtgttt ccaaatatat tactagacaa tattccatat  18660
agttattagt taagggtacc caattagaac acgtacgctt attatcatca tttggatcgt  18720
atttcataaa agttattgta ctatcgatgt caacacattc tacatttttt aatcgtctat  18780
atagtatttt tctgatattt tctataatat cagaattgtc ttccatcgga agttgtatac  18840
tatcggaatc agttacatgt ttaaataatt ctctgatgtc attccttata caatcaaatt  18900
cattattaaa cagtttaata gtctgtagac ctttatcgtc gtaaatatcc attgtcttat  18960
tagttacgct tatttttatg tgttttacat tgctttatta tattttataa gaatgattgt  19020
```

```
ttgacgaatc acgagaacta ttaagacaca ttattaggta tatattataa aaaagttttt  19080
gattacgatg ttataagagg aaagaggaca cattaacatc atacatcaat taactacatt  19140
cttataacat cgtaatcaaa agaattgcaa ttttgatgta taacaactgt caatgggtta  19200
tggaattgta tattacatat tatacggtat gttggtaacg acaaataccg gtcggtaatt  19260
gtctgccggt gtaatagaat tatatatata tctatctatt acaccggcct tgtatacata  19320
ataataagtt gtggtagtat gatctccata tttataattt aggactttgt attcagtatt  19380
tttggaatca taaaaaataa aaaaaagttt tactaattta aaatttaaaa agtatttaca  19440
ttttttcac tgtttagtcg cggatatgga attcgatcct gccaaaatca atacatcatc  19500
tatagatcat gtaacaatat tacaatacat agatgaacca aatgatataa gactaacagt  19560
atgcattatc cgaaatatta ataacattac atattatatc aatatcacaa aaataaatac  19620
acatttggct aatcaatttc gggcttggaa aaaacgtatc gccggaaggg actatataac  19680
taacttatct agagatacag gaatacaaca atcaaaactt actgaaacta tacgtaactg  19740
tcaaaaaaat agaaacatat atggtctata tatacactac aatttagtta ttaatgtggt  19800
tattgattgg ataaccgatg tgattgttca atcaatatta agagggttgg taaattggta  19860
catagctaat aatacctata cacccaataa tacaacaacc atttctgagt tggatatcat  19920
caaaatactg gataaatacg aggacgtgta tagagtaagt aaagaaaaag aatgtggaat  19980
ttgctatgaa gttgtttact caaaacgatt agaaaacgat agatactttg gtttattgga  20040
ttcgtgtaat catatatttt gcataacatg tatcaatata tggcataaaa cacgaagaga  20100
aaccggtgcg tcggataatt gtcctatatg tcgtacccgt tttagaaaca taacaatgag  20160
caagttctat aagctagtta actaataaat aaaaagttta atttgttgac gacgtatgtc  20220
gttatttttt ctcgtataaa agattaaatt caattcaatt cgttgtttct aatataatct  20280
gccgtattgg atggattctc aagacaattg catttagatt atattatcat gaataaaaat  20340
agtagcacac aactacttca gcaaatattc ttttttgaaa cgccatctat cgtagtgagg  20400
acacaagtga acctataatt atcaaattta ttagtatcag tcacatgaag gactttctgt  20460
agagtgacga ttccactatc tgtggtacga acggtttcat cttctttgat gccatcaccc  20520
agatgttcta taaacttggt atcctcgtcc gatttcatat cctttgccaa ccaatacata  20580
tagctaaact caggcatatg ttccacacat cctgaacaat gaaattctcc agaagatgtt  20640
acaatgtcta gatttggaca tttggtttca accgcgttaa catatgagtg aacacaccca  20700
tacatgaaag cgatgagaaa taggattctc atcttgccaa aatatcacta gaaaaaattt  20760
atttatcaat tttaaaggta taaaaaatac ttattgttgc tcgaatattt tgtatttgat  20820
ggtatacgga agattagaaa tgtaggtatt atcatcaact gattctatgg ttttatgtat  20880
tctatcatgt ttcactattg cgttggaaat aatatcatat gcttccacat atattttatt  20940
ttgttttaac tcataatact cacgtaattc tggattattg gcatatctat gaataatttt  21000
agctccatga tcagtaaata ttaatgagaa catagtatta ccacctacca ttattttttt  21060
catctcattc aattcttaat tgcaaagatc tatataatca ttatagcgtt gacttatgga  21120
ctctggaatc ttagacgatg tacagtcatc tataatcatg gcatatttaa tacattgttt  21180
tatagcatag tcgttatcta cgatgttaga tatttctctc aatgaatcaa tcacataatc  21240
taatgtaggt ttatgacata atagcatttt cagcagttca atgtttttag attcgttgat  21300
ggcaatggct atacatgtat atccgttatt tgatctaatg ttgacatctg aaccggattc  21360
```

```
tagcagtaaa gatactagag attgtttatt atatctaaca gccttgtgaa gaagtgtttc  21420
tcctcgtttg tcaatcatgt taatgtcttt aagataaggt aggcaaatgt ttatagtact  21480
aagaattggg caagcataag acatgtcaca aagacccttt ttgtatgtat aagtgtaaaa  21540
attataacat ccatagttgg atttacatag gtgtccaatc gggatctctc catcatcgag  21600
ataattgatg gcatctccct tcctttttta gtagatattt catcgtgtaa gaatcaatat  21660
taatatttct aaagtatccg tgtatagcct ctttatttac cacagttcca tattccacta  21720
gagggatatc gccgaatgtc atatactcaa ttagtatatg ttggaggaca tccgagttca  21780
ttgttttcaa tatcaaaaag atggtttcct tatcatttct ccatagtggt acaatactac  21840
acattatttc gtgcggcttt ccattttcca aaaacaattt gaccaaatct aaatctacat  21900
ctttattgta tctataatca ctatttagat aatcagccat aattcctcga gtgcaacatg  21960
ttagatcgtc tatatatgaa taagccgtgt tatctattcc tttcattaac aatttaacga  22020
tgtctatatc tatatgagat gacttaatat aatattgaag agctgtacaa tagtttttat  22080
ctataaaaga cggcttgatt ccgtgattaa ttagacattt aacaacttcc ggacgcacat  22140
atgctctcgt atccgacttt gaatacagat gagagatgat atacagatgc aatacggtac  22200
cgcaatttcg tagttgataa tcatcatacg cgtatcagta ctcgtcctca taaagaacac  22260
tgcagccatt ttctatgaac aaatcaataa ttttaggaac aggatcattg tcattacata  22320
attttctata actgaacgat ggttttcaca tttaacactc aagtcaaatc catgttctac  22380
caacaccttt atcaagtcaa cgtctacatt tttggatttc atatagctga atatattaaa  22440
gtcatttatg ttgctaaatc cagtggcttc tagtagagcc atcgctatat cctttaactt  22500
taacatgtct actatttgtg tattcttcta atggggtagc tgtctccaat ttttgcgtaa  22560
tggattagtg ccactgtcta gtagtagttt gacgacctcg acattattac aatgctcatt  22620
aaaaaggtat gcgtgtaaag cattattctt gaattggttc ctggtatcat taggatctct  22680
gtctctcaac atctgtttaa gttcatcgag agccacctcc tcattttcca aatagtcaaa  22740
cattttgact gaatgagcta ctgtgaactc tatacaccca cacaactaat gtcattaaat  22800
atcatgtcaa aaacttgtac aattattaat aaaaataatt tagtgtttaa attttaccag  22860
ttccagattt tacacctccg ttaatacctc cattaacccc actggacgat cctcctcccc  22920
acattccacc gccaccagat gtataagttt tagatccttt attactacca tcatgtccat  22980
ggataaagac actccacatg ccgccactac cccctttaga agacatatta ataagactta  23040
aggacaagtt taacaataaa attaatcacg agtaccctac taccaaccta cactattata  23100
tgattatagt ttctattttt acagtacctt gactaaagtc tctagtcaca agagcaatac  23160
taccaaccta cactattata tgattatagt ttctattttt ataggaacgc gtacgagaaa  23220
atcaaatgtc taatttctaa cggtagtgtt gataaacgat tatcgtcaat ggatacctcc  23280
tctatcatgt cgtctatttt cttactttgt tctattaact tattagcatt atatattatt  23340
tgattataaa acttatattg cttattagcc caatctgtaa atatcggatt attaacatat  23400
cgtttctttg taggtttatt taacatgtac atcactgtaa gcatgtccgt accatttatt  23460
ttaatttgac gcatatccgc aatttctttt tcgcagtcgg ttataaattc tatatatgat  23520
ggatacatgc tacatgtgta cttataatcg actaatatga agtacttgat acatattttc  23580
agtaacgatt tattattacc acctatgaat aagtacctgt gatcgtctag gtaatcaact  23640
gttttttttaa tacattcgat ggttggtaat ttactcagaa taatttccaa tatcttaata  23700
tataattctg ctatttctgg gatatattta tctgccagta taacacaaat agtaatacat  23760
```

-continued

```
gtaaacccat attttgttat tatattaatg tctgcgccat tatctattaa ccattctact  23820
aggctgacac tatgcgactc aatacaatga taaagtatac tacatccatg tttatctatt  23880
ttgtttatat cattaatata cggcttacaa agttttagta tcgataacac atccaactca  23940
cgcatagaga aggtagggaa taatggcata atatttatta ggttatcatc attgtcatta  24000
tctacaacta agtttccatt ttttaaaata tactcgacaa ctttaggatc tctattgcca  24060
aatttttgaa aatatttatt tatatgctta aatctatata atgtagctcc ttcatcaatc  24120
atacatttaa taacattgat gtatactgta tgataagata catattctaa caatagatct  24180
tgtatagaat ctgtatatct tttaagaatt gtggatatta ggatattatt acgtaaacta  24240
ttacacaatt ctaaaatata aaacgtatca cggtcgaata atagttgatc aactatataa  24300
ttatcgattt tgtgattttt cttcctaaac tgtttacgta aatagttaga tagaatattc  24360
attagttcat gaccactata gttactatcg aataacgcgt caaatatttc ccgtttaata  24420
tcgcatttgt caagataata atagagtgtg gtatgttcac gataagtata ataacgcatc  24480
tctttttcgt gtgaaattaa atagtttatt acgtccaaag atgtagcata accatcttgt  24540
gacctagtaa taatataata atagagaact gttttaccca ttctatcatc ataatcagtg  24600
gtgtagtcgt aatcgtaatc gtctaattca tcatcccaat tataatattc accagcacgt  24660
ctaatctgtt ctattttgat cttgtatcca tactgtatgt tgctacatgt aggtattcct  24720
ttatccaata atagtttaaa cacatctaca ttgggatttg atgttgtagc gtattttttct  24780
acaatattaa taccattttt gatactattt atttctatac ctttcgaaat tagtaatttc  24840
aataagtcta tatcgatgtt atcagaacat agatattcga atatatcaaa atcattgata  24900
tttttatagt cgactgacga caataacaaa atcacgacat cgtttttgat attattattt  24960
ttcttggtaa cgtatgcctt taatggagtt tcaccatcat actcatataa tggatttgca  25020
ccactttcta tcaatgattg tgcactgctg gcatcgatgt taaatgtttt acaactatca  25080
tagagtatct tatcgttaac catgattggt tgttgatgct atcgcatttt ttggtttctt  25140
tcatttcagt tatgtatgga tttagcacgt ttgggaagca tgagctcata tgatttcagt  25200
actgtagtgt cagtactatt agtttcgatc agatcaatgt ctagatctat agaatcaaaa  25260
cacgataggt cagaagataa tgaatatctg tacgcttctt gttgtactgt aacttctggt  25320
tttgttagat ggttgcatcg tgctttaacg tcaatggtac aaattttatc ctcgctttgt  25380
gtatcatatt cgtccctact ataaaattgt atattcagat tatcatgaga tgtgtatacg  25440
ctaacggtat caataaacgg agcacaccat ttagtcataa ccgtaatcca aaaattttta  25500
aagtatatct taacgaaaga agttgtgtca ttgtctacgg tgtatggtac tagatcctca  25560
taagtgtata tatctagagt aatgtttaat ttattaaatg gttgataata tggatcctca  25620
tgacaatttc cgaagatgga aataagacat aaacacgcaa taaatctaat tgcggacatg  25680
gttactcctt aaaaaaatac gaataatcac cttggctatt tagtaagtgt catttaacac  25740
tatactcata ttaatccatg gactcataat ctctatacgg gattaacgga tgttctatat  25800
acggggatga gtagttctct tctttaactt tatacttttt actaatcata tttagactga  25860
tgtatgggta atagtgtttg aagagctcgt tctcatcatc agaataaatc aatatctctg  25920
tttttttgtt atacagatgt attacagcct catatattac gtaatagaac gtgtcatcta  25980
ccttattaac tttcaccgca tagttgtttg caaatacggt taatcctttg acctcgtcga  26040
tttccgacca atctgggcgt ataatgaatc taaactttaa tttcttgtaa tcattcgaaa  26100
```

```
taatttttag tttgcatccg tagttatccc ctttatgtaa ctgtaaattt ctcaacgcga  26160
tatctccatt aataatgatg tcgaattcgt gctgtatacc catactgaat ggatgaacga  26220
ataccgacgg cgttaatagt aatttacttt ttcatcttta catattgggt actagtttta  26280
ctatcataag tttataaatt ccacaagcta ctatggaata agccaaccat cttagtataa  26340
cacacatgtc ttaaagttta ttaattaatt acatgttgtt ttatatatat cgctacgaat  26400
ttaaacagag aaatcagttt aggaaaaaaa attatctatc tacatcatca cgtctctgta  26460
ttctacgata gagtgctact ttaagatgcg acagatctgt gtcatcaaat atatactcca  26520
ttaaaatgat tattccggca gcgaacttga tattggatat atcacaacct ttgttaatat  26580
ctacgacaat agacagcagt cccatggttc cataaacagt gagtttatct ttctttgaag  26640
agatattttg tagagatctt ataaaactgt cgaatgacat cgcatttata tctttagcta  26700
aatcgtatat gttaccatcg taatatctaa ccgcgtctat cttaaacgtt tccatcgctt  26760
taaagacgtt tccgatagat ggtctcattt catcagtcat actgagccaa caaatataat  26820
cgtgtataac atctttgata gaatcagact ctaaagaaaa cgaatcggct ttattatacg  26880
cattcatgat aaacttaatg aaaaatgttt ttcgttgttt aagttggatg aatagtatgt  26940
cttaataatt gttattattt cattaattaa tatttagtaa cgagtacact ctataaaaac  27000
gagaatgaca taactagtta tcaaagtgtc taggacgcgt aattttcata tggtatagat  27060
cctgtaagca ttgtctgtat tctggagcta ttttctctat cgcattagtg agttcagaat  27120
atgttataaa tttaaatcga ataacgaaca taactttagt aaagtcgtct atattaactc  27180
ttttattttc tagccatcgt aataccatgt ttaagatagt atattctcta gttactacga  27240
tctcatcgtt gtctagaata tcacatactg aatctacatc caattttaga aattggtctg  27300
tgttacatat ctcttctata ttattgttga tgtattgtcg tagaaaacta ttacgtagac  27360
cattttcttt ataaaacgaa tatatagtac tccaattatc tttaccgata tatttgcaca  27420
cataatccat tctctcaatc actacatctt taagattttc gttgttaaga tatttggcta  27480
aactatataa ttctattaga tcatcaacag aatcagtata tatttttcta gatccaaaga  27540
cgaactcttt ggcgtcctct ataatattcc cagaaaagat attttcgtgt tttagtttat  27600
cgagatctga tctgttcata tacgccatga ttgtacggta cgttatgata accgcataaa  27660
ataaaaatcc attttcattt ttaaccaata ctattcataa ttgagattga tgtaatactt  27720
tgttactttg aacgtaaaaa cagtacacgg atccgtatct ccaacaagca cgtagtaatc  27780
aaatttggtg ttgttaaact tcgcaatatt catcaattta gatagaaact tatactcatc  27840
atctgtttta ggaatccatg tattattacc actttccaac ttatcattat cccaggctat  27900
gtttcgtcca tcatcgttgc gcagagtgaa taattctttt gtattcggta gttcaaatat  27960
atgatccatg catagatcag taaagctatt gtagatgtga tttttcctaa atctaatata  28020
aaactcgttt actagcaaac actttcctga tttatcgacc aagacacata tggtttctaa  28080
atctatcaag tggtggggat ccatagttat gacgcagtaa catatattat tacattcttg  28140
actgtcgcta atatctaaat atttattgtt atcgtattgg attctgcata tagatggctt  28200
gtatgtcaaa gatatagaac acataaccaa tttatagtcg cgctttacat tctcgaatct  28260
aaagttaaga gatttagaaa acattatatc ctcggatgat gttatcactg tttctggagt  28320
aggatatatt aaagtcttta cagatttcgt ccgattcaaa taaatcacta aataatatcc  28380
cacattatca tctgttagag tagtatcatt aaatctatta tattttatga aagatatatc  28440
actgctcacc tctatatttc gtacattttt aaactgtttg tataatatct ctctgataca  28500
```

-continued atcagatata tctattgtgt cggtagacga taccgttaca tttgaattaa tggtgttcca 28560
ttttacaact tttaacaagt tgaccaattc atttctaata gtatcaaact ctccatgatt 28620
aaatatttta atagtatcca ttttatatca ctacggacac aaagtagctg acataaacca 28680
ttgtataatt tttatgtttt atgtttatta gcgtacacat tttggaagtt ccggcttcca 28740
tgtatttcct ggagagcaag tagatgatga ggaaccagat agtttatatc cgtacttgca 28800
cttaaagtct acattgtcgt tgtatgagta tgatctttta aacccgctag acaagtatcc 28860
gtttgatatt gtaggatgtg gacatttaac aatctgacac gtgggtggat cggaccattc 28920
tcctcctgaa cacaggacac tagagttacc aatcaacgaa tatccactat tgcaactata 28980
agttacaacg ctcccatcgg tataaaaatc ctcgtatccg ttatgtcttc cgttggatat 29040
agatggaggg gattggcatt taacagattc acaaataggt gcctcgggat tccataccat 29100
agatccagta gatcctaatt cacaatacga tttagattca ccgatcaaat gatatccgct 29160
attacaagag tacgttatac tagagccaaa gtctactcca ccaatatcaa gttggccatt 29220
atcgatatct cgaggcgatg ggcatctccg tttaatacat tgattaaaga gtgtccatcc 29280
agtacctgta catttagcat atataggtcc catttttttgc tttctgtatc caggtagaca 29340
tagatattct atagtgtctc ctatgttgta attagcatta gcatcagtct ccacactatt 29400
cttaaatttc atattaatgg gtcgtgacgg aatagtacag catgatagaa cgcatcctat 29460
tcccaacaat gtcaggaacg tcacgctctc caccttcata tttatttatc cgtaaaaatg 29520
ttatcctgga catcgtacaa ataataaaaa gcccatatat gttcgctatt gtagaaattg 29580
tttttcacag ttgctcaaaa acgatggcag tgacttatga gttacgttac actttggagt 29640
ctcatcttta gtaaacatat cataatattc gatattacga gttgacatat cgaacaaatt 29700
ccaagtattt gattttggat aatattcgta ttttgcatct gctataatta agatataatc 29760
accgcaagaa cacacgaaca tctttcctac atggttaaag tacatgtaca attctatcca 29820
tttgtcttcc ttaactatat atttgtatag ataattacga gtctcgtgag taattccagt 29880
aattacatag atgtcgccgt cgtactctac agcataaact atactatgat gtctaggcat 29940
gggagacttt tttatccaac gatttttagt gaaacattcc acatcgttta atactacata 30000
tttttcatac gtggtataaa ctccacccat tacatatata tcatcgttta cgaataccga 30060
cgcgcctgaa tatctaggag taattaagtt tggaagtctt atccatttcg aagtgccgtg 30120
tttcaaatat tctgccacac ccgttgaaat agaaaattct aatcctccta ttacatataa 30180
ctttccatcg ttaacacaag tactaacttc tgattttaac gacgacatat tagtaaccgt 30240
tttccatttt ttcgtttcaa gatctacccg cgatacggaa taaacatgtc tattgttaat 30300
catgccgcca ataatgtata gacaattatg taaaacattt gcattataga attgtctatc 30360
tgtattaccg actatcgtcc aatattctgt tctaggagag taatgggtta ttgtggatat 30420
ataatcagag tttttaatga ctactatatt atgttttata ccatttcgtg tcactggctt 30480
tgtagatttg gatatagtta atcccaacaa tgatatagca ttgcgcatag tattagtcat 30540
aaacttggga tgtaaaatgt tgatgatatc tacatcgttt ggatttttat gtatccactt 30600
taataatatc atagctgtaa catcctcatg atttacgtta acgtcttcgt gggataagat 30660
agttgtcagt tcatcctttg ataattttcc aaattctgga tcggatgtca ccgcagtaat 30720
attgttgatt atttctgaca tcgacgcatt atatagtttt ttaattccat atcttttaga 30780
aaagttaaac atccttatac aatttgtgaa attaatatta tgaatcatag tttttacaca 30840

-continued

```
tagatctact acaggcggaa catcaattat tacggcagca actagtatca tttctacatt  30900
gtttatggtg atgtttatct tcttccagcg catatagtct aatagcgatt caaacgcgtg  30960
atagtttata ccattcaata taatcgcttc atcctttaga tggtgatcct gaatgcgttt  31020
aaaaaaatta tacggagacg ccgtaataat ttccttattc acttgtataa tttccccatt  31080
gatagaaaat atcacgcttt ccattcttaa agtactataa gtaattatag tataatgtaa  31140
acgtttatat attcaatatt tttataaaaa tcattttgac attaattcct ttttaaattt  31200
ccgtctatca tctatagaaa cgtattctat gaatttataa aatgctttta cgtgtcctat  31260
cgtaggcgat agaaccgcta aaaagcctat cgaatttcta caaaagaatc tgttatatgg  31320
tatagggaga gtataaaaca ttaaatgtcc gtacttatta aagtattcag tagccaatcc  31380
taactctttc gaatacttat taatggctct tgttctgtac gaatctattt ttttgaacaa  31440
cggacctagt ggtatatctt gttctatgta tctaaaataa tgtctgacta gatccgttag  31500
tttaatatcc tcagtcatct tgtctagaat ggcaaatcta actgcgggtt taggctttag  31560
tttagtttct atatctacat ctatgtcttt atctaacacc aaaaatataa tagctaatat  31620
tttattacaa tcatccggat attcttctac gatctcacta actaatgttt ctttggttat  31680
actagtatag tcactatcgg acaaataaag aaaatcagat gatcgatgaa taatacattt  31740
aaattcatca tctgtaagat ttttgagatg tctcattaga atattattag ggttagtact  31800
cattatcatt aggcagctat tacttatttt attatttttc accatataga tcaatcatta  31860
gatcatcaaa atatgtttca atcatcctaa agagtatggt gaatgactct tcccatctaa  31920
tttctgaacg ttcaccaatg tctctagcca ctttggcact aatagcgatc attcgcttag  31980
cgtcttctat attattaact ggttgattca atctatctag caatggaccg tcggacagcg  32040
tcattctcat gttcttaatc aatgtacata catcgccgtc atctaccaat tcatccaaca  32100
acataagctt tttaaaatca tcattataat aggtttgatc gttgtcattt ctccaaagaa  32160
tatatctaat aagtagagtc ctcatgctta gtaatttaac tattttagtt aacaactatt  32220
ttttatgtta aatcaattag tacaccgcta tgtttaatac ttattcatat tttagttttt  32280
aggattgaga atcaatacaa aaattaatgc atcattaatt ttagaaatac ttagtttcca  32340
cgtagtcaat gaaacatttg aactcatcgt acaggacgtt ctcgtacagg acgtaactat  32400
aaaccggttt atatttgttc aagatagata caaatccgat aacttttttt acgaattcta  32460
cgggatccac tttaaaagtg tcataccggg ttcttttttat tttttaaac agatcaatgg  32520
tgtgatgttg attaggtctt ttacaaattt gatatagaat agcgtttaca tattctccat  32580
aatggtcaat cgccatttgt tcgtatgtca taaattcttt aattatatga cactgtgtat  32640
tatttagttc atccttgttc attgttagga atctatccaa aatggcaatt atactagaac  32700
tataggtgcg ttgtatacac atattgatgt gtctgtttat acaatccatg atatttggat  32760
ccatgctact accttcgggt aaaattgtag catcatatac catttctagt actttaggtt  32820
cattattatc cattgcagag gacgtcatga tcgaatcata aaaaaatata ttatttttat  32880
gttattttgt taaaaataat catcgaatac ttcgtaagat actccttcat gaacataatc  32940
agttacaaaa cgtttatatg aagtaaagta tctacgattt ttacaaaagt ccggatgcat  33000
aagtacaaag tacgcgataa acggaataat aatagattta tctagtctat ctttttctat  33060
agctttcata gttagataca tggtctcaga agtaggatta tgtaacatca gcttcgataa  33120
aatgactggg ttatttagtc ttacacattc gctcatacat gtatgaccgt taactacaga  33180
gtctacacta aaatgattga acaatagata gtctaccatt gtttcgtatt cagatagtac  33240
```

```
agcgtagtac atggcatctt cacaaattat atcattgtct aatagatatt tgacgcatct  33300
tatggatccc acttcaacag ccatcttaaa atcggtagaa tcatattgct ttcctttatc  33360
attaataatt tctagaacat catctctatc ataaaagata caaatattaa ctgtttgatc  33420
cgtaataaca ttgctagtcg atagcaattt gttaataaga tgcgctgggc tcaatgtctt  33480
aataagaagt gtaagaggac tatctccgaa tttgttttgt ttattaacat ccgttgatgg  33540
aagtaaaaga tctataatgt ctacattctt gactgtttta gagcatacaa tatggagagg  33600
tgtatttcca tcatgatctg gttttgaggg actaattcct agtttcatca tccatgagat  33660
tgtagaagct tttggattgt ctgacataag atgtctatga atatgatttt tgccaaattt  33720
atccactatc ctggcttcga atccgatgga cattattttt ttaaacactc tttctgaagg  33780
atctgtacac gccaacaacg gaccacatcc ttcttcatca accgagttgt taatcttggc  33840
tccatactgt accaataaat ttattctctc tatgacttca tcatctgttc ccgagagata  33900
atatagaggc gttttatgct gtttatcaca cgcgtttgga tctgcgccgt gcgtcagcag  33960
catcgcgact attctattat tattaatttt agaagctata tgcaatggat aatttccatc  34020
atcatccgtc tcatttggag agtatcctct atgaagaagt tcttcgacaa atcgttcatc  34080
tagtccttta attccacaat acgcatgtag aatgtgataa ttatttccag aaggttcgat  34140
agcttgtagc atattcctaa atacatctaa atttttacta ttatatttgg cataaagaga  34200
tagataatac tcggccgaca taatgttgtc cattgtagta taaaaattaa tatttctatt  34260
tctatttctg tatatttgca acaatttact ctctataaca aatatcataa cttagttctt  34320
ttatgtcaag aaggcactgg tttagttcat ctataaatgt cacgccataa ctaccacgca  34380
tgccatactc agaattatga taaagatatt tatccttggg gtgtaggtaa tggggattaa  34440
tctttgttgg atcagtctct aagttaacac atgtcacaca tgatccattt atagttatat  34500
cacacgatga tgatttatga attgattccg gaagatcgct atcgtatttt gtggttccac  34560
aattcatttc catacatgtt attgtcacac taatattatg atgaacttta tctagccgct  34620
gagtggtaaa caacagaaca gatagtttat tatctttacc aacaccctca gccgctgcca  34680
caaatctctg atccgtatcc atgatggtca tgtttatttc tagtccgtat ccagtcaaca  34740
ctatgttagc atttctgtcg atatagcttt cactcatatg acactcacca ataatagtag  34800
aattaatgtc gtaatttaca ccaatagtga gttcggcggc aaagtaccaa taccggtaat  34860
cttgtcgagg aggacatata gtattcttgt attctaccga atacccgaga gatgcgatac  34920
aaaagagtaa gactaatttg taaaccatct tactcaaaat atgtaacaat agtacgatgc  34980
aatgagtaag acaataggaa atctatctta tatacacata attattctat caattttacc  35040
aattagttag tgtaatgtta acaaaaatgt gggagaatct aattagtttt tctttacaca  35100
attgacgtac atgagtttga gttccttgtt tttgctaatt atttcatcca atttattatt  35160
cttgacgata tcgagatctt ttgtatagga gtcagacttg tattcaacat gcttttctat  35220
aatcatttta gctatttcgg catcatccaa tagtacattt tccagattag cagaatagat  35280
attaatgtcg tatttgaaca gagcctgtaa catctcaatg tctttattat ctatagccaa  35340
tttaatgtcc ggaatgaaga gaagggaatt attggtgttt gtcgacgtca tatagtcgag  35400
caagagaatc atcatatcca cgtgtccatt ttttatagtg atgtgaatac aactaaggag  35460
aatagccaga tcaaaagtag atggtatctc tgaaagaaag taggaaacaa tacttacatc  35520
attaagcatg acggcatgat aaaatgaagt tttccatcca gttttcccat agaacatcag  35580
```

-continued

```
tctccaattt ttcttaacaa acagttttac cgtttgcatg ttaccactat caaccgcata  35640
atacaatgca gtgtttccct tgtcatcaaa ttgtgaatca tccagtccac tgaatagcaa  35700
aatctttact attttagtat cttccaatgt ggctgcctga tgtaatggaa attcattctc  35760
tagaagattt ttcaatgctc cagcgttcaa caacgtacat actagacgca cgttattatc  35820
agctattgca taatacaagg cactatgacc gttgatatcc gccttaaatg catctttgct  35880
agagagaaag cttttcagct gcttagactt ccaagtatta attcgtgaca gatccatgtc  35940
tgaaacaaga cgctaattag tgtatatttt ttcatttttt ataattttgt catattgcac  36000
cagaattaat aatatctcta atagatctga ttagtagata catggctatc gcaaaacaac  36060
atatacacat ttaataaaaa taatatttat taagaaaatt cagatttcac gtacccatca  36120
atataaataa aataatgatt ccttacaccg tacccatatt aaggagattc caccttaccc  36180
ataaacaata taaatccagt aatatcatgt ctgatgatga acacaaatgg tgtattaaat  36240
tccagttttt caggagatga tctcgccgta gctaccataa tagtagatgc ctctgctaca  36300
gttccttgtt cgtcgacatc tatctttgca ttctgaaaca ttttataaat atataatggg  36360
tccctagtca tatgtttaaa cgacgcatta tctggattaa acatactagg agccatcatt  36420
tcggctatcg acttaatatc cctcttattt tcgatagaaa atttagggag tttaagattg  36480
tacactttat tccctaattg aaacgaccaa tagtctaatt ttgcagccgt gatagaatct  36540
gtgaaatggg tcatattatc acctattgcc aggtacatac taatattagc atccttatac  36600
ggaaggcgta ccatgtcata ttctttgtca tcgattgtga ttgtatttcc ttgcaattta  36660
gtaactacgt tcatcatggg aaccgttttc gtaccgtact tattagtaaa actagcattg  36720
cgtgttttag tgatatcaaa cggatattgc catatacctt taaaatatat agtattaatg  36780
attgcccata gagtattatt gtcgagcata ttagaatcta ctacattaga cataccggat  36840
ctacgttcta ctatagaatt aattttatta accgcatctc gtctaaagtt taatctatat  36900
aggccgaatc tatgatattg ttgataatac gacggtttaa tacacacagt attatctacg  36960
aaactttgat aagttagatc agtgtacgta tatttagatg ttttcagctt agctaatcct  37020
gatattaatt ctgtaaatgc tggacccaga tctctttttc tcaaatccat agtcttcaat  37080
aattctattc tagtattacc tgatgcaggc aatagcgaca taaacataga aaacgaataa  37140
ccaaacggtg agaagacaat attatcatct tgaatatttt tatacgctac tataccggca  37200
ttggtaaatc cttgtagacg ataggcggac gctgaacacg ctaacgatag tatcaataac  37260
gcaatcatga ttttatggta ttaataatta accttatttt tatgttcggt ataaaaaaat  37320
tattgatgtc tacacatcct tttgtaattg acatctatat atccttttgt ataatcaact  37380
ctaatcactt taacttttac agttttccct accagtttat ccctatattc aacatatcta  37440
tccatatgca tcttaacact ctctgccaag atagcttcag agtgaggata gtcaaaaaga  37500
taaatatata gagcataatc attctcgtat actctgccct ttattacatc acccgcattg  37560
ggcaacgaat aacaaaatgc aagcatcttg ttaacgggct cgtaaattgg gataaaaatt  37620
atgtttttat tgtcttatat ctattttatt caagagaata ttcaggaatt tctttttccg  37680
gttgtatctc atcgcagtat atatcatttg tacattgttt tatatttttt aatagtttac  37740
acctttagt aggactagta tcgtacaatt catagctgta ttttgaattc caatcacgca  37800
taaaaatatc ttccaattgt tgacgaagac ctaatccatc atccggtgta atattaatag  37860
atgctccaca tgtatccgta aagtaatttc ctgtccaatt tgaggtacct atataggccg  37920
ttttatcggt taccatatat ttggcatggt ttaccctaga atacggaatg ggaggatcag  37980
```

catctggtac aataaatagc tttacttcta tatttatgtt tttagatttt agcatagcga 38040
tagatcttaa aaagtttctc atgataaacg aagatcgttg ccagcaacta atcaatagct 38100
taacggatac ttgtctgtct atagcggatc ttcttaattc atcttctata taaggccaaa 38160
acaaaatttt acccgccttc gaataaataa tagggataaa gttcataaca gatacataaa 38220
cgaatttact cgcatttcta atacatgaca ataaagcggt taaatcattg gttctttcca 38280
tagtacatag ttgttgcggc gcagaagcaa taaatacaga gtgtggaacg ccgcttacgt 38340
taatactaag aggatgatct gtattataat acgacggata aaagtttttc caattatatg 38400
gtagattgtt aactccaaga taccagtata cctcaaaaat ttgagtgaga tccgctgcca 38460
agttcctatt attgaagatc gcaataccca attctttgac ctgagttagt gatctccaat 38520
ccatgttagc gcttcctaaa taaatatgtg tattatcaga tatccaaaat tttgtatgaa 38580
gaactcctcc taggatattt gtaatatcta tgtatcgtac ttcaactccg gccatttgta 38640
gtctttcaac atcctttaat ggtttgttag atttattgac ggctactcta actcgtactc 38700
ctcttttggg taattgtaca atctcgttta atattatcgt gccgaaattc gtacccactt 38760
catccgataa actccaataa aaagatgata tatctagtgt ttttgtggta ttggatagaa 38820
tttccctcca catgttaaat gtagacaaat atactttatc aaattgcata cctataggaa 38880
tagtctctgt aatcactgcg attgtattat ccggattcat tttatttgtt aaaaaataat 38940
cctatatcac ttcactctat taaaaatcca agtttctatt tctttcatga ctgatttttt 39000
aacttcatcc gtttccttat gaagatgatg tttggcacct tcataaattt ttatttctct 39060
attacaattt gcatgttgca tgaaataata tgcacctaaa acatcgctaa tcttattgtt 39120
tgttccctgg agtatgagag tcggggggtg ttaatcttgg aaattatttt tctaaccttg 39180
ttggtagcct tcaagacctg actagcaaat ccagccttaa tttttttcatg attgactaat 39240 gggtcgtatt ggtatttata aacttcatcc atatctctag atactgattc tggacatagc 39300
tttccgactg gcgcatttgg tgtgatggtt cccataagtt tggcagctag cagattcagt 39360
cttgaaacag catctgcatt aactagagga gacattagaa tcattgctgt aaacaagttt 39420
ggattatcgt aagaggctag ctcccatgga atgacccaat aagtagattt aatagttacc 39480
acgtgctgta ccaaagtcat caatcatcat tttttcacca ttacttcttc catgtccaat 39540
atgatcatgt gagaatacta aaattcctaa cgatgatatg ttttcagcta gttcgtcata 39600
acgtccagaa tgtttaccag ctccatgact tataaatact aatgccttag gatatgtaat 39660
aggtttccaa tatttacaat atatgtaatc attgtccaga ttgaacatac agtttgcact 39720
catgattcac gttatataac tatcaatatt aacagttcgt ttgatgatca tattattttt 39780
atgttttatt gataattgta aaaacataca attaaatcaa tatagaggaa ggagacggct 39840
actgtctttt gtgagatagt catggcgact aaattagatt atgaggatgc tgttttttac 39900
tttgtggatg atgataaaat atgtagtcgc gactccatca tcgatctaat agatgaatat 39960
attacgtgga gaaatcatgt tatagtgttt aacaaagata ttaccagttg tggaagactg 40020
tacaaggaat tgatgaagtt cgatgatgtc gctatacggt actatggtat tgataaaatt 40080
aatgagattg tcgaagctat gagcgaagga gaccactaca tcaattttac aaaagtccat 40140
gatcaggaaa gtttattcgc taccatagga atatgtgcta aaatcactga acattgggga 40200
tacaaaaaga tttcagaatc tagattccaa tcattgggaa acattacaga tctgatgacc 40260
gacgataata taaacatctt gatacttttt ctagaaaaaa aattgaattg atgatatagg 40320

-continued ggtcttcata acgcataatt attacgttag cattctatat ccgtgttaaa aaaaattatc 40380
ctatcatgta tttgagagtt ttatatgtag caaacatgat agctgtgatg ccaataagct 40440
ttagatattc acgcgtgcta gtgttaggga tggtattatc tggtggtgaa atgtccgtta 40500
tataatctac aaaacaatca tcgcatatag tatgcgatag tagagtaaac atttttatag 40560
tttttactgg attcatacat cgtctaccca attcggttat aaatgaaatt gtcgccaatc 40620
ttacacccaa ccccttgtta tccattagta tagtattaac ttcgttattt atgtcataaa 40680
ctgtaaatga ttttgtagat gccatatcat acatgatatt catgtcccta ttataatcat 40740
tactaacttt atcacaatat atgttgataa tatctatata tgatctagtc tttgtgggca 40800
actgtctata caagtcgtct aaacgttgtt tactcatata gtatcgaaca gccatcatta 40860
catggtcccg tttcgttgat agataatcga gtatgttagt ggacttgtca aatctatata 40920
ccatattttc tggaagtgga tatacatagt cgtgatcaac attattgcta gcctcatctt 40980
ctatatcctg tactatacca ttatctatat catctacata atctacgata ttattacaca 41040
taaacatcga caacatacta ttgtttatta tctaagtcct gttgatccaa acccttgatc 41100
tcctctattt gtactatcta gagattgtac ttcttccagt tctggataat atatacgttg 41160
atagattagc tgagctattc tatctccagt atttacatta aacgtacatt ttccattatt 41220
aataagaatg actcctatgt ttcccctata atcttcgtct attacaccac ctcctatatc 41280
aatgcctttt agtgacagac cagacctagg agctattcta ccatagcaaa tcttaggcat 41340
ggacatacta atatctgtct taattaactg tctttctcct ggagggatag tataatcgta 41400
agcgctatac aaatcatatc cggcagcacc cggcgattgc ctagtaggag atttagctct 41460
gttagtttcc ttaacaaatc taactggtga gttaatattc atgttgaaca taaaactaat 41520
attttatttc aaaattattt accatcccat atattccatg aataagtgtg atgattgtac 41580
acttctatag tatctatata cgattcacga taaaatcctc ctatcaatag cagtttatta 41640
tccactatga tcaattctgg attatccctc ggataaatag gatcatctat cagagtccat 41700
gtattgctgg attcacaata aaattccgca tttctaccaa ccaagaataa ccttctaccg 41760
aacactaacg cgcatgattt ataatgagga taataagtgg atggtccaaa ctgccactga 41820
tcatgattgg gtagcaaata ttctgtagtt gtatcagttt cagaatgtcc tcccattacg 41880
tatataacat tgtttataga tgccactgct ggattacatc taggtttcag aagactcggc 41940
atattaaccc aagcagcatc cccgtggaac caacgctcaa cagatgtggg atttggtaga 42000
cctcctacta cgtataattt attgttagcg ggtatcccgc tagcatacag tctggggcta 42060
ttcatcggag gaattggaat ccaattgttt gatatataat ttacagctat agcattgtta 42120
tgtatttcat tgttcatcca tccaccgatg agatatacta cttctccaac atgagtactt 42180
gtacacatat ggaatatatc tataatttga tccatgttca taggatactc tatgaatgga 42240
tacttgtatg atttgcgtgg ttgtttatca caatgaaata ttttggtaca gtctagtatc 42300
cattttacat tatttatacc tctgggagaa agataatttg acctgattac atttttgata 42360
aggagtagca gatttcctaa tttatttctt cgcctcatat accacttaat gacaaaatca 42420
actacataat cctcatctgg aacatttagt tcatcgcttt ctagaataag tttcatagat 42480
agataatcaa aattgtctat gatgtcatct tccagttcca aaaagtgttt ggcaataaag 42540
tttttagtat gacataagag attggatagt ccgtattcta tacccatcat gtaacactcg 42600
acacaatatt cctttctaaa atctcgtaag ataaagttta tacaagtgta gatgataaat 42660
tctacagagg ttaatataga agcacgtaat aaattgacga cgttatgact atctatatat 42720

-continued

```
acctttccag tatatgagta aataactata gaagttaaac tgtgaatgtc aaggtctaga  42780
caaaccctcg taactggatc tttatttttc gtgtattttt gacgtaaatg tgtgcgaaag  42840
taaggagata actttttcaa tatcgtagaa ttgactatta tattgcctcc tatggcatca  42900
ataattgttt tgaatttctt agtcatagac aatgctaata tattcttaca gtacacagta  42960
ttgacaaata tcggcattta tgtttcttta aaagtcaaca tctagagaaa aatgattatc  43020
tttttgagac ataactccca ttttttggta ttcacccaca cgtttttcga aaaaattagt  43080
ttttccttcc aatgatatat tttccatgaa atcaaacgga ttggtaacat tataaatttt  43140
tttaaatccc aattcagaaa tcaatctatc cgcgacgaat tctatatatg ttttcatcat  43200
ttcacaattc attcctataa gtttaactgg aagagccgca gtaagaaatt cttgttcaat  43260
ggatactgca tctgttataa tagatctaac ggtttcttca ctcggtggat gcaataaatg  43320
tttaaacatc aaacatgcga aatcgcagtg cagaccctcg tctctactaa ttagttcgtt  43380
ggaaaacgtg agtccgggca ttaggccacg ctttttaagc caaaatatgg aagcgaatga  43440
tccggaaaag aagattcctt ctactgcagc aaaggcaata agtctctctc cataaccggc  43500
gctgtcatgt atccactttt gagcccaatc ggccttcttt tttacacaag gcatcgtttc  43560
tatggcatta aagagatagt ttttttcatt actatcttta acataagtat cgatcaaaag  43620
actatacatt tccgaatgaa tgttttcaat ggccatctga aatccgtaga aacatctagc  43680
ctcggtaatc tgtacttctg tacaaaatcg ttccgccaaa ttttcattca ctattccgtc  43740
actggctgca aaaaacgcca atacatgttt tataaaatat ttttcgtctg gtgttagttt  43800
attccaatca ttgatatctt tagatatatc tacttcttcc actgtccaaa atgatgcctc  43860
tgcctttttta tacatgttcc agatgtcatg atattggatt gggaaaataa caaatctatt  43920
tggatttggt gcaaggatgg gttccataac taaattaaca ataacaataa atttttttttc  43980
agttatctat atgcctgtac ttggatcttt tgtacatcga tatcgccgca atcactacaa  44040
taattacaag tattattgat agcattgtta ttagtactat cataattaaa ttatctacat  44100
tcatgggtgc tgaataatcg ttattatcat cattatcatt ttgtaattgt gacatcatac  44160
tagataaatc gtttgcgaga ttgttgtggg aagcgggcat ggaggatgca ttatcattat  44220
tatttaacgc cttccatttg gattcacaaa tgttacgcac attcaacatt ttatggaaac  44280
tataattttg tgaaaacaga taacaagaaa actcgtcatc gttcaaattt ttaacgatag  44340
taaaccgatt aaacgtcgag ctaatttcta acgctagcga ctctgttgga tatgggtttc  44400
cagatatata tcttttcagt tcccctacgt atctataatc atctgtagga aatggaagat  44460
atttccattt atctactgtt cctaatatca tatgtggtgg tgtagtagaa ccattaagcg  44520
cgaaagatgt tatttcgcat cgtattttaa cttcgcaata atttctggtt agataacgca  44580
ctctaccagt caagtcaatg atattagcct ttacagatat attcatagta gtcgtaacga  44640
tgactccatc ttttagatgc gatactcctt tgtatgtacc agaatcttcg tacctcaaac  44700
tcgatatatt taaacaagtt aatgagatat taacgcgttt tatgaatgat gatatataac  44760
cagaagtttt atcctcggtg gctagcgcta taaccttatc attataatac caactagtgt  44820
gattaatatg tgacacgtca gtgtgggtac aaatatgtac attatcgtct acgtcgtatt  44880
cgatacatcc gcatacagcc aacaaatata aaatgacaaa tactctaacg acgttcgtac  44940
ccatcttgat gcggtttaat aaatgttttg atttcaattt attgtaaaaa aagattcggt  45000
tttatactgt tcgatattct cattgcttat attttcatct atcatctcca cacagtcaaa  45060
```

-continued

```
tccgtggtta gcatgcacct catcaaccgg taaaagacta tcggactctt ctatcattat  45120
aactctagaa tatttaattt ggtcattatt aatcaagtca attatcttat ttttaacaaa  45180
cgtgagtatt ttactcattt tttataaaaa cttttagaaa tatacagact ctatcgtgtg  45240
tctatatctt ctttttatat ccaatgtatt tatgtctgat ttttcttcat ttatcatata  45300
taatggtcca aattctacac gtgcttcgga ttcatccaga tcattaaggt tcttataatt  45360
gtaacatcct tctcttccct cttctacatc ttccttctta ttcttattct tagcgtcaca  45420
gaatctacca cagcaggatc ccatgacgag cgtcatatta aactaatcca ttttcaatta  45480
taatatatga ttagtaatga ccattaaaat aaaaaatatt cttcataacc ggcaagaaag  45540
tgaaaagttc acattgaaac tatgtcagta gtatacatca tgaaatgaga tgaaatgaga  45600
tgaaatgatg atatatatac tctattttgg tggaggatta tatgatataa ttcgtggata  45660
atcattttta agacacattt ctttattcgt aaatcttttc acgttaaatg agtgtccata  45720
ttttgcaatt tcttcatatg atggcggtgt acgtggacga ggctgctcct gttcttgttg  45780
tagtcgccga ctgtcgtgtc tgcgtttaga tccctccatt atcgcgattg cgtagatgga  45840
gtactattat ataccttgta attaaatttt tttattaatt aaacgtataa aaacgttccg  45900
tatctgtatt taagagccag atttcgtcta atagaacaaa tagctacagt aaaaataact  45960
agaataattg ctacacccac tagaaaccac ggatcgtaat acggcaatcg gttttcgata  46020
ataggtggaa cgtatatttt atttaaggac ttaacaattg tctgtaaacc acaatttgct  46080
tccgcggatc ctgtattaac tatctgtaaa agcatatgtt gaccgggcgg agccgaacat  46140
tctccgatat ctaatttctg tatatctata atattattaa cctccgcata cgcattacag  46200
ttcttttcta gcttggatac cgcactaggt acatcgtcta gatctattcc tatttcctca  46260
gcgatagctc ttctatcctt ttccggaagc aatgaaatca cttcaataaa tgattcaacc  46320
atgagtgtga aactaagtcg agaattactc atgcatttgt tagttattcg gagcgcgcaa  46380
tttttaaact gtcctataac ctctcctata tgaatagcac aagtgacatt agtagggata  46440
gaatgttgag ctaatttttg taaataacta tctataaaaa gattatacaa agttttaaac  46500
tctttagttt ccgccattta tccagtctga gaaaatgtct ctcataataa atttttccaa  46560
gaaactaatt gggtgaagaa tggaaacctt taatctatat ttatcacagt ctgtcttggt  46620
acacatgatg aattcttcta atgccgtact aaattcgata tctttttcga tttctggata  46680
tgtttttaat aaagtatgaa caaagaaatg gaaatcgtaa taccagttat gttcaacttt  46740
gaaattgttt tttatttttct tgttaatgat tccagccact tgggaaaagt caaagtcgtt  46800
taatgccgat ttaatacgtt cattaaaaac aaacttttta tcctttagat gaattattat  46860
tggttcattg gaatcaaaaa gtaagatatt atcgggttta agatctgcgt gtaaaaagtt  46920
gtcgcagcat ggtagttcgt aaattttaat gtataacaga gccatctgta aaaagataaa  46980
ctttatgtat tgtaccaaag atttaaatcc taatttgata gctagctcgg tatctacttt  47040
atctgccgaa tacagtgcta ggggaaaaat tataatgttt cctctttcat attcgtagtt  47100
agttctcttt tcatgttcga aaaagtgaaa catgcggtta aaatagttta taacattaat  47160
attactgtta ataactgccg gataaaagtg ggatagtaat ttcacgaatt tgatactgtc  47220
ctttctctcg ttaaacgcct ttaaaaaaac tttagaagaa tatctcaatg agagttcctg  47280
accatccata gtttgtatca ataatagcaa catatgaaga acccgtttat acagagtatg  47340
taaaaatgtt aatttatagt ttaatcccat ggcccacgca cacacgatta atttttttc  47400
atctcccttt agattgttgt atagaaattt gggtactgtg aactccgccg tagtttccat  47460
```

```
gggactatat aattttgtgg cctcgaatac aaattttact acatagttat ctatcttaaa  47520
gactatacca tatcctcctg tagatatgtg ataaaaatcg tcgtttatag gataaaatcg  47580
tttatccttt tgttggaaaa aggatgaatt aatgtaatca ttctcttcta tctttagtag  47640
tgtttcctta ttaaaattct taaaataatt taacaatcta actgacggag cccaattttg  47700
gtgtaaatct aattgggaca ttatattgtt aaaatacaaa cagtctccta atataacagt  47760
atctgataat ctatggggag acatccattg atattcaggg gatgaatcat tggcaacacc  47820
catttattgt acaaaaagcc ccaatttaca aacgaaagtc caggtttgat agagacaaac  47880
aattaactat tttgtctctg tttttaacac ctccacagtt tttaatttct ttagtaatga  47940
aattattcac aatatcagta tcttctttat ctaccagaga ttttactaac ttgataacct  48000
tggctgtctc attcaatagg gtagtaatat ttgtatgtgt gatattgata tctttttgaa  48060
ttgtttcttt tagaagtgat tctttgatgg tgccagcata cgaattacaa taatgcagaa  48120
actcggttaa catgcaggaa ttatagtaag ccaattccaa ttgttgcctg tgttgtatta  48180
gagtgtcaat atgagcaatg gtgtccttgc gtttctctga tagaatgcga gcagcgattt  48240
tggcgttatc atttgacgat atttctggaa tgacgaatcc tgtttctact aactttttgg  48300
taggacaaag tgaaacaatc aagaagatag cttctcctcc tatttgtgga agaaattgaa  48360
ctcctctaga tgatctactg acgatagtat ctccttgaca gatattggac cgaattacag  48420
aagtacctgg aatgtaaagc cctgaaaccc cctcattttt taagcagatt gttgccgtaa  48480
atcctgcact atgcccaaga tagagagctc ctttggtgaa tccatctcta tgtttcagtt  48540
taaccaagaa acagtcagct ggtctaaaat ttccatctct atctaataca gcatctaact  48600
tgatgtcagg aactatgacc ggtttaatgt tatatgtaac attgagtaaa tccttaagtt  48660
cataatcatc actgtcatca gttatgtacg atccaaacaa tgtttctacc ggcatagtgg  48720
atacgaagat gctatccatc agaatgtttc cctgattagt attttctata tagctattct  48780
tctttaaacg attttccaaa tcagtaacta tgttcatttt tttaggagta ggacgcctag  48840
ccagtatgga agaggatttt ctagatcctc tcttcaacat ctttgatctc gatggaatgc  48900
aaaaccccat agtgaaacaa ccaacgataa aaataatatt gtttttcact ttttataatt  48960
ttaccatctg actcatggat tcattaatat ctttataaga gctactaacg tataattctt  49020
tataactgaa ctgagatata tacaccggat ctatggtttc cataattgag taaatgaatg  49080
ctcggcaata actaatggca aatgtataga acaacgaaat tatactagag ttgttaaagt  49140
taatattttc tatgagctgt tccaataaat tatttgttgt aactgcgttc aagtcataaa  49200
tcatcttgat actatccagt aaaccgtttt taagttctgg aatattatca tcccattgta  49260
aagcccctaa ttcgactatc gaatatcctg ctctgatagc agtttcaata tcgacggacg  49320
tcaatactgt aataaaggtg gtagtattgt catcatcgtg ataaactact ggaatatggt  49380
cgttagtagg tacggtaact ttacacaacg cgatatataa ctttcctttt gtaccatttt  49440
taacgtagtt gggacgtcct gcagggtatt gttttgaaga aatgatatcg agaacagatt  49500
tgatacgata tttgttggat tcctgattat tcactataat ataatctaga cagatagatg  49560
attcgataaa tagagaaggt atatcgttgg taggataata catccccatt ccagtattct  49620
cggatactct attgatgaca ctagttaaga acatgtcttc tattctagaa aacgaaaaca  49680
tcctacatgg actcattaaa acttctaacg ctcctgattg tgtctcgaat gcctcgtaca  49740
aggatttcaa ggatgccata gattctttga ccaacgattt agaattgcgt ttagcatctg  49800
```

-continued

```
atttttttat taaatcgaat ggtcggctct ctggtttgct accccaatga taacaatagt  49860
cttgtaaaga taaaccgcaa gaaaatttat acgcatccat ccaaataacc ctagcaccat  49920
cggatgatat taatgtatta ttatagattt tccatccaca attattgggc cagtatactg  49980
ttagcaacgg tatatcgaat agattactca tgtaacctac tagaatgata gttcgtgtac  50040
tagtcataat atctttaatc caatctaaga aatttaaaat tagatttttt acactgttaa  50100
agttaacaaa agtattaccc ggatacgtgg atatcatata tggcattggt ccattatcag  50160
taatagctcc ataaactgat acggcgatgg tttttatatg tgtttgatct aacgaggaag  50220
aaattcgcgc ccacaattca tctctagata tgtatttaat atcaaacggt aacacatcaa  50280
tttcgggacg cgtatatgtt tctaaatttt taatccaaat ataatgatga cctatatgcc  50340
ctattatcat actgtcaact atagtacacc tagggaactt acgatacatc tgtttcctgt  50400
aatcgttaaa ttttacaaat ctataacatg ctaaaccttt tgacgacaac cattcattaa  50460
tttctgatat ggaatctgta ttctcaatac cgtatcgttc taaagctagt gctatatctc  50520
cctgttcgtg ggaacgcttt cgtataatat cgatcaacgg ataatctgaa gtttttggag  50580
aataatatga ctcatgatct atttcgtcca taaacaatct agacatagga attggaggcg  50640
atgatcttaa ttttgtgcaa tgagtcgtca atcctataac ttctaatctt gtaatattca  50700
tcatcgacat aatactatct atgttatcat cgtatattag tataccacgg ccttcttcat  50760
ttcgtgccaa aatgatatac agtcttaaat agttacgcaa tatctcaata gtttcataat  50820
tgttagctgt tttcatcaag atttgtaccc tgtttaacat gatggcgttc tataacgtct  50880
ctattttcta tttttaattt tttaaatttt taacgattta ctgtggctag atacccaatc  50940
tctctcaaat atttttttag cctcgcttac aagctgttta tctatactat taaaactgac  51000
gaatccgtga ttttggtaat gggttccgtc gaaatttgcc gaagtgatat gaacatattc  51060
gtcgtcgact atcaacaatt ttgtattatt ctgaatagtg aaaaccttca cagatagatc  51120
attttgaaca cacaacgcat ctagactttt ggcggttgcc atagaatata cgtcgttctt  51180
atcccaatta ccaactagaa gtctgatctt aactcctcta ttaatggctg cttctataat  51240
ggagttgtaa atgtcgggcc aatagtagct attaccgtcg acacgtgtag tgggaactat  51300
ggccaaatgt tcaatatcta tactagtctt agccgacttg agtttatcaa taactacatc  51360
ggtatctaga tctctagaat atcccaatag gtgttccgga gaatcagtaa agaacactcc  51420
acctatagga ttcttaatat gatacgcagt gctaactggc aaacaacaag ccgcagagca  51480
taaattcaac catgaatttt ttgcgctatt aaaggcttta aaagtatcaa atcttctacg  51540
aagatctgtg gccagcgggg gataatcaga atatacacct aacgttttaa tcgtatgtat  51600
agatcctcca gtaaatgacg cgtttcctac ataacatctt tcatcatctg acacccaaaa  51660
acaaccgagt agtagtccca cattattttt tttatctata ttaacggtta taaaatttat  51720
atccgggcag tgactttgta gctctcccag atttcttttc cctcgttcat ctagcaaaac  51780
tattatttta atcccttttt cagatgcctc ttttagttta tcaaaaataa gcgcgcccct  51840
agtcgtactc agaggattac aacaaaaaga tgctatgtat atatatttct tagctagagt  51900
gataatttcg ttaaaacatt caaatgttgt caaatgatcg gatctaaaat ccatattttc  51960
tggtagtgtt tctaccagcc tacattttgc tcccgcaggt accgatgcaa atggccacat  52020
ttagttaaca taaaaactta tacatcctgt tctatcaacg attctagaat atcatcggct  52080
atatcgctaa aattttcatc aaagtcgaca tcacaaccta actcagtcaa tatattaaga  52140
agttccatga tgtcatcttc gtctatttct atatccgtat ccattgtaga ttgttgaccg  52200
```

attatcgagt ttaaatcatt actaatactc aatccttcag aatacaatct gtgtttcatt 52260
gtaaatttat aggcggtgta tttaagttgg tagattttca attatgtatt aatatagcaa 52320
cagtagtttt tgctcctcct tgattctagc atcctcttca ttattttctt ctacgtacat 52380
aagcatgtcc aatacgttag acaacacacc gacgatggcg gccgccacag acacgaatat 52440
gactaaaccg atgaccattt aaaaacccct ctctagcttt cacttaaact gtatcgatca 52500
ttcttttagc acatgtataa tataaaaaca ttattctatt tcgaatttag gcttccaaaa 52560
atttttcatc cgtaaaccga taataatata tatagacttg ttaatagtcg gaataaatag 52620
attaatgctt aaactatcat catctccacg attagagata caatatttac attctttttg 52680
ctgtttcgaa actttatcaa tacacgttaa tacaaaccca ggaaggagat attgaaactg 52740
aggctgttga aaatgaaacg gtgaatacaa taattcagat aatgtaaaat catgattccg 52800
tattctgatg atattagaac tgctaatgga tgtcgatggt atgtatctag gagtatctat 52860
tttaacaaag catcgatttg ctaatataca attatcattt tgattaattg ttattttatt 52920
catattctta aaaggtttca tatttatcaa ttcttctaca ttaaaaattt ccatttttaa 52980
tttatgtagc cccgcaatac tcctcattac gtttcatttt ttgtctataa tatccatttt 53040
gttcatctcg gtacatagat tatccaattg agaagcgcat ttagtagttt tgtacatttt 53100
aagtttattg acgaatcgtc gaaaactagt tatagttaac attttattat ttgataccct 53160
gatattaata cccctgccgt tactattatt tataactgat gtaacccacg taacattaga 53220
attaattatc gatagtaatg catcaacgct tccaaaattg tctattataa actcaccgat 53280
aatttttta ttgcatgttt tcatattcat taggattatc aaatctttaa tcttattacg 53340
attgtatgcg ttgatattac aagacgtcat tctaaaagac ggaggatttc catcaaatgc 53400
cagacaatca cgtacaaagt acatggaaat aggttttgtt ctattgcgca tcatagattt 53460
atatagaaca cccgtagaaa tactaatttg ttttactcta taaaatacta atgcatctat 53520
ttcatcgttt tgtataacgt ctttccaagt gtcaaattcc aaattttttt cattgatagt 53580
accaaattct tctatctctt taactacttg catagatagg taattacagt gatgcctaca 53640
tgccgttttt tgaaactgaa tagatgcgtc tagaagcgat gctacgctag tcacaatcac 53700
cactttcata tttagaatat atatatgtaa aaatatagta gaatttcatt ttgttttttc 53760
tatgctataa atgaattctc attttgcatc tgctcatact ccgttttata ttaataccaa 53820
agaaggaaga tatctggttc taaaagccgt taaagtatgc gatgttagaa ctgtagaatg 53880
cgaaggaagt aaagcttcct gcgtactcaa agtagataaa ccctcatcgc ccgcgtgtga 53940
gagaagacct tcgtccccgt ccagatgcga gagaatgaat aaccctggaa aacaagttcc 54000
gtttatgagg acggacatgc tacaaaatat gttcgcggct aatcgcgata atgtagcttc 54060
tagacttttg tcctaaaata ctattatatc cttttcgata ttaataaatc cgtgtcgtcc 54120
aggtttttta tctctttcag tatgtgaata gataggtatt ttatctctat tcatcatcga 54180
atttaagaga tccgataaac attgtttgta ttctccagat gtcagcatct gatacaacaa 54240
tatatgtgca cataaacctc tggcacttat ttcatgtacc ttccccttat cactaaggag 54300
aatagtattt gagaaatatg tatacatgat attatcatga attagatata cagaatttgt 54360
aacactctcg aaatcacacg atgtgtcggc gttaagatct aatatatcac tcgataacac 54420
attttcatct agatacacta gacatttttt aaagctaaaa tagtctttag tagtgacagt 54480
aactatgcga ttattttcat cgatgataca tttcatcggc atattattac gcttaccatc 54540

```
aaagactata ccatgtgtat atctaacgta ttctagcatg gttgccatac gcgcattaaa  54600
cttttcagga tctttggata gatcttccaa tctatctatt tgagaaaaca tttttatcat  54660
gttcaatagt tgaaacgtcg gatccactat atagatatta tctataaaga ttttaggaac  54720
tacgttcatg gtatcctggc gaatattaaa actatcaatg atatgattat cgttttcatc  54780
ttttatcacc atatagtttc taagatatgg gattttactt aatataatat tatttcccgt  54840
gataaatttt attagaaagg ccaaatctat aagaaaagtc ctagaattag tctgaagaat  54900
atctatatcg ccgtatagta tatttggatt aattagatat agagaatatg atccgtaaca  54960
tatacaactt ttattatggc gtctaagata ttcttccatc aacttattaa catttttgac  55020
tagggaagat acattatgac gtcccattac ttttgccttg tctattactg cgacgttcat  55080
agaatttagc atatctcttg ccaattcttc cattgatgtt acattataag aaattttaga  55140
tgaaattaca tttggagctt taatagtaag aactcctaat atgtccgtgt atgtggtcac  55200
taatacagat tgtagttcta taatcgtaaa taatttacct atattatatg tttgagtctg  55260
tttagaaaag tagctaagta tacgatcttt tatttctgat gcagatgtat caacatcgga  55320
aaaaaatctt tttttattct tttttactaa agatacaaat atgtctttgt taaaaacagt  55380
tattttctga atatttctag cttgtaattt taacatatga tattcgttca cactaggtac  55440
tctgcctaaa taggtttcta taatctttaa tgtaatatta ggaagagtat tctgatcagg  55500
attcctattc attttgagga tttaaaactc tgattattgt ctaatatggt ctctacgcaa  55560
actttttcac agagcgatag agtttttgat aactcgtttt tcttaagaaa tataaaacta  55620
ctgtttccag agctcgctct atcttttatt ttatctaatt cgatacaaac tcctgatact  55680
ggttcagaaa gtaattcatt aattttcagt cctttataga agatatttaa tatagataat  55740
acaaaatctt cagtttttga tatcgatctg attgatccta gaactagata tattaataac  55800
gtgctcatta ggcagtttat ggcagcttga taattagata tagtatattc cagttcatat  55860
ttattagata ccgcattgcc cagattttga tattctatga attcctctga aaataaatcc  55920
aaaataacta gacattctat tttttgtgga ttagtgtact ctcttccctc tatcatgttc  55980
actactggtg tccacgatga taaatatcta gagggaatat aatatagtcc ataggatgcc  56040
aatctagcaa tgtcgaataa ctgtaatttt attcttcgct cttcattatg aattgattct  56100
tgaggtataa acctaacaca aattatatta ttagactttt cgtatgtaat gtctttcatg  56160
ttataagttt ttaatcctgg aatagaatct attttaatga ggcttttaaa cgcagagttc  56220
tccaacgagt caaagcataa tactctgttg tttttcttat atacgatgtt acgattttct  56280
tctttgaatg gaataggttt ttgaattagt ttataattac aacataatag ataaggaagt  56340
gtgcaaatag tacgcggaaa aaacataata gctcccctgt tttcatccat ggttttaagt  56400
aaatgatcac tggcttcttt agtcaatgga tattcgaaca ttaaccgttt catcatcatt  56460
ggacagaatc catatttctt aatgtaaaga gtgatcaaat cattgtgttt attgtaccat  56520
cttgttgtaa atgtgtattc ggttatcgga tctgctcctt tttctattaa agtatcgata  56580
tcgatctcgt ctaagaattc aactatatcg acatatttca tttgtataca cataaccatt  56640
actaacgtag aatgtatagg aagagatgta acgggaacag ggtttgttga ttcgcaaact  56700
attctaatac ataattcttc tgttaatacg tcttgcacgt aatctattat agatgccaag  56760
atatctatat aattattttg taagatgatg ttaactatgt gatctatata agtagtgtaa  56820
taattcatgt attttgatat atgttccaac tctgtctttg tgatgtctag tttcgtaata  56880
tctatagcat cctcaaaaaa tatattcgca tatattccca agtcttcagt tctatcttct  56940
```

```
aaaaaatctt caacgtatgg aatataataa tctattttac ctcttctgat atcattaatg  57000
atatagtttt tgacactatc ttctgtcaat tgattcttat tcactatatc taagaaacgg  57060
atagcgtccc taggacgaac tactgccatt aatatctcta ttatagcttc tggacataat  57120
tcatctatta taccagaatt aatgggaact attccgtatc tatctaacat agttttaaga  57180
aagtcagaat ctaagacttg atgttcatat attggttcat acatgaaatg atctctattg  57240
atgatagtga ctatttcatt ctctgaaaat tggtaactca ttctatatat gctttccttg  57300
ttgatgaagg atagaatata ctcaatagaa tttgtaccaa caaactgttc tcttatgaat  57360
cgtatatcat catctgaaat aatcatgtaa ggcatacatt taacaattag agacttgtct  57420
cctgttatca atatactatt cttgtgataa tttatgtgtg aggcaaattt gtccacgttc  57480
tttaattttg ttatagtaga tatcaaatcc aatggagcta cagttcttgg cttaaacaga  57540
tatagttttt ctggaacaaa ttctacaaca ttattataaa ggactttggg tagataagtg  57600
ggatgaaatc ctattttaat taatgcgata gccttgtcct cgtgcagata tccaaacgct  57660
tttgtgatag tatggcattc attgtctaga aacgctctac gaatatctgt gacagatatc  57720
atctttagag aatatactag tcgcgttaat agtactacaa tttgtatttt ttaatctatc  57780
tcaataaaaa aattaatatg tatgattcaa tgtataacta aactactaac tgttattgat  57840
aactagaatc agaatctaat gatgacgtaa ccaagaagtt tatctactgc caatttagct  57900
gcattatttt tagcatctcg tttagatttt ccatcggcct tatcgaatac tcttccgtcg  57960
atatctacac aggcataaaa tgtaggagag ttactaggcc caactgattc aatacgaaaa  58020
gaccaatctc tcttagttat ttggcagtac tcattaataa cggtgacagg gttagcatct  58080
ttccaatcaa taattttttt agccggaata acatcatcaa aagacttatg atcctctctc  58140
attgattttt cgcgggatac atcatctatt atggcgtcag ccataacatc agcatccggc  58200
ttatccgcct ccgttgtcat aaaccaacga ggaggaatat cgtcggagct gtacaccata  58260
gcactacgtt gaagatcgta cagagcttta ttaacttctc gcttctccat attaagttgt  58320
ctagttagtt gtgcagcagt agctccttcg attccaatgg ttttaatagc ctcacacaca  58380
atctctgcgt cagaacgctc gtcaatatag atcttagaca tttttagaga gaactaacac  58440
aaccagcaat aaaactgaac ctactttatc atttttttat tcatcatcct ctggtggttc  58500
gtcgttccta tcgaatgtgg atctgattaa cccgtcatct ataggtgatg ctggttctgg  58560
agattctgga ggagatggat tattatctgg aagaatctct gttatttcct tgttttcatg  58620
tatcgattgc gttgtaacat taagattgcg aaatgctcta aatttgggag gcttaaagtg  58680
ttgtttgcaa tctctacacg cgtgtctaac tagtggaggt tcgtcagctg ctctagtttg  58740
aatcatcatc ggtgtagtat tcctactttt acagttagga cacggtgtat tgtatttctc  58800
gtcgagaacg ttaaaataat cgttgtaact cacatccttt attttatcta tattgtattc  58860
tactcctttc ttaatgcatt ttataccgaa taagagatag cgaaggaatt ctttttcggt  58920
gccgctagta cccttaatca tatcacatag tgttttatat tccaaatttg tggcaataga  58980
cggtttattt ctatacgata gtttgtttct ggaatccttt gagtattcta taccaatatt  59040
attctttgat tcgaatttag tttcttcgat attagatttt gtattaccta tattcttgat  59100
gtagtacttt gatgattttt ccatggccca ttctattaag tcttccaagt tggcatcatc  59160
cacatattgt gatagtaatt ctcggatatc agtagcggct accgccattg atgtttgttc  59220
attggatgag taactactaa tgtatacatt ttccatttat aacacttatg tattaacttt  59280
```

```
gttcatttat atttttcat tattatgttg atattaacaa aagtgaatat atatatgtta  59340
ataattgtat tgtggttata cggctacaat tttataatga gtgaaagtca gtgtccgatg  59400
atcaatgacg atagctttac tctgaaaaga aagtatcaaa tcgatagtgc ggagtcaaca  59460
ataaaaatgg ataagaagag gataaagttt cagaatagag ccaaaatggt aaaagaaata  59520
aatcagacaa taagagcagc acaaactcat tacgagacat tgaaactagg atacataaaa  59580
tttaagagaa tgattatgac tactactcta gaagatatag caccatctat tccaaataat  59640
cagaaaactt ataaactatt ctcggacatt tcagccatcg gcaaagcatc acagaatccg  59700
agtaagatgg tatatgctct gctgctttac atgtttccca atttgtttgg agatgatcat  59760
agattcattc gttatagaat gcatccaatg agtaaaatca aacacaagat cttctctcct  59820
ttcaaactta atcttattag aatattagtg gaagaaagat tctataataa tgaatgcaga  59880
tctaataaat ggagaataat tggaacacaa gttgataaaa tgttgatagc tgaatctgat  59940
aaatatacaa tagatgcaag gtataaccta aaacccatgt atagaatcaa gggagaatct  60000
gaagaagata ccctctttat caaacagatg gtagaacaat gtgtgacatc ccaggaattg  60060
gtggaaaaag tgttgaagat actgtttaga gatttgttca agagtggaga atacaaagcg  60120
tacagatacg atgatgatgt agaaaatgga tttattggat tggatacact aaaattaaac  60180
attgttcatg atatagttga accatgtatg cctgttcgta ggccagtggc taagatactg  60240
tgtaaagaaa tggtaaataa atactttgag aatccgctac atattattgg taaaaatctt  60300
caagagtgca ttgactttgt tagtgaatag gcatttcatc tttctccaat actaattcaa  60360
attgttaaat taataatgga tagtataaat agttattagt tataagatag taaaaataat  60420
tattagaata agagtgtagt atcatagata actctcttct ataaaaatgg attttattcg  60480
tagaaagtat cttatataca cagtagaaaa taatatagat tttttaaagg atgatacatt  60540
aagtaaagta aacaatttta ccctcaatca tgtactagct ctcaagtatc tagttagcaa  60600
ttttcctcaa cacgttatta ctaaggatgt attagctaat accaattttt ttgttttcat  60660
acatatggta cgatgttgta aagtgtacga agcggtttta cgacacgcat ttgatgcacc  60720
cacgttgtac gttaaagcat tgactaagaa ttatttatcg tttagtaacg caatacaatc  60780
gtacaaggaa accgtgcata aactaacaca agatgaaaaa tttttagagg ttgccgaata  60840
catggacgaa ttaggagaac ttataggcgt aaattatgac ttagttctta atccattatt  60900
tcacggaggg gaacccatca aagatatgga aatcattttt ttaaaactgt ttaagaaaac  60960
agacttcaaa gttgttaaaa aattaagtgt tataagatta cttatttggg catacctaag  61020
caagaaagat acaggcatag agtttgcgga taatgataga caagatatat atactctatt  61080
tcaacaaact ggtagaatcg tccatagcaa tctaacagaa acgtttagag attatatctt  61140
tcccggagat aagactagct attgggtgtg gttaaacgaa agtatagcta atgatgcgga  61200
tatcgttctt aatagacccg ccattaccat gtatgataaa attcttagtt atatatactc  61260
tgagataaaa caaggacgcg ttaataaaaa catgcttaag ttagtttata tctttgagcc  61320
tgaaaaagat atcagagaac ttctgctaga aatcatatat gatattcctg gagatatcct  61380
atctattatt gatgcaaaaa acgacgattg gaaaaaatat tttattagtt tttataaagc  61440
taattttatt aacggtaata catttattag tgatagaacg tttaacgagg acttattcag  61500
agttgttgtt caaatagatc ccgaatattt cgataatgaa cgaattatgt ctttattctc  61560
tacgagtgct gcggacatta aacgatttga tgagttagat attaataaca gttatatatc  61620
taatataatt tatgaggtga acgatatcac attagataca atggatgata tgaagaagtg  61680
```

-continued

```
tcaaatcttt aacgaggata cgtcgtatta tgttaaggaa tacaatacat acctgttttt  61740
gcacgagtcg gatcccatgg tcatagagaa cggaatacta aagaaactgt catctataaa  61800
atccaagagt agacggctga acttgtttag caaaaacatt ttaaaatatt atttagacgg  61860
acaattggct cgtctaggtc ttgtgttaga tgattataaa ggagacttgt tagttaaaat  61920
gataaaccat cttaagtctg tggaggatgt atccgcattc gttcgatttt ctacagataa  61980
aaaccctagt attcttccat cgctaatcaa aactatttta gctagttata atatttccat  62040
catcgtctta tttcaaaggt ttttgagaga taatctatat catgtagaag aattcttgga  62100
taaaagcatc catctaacca agacggataa gaaatatata cttcaattga taagacacgg  62160
tagatcatag aacagaccaa atatattatt aataatttgt atatacatag atataattat  62220
cacacatttt tgataaatgg gaactgctgc aacaattcag actcccacca aattaatgaa  62280
taaagaaaat gcagaaatga ttttggaaaa aattgttgat catatagtta tgtatattag  62340
tgacgaatca agtgattcag aaaataatcc tgaatatatt gattttcgta acagatacga  62400
agactataga tctctcatta taaaaagtga tcacgagttt gtaaagctat gtaaaaatca  62460
tgcggagaaa agttctccag aaacgcaaca aatgattatc aaacacatat acgaacaata  62520
tcttattcca gtatctgaag tactattaaa acttataatg tccatgggtg acataattac  62580
atataacgga tgtaaagaca atgaatggat gctagaacaa ctctctaccc taaactttaa  62640
caatctccgc acatggaact catgtagcat aggcaatgta acgcgtctgt tttatacatt  62700
ttttagttat ctgatgaaag ataaactaaa tatataagta taatcccatt ctaatacttt  62760
aacctgatgt attagcatct tattagaata ttaacctaac taaaagacat aacataaaaa  62820
ctcattacat agttgataaa aagcggtagg atataaatat tatggctgcc accgttccgc  62880
gttttgacga cgtgtacaaa aatgcacaaa gaagaattct agatcaagaa acatttttta  62940
gtagaggtct aagtagaccg ttaatgaaaa acacatatct atttgataat tacgcgtatg  63000
gatggatacc agaaactgca atttggagta gtagatacgc aaacttagat gcaagtgact  63060
attatcccat ttcgttggga ttacttaaaa agtttgagtt tctcatgtct ctatataaag  63120
gtcctattcc agtatacgaa gaaaaagtaa atactgaatt catagccaat ggatcgttct  63180
ctggtagata cgtatcatat cttcgaaagt tttctgctct tccaacaaac gagtttatta  63240
gtttttgtt actgacctcc atccctatct ataatatctt gttctggttt aaaaatactc  63300
agtttgatat tactaaacac acattattca gatacgttta tacagataat gccaaacacc  63360
tggcgttggc taggtatatg catcaaacag gagactataa gcctttgttt agtcgtctca  63420
aagagaatta tatatttacc ggtcccgttc caataagtat caaagatata gatcacccta  63480
atcttagtag agcaagaagt ccatccgatt atgagacatt agctaatatt agtactatat  63540
tgtactttac caagtatgat ccggtattaa tgtttttatt gttttacgta cctgggtatt  63600
caattactac aaaaattact ccagccgtag aatatctaat ggataaactg aatctaacaa  63660
agagcgacgt acaactgttg taaattattt tatgcttcgt aaaatgtagg ttttgaacca  63720
aacattcttt caaagaatga gatgcataaa actttattat ccaatagatt gactatttcg  63780
gacgtcaatc gtttaaagta aacttcgtaa aatattcttt gatcactgcc gagtttaaaa  63840
cttctatcga taattgtttc atatgtttta atatttacaa gtttttggt ccatggtaca  63900
ttagccggac aaatatatgc aaaataatat cgttctccaa gttctatagt ttctggatta  63960
tttttattat attcagtaac caaatacata ttagggttat ctgcggattt ataatttgag  64020
```

-continued

```
tgatgcattc gactcaacat aaataattct agaggagacg atctactatc aaattcggat  64080
cgtaaatctg tttctaaaga acggagaata tctatacata cctgattaga attcatccgt  64140
ccttcagaca acatctcaga cagtctggtc ttgtatgtct taatcatatt cttatgaaac  64200
ttggaaacat ctcttctagt ttcactagta cctttattaa ttctctcagg tacagatttt  64260
gaattcgacg atgccgagta tttcatcgtt gtatatttct tcttcgattg cataatcaga  64320
ttcttatata ccgcctcaaa ctctatttta aaattattaa acaatactct attattaatc  64380
agtcgttcta actctttcgc tatttctata gacttatcga catcttgact gtctatctct  64440
gtaaacacgg agtcggtatc tccatacacg ctacgaaaac gaaatctgta atctataggc  64500
aacgatgttt tcacaatcgg attaatatct ctatcgtcca tataaaatgg attacttaat  64560
ggattggcaa accgtaacat accgttagat aactctgctc catttagtac cgattctaga  64620
tacaagatca ttctacgtcc tatggatgtg caactcttag ccgaagcgta tgagtataga  64680
gcactatttc taaatcccat cagaccatat actgagttgg ctactatctt gtacgtatat  64740
tgcatggaat cataaatggc cttttcagtt gaactggtag cctgttttaa catcttttta  64800
tatctggctc tctctgccaa aaatgttctt aatagtctag gaatggttcc ttctatcgat  64860
ctatcgaaaa ttgctatttc agagatgagg ttcggtagtc taggttcaca atgaaccgta  64920
atatatctag gaggtggata tttctgaagc aagagctgat tatttatttc ttcttccaat  64980
ctattggtac taacaacgac accgactaat gtttccggag atagatttcc aaagatacac  65040
acattaggat acagactgtt ataatcaaag attaatacat tattactaaa catttttttgt  65100
tttggagcaa ataccttacc gccttcataa ggaaactttt gttttgtttc tgatctaact  65160
aagatagttt tagtttccaa caatagcttt aacagtggac ccttgatgac tgtactcgct  65220
ctatattcga ataccatgga ttgaggaagc acatatgttg acgcacccgc gtctgttttt  65280
gtttctactc cataatactc ccacaaatac tgacacaaac aagcatcatg aatacagtat  65340
ctagccatat ctaaagctat gtttagatta taatccttat acatctgagc taaatcaacg  65400
tcatcctttc cgaaagataa tttatatgta tcattaggta aagtaggaca taatagtacg  65460
actttaaatc cattttccca aatatcttta cgaattactt tacatataat atcctcatca  65520
acagtcacat aattacctgt ggttaaaacc tttgcaaatg cagcggcttt gcctttcgcg  65580
tctgtagtat cgtcaccgat gaacgtcatt tctctaactc ctctatttaa tactttaccc  65640
atgcaactga acgcgttctt ggatatagaa tccaatttgt acgaatccaa tttttcaaat  65700
ttttgaatga atgaatatag atcgaaaaat atagttccat tattgttatt aacgtgaaac  65760
gtagtattgg ccatgccgcc tactccctta tgactagact gatttctctc ataaatacag  65820
agatgtacag cttccttttt gtccggagat ctaaagataa tcttctctcc tgttaataac  65880
tctagacgat tagtaatata tctcagatca aagttatgtc cgttaaaggt aacgacgtag  65940
tcgaacgtta gttccaacaa ttgtttagct attcgtaaca aaactatttc agaacataga  66000
actagttctc gttcgtaatc catttccatt agtgactgta tcctcaaaca tcctctatcg  66060
acggcttctt gtatttcctg ttccgttaac atctcttcat taatgagcgt aaacaataat  66120
cgtttaccac ttaaatcgat ataacagtaa cttgtatgcg agattgggtt aataaataca  66180
gaaggaaact tcttatcgaa gtgacactct atatctagaa ataagtacga tcttgggata  66240
tcgaatctag gtattttttt agcgaaacag ttacgtggat cgtcacaatg ataacatcca  66300
ttgttaatct ttgtcaaata ttgctcgtcc aacgagtaac atccgtctgg agatatcccg  66360
ttagaaatat aaaaccaact aatattgaga aattcatcca tggtggcatt ttgtatgctg  66420
```

-continued

```
cgtttctttg gctcttctat caaccacata tctgcgacgg agcattttct atctttaata  66480
tctagattat aacttattgt ctcgtcaatg tctatagttc tcatctttcc caacggcctc  66540
gcattaaatg gaggaggaga caatgactga tatatttcgt ccgtcactac gtaataaaag  66600
taatgaggaa atcgtataaa tacggtctcg ccatttcgac atctggattt cagatataaa  66660
aatctgtttt caccgtgact ttcaaaccaa ttaatgcacc gaacatccat ttatagaatt  66720
tagaaatata ttttcattta aatgaatccc aaacattggg gaagagccgt atggaccatt  66780
atttttatag tactttcgca agcgggttta gacggcaaca tagaagcgtg taaacgaaaa  66840
ctatatacta tagttagcac tcttccatgt cctgcatgta gacggcacgc gactattgct  66900
ataaaggaca ataatgtcat gtctagcgat gatctgaatt atatttatta tttttttcatc  66960
agattattta acaatttggc atctgatccc aaatacgcga tcgatgtgac aaaggttaac  67020
cctttataaa cttaacccat tataaaactt atgattagtc acaactgaaa taaccgcgtg  67080
attatttttt ggtataattc tacacggcat ggtttctgtg actatgaatt caaccccccgt  67140
tacattagtg aaatctttaa caaacagcaa gggttcgtca aagacataaa actcattgtt  67200
tacaatcgaa atagaccccc tatcacactt aaaataaaaa atatccttat cctttaccac  67260
caaataaaat tctgattggt caatgtgaat gtattcactt aacagttcca caaatttatt  67320
tattaactcc gaggcacata catcgtcggt attttttatg gcaaacttta ctcttccagc  67380
atccgtttct aaaaaaatat taacgagttc catttatatc atccaatatt attgaaatga  67440
cgttgatgga cagatgatac aaataagaag gtacggtacc tttgtccacc atctcctcca  67500
attcatgctc tattttgtca ttaactttaa tgtatgaaaa cagtacgcca catgcttcca  67560
tgacagtgtg taacactttg gatacaaaat gtttgacatt agtataattg tccaagactg  67620
tcaatctata atagatagta gctataatat attctatgat ggtattgaag aagatgacaa  67680
ccttggcata ttgatcattt aacacagaca tggtatcaac agatagcttg aatgaaagag  67740
aatcagtaat tggaataagc gtcttctcga tagagtgtcc gtataccaac atgtctgata  67800
ttttgatgta ttccattaaa ttatttagtt ttttcttttt attctcgtta aacagcattt  67860
ctgtcaacgg accccaacat cgttgaccga ttaagttttg attgattttt ccgtgtaagg  67920
cgtatctagt cagatcgtat agcctatcca ataatccatc gtctgtgtgt agatcacatc  67980
gtacactttt taattctcta tagaagagcg acagacatct ggagcaatta cagacagcaa  68040
tttctttatt ctctacagat gtaagatact tgaagacatt cctatgatga tgcagaattt  68100
tggataacac ggtattgatg gtatctgtta ccataattcc tttgatggct gatagtgtca  68160
gagcacaaga tttccaatct ttgacaattt ttagcaccat tatctttgtt ttgatatcta  68220
tatcagacag catggtgcgt ctgacaacac agggattaag acggaaagat gaaatgattc  68280
tctcaacatc ttcaatggat accttgctat tttttctggc attatctata tgtgcgagaa  68340
tatcctctag cctgcaggtc aattcggtag ttgcgatata cataaactga tcactaattc  68400
caaacccacc cactttttat agtaagtttt tcacccataa ataataaata caataattaa  68460
tttctcgtaa aagtagaaaa tatattctaa tttattgcac ggtaaggaag tagtcgaaac  68520
gaattcgccc ttgcttgcaa gccaccatgg cctcctccga ggacgtcatc aaggagttca  68580
tgcgcttcaa ggtgcgcatg gagggctccg tgaacggcca cgagttcgag atcgagggcg  68640
agggcgaggg ccgcccctac gagggcaccc agaccgccaa gctgaaggtg accaagggcg  68700
gcccccctgcc cttcgcctgg gacatcctgt ccccccagtt ccagtacggc tccaaggtgt  68760
```

```
acgtgaagca ccccgccgac atccccgact acaagaagct gtccttcccc gagggcttca  68820
agtgggagcg cgtgatgaac ttcgaggacg gcggcgtggt gaccgtgacc caggactcct  68880
ccctgcagga cggctccttc atctacaagg tgaagttcat cggcgtgaac ttcccctccg  68940
acggccccgt aatgcagaag aagactatgg gctgggaggc ctccaccgag cgcctgtacc  69000
cccgcgacgg cgtgctgaag ggcgagatcc acaaggccct gaagctgaag gacggcggcc  69060
actacctggt ggagttcaag tccatctaca tggccaagaa gcccgtgcag ctgcccggct  69120
actactacgt ggactccaag ctggacatca cctcccacaa cgaggactac accatcgtgg  69180
agcagtacga gcgcgccgag ggccgccacc acctgttcct gtaggcgcgc ctataagggc  69240
gaattcgcgg cctcgacgct agagaatcag tatccttttt gatgatagtg gatctcaatg  69300
acatgggacg tctaaacctt cttattctat caccagattg catggtgatt tgtcttcttt  69360
cttttatcat aatgtaatct ctaaattcat cggcaaattg tctatatcta aaatcataat  69420
atgagatgtt tacctctaca aatatctgtt cgtccaatgt tagagtattt acatcagttt  69480
tgtattccaa attaaacatg gcaacggatt taattttata ttcctctatt aagtcctcgt  69540
cgataataac agaatgtaga taatcattta atccatcgta catggttgga agatgcttgt  69600
tgacaaaatc tttaattgtc ttgatgaagg tgggactata tctaacatct tgattaataa  69660
aatttataac attgtccata ggatactttg taactagttt tatacacatc tcttcatcgg  69720
taagtttaga cagaatatcg tgaacaggtg gtatattata ttcatcagat atacgaagaa  69780
caatgtccaa atctatattg tttaatatat tatatagatg tagcgtagct cctacaggaa  69840
tatctttaac taagtcaatg atttcatcaa ccgttagatc tattttaaag ttaatcatat  69900
aggcattgat tttaaaagg tatgtagcct tgactacatt ctcattaatt aaccattcca  69960
agtcactgtg tgtaagaaga ttatattcta tcataagctt gactacattt ggtcccgata  70020
ccattaaaga attcttatga tataaggaaa cagcttttag gtactcatct actctacaag  70080
aattttggag agccttaacg atatcagtga cgtttattat ttcaggagga aaaaacctaa  70140
cattgagaat gtcggagtta atagcttcca gatacagtga ttttggcaat agtccgtgta  70200
atccataatc cagtaacacg agctggtgct tgctagacac cttttcaatg tttaattttt  70260
ttgaaataag ctttgataaa gccttcctcg caaattccgg atacatgaac atgtcggcga  70320
catgattaag tattgttttt tcattatttt tatattttct caacaagttc tcaataccccc 70380
aatagatgat agaatatcac ccaatgcgtc catgttgtct atttccaaca ggtcgctata  70440
tccaccaata gaagttttc caaaaaagat tctaggaaca gttctaccac cagtaatttg  70500
ttcaaaataa tcacgcaatt cattttcggg tttaaattct ttaatatcga caatttcata  70560
cgctcctctt ttgaaactaa acttatttag aatatccagt gcatttctac aaaaaggaca  70620
tgtatacttg acaaaaattg tcactttgtt attggccaac ctttgttgta caaattcctc  70680
ggccatttta atatttaagt gatataaaac tatctcgact tatttaactc tttagtcgag  70740
atatatggac gcagatagct atatgatagc caactacaga aggcaaacgc tataaaaaac  70800
ataattacaa cgagcatatt tataaatatt tttattcagc attacttgat atagtaatat  70860
taggcacagt caaacattca accactctcg atacattaac tctctcattt tctttaacaa  70920
attctgcaat atcttcgtaa aaagattctt gaaacttttt agaatatcta tcgactctag  70980
atgaaatagc gttcgtcaac atactatgtt ttgtatacat aaaggcgcct attttaacag  71040
tttctagtga caaaatgcta gcgatcctag gatcctttag aatcacatag attgacgatt  71100
cgtctctctt agtaactcta gtaaaataat catacaatct agtacgcgaa ataatattat  71160
```

```
ccttgacttg aggagatcta aacaatctag ttttgagaac atcgataagt tcatcgggaa  71220
tgacatacat actatcttta atagaactct tttcatccag ttgaatggat tcgtccttaa  71280
ccaactgatt aatgagatct tctattttat cattttccag atgatatgta tgtccattaa  71340
agttaaattg tgtagcgctt ctttttagtc tagcagccaa tactttaaca tcactaatat  71400
cgatatacaa aggagatgat ttatctatgg tattaagaat tcgtttttcg acatctgtca  71460
aaaccaattc ctttttgcct gtatcatcca gttttccatc ctttgtaaag aaattatttt  71520
ctactagact attaataaga ctgataagga ttcctccata attgcacaat ccaaactttt  71580
taacaaaact agactttaca agatctacag gaatgcgtac ttcaggtttt ttagcttgtg  71640
attttttctt ttgcggacat tttctagtaa ccaactcatc taccatttca ttgattttag  71700
cagtgaaata agctttcaat gcacgggcac tgatactatt gaaaacgagt tgatcttcaa  71760
attccgccat ttaagttcac caaacaactt ttaaatacaa atatatcaat agtagtagaa  71820
taagaactat aaaaaaaata ataattaacc aataccaacc ccaacaaccg gtattattag  71880
ttgatgtggt agttttctca tcacttagaa cagatttaac aatttctata aagtctgtca  71940
aatcatcttc cggagacccc ataaatacac caaatatagc ggcgtacaac ttatccattt  72000
atacattgaa tattggcttt tctttatcgc tatcttcatc atattcatca tcaatatcaa  72060
caagtcccag attacgagcc agatcttctt ctacattttc agtcattgat acacgttcac  72120
tatctccaga gagtccgata acgttagcca ccacttctct atcaatgatt agtttcttga  72180
gcgcgaatgt aatttttgtt tccgttccgg atctatagaa gacgataggt gtgataattg  72240
ccttggccaa ttgtctttct cttttactga gtgattctag ttcaccttct atagatctga  72300
gaatggatga ttctccagtc gaaacatatt ctaccatgga tccgtttaat ttgttgatga  72360
agatggattc atccttaaat gtttctctg taatagtttc caccgaaaga ctatgcaaag  72420
aatttggaat gcgttccttg tgcttaatgt ttccatagac ggcttctaga agttgataca  72480
acataggact agccgcggta acttttattt ttagaaagta tccatcgctt ctatcttgtt  72540
tagatttatt tttataaagt ttagtctctc cttccaacat aataaaagtg gaagtcattt  72600
gactagataa actatcagta agttttatag agatagacga acaattagcg tattgagaag  72660
catttagtgt aacgtattcg atacattttg cattagattt actaatcgat tttgcatact  72720
ctataacacc cgcacaagtc tgtagagaat cgctagatgc agtaggtctt ggtgaagttt  72780
caactctctt cttgattacc ttactcatga ttaaacctaa ataattgtac tttgtaatat  72840
aatgatatat attttcactt tatctcattt gagaataaaa atgtttttgt ttaaccactg  72900
catgatgtac agatttcgga atcgcaaacc accagtggtt ttattttatc cttgtccaat  72960
gtgaattgaa tgggagcgga tgcgggtttc gtacgtagat agtacattcc cgtttttaga  73020
ccgagactcc atccgtaaaa atgcatactc gttagtttgg aataactcgg atctgctata  73080
tggatattca tagattgact ttgatcgatg aaggctcccc tgtctgcagc catttttatg  73140
atcgtctttt gtggaatttc ccaaatagtt ttataaactc gcttaatatc ttctggaagg  73200
tttgtattct gaatggatcc accatctgcc ataatcctat tcttgatctc atcattccat  73260
aattttctct cggttaaaac tctaaggaga tgcggattaa ctacttgaaa ttctccagac  73320
aatactctcc gagtgtaaat attactggta tacggttcca ccgactcatt atttcccaaa  73380
atttgagcag ttgatgcagt cggcataggt gccaccaata aactatttct aagaccgtat  73440
gttctgattt tatcttttag aggttcccaa ttccaaagat ccgacggtac aacattccaa  73500
```

```
agatcatatt gtagaatacc gttactggcg tacgatccta catatgtatc gtatggtcct  73560
tccttctcag ctagttcaca actcgcctct aatgcaccgt aataaatggt ttcgaagatc  73620
ttcttattta gatcttgtgc ttccaggcta tcaaatggat aatttaagag aataaacgcg  73680
tccgctaatc cttgaacacc aataccgata ggtctatgtc tcttattaga gatttcagct  73740
tctggaatag gataataatt aatatctata attttattga gatttctgac aattactttg  73800
accacatcct tcagtttgag aaaatcaaat cgcccatcta ttacaaacat gttcaaggca  73860
acagatgcca gattacaaac ggctacctca ttagcatccg catattgtat tatctcagtg  73920
caaagattac tacacttgat agttcctaaa ttttgttgat tactcttttt gttacacgca  73980
tccttataaa gaatgaatgg agtaccagtt tcaatctgag attctataat cgctttccag  74040
acgactcgag cctttattat agatttgtat ctcctttctc tttcgtatag tgtatacaat  74100
cgttcgaact cgtctcccca aacattgtcc aatccaggac attcatccgg acacatcaac  74160
gaccactctc cgtcatcctt cactcgtttc ataaagagat caggaatcca aagagctata  74220
aatagatctc tggttctatg ttcctcgttt cctgtattct ttttaagatc gaggaacgcc  74280
ataatatcag aatgccacgg ttccaagtat atggccataa ctccaggccg tttgtttcct  74340
ccctgatcta tgtatctagc ggtgttatta taaactctca acattggaat aataccgttt  74400
gatataccat tggtaccgga gatatagctt ccactggcac gaatattact aattgataga  74460
cctattcccc ctgccatttt agagattaat gcgcatcgtt ttaacgtgtc atagataccc  74520
tctatgctat catcgatcat gttaagtaga aaacagctag acatttggtg acgactagtt  74580
cccgcattaa ataaggtagg agaagcgtgc gtaaaccatt tttcagaaag tagattgtac  74640
gtctcaatag ctgagtctat atcccattga tgaattccta ctgcgacacg cattaacatg  74700
tgctgaggtc tttcaacgat cttgttgttt attttcaaca agtaggattt ttccaaagtt  74760
ttaaaaccaa aatagttgta tgaaaagtct cgttcgtaaa taataaccga gttgagttta  74820
tccttatatt tgttaactat atccatggtg atacttgaaa taatcggaga atgtttccca  74880
tttttaggat taacatagtt gaataaatcc tccatcactt cactaaatag tttttttgtt  74940
tccttgtgta gatttgatac ggctattctg gcggctaaaa tggcataatc cggatgttgt  75000
gtagtacaag tggctgctat ttcggctgcc agagtgtcca attctaccgt tgttactcca  75060
ttatatattc cttgaataac cttcatagct attttaatag gatctatatg atccgtgttt  75120
aagccataac ataattttct aatacgagac gtgattttat caaacatgac attttccttg  75180
tatccatttc gtttaatgac aaacattttt gttggtgtaa taaaaaaatt atttaacttt  75240
tcattaatag ggatttgacg tacgtagcgt acaaaatgat cgttcctggt atatagataa  75300
agagtcctat atatttgaaa atcgttacgg ctcgattaaa ctttaatgat tgcatagtga  75360
atatatcatt aggatttaac tccttgacta tcatggcggc gccagaaatt accatcaaaa  75420
gcattaatac agttatgccg atcgcagtta gaacggttat agcatccacc atttatatct  75480
aaaaattaga tcaaagaata tgtgacaaag tcctagttgt atactgagaa ttgacgaaac  75540
aatgtttctt acatattttt ttcttattag taactgactt aatagtagga actggaaagc  75600
tagacttgat tattctataa gtatagatac ccttccaaat aatattctct ttgataaaag  75660
ttccagaaaa tgtagaattt tttaaaaagt tatcttttgc tattaccaag attgtgttta  75720
gacgcttatt attaatatga gtgatgaaat ccacaccgcc tctagatatc gcctttattt  75780
ccacattaga tggtaaatcc aatagtgaaa ctatcttttt aggaatgtat ggactcgcgt  75840
ttagaggagt gaacgtcttg ggcgtcggaa aggatgattc gtcaaacgaa taaacaattt  75900
```

```
cacaaatgga tgttaatgta ttagtaggaa atttcttgac gctattggaa ttgaagattc  75960
taatggatga tgttctacct atttcatccg ataacatgtt aatttccgac accaacggtt  76020
ttaatatttc gatgatatac ggtagtctct ctttcggact tatatagctt attccacaat  76080
acgagtcatt atatactcca aaaaacaaaa taactagtat aaaatctgta tcgaatggga  76140
aaaacgaaat tatcgacata ggtatagaat ccggaacatt gaacgtatta atacttaatt  76200
ctttttctgt ggtaagtacc gataggttat tgacattgta tggttttaaa tattctataa  76260
cttgagactt gatagatatt agtgatgaat tgaaaattat ttttatcacc acgtgtgttt  76320
caggatcatc gtcgacgcct gtcaaccaac cgaatggagt aaaataaata tcattaatat  76380
atgctctaga tattagtatt tttatcaatc ctttgattat catcttctcg taggcgaatg  76440
attccatgat caagagtgat ttgagaacat cctccggagt attaatgggc ttagtaaaca  76500
gtccatcgtt gcaataataa aagttatcca agttaaagga tattatgcat tcgtttaaag  76560
atatcacctc atctgacgga gacaattttt tggtaggttt tagagacttt gaagctactt  76620
gtttaacaaa gttattcatc gtcgtctact attctattta attttgtagt taatttatca  76680
catatcacat taattgactt tttggtccat ttttccatac gtttatattc ttttaatcct  76740
gcgttatccg tttccgttat attcagggat agatcttgca agttaaatag aatgctctta  76800
aataatgtca ttttcttatc cgctaaaaat ttaaagaatg tataaacctt tttcagagat  76860
ttgaaactct taggtggtgt cctagtacac aatatcataa acaaactaat aaacattcca  76920
cattcagatt ccaacagctg attaacttcc acattaatac agcctatttt cgctccaaat  76980
gtacattcga aaaatctgaa taaaacatcg atgtcacaat ttgtattatc caatacagaa  77040
tgtttgtgat tcgtgttaaa accatcggag aaggaataga aataaaaatt attatagtgg  77100
tggaattcag ttggaatatt gcctccggag tcataaaagg atactaaaca ttgtttttta  77160
tcataaatta cacatttcca atgagacaaa taacaaaatc caaacattac aaatctagag  77220
gtagaacttt taattttgtc tttaagtata tacgataaga tatgtttatt cataaacgcg  77280
tcaaattttt catgaatcgc taaggagttt aagaatctca tgtcaaattg tcctatataa  77340
tccacttcgg atccataagc aaactgagag actaagttct taatacttcg attgctcatc  77400
caggctcctc tctcaggctc tattttcatc ttgacgacct ttggatttc accagtatgt  77460
attcctttac gtgataaatc atcgattttc aaatccattt gtgagaagtc tatcgcctta  77520
gatacttttt cccgtagtcg aggtttaaaa aaatacgcta acggtatact agtaggtaac  77580
tcaaagacat catatataga atggtaacgc gtctttaact cgtcggttaa ctctttcttt  77640
tgatcgagtt cgtcgctact attgggtctg ctcaggtgcc ccgactctac tagttccaac  77700
atcataccga taggaataca agacactttg ccggcggttg tagatttatc atatttttcc  77760
actacatatc cgttacaatt tgttaaaaat ttagatacat ctatattgct acataatcca  77820
gctagtgaat atatatgaca taataaattg gtaaatccta gttctggtat tttactaatt  77880
actaaatctg tatatctttc catttatcat ggaaaagaat ttaccagata tcttcttttt  77940
tccaaactgc gttaatgtat tctcttacaa atattcacaa gatgaattca gtaatatgag  78000
taaaacggaa cgtgatagtt tctcattggc cgtgtttcca gttataaaac atagatggca  78060
taacgcacac gttgtaaaac ataaaggaat atacaaagtt agtacagaag cacgtggaaa  78120
aaaagtatct cctccatcac taggaaaacc cgcacacata aacctaaccg cgaagcaata  78180
tatatacagt gaacacacaa taagctttga atgttatagt tttctaaaat gtataacaaa  78240
```

-continued

```
tacagaaatc aattcgttcg atgagtatat attaagagga ctattagaag ctggtaatag  78300
tttacagata ttttccaatt ccgtaggtaa acgaacagat actataggtg tactagggaa  78360
taagtatcca tttagcaaaa ttccattggc ctcattaact cctaaagcac aacgagagat  78420
attttcagcg tggatttctc atagacctgt agttttaact ggaggaactg gagtgggtaa  78480
gacgtcacag gtacccaagt tattgctttg gtttaattat ttatttggtg gattctctac  78540
tctagataaa atcactgact ttcacgaaag accagtcatt ctatctcttc ctaggatagc  78600
tttagttaga ttgcatagca ataccatttt aaaatcattg ggatttaagg tactagatgg  78660
atctcctatt tctttacggt acggatctat accggaagaa ttaataaaca aacaaccaaa  78720
aaaatatgga attgtatttt ctacccataa gttatctcta acaaaactat ttagttatgg  78780
cactcttatt atagacgaag ttcatgagca tgatcaaata ggagatatta ttatagcagt  78840
agcgagaaag catcatacga aaatagattc tatgttttta atgactgcca cattagagga  78900
tgaccgagaa cggctaaaag tatttttacc taatcccgca tttatacata ttcctggaaa  78960
tacactgttt aaaattagcg aggtatttat tcataataag ataaatccat cttccagaat  79020
ggcatacata gaagaagaaa agagaaattt agttactgct atacagatgt atactcctcc  79080
tgatggatca tccggtatag tctttgtggc atccgttgca cagtgtcacg aatataaatc  79140
atatttagaa aaaagattac cgtatgatat gtatattatt catggtaagg tcttagatat  79200
agacgaaata ttagaaaaag tgtattcatc acctaatgta tcgataatta tttctactcc  79260
ttatttggaa tccagcgtta ctatacgcaa tgttacacac atttatgata tgggtagagt  79320
ttttgtcccc gctcctttg gaggatcgca acaatttatt tctaaatcta tgagagatca  79380
acgaaaagga agagtaggaa gagttaatcc tggtacatac gtctatttct atgatctgtc  79440
ttatatgaag tctatacagc gaatagattc agaatttcta cataattata tattgtacgc  79500
taataagttt aatctaacac tccccgaaga tttgtttata atccctacaa atttggatat  79560
tctatggcgt acaaaggaat atatagactc gttcgatatt agtacagaaa catggaataa  79620
attattatcc aattattata tgaagatgat agagtatgct aaactttatg tactaagtcc  79680
tattctcgct gaggagttgg ataactttga gaggacggga gaattaacta gtattgtacg  79740
agaagccatt ttatctctaa atttacgaat taagatttta aattttaaac ataaagatga  79800
tgatacgtat atacactttt gtaaaatatt attcggtgtc tataacggaa caaacgctac  79860
tatatattat catagacctc taacgggata tatgaatatg atttcagata ctatatttgt  79920
tcctgtagat aataactaaa aatcaaactc taatgaccac atcttttttt agagatgaaa  79980
aattttccac atctcctttt gtagacacga ctaaacattt tgcagaaaaa agtttattag  80040
tgtttagata atcgtatact tcatcagtgt agatagtaaa tgtgaacaga taaaaggtat  80100
tcttgctcaa tagattggta aattccatag aatatattaa tcctttcttc ttgagatccc  80160
acatcatttc aaccagagac gttttatcca atgatttacc tcgtactata ccacatacaa  80220
aactagattt tgcagtgacg tcgtacctgg tattcctacc aaacaaaatt ttacttttag  80280
ttcttttaga aaattctaag gtagaatctc tatttgccaa tatgtcatct atggaattac  80340
cactagcaaa aaatgataga aatatatatt gatacatcgc agctggtttt gatctactat  80400
actttaaaaa cgaatcagat tccataattg cctgtatatc atcagctgaa aaactatgtt  80460
ttacacgtat tccttcggca tttcttttta atgatatatc ttgtttagac aatgataaag  80520
ttatcatgtc catgagagac gcgtctccgt atcgtataaa tatttcatta gatgttagac  80580
gcttcattag ggtatactt ctataaggtt tcttaatcag tccatcattg gttgcgtcaa  80640
```

gaactactat cggatgttgt tgggtatctc tagtgttaca catggcctta ctaaagtttg 80700
ggtaaataac tatgatatct ctattaatta tagatgcata tatttcattt gtcaaggata 80760
ttagtatcga cttgctatcg tcattaatac gtgtaatgta atcatataaa tcatgcgata 80820
gccaaggaaa atttaaatag atgttcatca tataatcgtc gctataattc atattaatac 80880
gttgacattg actaatttgt aatatagcct cgccacgaag aaagctctcg tattcagttt 80940
catcgataaa ggataccgtt aaatataact ggttgccgat agtctcatag tctattaagt 81000
ggtaagtttc gtacaaatac agaatcccta aaatattatc taatgttgga ttaatcttta 81060
ccataactgt ataaaatgga gacggagtca taactatttt accgtttgta cttactggaa 81120
tagatgaagg aataatctcc ggacatgctg gtaaagaccc aaatgtctgt ttgaagaaat 81180
ccaatgttcc aggtcctaat ctcttaacaa aaattacgat attcgatccc gatatccttt 81240
gcattctatt taccagcata tcacgaacta tattaagatt atctatcatg tctattctcc 81300
caccgttata taaatcgcct ccgctaagaa acgttagtat atccatacaa tggaatactt 81360
catttctaaa atagtattcg ttttctaatt ctttaatgtg aaatcgtata ctagaaaggg 81420
aaaaattatc tttgagtttt ccgttagaaa agaaccacga aactaatgtt ctgattgcgt 81480
ccgattccgt tgctgaatta atggatttac accaaaaact catataactt ctagatgtag 81540
aagcattcgc taaaaaatta gtagaatcaa aggatataag tagatgttcc aacaagtgag 81600
caattcccaa gatttcatct atatcattct cgaatccgaa attagaaatt cccaagtaga 81660
tatccttttt catccgatcg ttgatgaaaa tacgaacttt attcggtaag acaatcattt 81720
actaaggagt aaaataggaa gtaatgttcg tatgtcgtta tcatcgtata aattaaaggt 81780
gtgtttttta ccattaagtg acattataat tttaccaata ttggaattat aatataggtg 81840
tatttgcgca ctcgcgacgg ttgatgcatc ggtaaatata gctgtatcta atgttctagt 81900
cggtatttca tcatttcgct gtctaataat agcgttttct ctatctgttt ccattacagc 81960
tgcctgaagt ttattggtcg gataatatgt aaaataataa gaaatacata cgaataacaa 82020
aaataaaata agatataata aagatgccat ttagagatct aattttgttc aacttgtcca 82080
aattcctact tacagaagat gaggaatcgt tggagatagt gtcttcctta tgtagaggat 82140
ttgaaatatc ttataatgac ttgataactt actttccaga taggaaatac cataaatata 82200
tttataaagt atttgaacat gtagatttat cggaggaatt aagtatggaa ttccatgata 82260
caactctgag agatttagtc tatcttagat tgtacaagta ttccaagtgt atacggccgt 82320
gttataaatt aggagataat ctaaaaggca tagttgttat aaaggacagg aatatttata 82380
ttagggaagc aaatgatgac ttgatagaat atctcctcaa ggaatacact cctcagattt 82440
atacatattc taatgagcgc gtccccataa ctggttcaaa attaattctt tgtggatttt 82500
ctcaagttac atttatggcg tatacaacgt cgcatataac aacaaataaa aaggtagatg 82560
ttctcgtttc caaaaaatgt atagatgaac tagtcgatcc aataaattat caaatacttc 82620
aaaatttatt tgataaagga agcggaacaa taaacaaaat actcaggaag atattttatt 82680
cggtaacagg tggccaaact ccataggtag ctttttctat ttcggatttt agaatttcca 82740
aattcaccag cgatttatcg gttttggtga aatccaagga tttattaatg tccacaaatg 82800
ccatttgttt tgtctgtgga ttgtatttga aaatggaaac gatgtagtta gatagatgcg 82860
ctgcgaagtt tcctattagg gttccgcgct tcacgtcacc cagcatactt gaatcaccat 82920
cctttaaaaa aatgataaga tatcaacatg gagtatatca tactcggatt ttaattcttc 82980
tactgactca ctgacatttt cacaaatact acaatacggt ttaccgaaaa taatcagtac 83040
gttcttcatt tatgggtatc aaaaacttaa aatcgttact gctggaaaat aaatcactga 83100
cgatattaga tgataattta tacaaagtat acaatggaat atttgtggat acaatgagta 83160
tttatatagc cgtcgccaat tgtgtcagaa acttagaaga gttaactacg gtattcataa 83220
aatacgtaaa cggatgggta aaaaagggag ggcatgtaac ccttttatc gatagaggaa 83280
gtataaaaat taaacaagac gttagagaca agagacgtaa atattctaaa ttaaccaagg 83340
acagaaaaat gctagaatta gaaaagtgta catccgaaat acaaaatgtt accggattta 83400
tggaagaaga aataaaggca gaaatgcaat taaaaatcga taaactcaca tttcaaatat 83460
atttatctga ttctgataac ataaaaatat cattgaatga gatactaaca catttcaaca 83520
ataatgagaa tgttacatta ttttattgtg atgaacgaga cgcagaattc gttatgtgtc 83580
tcgaggctaa aacacatttc tctaccacag gagaatggcc gttgataata agtaccgatc 83640
aggatactat gctatttgca tctgctgata atcatcctaa gatgataaaa aacttaactc 83700
aactgtttaa atttgttccc tcggcagagg ataactattt agcaaaatta acggcgttag 83760
tgaatggatg tgatttcttt cctggactct atggggcatc tataacaccc accaacttaa 83820
acaaaataca attgtttagt gattttacaa tcgataatat agtcactagt ttggcaatta 83880
aaaattatta tagaaagact aactctaccg tagacgtgcg taatattgtt acgtttataa 83940
acgattacgc taatttagac gatgtctact cgtatattcc tccttgtcaa tgcactgttc 84000
aagaatttat attttccgca ttagatgaaa aatggaatga atttaaatca tcttatttag 84060
agaccgttcc gttaccctgt caattaatgt acgcgttaga accacgtaag gagattgatg 84120
tttcagaagt taaaacttta tcatcttata tagatttcga aaatactaaa tcagatatcg 84180
atgttataaa atctatatcc tcgatcttcg gatattctaa cgaaaactgt aacacgatag 84240
tattcggcat ctataaggat aatttactac tgagtataaa tagttcattt tactttaacg 84300
atagtctgtt aataaccaat actaaaagtg ataatataat aaatataggt tactagatta 84360
aaaatggtgt tccaactcgt gtgctctacg tgcggcaaag atatttctca cgaacgatat 84420
aaattgatta tacgaaaaaa atcattaaag gatgtactcg tcagtgtaaa gaacgaatgt 84480
tgtaggttaa aattatctac acaaatagaa cctcaacgta acttaacagt gcaacctcta 84540
ttggatataa actaatatgg atccggttaa ttttatcaag acatatgcgc ctagaggttc 84600
tattattttt attaattata ccatgtcatt aacaagtcat ttgaatccat cgatagaaaa 84660
acatgtgggt atttattatg gtacgttatt atcggaacac ttggtagttg aatctaccta 84720
tagaaaagga gttcgaatag tcccattgga tagttttttt gaaggatatc ttagtgcaaa 84780
agtatacatg ttagagaata ttcaagttat gaaaatagca gctgatacgt cattaacttt 84840
attgggtatt ccgtatggat ttggtcatga tagaatgtat tgttttaaat tggtagctga 84900
ctgttataaa aatgccggta ttgatacatc gtctaaacga atattaggta aagatatttt 84960
tctgagccaa aacttcacag acgataatag atggataaag atatatgatt ctaataattt 85020
aacattttgg caaattgatt accttaaagg gtgagttaat atgcataact actcctccgt 85080
tgttttttcc ctcgttcttt ttcttaacgt tgtttgccat cactctcata atgtaaagat 85140
attctaaaat ggtaaacttt tgcatatcgg acgcagaaat tggtataaat gttgtaattg 85200
tattatttcc cgtcaatgga ctagtcacag ctccatcagt tttatatcct ttagagtatt 85260
tctcactcgt gtctagcatt ctagagcatt ccatgatctg tttatcgttg atattggccg 85320
gaaagataga ttttttattt tttattatat tactattggc aattgtagat ataacttctg 85380
gtaaatattt ttctaccttt tcaatctctt ctattttcaa gccggctata tattctgcta 85440
tattgttgct agtatcaata ccttttctgg ctaagaagtc atatgtggta ttcactatat 85500
cagttttaac tggtagttcc attagccttt ccacttctgc agaataatca gaaattggtt 85560
ctttaccaga aaatccagct actataatag gctcaccgat gatcattggc aaaatcctat 85620
attgtaccag attaatgaga gcatatttca tttccaataa ttctgctagt tcttgagaca 85680
ttgatttatt tgatgaatct agttggttct ctagatactc taccatttct gccgcataca 85740
ataacttgtt agataaaatc agggttatca aagtgtttag cgtggctaga atagtgggct 85800
tgcatgtatt aaagaatgcg gtagtatgag taaaccgttt taacgaatta tatagtctcc 85860
agaaatctgt ggcgttgcat acatgagccg aatgacatcg aagattgtcc aatattttta 85920
atagctgctc tttgtccatt atttctatat ttgactcgca acaattgtag ataccattaa 85980
tcaccgattc ctttttcgat gctggacaat agcacaattg tttagctttg gactctatgt 86040
attcagaatt aatagatata tctctcaata cagattgcac tatacatttt gaaactatgt 86100
caaaaattgt agaacgacgc tgttctgcag ccatttaact ttaaataatt tacaaaaatt 86160
taaaatgagc atccgtataa aaatcgataa actgcgccaa attgtggcat atttttcaga 86220
gttcagtgaa gaagtgtcta taaatgtaga ctcgacggat gagttaatgt atatttttgc 86280
cgccttgggc ggatctgtaa acatttgggc cattatacct ctcagtgcat cagtgtttta 86340
ccgaggagcc gaaaacattg tgtttaatct tcctgtgtcc aaggtaaaat cgtgtttgtg 86400
tagttttcac aatgatgcca tcatagatat agaacctgat ctggaaaata atctagtaaa 86460
actttctagt tatcatgtag taagtgtcga ttgtaataag gaactgatgc ctattaggac 86520
agatactact atttgtctaa gtatagatca aaagaaatct tatgtgttta attttcacaa 86580
gtatgaagaa aaatgttgtg gtagaaccgt cattcattta gaatggttgt tgggctttat 86640
caagtgtatt agtcagcatc agcatctggc tattatgttt aaagatgaca atattattat 86700
gaagactcct ggtaatactg atgcattttc cagggaatat tctatgactg aatgttctca 86760
agaactacaa aagttttctt tcaaaatagc tatctcgtct ctcaacaaac tacgaggatt 86820
caaaaagaga gtcaatgttt ttgaaactag aatcgtaatg gataatgacg ataacatttt 86880
aggaatgttg ttttcggata gagttcaatc ctttaagatc aacatcttta tggcgttttt 86940
agattaatac tttcaatgag ataaatatgg gtggcagagt aagtgttgag ctccctaaac 87000
gggatccgcc tccgggagta cccactgatg agatgttatt aaacgtggat aaaatgcatg 87060
acgtgatagc tcccgctaag cttttagaat atgtgcatat aggaccacta gcaaaagata 87120
aagaggataa agtaaagaaa agatatccag agtttagatt agtcaacaca ggacccggtg 87180
gtctttcggc attgttaaga caatcgtata atggaaccgc acccaattgc tgtcgcactt 87240
ttaatcgtac tcattattgg aagaaggatg gaaagatatc agataagtat gaagagggtg 87300
cagtattaga atcgtgttgg ccagacgttc acgacactgg aaaatgcgat gttgatttat 87360
tcgactggtg tcagggggat acgttcgata gaaacatatg ccatcagtgg atcggttcag 87420
cctttaatag gagtaataga actgtagagg gtcaacaatc gttaataaat ctgtataata 87480
agatgcaaac attatgtagt aaagatgcta gtgtaccaat atgcgaatca tttttgcatt 87540
atttacgcgc acacaataca gaagatagca aagagatgat cgattatatt ctaagacaac 87600
agtctgcgga ctttaaacag aaatatatga gatgtagtta tcccactaga gataagttag 87660
aagagtcatt aaaatatgcg gaacctcgag aatgttggga tccagagtgt tcgaatgcca 87720

-continued

```
atgttaattt cttactaaca cgtaattata ataatttagg actttgcaat attgtacgat  87780
gtaataccag cgtgaacaac ttacagatgg ataaaacttc ctcattaaga ttgtcatgtg  87840
gattaagcaa tagtgataga ttttctactg ttcccgtcaa tagagcaaaa gtagttcaac  87900
ataatattaa acattcgttc gacctaaaat tgcatttgat cagtttatta tctctcttgg  87960
taatatggat actaattgta gctatttaaa tgggtgccgc ggcaagcata cagacgacgg  88020
tgaatacact cagcgaacgt atctcgtcta aattagaaca agaagcgaac gctagtgctc  88080
aaacaaaatg tgatatagaa atcggaaatt tttatatccg acaaaaccat ggatgtaacc  88140
tcactgttaa aaatatgtgc tctgcggacg cggatgctca gttggatgct gtgttatcag  88200
ccgctacaga aacatatagt ggattaacac cggaacaaaa agcatacgtg ccagctatgt  88260
ttactgctgc gttaaacatt cagacgagtg taaacactgt tgttagagat tttgaaaatt  88320
atgtgaaaca gacttgtaat tctagcgcgg tcgtcgataa caaattaaag atacaaaacg  88380
taatcataga tgaatgttac ggagccccag gatctccaac aaatttggaa tttattaata  88440
caggatctag caaaggaaat tgtgccatta aagcgttgat gcaattgacg actaaggcca  88500
ctactcaaat agcacctaga caagttgctg gtacaggagt tcagttttat atgattgtta  88560
tcggtgttat aatattggca gcgttgttta tgtactatgc caagcgtatg ttgttcacat  88620
ccaccaatga taaaatcaaa cttattttag ccaataagga aaacgtccat tggactactt  88680
acatggacac attctttaga acttctccga tggttattgc taccacggat atgcaaaact  88740
gaaaatatat tgataatatt ttaatagatt aacatggaag ttatcgctga tcgtctagac  88800
gatatagtga aacaaaatat agcggatgaa aaatttgtag attttgttat acacggtcta  88860
gagcatcaat gtcctgctat acttcgacca ttaattaggt tgtttattga tatactatta  88920
tttgttatag taatttatat ttttacggta cgtctagtaa gtagaaatta tcaaatgttg  88980
ttggtggcgc tagtcatcac attaactatt ttttattact ttatactata atagtactag  89040
actgacttct aacaaacatc tcacctgcca taaataaatg cttgatatta aagtcttcta  89100
tttctaacac tattccatct gtggaaaata atactctgac attatcgcta attgacacat  89160
cggtgagtga tatgcctata aagtaataat cttctttggg cacatatacc agtgtaccag  89220
gttctaacaa cctatttact ggtgctcctg tagcatactt tttctttacc ttgagaatat  89280
ccatcgtttg cttggtcaat agcgatatgt gattttttat caaccactcg aaaaagtaat  89340
tggagtgttc atatcctcta cgggctattg tctcatggcc gtgtatgaaa tttaagtaac  89400
acgactgtgg tagatttgtt ctatagagcc gattgccgca aatagataga actaccaata  89460
tgtctgtaca aatgttaaac attaattgat taacagaaaa aacaatgttc gttctgggaa  89520
tagaaaccag atcaaaacaa aattcgttag aatatatgcc acgtttatac atggaatata  89580
aaataactac agtttgaaaa ataacagtat catttaaaca tttaacttgc ggggttaatt  89640
tcacaacttt actgttttta aactgttcaa aatatagcat cgatccgtga gaaatacgtt  89700
tagccgcctt taatagagga aatcccaccg cctttctgga tctcaccaac gacgatagtt  89760
ctgaccagca actcatttct tcatcatcca cctgttttaa catataatag gcaggagata  89820
gatatccgtc attgcaatat tccttctcgt aggcacacaa tctaatattg ataaaatctc  89880
cattctcttc tctgcattta ttatcttgtt tcggtggctg attaggctgt agtcttggtt  89940
taggctttgg tatatcgttg ttgaatctat tttggtcatt aaatctttca tttcttcctg  90000
gtatattttt atcacctcgt ttggttggat ttttgtctat attatcgttt gtaacatcgg  90060
tacgggtatt catttatcac aaaaaaaact tctctaaatg agtctactgc tagaaaacct  90120
```

-continued

```
catcgaagaa gataccatat tttttgcagg aagtatatct gagtatgatg atttacaaat  90180
ggttattgcc ggcgcaaaat ccaaatttcc aagatctatg ctttctattt ttaatatagt  90240
acctagaacg atgtcaaaat atgagttgga gttgattcat aacgaaaata tcacaggagc  90300
aatgtttacc acaatgtata atataagaaa caatttgggt ctaggagatg ataaactaac  90360
tattgaagcc attgaaaact atttcttgga tcctaacaat gaagttatgc ctcttattat  90420
taataatacg gatatgactg ccgtcattcc taaaaaaagt ggtaggagaa agaataagaa  90480
catggttatc ttccgtcaag gatcatcacc tatcttgtgc attttcgaaa ctcgtaaaaa  90540
gattaatatt tataaagaaa atatggaatc cgcgtcgact gagtatacac ctatcggaga  90600
caacaaggct ttgatatcta aatatgcggg aattaatgtc ctgaatgtgt attctccttc  90660
cacatccata agattgaatg ccatttacgg attcaccaat aaaaataaac tagagaaact  90720
tagtactaat aaggaactag aatcgtatag ttctagccct cttcaagaac ccattaggtt  90780
aaatgatttt ctgggactat tggaatgtgt taaaaaaaat attcctctaa cagatattcc  90840
gacaaaggat tgattactat aaatggagaa tgttcctaat gtatacttta atcctgtgtt  90900
tatagagccc acgtttaaac attctttatt aagtgtttat aaacacagat taatagtttt  90960
atttgaagta ttcgttgtat tcattctaat atatgtattt tttagatctg aattaaatat  91020
gttcttcatg cctaaacgaa aaatacccga tcctattgat agattacgac gtgctaatct  91080
agcgtgtgaa gacgataaat taatgatcta tggattacca tggatgacaa ctcaaacatc  91140
tgcgttatca ataaatagta aaccgatagt gtataaagat tgtgcaaagc ttttgcgatc  91200
aataaatgga tcacaaccag tatctcttaa cgatgttctt cgcagatgat gattcatttt  91260
ttaagtattt ggctagtcaa gatgatgaat cttcattatc tgatatattg caaatcactc  91320
aatatctaga ctttctgtta ttattattga tccaatcaaa aaataaatta gaagccgtgg  91380
gtcattgtta tgaatctctt tcagaggaat acagacaatt gacaaaattc acagactctc  91440
aagattttaa aaaactgttt aacaaggtcc ctattgttac agatggaagg gtcaaactta  91500
ataaaggata tttgttcgac tttgtgatta gtttgatgcg attcaaaaaa gaatcctctc  91560
tagctaccac cgcaatagat cctattagat acatagatcc tcgtcgtgat atcgcatttt  91620
ctaacgtgat ggatatatta aagtcgaata aagtgaacaa taattaattc tttattgtca  91680
tcatgaacgg cggacatatt cagttgataa tcggccccat gttttcaggt aaaagtacag  91740
aattaattag acgagttaga cgttatcaaa tagctcaata taaatgcgtg actataaaat  91800
attctaacga taatagatac ggaacgggac tatggacgca tgataagaat aattttgaag  91860
cattggaagc aactaaacta tgcgatgtct tggaatcaat tacagatttc tccgtgatag  91920
gtatcgatga aggacagttc tttccagaca ttgttgaatt ctgtgagcgt atggcaaacg  91980
aaggaaaaat agttatagta gccgcactcg atgggacatt tcaacgtaaa ccgtttaata  92040
atattttgaa tcttattcca ttatctgaaa tggtggtaaa actaactgct gtgtgtatga  92100
aatgctttaa ggaggcttcc ttttctaaac gattgggtga ggaaaccgag atagaaataa  92160
taggaggtaa tgatatgtat caatcggtgt gtagaaagtg ttacatcgac tcataatatt  92220
atatttttta tctaaaaaac taaaaataaa cattgattaa attttaatat aatacttaaa  92280
aatggatgtt gtgtcgttag ataaaccgtt tatgtatttt gaggaaattg ataatgagtt  92340
agattacgaa ccagaaagtg caaatgaggt cgcaaaaaaa ctgccgtatc aaggacagtt  92400
aaaactatta ctaggagaat tattttttct tagtaagtta cagcgacacg gtatattaga  92460
```

-continued

```
tggtgccacc gtagtgtata taggatctgc tcccggtaca catatacgtt atttgagaga  92520
tcatttctat aatttaggag tgatcatcaa atggatgcta attgacggcc gccatcatga  92580
tcctatttta aatggattgc gtgatgtgac tctagtgact cggttcgttg atgaggaata  92640
tctacgatcc atcaaaaaac aactgcatcc ttctaagatt attttaattt ctgatgtaag  92700
atccaaacga ggaggaaatg aacctagtac ggcggattta ctaagtaatt acgctctaca  92760
aaatgtcatg attagtattt taaaccccgt ggcatctagt cttaaatgga gatgcccgtt  92820
tccagatcaa tggatcaagg acttttatat cccacacggt aataaaatgt tacaaccttt  92880
tgctccttca tattcagctg aaatgagatt attaagtatt tataccggtg agaacatgag  92940
actgactcga gttaccaaat tagacgctgt aaattatgaa aaaaagatgt actaccttaa  93000
taagatcgtc cgtaacaaag tagttgttaa ctttgattat cctaatcagg aatatgacta  93060
ttttcacatg tactttatgc tgaggaccgt gtactgcaat aaaacatttc ctactactaa  93120
agcaaaggta ctatttctac aacaatctat atttcgtttc ttaaatattc caacaacatc  93180
aactgaaaaa gttagtcatg aaccaataca acgtaaaata tctagcaaaa attctatgtc  93240
taaaaacaga aatagcaaga gatccgtacg cggtaataaa tagaaacgta ctactgagat  93300
atactaccga tatagagtat aatgatttag ttactttaat aaccgttaga cataaaattg  93360
attctatgaa aactgtgttt caggtattta acgaatcatc cataaattat actccggttg  93420
atgatgatta tggagaacca atcattataa catcgtatct tcaaaaaggt cataacaagt  93480
ttcctgtaaa ttttctatac atagatgtgg taatatctga cttatttcct agctttgtta  93540
gactagatac tacagaaact aatatagtta atagtgtact acaaacaggt gatggtaaaa  93600
agactcttcg tcttcccaaa atgttagaga cggaaatagt tgtcaagatt ctctatcgcc  93660
ctaatatacc attaaaaatt gttagatttt tccgcaataa catggtaact ggagtagaga  93720
tagccgatag atctgttatt tcagtcgctg attaatcaat tagtagagat gagataagaa  93780
cattataata atcaataata tatcttatat cttatatctt atatcttata tcttgtttag  93840
aaaaatgcta atattaaaat agctaacgct agtaatccaa tcggaagcca tttgatatct  93900
ataatagggt atctaatttc ctgatttaaa tagcggacag ctatattctc ggtagctact  93960
cgtttggaat cacaaacatt atttacatct aatttactat ctgtaatgga aacgtttccc  94020
aatgaaatgg tacaatccga tacattgcat tttgttatat tttttttaa agaggctggt  94080
aacaacgcat cgcttcgttt acatggctcg taccaacaat aatagggtaa tcttgtatct  94140
attcctatcc gtactatgct tttatcagga taaatacatt tacatcgtat atcgtctttg  94200
ttagcatcac agaatgcata aatttgttcg tccgtcatga taaaaattta aagtgtaaat  94260
ataactatta tttttatagt tgtaataaaa agggaaattt gattgtatac tttcggttct  94320
ttaaaagaaa ctgacttgat aaaaatggct gtaatctcta aggttacgta tagtctatat  94380
gatcaaaaag agattaatgc tacagatatt attattagtc atgttaaaaa tgacgacgat  94440
atcggtaccg ttaaagatgg taaactaggt gctatggatg gggcattatg taagacttgt  94500
gggaaaacgg aattggaatg tttcggtcac tggggtaaag taagtattta taaaactcat  94560
atagttaagc ctgaatttat ttcagaaatt attcgtttac tgaatcatat atgtattcac  94620
tgcggattat tgcgttcacg agaaccgtat tccgacgata ttaacctaaa agagttatcg  94680
ggacacgctc ttaggagatt aaaggataaa atattatcca agaaaaagtc atgttggaac  94740
agcgaatgta tgcaaccgta tcaaaaaatt actttttcaa agaaaaaggt ttgtttcgtc  94800
aacaagttgg atgatattaa cgttcctaat tctctcatct atcaaaagtt aatttctatt  94860
```

catgaaaagt tttggccatt attagaaatt catcaatatc cagctaactt attttataca 94920
gactactttc ccatccctcc gttgattatt agaccggcta ttagtttttg gatagatagt 94980
atacccaaag aaaccaatga attaacttac ttattaggta tgatcgttaa gaattgtaac 95040
ttgaatgctg atgaacaggt tatccagaag gcggtaatag aatacgatga tattaaaatt 95100
atttctaata acactaccag tatcaattta tcatatatta catccggcaa aaataatatg 95160
attagaagtt atatcgtcgc ccggcgaaaa gatcagaccg ctagatctgt aattggtccc 95220
agtacatcta tcaccgttaa tgaggtagga atgcccgcat atattagaaa tacacttaca 95280
gaaaagatat ttgttaatgc ctttacagtg gataaagtta aacaactatt agcgtcaaac 95340
caagttaaat tttactttaa taaacgatta aaccaattaa caagaatacg ccaaggaaag 95400
tttattaaaa ataaaataca tttattgcct ggtgattggg tagaagtagc tgttcaagaa 95460
tatacaagta ttatttttgg aagacagccg tctctacata gatacaacgt catcgcttca 95520
tctatcagag ctaccgaagg agatactatc aaaatatctc ccggaattgc caactctcaa 95580
aatgctgatt tcgacgggga tgaggaatgg atgatattag aacaaaatcc taaagctgta 95640
attgaacaaa gtattcttat gtatccgacg acgttactca aacacgatat tcatggagcc 95700
cccgtttatg gatctattca agatgaaatc gtagcagcgt attcattgtt taggatacaa 95760
gatctttgtt tagatgaagt attgaacatc ttggggaaat atggaagaga gttcgatcct 95820
aaaggtaaat gtaaattcag cggtaaagat atctatactt acttgatagg tgaaaagatt 95880
aattatccgg gtctcttaaa ggatggtgaa attattgcaa acgacgtaga tagtaatttt 95940
gttgtggcta tgaggcatct gtcattggct ggactcttat ccgatcataa gtcgaacgtg 96000
gaaggtatca actttattat caagtcatct tatgttttta agagatatct atctatttac 96060
ggttttgggg tgacattcaa agatctgaga ccaaattcga cgttcactaa taaattggag 96120
gccatcaacg tagaaaaaat agaacttatc aaagaagcat acgccaaata tctcaacgat 96180
gtaagagacg ggaaaatagt tccattatct aaagctttag aggcggacta tgtggaatcc 96240
atgttatcca acttgacaaa tcttaatatc cgagagatag aagaacatat gagacaaacg 96300
ctgatagatg atccagataa taacctcctg aaaatggcca aagcgggtta taaagtaaat 96360
cctacagaac taatgtatat tctaggtacg tatggacaac aaaggattga tggtgaacca 96420
gcagagactc gagtattggg tagagtttta ccttactatc ttccagactc taaggatcca 96480
gaaggaagag gttacattct taattcttta acaaaaggat taacgggttc tcaatattac 96540
ttttcgatgc tggttgccag atctcaatct actgatatcg tctgtgaaac atcacgtacc 96600
ggaacactgg ctagaaaaat cattaaaaag atggaggata tggtggtcga cggatacgga 96660
caagtagtta taggtaatac gctcatcaag tacgccgcca attataccaa aattctaggc 96720
tcagtatgta aacctgtaga tcttatctat ccagatgagt ccatgacttg gtatttggaa 96780
attagtgctc tgtggaataa aataaaacag ggattcgttt actctcagaa acagaaactt 96840
gcaaagaaga cattggcgcc gtttaatttc ctagtattcg tcaaacccac cactgaggat 96900
aatgctatta aggttaagga tctgtacgat atgattcata acgtcattga tgatgtgaga 96960
gagaaatact tctttacggt atctaatata gattttatgg agtatatatt cttgacgcat 97020
cttaatcctt ctagaattag aattacaaaa gaaacggcta tcactatctt tgaaaagttc 97080
tatgaaaaac tcaattatac tctaggtggt ggaactccta ttggaattat ttctgcacag 97140
gtattgtctg agaagtttac acaacaagcc ctgtccagtt ttcacactac tgaaaaaagt 97200

```
ggtgccgtca aacaaaaact tggtttcaac gagtttaata acttgactaa tttgagtaag  97260
aataagaccg aaattatcac tctggtatcc gatgatatct ctaaacttca atctgttaag  97320
attaatttcg aatttgtatg tttgggagaa ttaaatccag acatcactct tcgaaaagaa  97380
acagataggt atgtagtaga tataatagtc aatagattat acatcaagag agcagaaatt  97440
accgaattag tcgtcgaata tatgattgaa cgatttatct cctttagcgt cattgtaaag  97500
gaatggggta tggaaacatt cattgaggat gaggataata ttagatttac tgtctatcta  97560
aatttcgttg aaccagagga attgaatctt agtaagttta tgatggttct tccgggtgcc  97620
gccaacaagg gcaagattag taaattcaag attcctatct ctgattatac gggttatgac  97680
gacttcaatc aaacaaaaaa gctcaataag atgactgtag aactcatgaa tctaaaagaa  97740
ttgggttctt tcgatttgga aaacgtcaac gtgtatcctg gagtatggaa tacatacgat  97800
atcttcggta tcgaggccgc tcgtgaatac ttgtgcgaag ccatgttaaa cacctatgga  97860
gaagggttcg attatctgta tcagccttgt gatcttctcg ctagtttact atgtgctagt  97920
tacgaaccag aatcagtgaa taaattcaag ttcggcgcag ctagtactct taagagagct  97980
acgttcggag acaataaagc attgttaaac gcggctcttc ataaaaagtc agaacctatt  98040
aacgataata gtagctgcca ctttttagc aaggtcccta atataggaac tggatattac  98100
aaatacttta tcgacttggg tcttctcatg agaatggaaa ggaaactatc tgataagata  98160
tcttctcaaa agatcaagga aatggaagaa acagaagact tttaattctt atcaataaca  98220
tatttttcta tgatctgtct tttaaacgat ggattttcca caaatgcgcc tctcaagtcc  98280
ctcatagaat gatacacgta taaaaaatat agcataggca atgactcctt atttttagac  98340
attagatatg ccaaaatcat agccccgctt ctatttactc ccgcagcaca atgaaccaac  98400
acgggctcgt ttcgttgatc acatttagat aaaaaggcgg ttacgtcgtc aaaatattta  98460
ctaatatcgg tagttgtatc atctaccaac ggtatatgaa taatattaat attagagtta  98520
ggtaatgtat atttatccat cgtcaaattt aaaacatatt tgaacttaac ttcagatgat  98580
ggtgcatcca tagcattttt ataatttccc aaatacacat tattggttac tcttgtcatt  98640
atagtgggag atttggcttt gtgcatatct ccagttgaac gtagtagtaa gtatttatac  98700
aaacttttct tatccattta taacgtacaa atggataaaa ctactttatc ggtaaacgcg  98760
tgtaatttag aatacgttag agaaaaggct atagtaggcg tacaagcagc caaaacatca  98820
acacttatat tctttgttat tatattggca attagtgcgc tattactctg gtttcagacg  98880
tctgataatc cagtctttaa tgaattaacg agatatatgc gaattaaaaa tacggttaac  98940
gattggaaat cattaacgga tagcaaaaca aaattagaaa gtgatagagg tagacttcta  99000
gccgctggta aggatgatat attcgacttc aaatgtgtgg atttcggcgc ctattttata  99060
gctatgcgat tggataagaa aacatatctg ccgcaagcta ttaggcgagg tactggagac  99120
gcgtggatgg ttaaaaaggc ggcaaaggtc gatccatctg ctcaacaatt ttgtcagtat  99180
ttgataaaac acaagtctaa taatgttatt acttgtggta atgagatgtt aaatgaatta  99240
ggttatagcg gttattttat gttaccgcat tggtgttccg attttagtaa tatggaatag  99300
tgttagataa atgcggtaac aaatgttcct gtaaggaacc ataacagttt agatttaacg  99360
ttaaagatga gcataaacat aataaacaaa attacaatca aacctataac attaatatca  99420
aacaatccaa aaaatgaaat cagtggagta gtaaacgcgt acataactcc tggataacgt  99480
ttagcagctg ccgttcctat tctagaccaa aaattcggtt tcatgttttc gaaacggtat  99540
tctgcaacaa gtcgaggatc gtgttctaca tatttggcgg cgttatccag tatctgccta  99600
```

```
ttgatcttca tttcgttttc gattctggct atttcaaaat aaaatcccga tgatagacct  99660
ccagacttta taatttcatc tacgatgttc agcgccgtag taactctaat aatataggct  99720
gataagctaa catcataccc tcctgtatat gtgaatatgg catgattttt gtccattaca  99780
agctcggttt taactttatt gcctgtaata atttctctca tctgtaggat atctattttt  99840
ttgtcatgca ttgccttcaa gacgggacga agaaacgtaa tatcctcaat aacgttatcg  99900
ttttctacaa taactacata ttctaccttt ttattttcta actcagtaaa aaaattagaa  99960
tcccataggg ctaaatgtct agcgatattt cttttcgttt cctctgtaca catagtgtta 100020
caaaaccctg aaaagaagtg agtatacttg tcatcatttc taatgtttcc tccagtccac 100080
tgtataaacg cataatcctt gtaatgatct ggatcatcct tgactaccac aacatttctt 100140
ttttctggca taacttcgtt gtcctttaca tcatcgaact tctgatcatt aatatgctca 100200
tgaacattag gaaatgtttc tgatggaggt ctatcaataa ctggcacaac aataacagga 100260
gttttcaccg ccgccattta gttattgaaa ttaatcatat acaactcttt aatacgagtt 100320
atattttcgt ctatccattg tttcacattg acatatttcg acaaaaagat ataaaatgcg 100380
tattccaatg cttctctgtt taatgaatta ctaaaatata caaacacgtc actgtctggc 100440
aataaatgat atcttagaat attgtaacaa tttattttgt attgcacatg ttcgtgatct 100500
atgagttctt cttcgaatgg cataggatct ccgaatctga aaacgtataa ataggagtta 100560
gaataataat atttgagagt attggtaata tataaactct ttagcggtat aattagtttt 100620
tttctctcaa tttctatttt tagatgtgat ggaaaaatga ctaattttgt agcattagta 100680
tcatgaactc taatcaaaat cttaatatct tcgtcacacg ttagctcttt gaagtttta 100740
agagatgcat cagttggttc tacagatgga gtaggtgcaa caatttttttg ttctacacat 100800
gtatgtactg gagccattgt tttaactata atggtgcttg tatcgaaaaa ctttaatgca 100860
gatagcggaa gctcttcgcc gcgactttct acatcgtaat tgggttctaa cgccgatctc 100920
tgaatggata ctagttttct aagttctaat gtgattctct gaaaatgtaa atccaattcc 100980
tccggcatta tagatgtgta tacatcggta aataaaacta tagtatccaa cgatcccttc 101040
tcgcaaattc tagtcttaac caaaaaatcg tatataacca cggagatggc gtatttaaga 101100
gtggattctt ctaccgtttt gttcttggat gtcatatagg aaactataaa gtccgcacta 101160
ctgttaagaa tgattactaa cgcaactata tagtttaaat taagcatttt ggaaacataa 101220
aataactctg tagacgatac ttgactttcg aataagtttg cagacaaacg aagaaagaac 101280
agacctctct taatttcaga agaaaacttt ttttcgtatt cctgacgtct agagtttata 101340
tcaataagaa agttaagaat tagtcggtta atgttgtatt tcattaccca agtttgagat 101400
ttcataatat tatcaaaaga catgataata ttaaagataa agcgctgact atgaacgaaa 101460
tagctatatg gttcgctcaa gaatatagtc ttgttaaacg tggaaacgat aactgtattt 101520
ttaatcacgt cagcggcatc taaattaaat ataggtatat ttattccaca cactctacaa 101580
tatgccacac catcttcata ataaataaat tcgttagcaa aattattaat tttagtgaaa 101640
tagttagcgt caactttcat agcttccttc aatctaattt gatgctcaca cggtgcgaat 101700
tccactctaa catccctttt ccatgcctca ggttcatcga tctctataat atctagtttt 101760
ttgcgtttca caaacacagg ctcgtctctc gcgatgagat ctgtatagta actatgtaaa 101820
tgataactag atagaaagat gtagctatat agatgacgat cctttaagag aggtataata 101880
actttacccc aatcagatag actgttgtta tggtcttcgg aaaaagaatt tttataaatt 101940
```

```
tttccagtat tttccaaata tacgtactta acatctaaaa aatccttaat gataatagga 102000
atggataatc cgtctatttt ataaagaaat acatatcgca cattatactt ttttttggaa 102060
atgggaatac cgatgtgtct acataaatat gcaaagtcta aatatttttt agagaatctt 102120
agttggtcca aattcttttc caagtacggt aatagatttt tcatattgaa cggtatcttc 102180
ttaatctctg gttctagttc cgcattaaat gatgaaacta agtcactatt tttataacta 102240
acgattacat cacctctaac atcatcattt accagaatac tgatcttctt ttgtcgtaaa 102300
tacatgtcta atgtgttaaa aaaaagatca tacaagttat acgtcatttc atctgtggta 102360
ttcttgtcat tgaaggataa actcgtacta atctcttctt taacagcctg ttcaaattta 102420
tatcctatat acgaaaaaat agcaaccagt gtttgatcat ccgcgtcaat attctgttct 102480
atcgtagtgt ataacaatcg tatatcttct tctgtgatag tcgatacgtt ataaaggttg 102540
ataacgaaaa tatttttatt ttgtgaaata aagtcatcgt aggattttgg acttatattc 102600
gcgtctagta gatatgcttt tatttttgga atgatctcaa ttagaatagt ctctttagag 102660
tccatttaaa gttacaaaca actaggaaat tggtttatga tgtataattt ttttagtttt 102720
tatagattct ttattctata cttaaaaaat gaaaataaat acaaaggttc ttgagggttg 102780
tgttaaattg aaagcgagaa ataatcataa attatttcat tatcgcgata tccgttaagt 102840
ttgtatcgta atggcgtggt caattacgaa taaagcggat actagtagtt tcacaaagat 102900
ggctgaaatc agagctcatc taaaaaatag cgctgaaaat aaagataaaa acgaggatat 102960
tttcccggaa gatgtaataa ttccatctac taagcccaaa accaaacgag ccactactcc 103020
tcgtaaacca gcggctacta aaagatcaac caaaaaggag gaagtggaag aagaagtagt 103080
tatagaggaa tatcatcaaa caactgaaaa aaattctcca tctcctggag tcagcgacat 103140
tgtagaaagc gtggccgctg tagagctcga tgatagcgac ggggatgatg aacctatggt 103200
acaagttgaa gctggtaaag taaatcatag tgctagaagc gatctttctg acctaaaggt 103260
ggctaccgac aatatcgtta aagatcttaa gaaaattatt actagaatct ctgcagtatc 103320
gacggttcta gaggatgttc aagcagctgg tatctctaga caatttactt ctatgactaa 103380
agctattaca acactatctg atctagtcac cgagggaaaa tctaaagttg ttcgtaaaaa 103440
agttaaaact tgtaagaagt aaatgcgtgc actttttttat aaagatggta aactctttac 103500
cgataataat tttttaaatc ctgtatcaga cgataatcca gcgtatgagg ttttgcaaca 103560
tgttaaaatt cctactcatt taacagatgt agtagtatat gaacaaacgt gggaggaggc 103620
gttaactaga ttaatttttg tgggaagcga ttcaaaagga cgtagacaat acttttacgg 103680
aaaaatgcat gtacagaatc gcaacgctaa aagagatcgt atttttgtta gagtatataa 103740
cgttatgaaa cgaattaatt gttttataaa caaaaatata aagaaatcgt ccacagattc 103800
caattatcag ttggcggttt ttatgttaat ggaaactatg tttttttatta gatttggtaa 103860
aatgaaatat cttaaggaga atgaaacagt agggttatta acactaaaaa ataaacacat 103920
agaaataagt cccgatgaaa tagttatcaa gtttgtagga aaggacaaag tttcacatga 103980
atttgttgtt cataagtcta atagactata taaaccgcta ttgaaactga cggatgattc 104040
tagtcccgaa gaatttctgt tcaacaaact aagtgaacga aaggtatacg aatgtatcaa 104100
acagtttggt attagaatca aggatctccg aacgtatgga gtcaattata cgtttttata 104160
taatttttgg acaaatgtaa agtccatatc tcctcttccg tcaccaaaaa agttaatagc 104220
attaactatc aaacaaactg ctgaagttgt aggtcatact ccatcaattt caaaaagagc 104280
ttatatggca acgactattt tagaaatggt aaaggataaa aattttttag atgtagtatc 104340
```

-continued taaaactacg ttcgatgaat tcctatctat agtcgtagat cacgttaaat catctacgga 104400
tggatgatat agatctttac acaaataatt acaagaccga taaatggaaa tggataagcg 104460
tatgaaatct ctcgcaatga cagctttctt cggagagcta aacacattag atattatggc 104520
attgataatg tctatattta aacgccatcc aaacaatacc attttttcag tggataagga 104580
tggtcagttt atgattgatt tcgaatacga taattataag gcttctcaat atttggatct 104640
gaccctcact ccgatatctg gagatgaatg caagactcac gcatcgagta tagccgaaca 104700
attggcgtgt gcggatatta ttaaagagga tattagcgaa tacatcaaaa ctactccccg 104760
tcttaaacga tttataaaaa aataccgcaa tagatcagat actcgcatca gtcgagatac 104820
agaaaagctt aaaatagctc tagctaaagg catagattac gaatatataa aagacgcttg 104880
ttaataagta aatgaaaaaa aactagtcgt ttataataaa acacgatatg gatgccaacg 104940
tagtatcatc ttctactatt gcgacgtata tagacgcttt agcgaagaat gcttcagaat 105000
tagaacagag gtctaccgca tacgaaataa ataatgaatt ggaactagta tttattaagc 105060
cgccattgat tactttgaca aatgtagtga atatctctac gattcaggaa tcgtttattc 105120
gatttaccgt tactaataag gaaggtgtta aaattagaac taagattcca ttatctaagg 105180
tacatggtct agatgtaaaa aatgtacagt tagtagatgc tatagataac atagtttggg 105240
aaaagaaatc attagtgacg gaaaatcgtc ttcacaaaga atgcttgttg agactatcga 105300
cagaggaacg tcatatattt ttggattaca agaaatatgg atcctctatc cgactagaat 105360
tagtcaatct tattcaagca aaaacaaaaa actttacgat agactttaag ctaaaatatt 105420
ttctaggatc cggtgcccag tctaaaagtt ctttattaca cgctattaat catccaaagt 105480
caaggcctaa tacatctctg gaaatagaat tcacacctag agacaatgaa acagttccat 105540
atgatgaact aataaaggaa ttgacgactc tatcacgtca tatatttatg gcttctccag 105600
agaatgtaat tctttctccg cctattaacg cgcctataaa aacctttatg ttgcctaaac 105660
aagatatagt aggtttggat ctggaaaatc tatatgccgt aactaagact gacggcattc 105720
ctataactat cagagttaca tcaaacgggt tgtattgtta ttttacacat cttgggtata 105780
ttattagata tccagttaag agaataatag attccgaagt agtagtcttt ggtgaggcag 105840
ttaaggataa gaactggacc gtatatctta ttaagctaat agagcctgtg aatgctatca 105900
gtgatagact agaagaaagt aagtatgttg aatctaaact agtggatatt tgtgatcgga 105960
tagtattcaa gtcaaagaaa tacgaaggtc cgtttactac aactagtgaa gtcgtcgata 106020
tgttatctac atatttacca aagcaaccag aaggtgttat tctgttctat tcaaagggac 106080
ctaaatctaa cattgatttt aaaattaaaa aggaaaatac tatagaccaa actgcaaatg 106140
tagtatttag gtacatgtcc agtgaaccaa ttatctttgg agaatcgtct atctttgtag 106200
agtataagaa atttagcaac gataaaggct ttcctaaaga atatggttct ggtaagattg 106260
tgttatataa cggcgttaat tatctaaata atatctattg tttggaatat attaatacac 106320
ataatgaagt gggtattaag tccgtggttg tacctattaa gtttatagca gaattcttag 106380
ttaatggaga aatacttaaa cctagaattg ataaaaccat gaaatatatt aactcagaag 106440
attattatgg aaatcaacat aatatcatag tcgaacattt aagagatcaa agcatcaaaa 106500
taggagatat ctttaacgag gataaactat cggatgtggg acatcaatac gccaataatg 106560
ataaatttag attaaatcca gaagttagtt attttacgaa taaacgaact agaggaccgt 106620
tgggaatttt atcaaactac gtcaagactc ttcttatttc tatgtattgt tccaaaacat 106680

-continued

```
ttttagacga ttccaacaaa cgaaaggtat tggcgattga ttttggaaac ggtgctgacc 106740
tggaaaaata cttttatgga gagattgcgt tattggtagc gacggatccg gatgctgatg 106800
ctatagctag aggaaatgaa agatacaaca aattaaactc tggaattaaa accaagtact 106860
acaaatttga ctacattcag gaaactattc gatccgatac atttgtctct agtgtcagag 106920
aagtattcta ttttggaaag tttaatatca tcgactggca gtttgctatc cattattctt 106980
ttcatccgag acattatgct accgtcatga ataacttatc cgaactaact gcttctggag 107040
gcaaggtatt aatcactacc atggacggag acaaattatc aaaattaaca gataaaaaga 107100
cttttataat tcataagaat ttacctagta gcgaaaacta tatgtctgta gaaaaaatag 107160
ctgatgatag aatagtggta tataatccat caacaatgtc tactccaatg actgaataca 107220
ttatcaaaaa gaacgatata gtcagagtgt ttaacgaata cggatttgtt cttgtagata 107280
acgttgattt cgctacaatt atagaacgaa gtaaaaagtt tattaatggc gcatctacaa 107340
tggaagatag accgtctaca aaaaactttt tcgaactaaa tagaggagcc attaaatgtg 107400
aaggtttaga tgtcgaagac ttacttagtt actatgttgt ttatgtcttt tctaagcggt 107460
aaataataat atggtatggg ttctgatatc cccgttctaa atgcattaaa taattccaat 107520
agagcgattt ttgttcctat aggaccttcc aactgtggat actctgtatt gttaatagat 107580
atattaatac ttttgtcggg taacagaggt tctacgtctt ctaaaaataa aagttttata 107640
acatctggcc tgttcataaa taaaaacttg gcgattctat atatactctt attatcaaat 107700
ctagccattg tcttatagat gtgagctact gtaggtgtac catttgattt tctttctaat 107760
actatatatt tctctcgaag aagttcttgc acatcatctg ggaataaaat actactgttg 107820
agtaaatcag ttattttttt tatatcgata ttgatggaca tttttatagt taaggataat 107880
aagtatccca aagtcgataa cgacgataac gaagtattta tacttttagg aaatcacaat 107940
gactttatca gattaaaatt aacaaaatta aaggagcatg tatttttttc tgaatatatt 108000
gtgactccag atacatatgg atctttatgc gtcgaattaa atgggtctag ttttcagcac 108060
ggtggtagat atatagaggt ggaggaattt atagatgctg gaagacaagt tagatggtgt 108120
tctacatcca atcatatatc taaagatata cccgaagata tgcacactga taaatttgtc 108180
atttatgata tatacacttt tgacgctttc aagaataaac gattggtatt cgtacaggtg 108240
cctccgtcgt taggagatga tagtcatttg actaatccgt tattgtcacc gtattatcgt 108300
aattcagtag ccagacaaat ggtcaatgat atgattttta atcaagattc atttttaaaa 108360
tatttattag aacatctgat tagaagccac tatagagttt ctaaacatat aacaatagtt 108420
agatacaagg ataccgaaga attaaatcta acgagaatat gttataatag agataagttt 108480
aaggcgtttg tattcgcttg gtttaacggc gtttcggaaa atgaaaaggt actagatacg 108540
tataaaaagg tatctaattt gatataatga attcagtgac tgtatcacac gcgccatata 108600
ctattactta tcacgatgat tgggaaccag taatgagtca attggtagag ttttataacg 108660
aagtagccag ttggctgcta cgagacgaga cgtcgcctat tcctgataag ttctttatac 108720
agttgaaaca accgcttaga aataaacgag tatgtgtgtg tggtatagat ccgtatccga 108780
aagatggaac tggtgtaccg ttcgaatcac caaattttac aaaaaaatca attaaggaga 108840
tagcttcatc tatatctaga ttaaccggag taattgatta taaaggttat aaccttaata 108900
taatagacgg ggttataccc tggaattatt acttaagttg taaattagga gaaacaaaaa 108960
gtcacgcgat ttactgggat aaaatttcta agttactgct gcagcatata actaaacacg 109020
ttagtgttct ttattgtttg ggtaaaacag atttctcgaa tatacgggcc aagttagaat 109080
```

```
ccccggtaac taccatagtc ggatatcatc cagcggctag agaccgccaa ttcgagaaag 109140
atagatcatt tgaaattatc aacgttttac tggaattaga caacaaggca cctataaatt 109200
gggctcaagg gtttatttat taatgcttta gtgaaatttt aacttgtgtt ctaaatggat 109260
gcggctatta gaggtaataa tgttatcttt gttcttaaga ctataggtgt cccgtcagcg 109320
tgcagacaaa atgaagatcc aagatttgta gaagcattta aatgcgacga gttagaaaga 109380
tatattgaga ataatccaga atgtacacta ttcgaaagtc ttagggatga ggaagcatac 109440
tctatagtca gaattttcat ggatgtagat ttagacgcgt gtctagacga aatagattat 109500
ttaacggcta ttcaagattt tattatcgag gtgtcaaact gtgtagctag attcgcgttt 109560
acagaatgcg gcgccattca tgaaaatgta ataaaatcca tgagatctaa tttttcattg 109620
actaagtcta caaatagaga taaaacaagt tttcatatta tctttttaga cacgtatacc 109680
actatggata cattgatagc tatgaaacga acactattag aattaagtag atcatctgaa 109740
aatccactaa ccagatcgat agacactgcc gtatatagga gaaaaacaac tcttcgggtt 109800
gtaggtacta ggaaaaatcc aaattgcgac actattcatg taatgcaacc accgcatgat 109860
aatatagaag attacctatt cacttacgtg gatatgaaca acaatagtta ttacttttct 109920
ctacaacgac gattggagga tttagttcct gataagttat gggaaccagg gtttatttca 109980
ttcgaagacg ctataaaaag agtttcaaaa atattcatta attctataat aaactttaat 110040
gatctcgatg aaaataattt tacaacggta ccactggtca tagattacgt aacaccttgt 110100
gcattatgta aaaaacgatc gcataaacat ccgcatcaac tatcgttgga aaatggtgct 110160
attagaattt acaaaactgg taatccacat agttgtaaag ttaaaattgt tccgttggat 110220
ggtaataaac tgtttaatat tgcacaaaga attttagaca ctaactctgt tttattaacc 110280
gaacgaggag accatatagt ttggattaat aattcatgga aatttaacag cgaagaaccc 110340
ttgataacaa aactaatttt gtcaataaga catcaactac ctaaggaata ttcaagcgaa 110400
ttactctgtc caagaaaacg aaagactgta gaagctaaca tacgagacat gttagtagat 110460
tcagtagaga ccgataccta tccggataaa cttccgttta aaaatggtgt attggacctg 110520
gtagacggaa tgttttactc tggagatgat gctaaaaaat atacgtgtac tgtatcaacc 110580
ggatttaaat ttgacgatac aaagttcgtc gaagacagtc cagaaatgga agagttaatg 110640
aatatcatta acgatatcca accattaacg gatgaaaata agaaaaatag agagctatat 110700
gaaaaaacat tatctagttg tttatgtggt gctaccaaag gatgtttaac attctttttt 110760
ggagaaactg caactggaaa gtcgacaacc aaacgtttgt taaagtctgc tatcggtgac 110820
ctgtttgttg agacgggtca aacaatttta acagatgtat tggataaagg acctaatcca 110880
tttatcgcta acatgcattt gaaaagatct gtattctgta gcgaactacc tgattttgcc 110940
tgtagtggat caaagaaaat tagatctgac aatattaaaa agttgacaga accttgtgtc 111000
attggaagac cgtgtttctc caataaaatt aataatagaa accatgcgac aatcattatc 111060
gatactaatt acaaacctgt ctttgatagg atagataacg cattaatgag aagaattgcc 111120
gtcgtgcgat tcagaacaca cttttctcaa ccttctggta gagaggctgc tgaaaataat 111180
gacgcgtacg ataaagtcaa actattagac gaggggttag atggtaaaat acaaaataat 111240
agatatagat ttgcatttct atacttgttg gtgaaatggt acagaaaata tcatgttcct 111300
attatgaaac tatatcctac accggaagag attcctgact ttgcattcta tctcaaaata 111360
ggtactctgt tagtatctag ctctgtaaag catattccat taatgacgga cctctccaaa 111420
```

-continued aagggatata tattgtacga taatgtggtc actcttccgt tgactacttt ccaacagaaa 111480
atatccaagt attttaattc tagactattt ggacacgata tagagagctt catcaataga 111540
cataagaaat ttgccaatgt tagtgatgaa tatctgcaat atatattcat agaggatatt 111600
tcatctccgt aaatatatgc tcatatattt atagaagata tcacatatct aaatgaatac 111660
cggaatcata gatttatttg ataatcatgt tgatagtata ccaactatat tacctcatca 111720
gttagctact ctagattatc tagttagaac tatcatagat gagaacagaa gcgtgttatt 111780
gttccatatt atgggatcag gtaaaacaat aatcgctttg ttgttcgcct tggtagcttc 111840
cagatttaaa aaggtttaca ttctagtgcc gaacatcaac atcttaaaaa ttttcaatta 111900
taatatgggt gtagctatga acttgtttaa tgacgaattc atagctgaaa atatctttat 111960
tcattccaca acaagttttt attctcttaa ttataacgat aacgtcatta attataacgg 112020
attatctcgc tacaataact ctatttttat cgttgatgag gcacataata tctttgggaa 112080
taatactgga gaacttatga ccgtgataaa aaataaaaac aagattcctt ttttactatt 112140
gtctggatct cccattacta acacacctaa tactctgggt catattatag atttaatgtc 112200
cgaagagacg atagattttg gtgaaattat tagtcgtggt aagaaagtaa ttcagacact 112260
tcttaacgaa cgaggtgtga atgtacttaa ggatttgctt aaaggaagaa tatcatatta 112320
cgaaatgcct gataaagatc taccaacgat aagatatcac ggacgtaagt ttctagatac 112380
tagagtagta tattgtcaca tgtctaaact tcaagagaga gattatatga ttactagacg 112440
acagctatgt tatcatgaaa tgtttgataa aaatatgtat aacgtgtcaa tggcagtatt 112500
gggacaactt aatctgatga ataatttaga tactttattt caggaacagg ataaggaatt 112560
gtacccaaat ctgaaaataa ataatggcgt gttatacgga gaagaattgg taacgttaaa 112620
cattagttcc aaatttaagt actttattaa tcggatacag acactcaacg gaaaacattt 112680
tatatacttt tctaattcta catatggcgg attggtaatt aaatatatca tgctcagtaa 112740
tggatattct gaatataatg gttctcaggg aactaatcca catatgataa acggcaaacc 112800
aaaaacattt gctatcgtta ctagtaaaat gaaatcgtct ttagaggatc tattagatgt 112860
gtataattct cctgaaaacg atgatggtag tcaattgatg tttttgtttt cgtcaaacat 112920
tatgtccgaa tcctatactc tgaaagaggt aaggcatatt tggtttatga ctatcccaga 112980 tacttttttct caatacaacc aaattcttgg acgatctatt agaaaattct cttacgccga 113040
tatttctgaa ccagttaatg tatatctttt agccgccgta tattccgatt tcaatgacga 113100
agtgacgtca ttaaacgatt acacacagga tgaattaatt aatgttttac catttgacat 113160
caaaaagctg ttatatctaa aatttaagac gaaagaaacg aatagaatat actctattct 113220
tcaagagatg tctgaaacgt attctcttcc accacatcca tcaattgtaa aagttttatt 113280
gggagaattg gtcagacaat ttttttataa taattctcgt attaagtata acgataccaa 113340
gttacttaaa atggttacat cagttataaa aaataaagaa gacgctagga attacataga 113400
tgatattgta aacggtcact tctttgtatc gaataaagta tttgataaat ctcttttata 113460
caaatacgaa aacgatatta ttacagtacc gtttagactt tcctacgaac catttgtttg 113520
gggagttaac tttcgtaaag aatataacgt ggtatcttct ccataaaact gatgagatat 113580
ataaagaaat aaatgtcgag ctttgttacc aatggatacc tttccgttac attggaacct 113640
catgagctga cgttagacat aaaaactaat attaggaatg ccgtatataa gacgtatctc 113700
catagagaaa ttagtggtaa aatggccaag aaaatagaaa ttcgtgaaga cgtggaatta 113760
cctctcggcg aaatagttaa taattctgta gttataaacg ttccgtgtgt aataacctac 113820
gcgtattatc acgttgggga tatagtcaga ggaacattaa acatcgaaga tgaatcaaat 113880
gtaactattc aatgtggaga tttaatctgt aaactaagta gagattcggg tactgtatca 113940
tttagcgatt caaagtactg ctttttcga aatggtaatg cgtatgacaa tggcagcgaa 114000
gtcactgccg ttctaatgga ggctcaacaa ggtatcgaat ctagttttgt ttttctcgcg 114060
aatatcgtcg actcataaga aagagaatag cggtaagtat aaacacgaat actatggcaa 114120
taattgcgaa tgttttattc tcttcgatat atttttgata atatgaaaaa catgtctctc 114180
tcaaatcgga caaccatctc ataaaatagt tatctcgcgc tggcgaggtg gttgctgctc 114240
gtataatctc cccagaataa tatacttgcg tgtcgtcgtt caatttatac ggatttctat 114300
agttctctgt tatataatgc ggttttctat catgattaga cgacgacaat agtgttctaa 114360
atttagatag ttgatcagaa tgaatgttta ttggcgttgg aaaaaattatc catacagcgt 114420
ctgcagagtg gttgatagtt gttcctagat atgtaaaata atccaactta ctaggcagca 114480
aattgtctag ataaaatact gaatcaaacg gtgcagacgt attggcggat ctaatggaat 114540
ccaattgatt aactatcttt tgaaaatata catttttatg atccaatact tgtaagaata 114600
tagaaataat gataagtcca tcatcgtgtt tttttgcctc ttcataagaa ctatattttt 114660
tcttattcca atgaacaaga ttaatctctc cagagtattt gtacacatct atcaagtgat 114720
tggatccata atcgtcttcc tttccccaat atatatgtag tgatgataac acatattcat 114780
tggggagaaa ccctccactt atatatcctc ctttaaaatt aatccttact agttttccag 114840
tgttctggat agtggttggt ttcgactcat tataatgtat gtctaacggc ttcaatcgcg 114900
cgttagaaat tgctttttta gtttctatat taataggaga tagttgttgc ggcatagtaa 114960
aaatgaaatg ataactgttt aaaaatagct cttagtatgg gaattacaat ggatgaggaa 115020
gtgatatttg aaactcctag agaattaata tctattaaac gaataaaaga tattccaaga 115080
tcaaaagaca cgcatgtgtt tgctgcgtgt ataacaagtg acggatatcc gttaatagga 115140
gctagaagaa cttcattcgc gttccaggcg atattatctc aacaaaattc agattctatc 115200
tttagagtat ccactaaact attacggttt atgtactaca atgaactaag agaaatcttt 115260
agacggttga gaaaaggttc tatcaacaat atcgatcctc actttgaaga gttaatatta 115320
ttgggtggta aactagataa aaaggaatct attaaagatt gtttaagaag agaattaaaa 115380
gaggaaagtg atgaacgtat aacagtaaaa gaatttggaa atgtaattct aaaacttaca 115440
acacgggata aattatttaa taaagtatat ataagttatt gcatggcgtg ttttattaat 115500
caatcgttgg aggatttatc gcatactagt atttacaatg tagaaattag aaagattaaa 115560
tcattaaatg attgtattaa cgacgataaa tacgaatatc tgtcttatat ttataatatg 115620
ctagttaata gtaaatgaac ttttacagat ctagtataat tagtcagatt attaagtata 115680
atagacgact agctaagtct attatttgcg aggatgactc tcaaattatc acactcacgg 115740
cattcgttaa ccaatgccta tggtgtcata aacgagtatc cgtgtccgct attttattaa 115800
ctactgataa caaaatatta gtatgtaaca gacgagatag ttttctctat tctgaaataa 115860
ttagaactag aaacatgttt agaaagaaac gattatttct gaattattcc aattatttga 115920
acaaacagga aagaagtata ctatcgtcat ttttttctct agatccagct actactgata 115980
atgatagaat agacgctatt tatccgggtg gcatacccaa aaggggtgag aatgttccag 116040
agtgtttatc cagggaaatt aaagaagaag ttaatataga caattctttt gtattcatag 116100
acactcggtt ttttattcat ggcatcatag aagataccat tattaataaa ttttttgagg 116160

-continued taatcttctt tgtcggaaga atatctctaa cgagtgatca aatcattgat acatttaaaa 116220
gtaatcatga aatcaaggat ctaatatttt tagatccgaa ttcaggtaat ggactccaat 116280
acgaaattgc aaaatatgct ctagatactg caaaacttaa atgttacggc catagaggat 116340
gttattacga atcattaaaa aaattaactg aggatgattg attagaaaat ataaattaat 116400
ttaccatcgt gtatttttat aacgggattg tccggcatat catgtagata gttaccgtct 116460
acatcgtata ctcgaccatc tacgccttta aatcctctat ttattgacat taatctatta 116520
gaattggaat accaaatatt agtaccctca attagtttat tggtaatatt ttttttagac 116580
gatagatcga tggctcttga aaccaaggtt ttccaaccgg actcattgtc gatcggtgag 116640
aagtcttttt cattagcatg aatccattct aatgatgtat gtttaaacac tctaaacaat 116700
tggacaaatt cttttgattt gctttgaatg atttcaaata ggtcttcgtc tacagtaggc 116760
ataccattag ataatctagc cattataaag tgcacgttta catatctacg ttctggagga 116820
gtaagaacgt gactattgag acgaatggct cttcctacta tctgacgaag agacgcctcg 116880
ttccatgtca tatctaaaat gaagatatca ttaattgaga aaaaactaat accctcgcct 116940
ccactagaag agaatacgca tgttttaatg cattctccgt tagtgtttga ttcttggtta 117000
aactcagcca ccgccttgat tctagtatct tttgttctag atgagaactc tatattagag 117060
ataccaaaga ctttgaaata tagtaataag atttctattc ctgactgatt aacaaatggt 117120
tcaaagacta gacatttacc atgggatgct aatattccca aacatacatc tataaatttg 117180
acgcttttct cttttaattc agtaaataga gagatatcag ccgcactagc atccccttc 117240 aatagttctc cctttttaaa ggtatctaat gcggatttag aaaactctct atctcttaat 117300
gaatttttaa aatcattata tagtgttgct atctcttgcg cgtattcgcc cggatcacga 117360
ttttgtcttt caggaaagct atcgaacgta aacgtagtag ccatacgtct cagaattcta 117420
aatgatgata tacctgtttt tatttcagcg agtttagcct tttgataaat ttcttcttgc 117480
tttttcgaca tattaacgta tcgcattaat actgttttct tagcgaatga tgcagaccct 117540
tctacgtcat caaaaataga aaactcgtta ttaactatgt acgaacatag gcctcctagt 117600
ttggagacta attctttttc atcgactaga cgtttattct caaatagcga ttggtgttgt 117660
aaggatcctg gtcgtagtaa gttaaccaac atggtgaatt cttgcacact attgacgata 117720
ggtgtagccg ataaacaaat catcttatgg tttttttaacg caatggtctt agataaaaaa 117780
ttatatactg aacgagtagg acggatctta ccatcttctt tgattaatga tttagaaatg 117840
aagttatgac attcatcaat gatgacgcat attctactct tggcattaat agttttgata 117900
ttagtaaaaa atttatttct aaaattttga tcatcgtaat taataaaaat acaatccttc 117960
gttatctctg gagcgtatct gagtatagtg ttcatccaag gatcttctat caaagccttt 118020
ttcaccaata agataatagc ccaattcgta taaatatcct taagatgttt gagaatatat 118080
acagtagtca ttgttttacc gacacccgtt tcatggaaca ataaaagaga atgcatactg 118140
tctaatccta agaaaactct tgctacaaaa tgttgataat ccttgaggcg tactacgtcc 118200
gaccccatca tttcaacggg catattagta gttctgcgca atgcataatc gatataggcc 118260
gcgtgtgatt tactcattta tgagtgataa gtaataacta tgttttaaaa atcacagcag 118320
tagtttaact agtcttctct gatgtttgtt ttcgatactt tttgaatcag aagtcatact 118380
agaataaagc aacgagtgaa cgtaatagag agcttcgtat actctattcg aaaactctaa 118440
gaacttatta atgaattccg tatccactgg attgtttaaa atactaaatt gaacactgtt 118500
cacatccttc caagaagaag acttagtgac ggacttaaca tgagacataa ataaatccaa 118560 attttttta caaacatcac tagccaccat aatggcgcta tctttcaacc agctatcgct 118620
tacgcatttt agcagtctaa catttttaaa gagactacaa tatattctca tagtatcgat 118680
tacacctcta ccgaatagag taggaagttt aataatacaa tatttttcgt ttacaaaatc 118740
aaataatggt cgaaacacgt cgaaggttaa catcttataa tcgctaatgt atagattgtt 118800
ttcagtgaga tgattattag atttaatagc atctcgttca cgtttgaaca gtttattgcg 118860
tgcgctgagg tcggcaacta cggcgtccgc tttagtactc ctcccataat actttacgct 118920
attaatcttt aaaatttcat agactttatc tagatcgctt tctggtaaca tgatatcatg 118980
tgtaaaaagt tttaacatgt cggtcggcat tctatttaga tcattaactc tagaaatctg 119040
aagaaagtaa ttagctccgt attccagact aggtaatggg cttttaccta gagacagatt 119100
aagttctggc aatgtttcat aaaatggaag aaggacatgc gttccctccc ggatattttt 119160
tacaatttca tccatttaca actctatagt ttgttttcat tattattagt tattatctcc 119220
cataatcttg gtaatactta ccccttgatc gtaagatacc ttatacaggt cattacatac 119280
aactaccaat tgtttttgta cataatagat tggatggttg acatccatgg tggaataaac 119340
tactcgaaca gatagtttat ctttccccct agatacatta gccgtaatag ttgtcggcct 119400
aaagaatatc tttggtgtaa agttaaaagt tagggttctt gttccattat tgctttttgt 119460
cagtagttca ttataaattc tcgagatggg tccgttctct gaatatagaa catcatttcc 119520
aaatctaact tctagtctag aaataatatc ggtcttattc ttaaaatcta ttcccttgat 119580
gaagggatcg ttaatgaaca aatccttggc ctttgattcg gctgatctat tatctccgtt 119640
atagacgtta cgttgactag tccaaagact tacaggaata gatgtatcga tgatgttgat 119700
actatgtgat atgtgagcaa agattgttct cttagtggca tcactatatg ttccagtaat 119760
ggcggaaaac tttttagaaa tgttatatat aaaagaattt tttcgtgttc caaacattag 119820
cagattagta tgaagataaa cactcatatt atcaggaaca ttatcaattt ttacatacac 119880
atcagcatct tgaatagaaa cgataccatc ttctggaacc tctacgatct cggcagactc 119940
cggataacca gtcggtggac catcgctaac aataactaga tcatccaaca atctactcac 120000
atatgcatct atataatctt tttcatcttg tgagtaccct ggatacgaaa taaatttatt 120060
atccgtattt ccataataag gtttagtata aacagagaga gatgttgccg catgaacttc 120120
agttacagtc gccgttggtt ggtttatttg acctattact ctcctaggtt tctctataaa 120180
cgatggttta atttgtacat tcttaaccat atatccaata aagctcaatt caggaacata 120240
aacaaattct ttgttgaacg tttcaaagtc gaacgaagag tcacgaataa cgatatcgga 120300
tactggattg aaggtcaccg ttacggtaat ttttgaatcg gatagtttaa gactgctgaa 120360
tgtatcttcc acatcaaacg gagttttaat ataaacgtat actgtagatg gttctttaat 120420
agtgtcatta ggagttaggc caatagaaat atcattaagt tcactagaat atccagagtg 120480
tttcaaagca attgtattat tgatacaatt attatataat tcttcgccct caatttccca 120540
aataacaccg ttacacgaag agatagatac gtgattaata catttatatc caacatatgg 120600
tacgtaaccg aatcttccca tacctttaac ttctggaagt tccaaactca gaaccaaatg 120660
attaagcgca gtaatatact gatccctaat ttcgaagcta gcgatagcct gattgtctgg 120720
accatcgttt gtcataactc cggatagaga aatatattgc ggcatatata aagttggaat 120780
ttgactatcg actgcgaaga cattagaccg tttaatagag tcatccccac cgatcaaaga 120840
attaatgata gtattattca ttttctattt aaaatggaaa aagcttacaa taaactccgt 120900
agagaaatat ctataatttg tgagttttcc ttaaagtaac agcttccgta aacgccgtct 120960
ttatctctta gtaagtttat tgtatttatg accttttcct tatcttcata gaatactaaa 121020
ggcaacaaag aaatttttgg ttcttctcta agagctacgt gagacttaac catagacgcc 121080
aacgaatccc tacatatttt agaacagaaa taccctactt caccaccctt gtatgtctca 121140
atactaatag gtctaaaaac caaatcttga ttacaaaacc aacacttatc aattacacta 121200
tttgtcttaa tagacacatc tgccatagat ttataatact ttggtagtat acaagcgagt 121260
gcttcttctt tagcgggctt aaagactgct ttaggtgctg aaataaccac atctggaagg 121320
cttactcgct tagccattta attacggaac tatttttta tacttctaat gagcaagtag 121380
aaaacctctc atctacaaaa acgtactcgt gtccataatc ctctaccata gtaacacgtt 121440
ttttagatct catatgtgct aaaaagtttt cccatactaa ttggttacta ttatttttcg 121500
tataattttt aacagtttga ggttttagat ttttagttac agaagtgata tcgaatattt 121560
tatccaaaaa gaatgaataa ttaattgtct tagaaggagt gttttcttgg caaaagaata 121620
ccaagtgctt aaatatttct actacttcat taatcttttc tgtactcaga ttcagtttct 121680
catcttttac ttgattgatt atttcaaaga ctaacttata atccttttta tttattctct 121740
cgttagcctt aagaaaacta gatacaaaat ttgcatctac atcatccgtg gatatttgat 121800 tttttccat gatatccaag agttccgaga taatttctcc agaacattga tgagacaata 121860
atctccgcaa tacatttctc aaatgaataa gtttattaga cacgtggaag tttgactttt 121920
tttgtacctt tgtacatttt tgaaataccg actcgcaaaa aatacaatat tcatatcctt 121980
gttcagatac tataccgttg tgtctacaac cgctacataa tcgtagattc atgttaacac 122040
tctacgtatc tcgtcgtcca atattttata taaaaacatt ttatttctag acgttgccag 122100
aaaatcctgt aatattttta gttttttggg ctgtgaataa agtatcgccc taatatggtt 122160
accgtcctcc gccaatatag tagttaaatt atccgcacat gcagaagaac accgcttagg 122220
cggattcagt acaatgttat atttttcgta ccaactcatt taaatatcat aatctaaaat 122280
agttctgtaa tatgtctagc gctaatatat tgatcataat cctgtgcata aattaagata 122340
caacaatgtc tcgaaatcat cgacatggct tcttccatag ttagaagatc gtcgtcaaag 122400
ttagcaacgt gattcatcaa catttgctgt tttgaggcag caaatactga accgtcgcca 122460
ttcaaccatt cataaaaacc atcgtctgaa tccattgata atttcttgta ctggtttttg 122520
agagctcgca tcaatctagc atttctagct cccggattga aaacagaaag aggatcgtac 122580
atccagggtc cattttctgt aaatagaatc gtataatgtc ccttcaagaa gatatcagac 122640
gatccacaat caaagaattg gtctccgagt ttgtaacaga cagcggactt taacctatac 122700
atgataccgt ttagcataat ttctggtgat acgtcaatcg gagtatcatc tattagagat 122760
ctaaagccgg tgtaacattc tccaccaaac atattcttat tctgacgtcg ttctacataa 122820
aacatcattg ctccattaac gataacaggg gaatgaacag cactacccat cacattagtt 122880
cccaatggat caatgtgtgt aactccagaa catcttccat agcctatgtt aggaggagcg 122940
aacaccactc ttccactatt gccatcgaat gccatagaat aaatatcctt ggaattgata 123000
gaaatcggac tgtcggatgt tgtgatcatc ttcataggat taacaactat gtatggtgcc 123060
gcctgaagtt tcatatcgta actgatgccg tttataggtc tagccacaga aaccaacgta 123120
ggtctaaatc caactataga caaaatagaa gccaatatct gttcctcatc tgtcataact 123180
tgagagcatc cagtatgaat aatcttcatt agatggggat ctaccgcatc atcatcgtta 123240
caataaaaaa ttcccattct aatgttcata attgcttttc taatcatggt atgcatgttt 123300
gctctctgaa tctctgtgga aattagatct gatacacctg taatcactat cggattatcc 123360
tccgtaagac gattaaccaa caacatataa ttataagact ttacttttct aaattcataa 123420
agttgctgga ttaggctata ggtgtctcca tgtacatacg cgttctcgag cgcaggaagt 123480
ttaataccga atagtgccat cagaatagga tgaatatagt aattagtttc tggttttcta 123540
taaataaaag acaaatcttg tgaactagac atatcggtaa aatgcatgga ttggaatcgt 123600
gtagtcgaca gaagaatatg atgattagat ggagagtata ttttatctaa ctctttgagt 123660
tggtcaccga ttctaggact agctcgagaa tgaataagta ctaaaggatg agtacatttc 123720
acagaaacac tagcattgtt caatgtgctc tttacatggg taaggagttg aaatagctcg 123780
tttctatttg ttctgacaat atttagttta ttcataatgt taagcatatc ctgaatagta 123840
aagttagatg tgtcatactt gttagtagtt agatatttag caattgcatt cccatcattt 123900
ctcaatctcg tactccaatc atgcgtggat gctacttcgt cgatggaaac catacaatcc 123960
tttttggtag tctgttgagc ttgatcattt cctgcacgtt taggtttggt acgttgattt 124020
ctagcccctg cggatataaa gtcatcgtct acaatttggg acaatgaatt gcatacacta 124080
caagacaaag atttatcaga agtgtgaata tgatcttcat ctaccaaaga aagagtttga 124140
ttagtataac tagattttag tcctgcgtta gatgttaaaa aaacatcgct attgaccacg 124200
gcttccatta tttatattcg tagtttttac tcgaaagcgt gattttaata tccaatctta 124260
ttacttttgg aatcgttcaa aacctttgac taattgtaga atttgattta ttgccctacg 124320
cgtatactcc cttgcatcat atacgttcgt caccagatcg tttgtttcgg cctgaagttg 124380
gtgcatatct ctttcaacat tcgacatgag atccttaagg gccatatcgt ctagattttg 124440
ttgagatgct gctcctggat ttggattttg ttgtgctgtt gtacatactg taccaccagt 124500
aggtgtagga gtacatacag tggccacaat aggaggttga ggaggtgtaa ccgttggagt 124560
agtacaagaa atatttccat ccgattgttg tgtacatgta gttgttggta acgtctgaga 124620
aggttgggta gatggcggtg tcgtcgtctt ttgatcttta ttaaatttag agataatatc 124680
ctgaacagca ttgctcggcg tcaacgctgg aaggagtgaa ctcgccggcg catcagtatc 124740
ttcagacagc caatcaaaaa gattagacat atcagatgat gtattagttt gttgtcgtgg 124800
ttttggtgta ggagcagtac tactaggtag aagaatagga gccggtgtag ctgttggaac 124860
cggctgtgga gttatatgaa tagttggttg tagcggttgg ataggctgtc tgctggcggc 124920
catcatatta tctctagcta gttgttctcg caactgtctt tgataatacg actcttgaga 124980
ctttagtcct atttcaatcg cttcatcctt tttcgtatcc ggatcctttt cttcagaata 125040
atagattgac gactttggtg tagaggattc tgccagcctc tgtgagaact tgttaaagaa 125100
gtccatttaa ggctttaaaa ttgaattgcg attataagat taaatggcag acacagacga 125160
tattatcgac tatgaatccg atgatctcac cgaatacgag gatgatgaag aagaggaaga 125220
agatggagag tcactagaaa ctagtgatat agatcccaaa tcttcttata agattgtaga 125280
atcagcatcc actcatatag aagatgcgca ttccaatctt aaacatatag ggaatcatat 125340
atctgctctt aaacgacgct atactagacg tataagtcta tttgaaatag cgggtataat 125400
agcagaaagc tataacttgc ttcaacgagg aagattacct ctagtttcag aattttctga 125460
cgaaacgatg aagcaaaata tgctacatgt aattatacaa gagatagagg agggttcttg 125520
tcctatagtc atcgaaaaga acggagaatt gttgtcggta aacgattttg acaaagatgg 125580
tctaaaattc catctagact atattatcaa aatttggaaa cttcaaaaac gatattagaa 125640

-continued tttatacgaa tatcgttctc taaatgtcac aatcaagtct cgcatgttca gcaatttatt 125700
gtcgtacttt atatcgtgtt cattaacgat atcttgcaaa atagtaatga ttctatcttc 125760
cttcgataga tattcttcag agattattgt cttatattct ttcttgttat ccgatatgaa 125820
tttgataaga ctttgaacat tattgatacc cgtctgttta attttttcta cagatatttt 125880
agttttggca gattctatcg tatctgtcaa tagacatcca acatcgacat tcgacgtcaa 125940
ttgtctataa atcagagtat aaattttaga aataacatta gcgaattgtt gtgcgttgat 126000
gtcgttattc tgaaacagta tgattttagg tagcattttc ttaacaaaga gaacgtattt 126060
attgttactc agttgaacag atgatatatc cagattacta acgcatctga ttccgtatac 126120
caaactttca gaagaaatgg tgtacaattg tttgtattca ttcaatgtct ctttttcaga 126180
aattagttta gagtcgaata ctgcaataat tttcaagaga tagttttcat cagataagat 126240
tttatttagt gtagatatga taaaactatt gttttgttgg agaacttgat acgccgcgtt 126300
ctctgtagtc gacgctctca aatgggaaac gatctccatt atttttttgg aatcggatac 126360
aatatcttcg gtatcttgac gcagtctagt atacatagag ttaagagaga ttagagtttg 126420
tacattaagc aacatgtctc taaatgtggc tacaaacttt tccttttca catcatctag 126480
tttattatat accgatttca caacggcacc agatttaagg aaccagaatg aaaaactctg 126540
ataactacaa tatttcatca tagttacgat tttatcatct tctatagttg gtgtaatagc 126600
gcatacettt ttctccaaga ctggaaccaa cgtcataaaa atgtttaaat caaaatccat 126660
atcaacatct gatgcgctaa gaccagtctc gcgttcaaga ttatctttac taatggtgac 126720
gaactcatcg tatagaactc taagtttgtc cattatttat ttacagattt agttgtttaa 126780
tttatttgtg ctcttccaga gttgggatag tatttttcta acgtcggtat tatattatta 126840
ggatctacgt tcatatgtat cataatatta atcatccacg ttttgataaa tctatcttta 126900
gcttctgaaa taacgtattt aaacaaagga gaaaaatatt tagctacggc atcagacgca 126960
ataacatttt ttgtaaatgt aacgtattta gacgacagat cttcgttaaa aagttttcca 127020
tctatgtaga atccatcggt tgttaacacc attcccgcgt cagattgaat aggagtttga 127080
atagtttgtt ttggaaatag atccttcaat aacttatagt tgggtgggaa aaaatcgatt 127140
ttatcactag actctttctt ttttactatc attacctcat gaactatttc ttgaatgagt 127200
atatgtattt tctttcctat atcggacgcg ttcattggaa aatataccat gtcgttaact 127260
ataagaatat ttttatcctc gtttacaaac tgaataatat cagatgtagt tcgtaaacga 127320
actatatcat caccagcaca acatctaact atatgatatc cactagtttc ctttagtcgt 127380
ttattatctt gttccatatt agcagtcatt ccatcattta agaaggcgtc aaaaataata 127440
gggagaaatg acattttgga ttctgttaca actttaccaa aattaaggat atacggactt 127500
actatctttt tctcaacgtc aatttgatga acacacgatg aaaatgtact tcgatgagat 127560
tgatcatgta gaaaacaaca agggatacaa tatttccgca tatcatgaaa tatattaaga 127620
aatcccacct tattatattt ccccaaagga tccatgcatg taaacattat gccgttatca 127680
ttaataaaga cttctttctc atcggatctg taaaagttgt tactgatttt tttcattcca 127740
ggatctagat aattaataat gatgggtttt ctattcttat tctttgtatt ttggcatatc 127800
ctagaccagt aaacagtttc cactttggta aaatcagcag acttttgaac gctattaaac 127860
atggcattaa tggcaataac taaaaatgta aaatattttt ctatgttagg aatatggttt 127920
ttcactttaa tagatatatg gtttttggcc aaaatgatag atattttttt atccgaggat 127980
agtaaaatat tattagtcgc cgtctctata aaaatgaagc tagtctcgat atccaatttt 128040
attctagaat tgataggagt cgccaaatgt accttatacg ttatatctcc cttgatgcgt 128100
tccatttgtg tatctatatc ggacacaaga tctgtaaata gttttacgtt attaatcatc 128160
acggtatcgc cgtcgctaga taacgctaat gtaccatcca agtcccaaat ggagagattt 128220
aactgttcat cgtttagaat aaaatgatta ccggtcatat taataaagtg ttcatcgtat 128280
ctagataaca acgacttata attaatgtcc aagtcttgaa ctcgctgaat gatctttttt 128340
aacccagtta gttttagatt ggtacgaaat atattgttaa actttgattc tacagtaatg 128400
tccaaatcta gttgtggaaa tacttccatc aacattgttt caaacttgat aatattatta 128460
tctacatctt cgtacgatcc aaattccgga atagatgtat cgcacgctct ggccacccag 128520
ataaccaaaa agtcacacgc tccaggatat acattgtata aaaagctatc gttttttagt 128580
agggtttttt tctgcgtgta tacgaaggga ttaaaaatag tattatcaac gtaactatat 128640
tccaaattat tcttatgaga atagataata atatcgtcct taatatctaa caaatttcct 128700
aaatatccct ttaattgagt cattcgaagc gtcaatagaa tatgtctctt aactatttcc 128760
ggctgttgta tatttaaatg acttcgtaaa aaataatata tgggcgactt ctcatctatg 128820
taatcatatg gagtgagata tagggctcgt tctacctcct gccccttacc cacctgtaat 128880
accaattgcg gacttactat atatcgcata tttatatcgt ggggtaaagt gaaaatctac 128940
taccgatgat gtaagtctta caatgttcga accagtacca gatcttaatt tggaggcctc 129000
cgtagaacta ggggaggtaa atatagatca aacaacacct atgataaagg agaatagcgg 129060
ttttatatcc cgtagtagac gtctattcgc ccatagatct aaggatgatg agagaaaact 129120
agcactacga ttctttttac aaagacttta tttttagat catagagaga ttcattattt 129180
gttcagatgc gttgacgctg taaaagacgt cactattacc aaaaaaaata acattatcgt 129240
ggcgccttat atagcacttt taactatcgc atcaaaagga tgcaaactta cagaaacaat 129300
gattgaagca ttctttccag aactatataa tgaacatagt aagaaattta aattcaactc 129360
tcaagtatcc atcatccaag aaaaactcgg ataccagttt ggaaactatc acgtttatga 129420
ttttgaaccg tattactcta cagtagctct ggctattcga gatgaacatt catctggcat 129480
ttttaatatc cgtcaagaga gttatctggt aagttcatta tctgaaataa catatagatt 129540
ttatctaatt aatctaaaat ctgatcttgt tcaatggagt gctagtacgg gcgctgtaat 129600
taatcaaatg gtaaatactg tattgattac agtgtatgaa aagttacaac tggtcataga 129660
aaatgattca caatttacat gttcattggc tgtggaatca aaacttccaa taaaattact 129720
taaagataga aatgaattat ttacaaaatt cattaacgag ttaaaaaaga ccagttcatt 129780
caagataagc aaacgcgata aggatacgct actaaaatat tttacttagg actggagtta 129840
gaatttatag acgactcatt tcgtttatca ttgttactat tattactatt actatcatta 129900
ttagtgttgg cattattagt attcttcttg tcatcttgtt cagaaatata cagcaatgct 129960
atacctaata ctaaatacat tatcatgctc gcaatggctc taacaacaac gaaccaaaat 130020
gaatttggtc gtagcttttg ttcacaaaaa tacataaaga aatgtctaca taaatctatg 130080
gcgccattgg ctacttgaaa tagcgccagt cctcctacag attttaatat agctgtataa 130140
catgacattt attcatcatc aaaagagaca gagtcaccat ctgtcatatt tagatttttt 130200
ttcatgtgtt caaagtatcc tctactcatt tcattataat agtttatcat acttagaatt 130260
ttaggacgga tcaatgagta agacttgact agatcgtcag tagtaatttg tgcatcgtct 130320
attctgcatc cgcttcgtcg aataatgtat agcatcgctt tgagattctc catagctatc 130380

-continued aagtctttat acaatgacat ggaaatatct gtgaatactt tatacttctc caacatcgat 130440
gccttaacat catcgcctac tttagcattg aaaatacgtt ctattgtgta gatggatgta 130500
gcaagatttt taaacaacaa tgccatctta cacgatgatt gcctcaagtc tccaatcgtt 130560
tgtttagaac gattagctac agagtccaat gcttggctga ctagcatatt attatcttta 130620
gaaattgtat tcttcaatga ggcgtttatc atatctgtga tttcgttagt catattacag 130680
tctgactggg ttgtaatgtt atccaacata tcacctatgg atacggtaca cgtaccagca 130740
tttgtaataa tcctatctaa gatgttgtat ggcattgcgc agaaaatatc ttctcctgta 130800
atatctccac tctcgataaa tctactcaga ttattcttaa atgccttatt ctctggagaa 130860
aagatatcag tgtccatcat ttcattaata gtatacgcag aaaagatacc acgagtatca 130920
attctatcca agatacttat cggttccgag tcacagataa tggtttcctc tccttcggga 130980
gatcctgcat agaaatatct aggacaatag tttctatact gtctgtaact ctgataatct 131040
ctaaagtcac taactgatac catgaaattg agaagatcaa acgctgaagt aattaatttt 131100
tctgcctcgt ttttactaca actagttttc atcaatgtag tgacgatgta ttgtttagtt 131160
acttttggtc taatactgat gatagagata ttattgcttc ccataatgga tcttctagta 131220
gtcaccttaa agcccattga tgcgaatagc agatagataa agtcttggta tgactccttt 131280
ctaatatagt acggactacc tttgtcaccc aactttatac ccacataagc cataacaacc 131340
tctttaatag ccgtttcatg aggtttatca gccatgagcc tgagtagttg gaagaatctc 131400
atgaatcccg tctcagaaag tcctatatgc atgatagatt tatctttcct gggaaactct 131460
cgtatagtca tagatgaaat actcttcaaa gtttctgaaa taagattagt aacagtctta 131520
cctccgacta ctctaggtaa caaacaaact ctaataggtg ttttctctgc ggagataata 131580
tcagaaagga tagagcaata agtagtatta ttgtgattat aaagaccgaa tacataacag 131640
gtagaattta taaacatcat gtcctgaagg tttttagact tgtattcctc gtaatccata 131700
ccgtcccaaa acatggattt ggtaactttg atagccgtag atctttgttc cttcgccaac 131760
aggttaaaga aattaataaa gaatttgttg tttctattta tgtccacaaa ttgcacgttt 131820
ggaagcgcca cggttacatt cactgcagca ttttgaggat cgcgagtatg aagtacgatg 131880
ttattgttta ctggtatatc tggaaagaaa tctaccagtc taggaataag agattgatat 131940
cgcatagaaa tagtaaagtt tataatctca tcatcgaaga gcattttgtt accattgtaa 132000
taaatatcca ctctgtcata tgtataaatg aagtactgtt caaacatgat gagatgttta 132060
tatgttggca tagtagtgag atcgacgttt ggtaatggca atgtattaag attaactcca 132120
taatgtctag cagcatctgc gatgttataa gcgtcgtcaa agcggggtcg atcttgtatt 132180
gttatatatt gtctaacacc tataagatta tcaaaatctt gtctgcttaa tacaccgtta 132240
acaatttttg ccttgaattc ttttattggt gcattaataa catccttata gaggatgtta 132300
aacaaataag tgttatcaaa gttaagatct ggatatttct tttctgctag aacatccatt 132360
gagtcggagc catctggttt aatataacca ccgataaatc tagctctgta ttctgtatcc 132420
gtcaatctaa tattaagaag gtgttgagtg aaaggtggaa gatcgtaaaa gctgtgagta 132480
ttaatgatag gattagtttc cgaactaatg ttaattgggg tattaataat atctatattt 132540
ccagcgttaa gtgtaacatt aaacagtttt aattcacgtg acgtggtatc aattaaataa 132600
ttaatgccca atttggatat agcagcctga agctcatctt gtttagttac ggatcctaat 132660
gagttattaa gcaatatatc gaacggatga acgaaggttg ttttgagttt gtcgcatact 132720
ttgtaatcta gacatagatg cggaagaacg gtagaaacta tacgaaataa atattcagag 132780

```
tcctctaatt gatcaagagt aactattgac ttaataggca tcatttattt agtattaaat 132840
gacgaccgta ccagtgacgg atatacaaaa cgatttaatt acagagtttt cagaagataa 132900
ttatccatct aacaaaaatt atgaaataac tcttcgtcaa atgtctattc taactcacgt 132960
taacaacgtg gtagatagag aacataatgc cgccgtagtg tcatctccag aggaaatatc 133020
ctcacaactt aatgaagatc tatttccaga tgatgattca ccggccacta ttatcgaacg 133080
agtacaacct catactacta ttattgacga tactccacct cctacgtttc gtagagagtt 133140
attaatatcg gaacaacgtc aacaacgaga aaaaagattt aatattacag tatcgaaaaa 133200
tgctgaagca ataatggaat ctagatctat aataacttct atgccaacac aaacaccatc 133260
cttgggagta gtttatgata aagataaaag aattcagatg ttagaggatg aagtggttaa 133320
tcttagaaat caacgatcta atacaaaatc atctgataat ttagataatt ttaccaaaat 133380
actatttggt aagactccgt ataaatcaac agaagttaat aagcgtatag ccatcgttaa 133440
ttatgcaaat ttgaacgggt ccccccttatc agtcgaggac ttggatgttt gttcggagga 133500
tgaaatagat agaatctata aaacgattaa acaatatcac gaaagtagaa aacgaaaaat 133560
tatcgtcact aacgtgatta ttattgtcat aaacattatc gagcaggcat tgctaaaact 133620
cggatttgaa gaaatcaaag gactgagtac cgatatcact tcagaaatta tcgatgtgga 133680
gatcggagat gactgcgatg ctgtagcatc aaaactagga atcggtaaca gtccggttct 133740
taatattgta ttgtttatac tcaagatatt cgttaaacga attaaaatta tttaatttaa 133800
tacattccca tatccagaca acaatcgtct ggattaatct gttcctgtcg tctcataccg 133860
gacgacatat taatcttttt attagtgggc atctttttag atggtttctt tttcccagca 133920
ttaactgatt cgatacctag aagatcgtga ttgatctctc cgaccattcc acgaacttct 133980
aattggccgt ctctgacggt accataaact attttaccag cattagtaac agcttggaca 134040
atctgaccat ccatcgcatt gtacgatgta gtagtaactg ttgttctacg tctaggagca 134100
ccagaagtat ttttggagcc cttggaggct gatgtagaag aagacgagga ttttgatttt 134160
ggtttacatg taatacattt tgaactcttt gattttgtat cacatgcgcc ggcagtcaca 134220
tctgtttgag aattaagatt attgttgcct cctttgacgg ctgcatctcc accgatttgc 134280
gctagtagat ttttaagctg tggtgtaatc ttattaactg tttcgatata atcatcgtaa 134340
ctgcttctaa cggctaaatt ttttttatcc gccatttaga agctaaaaat atttttattt 134400
atgcagaaga tttaactaga ttatacaatg aactaatatg atccttttcc agattattta 134460
caaacttggt attttttggt tctggaggag gcgaatttaa attcggactt ggattcggat 134520
tttgtaagtt cttgatctta ttatacatcg agtataggat ggcgacagta actgctacac 134580
aaataccgat caaaagaaga ataccaatca tttattgaca ataacttcac tattgatcaa 134640
gtatgcaata tatcatcttt tcactaaata agtagtaata atgattcaac aatgtcgaga 134700
tatatggacg ataataattt agttcatgga aatatcgcta tgattggtgt gaatgactcc 134760
gctaactctg tggggtgcgc agtgctttcc ccacatagaa taaattagca ttccgactgt 134820
gataataata ccaagtataa acgccataat actcaatact ttccatgtac gagtgggact 134880
agtagactta ctaaagtcaa taaaggcgaa gatacacgaa agaatcaaaa gaatgattcc 134940
agcgattagc acgccggaaa aataatttcc aatcataagc atcatgtcca tttaactaat 135000
aaaaatttta aatcgccgaa tgaacaaagt ggaatataaa ccatataaaa acaatagttt 135060
gtactgcaaa aataatatct atttttgttt tcgaagatat ggtaaaatta aatagtagta 135120
```

-continued

```
cacagcatgt tataactaac agcagcaacg gctcgtaatt acttatcatt tactagacga 135180
aaaggtggtg ggatattttc ttgctcaaat aatacgaata tatcacccat ccattttatg 135240
cgatgtttat atactctaat ctttaataga tctatagacg acgggtttac caacaatata 135300
gattttatcg attcatctaa tttaaaccct tccttaaacg tgaatgatct attatctggc 135360
ataacgatga ccctacctga tgaatcggac aatgtactgg gccatgtaga ataaattatc 135420
aacgaattat cgtctacgaa catttatatc atttgtttta attttaggac gcgaataaat 135480
ggatataaaa tagaaaataa cagatattac aaccagtgtt atggccgcgc ccaaccaggt 135540
aggcagtttt attttatctt ttactacagg ttctcctgga tgtacgtcac caacggcgga 135600
cgtagttcta gtacaattag acgtaagttc cgcttgggaa tttttaacg ctaaagagtt 135660
aacgttaatc gtgcacccaa cgtatttaca tctagttctt tgaacatctt gattataata 135720
taaccatttt ctatctctag attcgtcagt gcactcatgt aaccaacata ccctaggtcc 135780
taaatattta tctccggaat tagattttgg ataattcgcg caccaacaat ttctatttcc 135840
tttatgatcg ttacaaaaga cgtataatgc cgtatcccca aaagtaaaat aatcaggacg 135900
aataattcta ataaactcag aacaatatct cgcatccata tgtttggagc aaatatcgga 135960
ataagtagac atagccggtt tccgttttgc acgtaaccat tctaaacaat tggggtttcc 136020
aggatcgttt ctacaaaatc cagtcatgaa atcatcacaa tgttctgtct tgtaattatt 136080
attaaatatt tttggacagt gtttggtatt tgtcttagaa caacattttg ccacgctatc 136140
actatcgccc aggagataat cctttttttat aaaatgacat cgttgcccgg atgctatata 136200
atcagtggcg tgttttaaat ccttaatata ttcaggagtt acctcgttct gataatagat 136260
taatgatcca ggacgaaatt tgaaagaact acatggttct ccatgaatta atacatattg 136320
tttagcaaat tcaggaacta taaaactact acaatgatct atcgacatac catctatcaa 136380
acaaaacttg ggtttaattt ctcccggaga tgtttcataa tagtacgtat aactttcttc 136440
tgcaaactta acagctctat tatattcagg ataattaaaa cctaattcca tatatttgtc 136500
tcgtatatct gctattcctg gtgctatttt gattctatta agagtaacag ctgcccccat 136560
tcttaataat cgtcagtatt taaactgtta aatgttggta tatcaacatc taccttattt 136620
cccgcagtat aaggtttgtt gcaggtatac tgttcaggaa tggttacatt tatacttctt 136680
ctatagtcct gtctttcgat gttcatcaca tatgcaaaga acagaataaa caaaataatg 136740
taagaaataa tattaaatat ctgtgaattc gtaaatacat tgattgccat aataattaca 136800
gcagctacaa tacacacaat agacattccc acagtgttgc cattacctcc acgatacatt 136860
tgagttacta agcaataggt aataactaag ctagtaagag gcaatagaaa agatgagata 136920
aatatcatca atatagagat tagaggaggg ctatatagag ccaagacgaa caaaatcaaa 136980
ccgagtaacg ttctaacatc attatttttg aagattccca aataatcatt cattcctcca 137040
taatcgtttt gcatcatacc tccatcttta ggcataaacg attgctgctg ttcctctgta 137100
aataaatctt tatcaagcac tccagcaccc gcagagaagt cgtcaagcat attgtaatat 137160
cttaaataac tcatttatat attaaaaaat gtcactatta aagatggagt ataatcttta 137220
tgccgaacta aaaaaaatga cttgtggtca acccctaagt ctttttaacg aagacgggga 137280
tttcgtagaa gttgaaccgg gatcatcctt taagtttctg atacctaagg gatttacgc 137340
ctctccttcc gtaaagacga gtctagtatt cgagacatta acaacgaccg ataataaaat 137400
cactagtatc aatccaacaa atgcgccaaa gttatatcct cttcaacgca aagtcgtatc 137460
tgaagtagtt tctaatatga ggaaaatgat cgaatcaaaa cgtcctctat acattactct 137520
```

```
tcacttggcg tgtggatttg gtaagactat taccacgtgt tatcttatgg ctacacacgg 137580
tagaaaaacc gtcatttgcg tacccaataa aatgttaata catcaatgga agacacaggt 137640
agaggcagtc ggattggaac ataagatatc catagatgga gtaagtagtc tattaaagga 137700
actaaagact caaagtccgg atgtattaat agtagtcagt agacatctga caaacgatgc 137760
cttttgtaaa tatatcaata agcattatga tttgttcatc ttggatgaat cacatacgta 137820
taatctgatg aacaatacag cagttacaag atttttagcg tattatcctc cgatgatgtg 137880
ttatttttta actgctacac ctagaccagc taacagaatt tattgtaaca gtattattaa 137940
tattgccaag ttatccgatc taaaaaaaac tatctatgcg gtagatagtt tttttgagcc 138000
atattccaca gacaatatta gacatatgat aaaacgatta gatggaccat ctaataaata 138060
tcatatatat actgagaagt tattatctgt agacgagcct agaaatcaac ttattcttga 138120
taccctggta gaagaattca agtcaggaac tattaatcgc attttagtta ttactaaact 138180
acgtgaacat atggtattat tctacaaacg attattagat cttttcggac cagaggttgt 138240
atttatagga gacgcccaaa atagacgtac tccagatatg gtcaaatcaa tcaaggaact 138300
aaatagattt atattcgtat ccaccttatt ttattccggt actggtttag atattcctag 138360
tttggattcg ttgttcattt gctcggcagt aatcaacaat atgcaaatag agcaattact 138420
agggagggta tgtcgagaaa cagaactatt agataggacg gtatatgtat ttcctaacac 138480
atccatcaaa gaaataaagt acatgatagg aaatttcatg caacgaatta ttagtctgtc 138540
tgtagataaa ctaggattta aacaaaaaag ttatcggaaa catcaagaat ccgatcccac 138600
ttttgtatgt acaacatcct ccagagaaga acgtgtatta aatagaatat ttaactcgca 138660
aaatcgttaa gaagtttaag cgacgatccg catgctgcac aggccagtgt attacccctc 138720
atagtattaa tataatccaa tgatactttt gtgatgtcgg aaatcttaac caatttagac 138780
tgacaggcag aacacgtcat gcaatcatca tcgtcatcga taactgtagt cttgggcttc 138840
tttttgcggc tcttcattcc ggaacgcaca ttggtgctat ccatttaggt agtaaaaaat 138900
aagtcagaat atgccctata acacgatcgt gcaaaacctg gtatatcgtc tctatcttta 138960
tcacaatata gtgtatcaac atctttatta ttattgacct cgtttatctt ggaacatgga 139020
atgggaacat ttttgttatc aacggccacc tttgccttaa ttccagatgt tgtaaaatta 139080
taactaaaca gtctatcatc gacacaaatg aaattcttgt ttagacgttt gtagtttacg 139140
tatgcggctc gttcgcgtct catttttca gatattgcag gtactataat attaaaaata 139200
agaatgaaat aacataggat taaaaataaa gttatcatga cttctagcgc tgatttaact 139260
aacttaaaag aattacttag tctgtacaaa agtttgagat tttcagattc tgcggctata 139320
gaaaagtata attctttggt agaatgggga acatctactt actggaaaat aggcgtgcaa 139380
aaggtagcta atgtcgagac gtcaatatct gattattatg atgaggtaaa aaataaaccg 139440
tttaatattg atccgggcta ttacattttc ttaccggtat attttgggag cgtctttatt 139500
tattcgaagg gtaaaaatat ggtagaactt ggatctggaa actcttttca aataccagat 139560
gatatgcgaa gtgcgtgtaa caaagtatta gacagcgata acggaataga ctttctgaga 139620
tttgttttgt taaacaatag atggataatg gaagatgcta tatcaaaata tcagtctcca 139680
gttaatatat ttaaactagc tagtgagtac ggattaaaca tacccaaata tttagaaatt 139740
gaaatagagg aagacacatt atttgacgac gagttatact ctattataga acgctctttc 139800
gatgataaat ttccaaaaat atccatatcg tatattaagt tgggagaact tagacggcaa 139860
```

gttgtagact ttttcaaatt ctcattcatg tatattgagt ccatcaaggt agatcgtata 139920
ggagataata tttttattcc tagcgttata acaaaatcag gaaaaaagat attagtaaaa 139980
gatgtagacc atttaatacg atctaaggtt agagaacata catttgtaaa agtaaaaaag 140040
aaaaacacat tttccatttt atacgactat gatggaaacg gaacagaaac tagaggagaa 140100
gtaataaaac gaattataga cactatagga cgagactatt atgttaacgg aaagtatttc 140160
tctaaggttg gtagtgcagg cttaaagcaa ttgactaata aattagatat taatgagtgc 140220
gcaactgtcg atgagttagt tgatgagatt aataaatccg gaactgtaaa acgaaaaata 140280
aaaaaccaat cagcatttga tttaagcaga gaatgtttgg gatatccaga agcggatttt 140340
ataacgttag ttaataacat gcggttcaaa atagaaaatt gtaaggttgt aaatttcaat 140400
attgaaaata ctaattgttt aaataacccg agtattgaaa ctatatatgg aaactttaac 140460
cagttcgtct caatctttaa tgtcgtcacc gatgtcaaaa aaagattatt cgagtgaaat 140520
aatatgcgcc tttgatatag gtgcaaaaaa tcctgccaga actgttttag aagtcaagga 140580
taactccgtt agggtattgg atatatcaaa attagactgg agttctgatt gggaaaggcg 140640
catagctaaa gatttgtcac aatatgaata cactacagtt cttctagaac gtcagcctag 140700
aaggtcgccg tatgttaaat ttatctattt tattaaaggc tttttatatc atacatcggc 140760
tgccaaagtt atttgcgtct cgcctgtcat gtctggtaat tcatatagag atcgaaaaaa 140820
gagatcggtc gaagcatttc ttgattggat ggacacattc ggattgcgag actccgttcc 140880
ggatagacgc aaattagacg atgtagcgga tagtttcaat ttggctatga gatacgtatt 140940
agataaatgg aatactaatt atacacctta taataggtgt aaatctagaa attacataaa 141000
aaaaatgtaa taacgttagt aacgccatta tggataatct atttaccttt ctacatgaaa 141060
tagaagatag atatgccaga actattttta actttcatct aataagttgc gatgaaatag 141120
gagatatata tggtcttatg aaagaacgca tttcctcaga ggatatgttt gataatatag 141180
tgtataataa agatatacat cctgccatta agaaactagt gtattgcgac atccaactta 141240
ctaaacacat tattaatcag aatacgtatc cggtatttaa cgattcttca caagtgaaat 141300
gttgtcatta tttcgacata aactcagata atagcaatat tagctctcgt acagtagaga 141360
tatttgagag ggaaaagtca tctcttgtat catatattaa aactaccaat aagaagagaa 141420
aggtcaatta cggcgaaata aagaaaactg ttcatggagg cactaatgca aattactttt 141480
ccggtaaaaa gtctgacgag tatctgagta ctacagttag atccaacatt aatcaacctt 141540
ggatcaaaac catttctaag agaatgagag tagatatcat taatcactct atagtaacgc 141600
gtggaaaaag ctctatatta caaactatag aaattatttt tactaataga acatgtgtga 141660
aaatattcaa ggattctact atgcacatta ttctatccaa ggacaaggat gaaaaggggt 141720
gtatacacat gattgacaaa ttattctatg tctattataa tttatttctg ttgttcgaag 141780
atatcatcca aaacgagtac tttaaagaag tagctaatgt tgtaaaccac gtactcacgg 141840
ctacggcatt agatgagaaa ttattcctaa ttaagaaaat ggctgaacac gatgtttatg 141900
gagttagcaa tttcaaaata gggatgttta acctgacatt tattaagtcg ttggatcata 141960
ccgttttccc ctctctgtta gatgaggata gcaaaataaa gtttttttaag gggaaaaagc 142020 tcaatattgt agcattacga tctctggagg attgtataaa ttacgtgact aaatccgaga 142080
atatgataga aatgatgaag gaaagatcga ctattttaaa tagcatagat atagaaacgg 142140
aatcggtaga tcgtctaaaa gaattgcttc taaaatgaaa aaaaacactg attcagaaat 142200
ggatcaacga ctcggatata agtttttggt gcctgatcct aaagccggag tttttatag 142260 accgttacat ttccaatatg tatcgtattc taattttata ttgcatcgat tgcatgaaat 142320
cttgaccgtc aagcggccac tcttatcgtt taagaataat acagaacgaa ttatgataga 142380
aattagcaat gttaaagtga ctcctccaga ttactcacct ataatcgcga gtattaaagg 142440
taagagttat gacgcattag ccacgttcac tgtaaatatc tttaaagagg taatgaccaa 142500
agagggtata tccatcacta aaataagtag ttatgaggga aaagattctc atttgataaa 142560
aattccgcta ctaataggat acgggaataa aaatccactt gatacagcca agtatcttgt 142620
tcctaatgtc ataggtggag tctttatcaa taaacaatct gtcgaaaaag taggaattaa 142680
tctagtagaa aagattacaa catggccaaa atttagggtt gttaagccaa actcattcac 142740
tttctcgttt tcctccgtat cccctcctaa tgtattaccg acaagatatc gccattacaa 142800
gatatctctg gatatatcac aattggaagc gttgaatata tcatcgacaa agacatttat 142860
aacggtcaat attgttttgc tgtctcaata tttatctaga gtgagtctag aattcattag 142920
acgtagttta tcatacgata tgcctccaga agttgtctat ctagtaaacg cgataataga 142980
tagtgctaaa cgaattactg aatctattac tgactttaat attgatacat acattaatga 143040
cctggtggaa gctgaacaca ttaaacaaaa atctcagtta acgatcaacg agttcaaata 143100
tgaaatgctg cataactttt tacctcatat gaactataca cccgatcaac taaagggatt 143160
ttatatgata tctttactaa gaaagtttct ctactgtatc ttccacactt ctagatatcc 143220
agatagagat tcgatggttt gtcatcgcat cctaacgtac ggcaaatatt ttgagacgtt 143280
ggcacatgat gaattagaga attacatagg caacatccga aacgatatca tgaacaatca 143340
caagaacaga ggcacttacg cggtaaacat tcatgtacta acaactcccg gacttaatca 143400
tgcattttct agtctattga gtggaaagtt caaaaagtca gacggtagtt atcgaacaca 143460
tcctcactat tcatggatgc agaatatttc tattcctagg agtgttggat tttatccgga 143520
tcaagtaaag atttcaaaga tgttttctgt cagaaaatac catccaagtc aatatcttta 143580
cttttgttca tcagacgttc cggaaagagg tcctcaggta ggtttagtat ctcaattgtc 143640
tgtcttgagt tccattacaa atatactaac gtctgagtat ttggatttgg aaaagaaaat 143700
ttgtgagtat atcagatcat attataaaga tgatataagt tactttgaaa caggatttcc 143760
aatcactata gaaaatgctc tagtcgcatc tcttaatcca aatatgatat gtgattttgt 143820
aactgacttt agacgtagaa aacggatggg attcttcggt aacttggagg taggtattac 143880
tttagttagg gatcacatga atgaaattcg cattaatatt ggagcgggaa gattagtcag 143940
accattcttg gttgtggata acggagagct catgatggat gtgtgtccgg agttagaaag 144000
cagattagac gacatgacat tctctgacat tcagaaagag tttccgcatg tcatcgaaat 144060
ggtagatata gaacaattta cttttagtaa cgtatgtgaa tcggttcaaa aatttagaat 144120
gatgtcaaag gatgaaagaa agcaatacga tttatgtgac tttcctgccg aatttagaga 144180
tggatatgtg gcatcttcat tagtgggaat caatcacaat tctggaccca gagctattct 144240
tggatgtgct caagctaaac aagctatctc ttgtctgagt tcggatatac gaaataaaat 144300
agacaatgga attcatttga tgtatccaga gaggccaatc gtgattagta aggctttaga 144360
aacttcaaag attgcggcta attgcttcgg ccaacatgtt actatagcat taatgtcgta 144420
caaaggtatc aatcaagagg atggaattat cattaaaaaa caatttattc agagaggcgg 144480
tctcgatatt gttacagcca agaaacatca agtagaaatt ccgttggaaa actttaataa 144540
caaagaaaga gataggtcta acgcctattc aaaattagaa agtaatggat tagttagact 144600

-continued

```
gaatgctttc ttggaatccg gagacgctat ggcacgaaat atctcatcaa gaactcttga 144660
agatgatttt gctagagata atcagattag cttcgatgtt tccgagaaat ataccgatat 144720
gtacaaatct cgcgttgaac gagtacaagt agaacttact gacaaagtta aggtacgagt 144780
attaaccatg aaagaaagaa gacccattct aggagacaaa tttaccacta gaacgagtca 144840
aaagggaaca gtcgcgtatg tcgcggatga aacggaactt ccatacgacg aaaatggtat 144900
cacaccagat gtcattatta attctacatc catcttctct agaaaaacta tatctatgtt 144960
gatagaagtt attttaacag ccgcatattc tgctaagccg tacaacaata agggagaaaa 145020
ccgacctgtc tgttttccta gtagtaacga aacatccatc gatacatata tgcaattcgc 145080
taaacaatgt tatgagcatt caaatccgaa attgtccgat gaagaattat cggataaaat 145140
cttttgtgaa aagattctct atgatcctga aacggataag ccttatgcat ccaaagtatt 145200
ttttggacca atttattact tgcgtctgag gcatttaact caggacaagg caaccgttag 145260
atgtagaggt aaaaagacga agctcattag acaggcgaat gagggacgaa aacgtggagg 145320
aggtatcaag ttcggagaaa tggagagaga ctgtttaata gcgcatggtg cagccaatac 145380
tattacagaa gttttgaaag attcggaaga agattatcaa gatgtgtatg tttgtgaaaa 145440
ttgtggagac atagcagcac aaatcaaggg tattaataca tgtcttagat gttcaaaact 145500
taatctctct cctctcttaa caaaaattga taccacacac gtatctaaag tatttcttac 145560
tcaaatgaac gccagaggcg taaaagtcaa attagatttc gaacgaagac ctccttcgtt 145620
ttataaacca ttagataaag ttgatctcaa gccgtctttt ctggtgtaat attctagttt 145680
ggtagtagat acatatcaat atcatcaaat tcgagatccg aattataaaa tgggcgtgga 145740
ttgttaacta tagaatcgga cgtctgatat tcgaaaatct gtggagtttc aggttttggt 145800
ggaggtgtaa ctgctacttg ggatactgaa gtctgatatt cagaaagctg tggatgttct 145860
ggttcggcat ccaccgatgg tgttacacca ctactaattg gttcagtaac gtctgtggac 145920
gatggaggca ccacttctac agaacctgta gcctcagtca tcaacggagc tacttcaatg 145980
cgaggaaatg tataatttgg taatggtttc tcatgtggat ctgaagaaga ggtaagatat 146040
ctactagaaa gataccgatc acgttctagt tctcttttgt agaacttaac tttttctttc 146100
tccgcatcta gttgatattc caacctcttc acgttactac gttcagattc caattcacgt 146160
tcgcatgggt tacctccaca gtttttacga gcgatttcac gttcagcctt catgcgtctc 146220
tccctctctc tatcgagttt atcagagcag tctttctgaa ggcgatcgaa ctccataaat 146280
ttctccaacg ctttgattgt ttccatagat ttccgaagtt cagcttttag gactgtgatt 146340
ctttttcttt cgaattcaca gctggatgta caaccgtttc cattaccgcc atctctaagt 146400
ttcttttcta gatcggcaac atttcatccc catgcctttt acattcctcg agtctactgt 146460
cgtcgaaata tcgttccagc tccttttcga catcaataac tttagcacgt tgtctctcaa 146520
gctctctttt gtagttatct gattccctgg cacgtttaag atcttcatgc aattgagtca 146580
gctcttaact tcctctcttg cttcttcgtc atagtactta caatcactat gggatccatt 146640
gttaccacgt ctacactcgg cgagctcgcg tttaagagat tcaatttccc gtttgtattg 146700
gtccatgttt ccattgctac caccattaga tttacaggct gctagttgtc gttcgagatc 146760
agaaatacgg gttttcttgg aattgatttc gtcgatgtac ttggcatcga aacacttatt 146820
aagttctttt tccaattcta cgattttatt tctttcgcga gtcaattccc tcctgtagta 146880
actatctgtt ttgtcagatt cacgctctct acgtagactt tcttgcaagt tactaatttg 146940
ttccctagca cgtccgagtt tagttttata tgctgaatag agttctgatt catcctttga 147000
```

gcagatctct agcgatcgtt taagattcct gattctagtc tttagcctat ttacctcctc 147060
agaagatgtt ccgttaccgt tgcgtttaca ctcgttaagc tgtctatcaa gatccatgat 147120
tctatctcta aaacgttgca tctctctttc catatcagca ttgctttcat tattacgtct 147180
gcagtcactc aactgtcttt caatatctga gattctatct ctaagacgtc gcatctctct 147240
ctgtttcggc attggtttca ttattacgtc tacagtcgtt caactgtctt tcaagatctg 147300
atattctaga ttggagtctg ctaatctctg tagcattttc acggcattca ctcagttgtc 147360
tttcaagatc tgaaatttta gattggagtc tgctaatctc tgtaagattt cctcctccgc 147420
tctcgatgca gtcggtcaac ttattctcta gttctctaat acgcgaacgc agtgcatcaa 147480
cttcttgcgt gtcttcctgg ttgcgtgtac attcatcgag tctagattcg agatctctaa 147540
cgcgtcgtcg ttcttcctca agttctctgc gtactacaga aagcgtgtcc ttatcttgtt 147600
gatatttagc aatttctgat tctagagtac tgattttgct tacgtagtta ctaatagttg 147660
tcttggcctt atcaagatcc tccttgtatt tgtcgcattc cttgatatcc ctacgaagtc 147720
tggacagttc ccattcgaca ttacgacgtt tatcgatttc agctcggaga tcgtcatcgc 147780
gttgttttag ccacatacga ctgagttcaa gttctcgttg acaagatcca tctacttttc 147840
cattcctaat agtatccagt tccttttcta gttctgaacg catttcttgt tccctatcaa 147900
gcgattctct caattctcgg atagtcttct tatcaatttc taataaatct gaaccatcat 147960
ctgtcccatt ttgaatatcc ctgtgttctt tgatctcttt tgtaagtcgg tcgattcttt 148020
cggttttata aacagaatcc ctttccaaag tcctaatctt actgagttta tcactaagtt 148080
ctgcattcaa ttcggtgagt tttctcttgg cttcttccaa ctctgtttta aactctccac 148140
tattttcgca ttcttcctcg catttatcta accattcaat tagtttatta ataactagtt 148200
ggtaatcagc gattcctata gccgttcttg taattgtggg aacataatta ggatcttcta 148260
atggattgta tggcttgata gcatcatctt tatcattatt agggggatgg acaaccttaa 148320
ttggttggtc ctcatctcct ccagtagcgt gtggttcttc aataccagtg ttagtaatag 148380
gcttaggcaa atgcttgtcg tacgcgggca cttcctcatc catcaagtat ttataatcgg 148440
gttctacttc agaatattct tttctaagag acgcgacttc gggagttagt agaagaactc 148500
tgtttctgta tctatcaacg ctggaatcaa tactcaagtt aaggatagcg aatacctcat 148560
cgtcatcatc cgtatcctct gaaacgccat catatgacat ttcatgaagt ctaacgtatt 148620
gataaataga atcagattta gtattaaaca gatccttaac ctttttagta aacgcatatg 148680
tatattttag atctccagat ttcataatat gatcacatgc cttaaatgtc agtgcttcca 148740
tgatataatc tggaacacta atgggtgacg aaaaagatac agcaccatat gctacgttga 148800
taaataaatc tgaaccacta agtagataat gattaatgtt aaggaaaaga aaatattcag 148860
tgtataggta tgtcttggcg tcatatcttg tactaaacac gctaaacagt ttgttaatgt 148920
gatcaatttc caatagatta attagagcag cgggaatacc aacaaacata ttaccacatc 148980
cgtattttct atgaatatca catatcatgt taaaaaatct tgatagaaga gcgaatatct 149040
cgtctgactt aatgagtcgt agttcagcag caacataagt cataactgta aatagaacat 149100
actttcctgt agtgttgatt ctagactcca catcaacacc attattaaaa atagttttat 149160
atacatcttt aatctgctct ccgttaatcg tcgaacgttc tagtatacgg aaacactttg 149220
atttcttatc tgtagttaat gacttagtga tatcacgaag aatattacga attacatttc 149280
ttgtttttct tgagagacct gattcagaac tcaactcatc gttccatagt tttctacct 149340 cagtggcgaa atctttggag tgcttggtac atttttcaat aaggttcgtg acctccattt 149400
attataaaaa atttattcaa aacttaacta caatcgggta attataagat cgtagatctc 149460
ccatgtggcg gaatactacc atctatcgca tgtggatgga cagtaggtaa tggccatggg 149520
aacagtaatg attgcatatt tatctttctt gctagtatta ctgcatattg tcccaatgtt 149580
tcgatgtgat gttctaacct atcaactgcc gctgtatcac aacaatagtg tccgatgaaa 149640
ttaagattat gatccaatgt gtttaatata tgattatcaa gtcttatacg atccgcgtct 149700
tttttgacag gatcaggttc ttctacagga agaagtttcg gcctcttatg atattcatgt 149760
ctgggaaacg gtggtctagg gtgaggctcc ggtatcggag tgggttttgg attataatca 149820
tcatcgtcta tgacatcatc atcatcttcg acttcgatat ttattttgct atcttgatga 149880
tgtcctgtat cagttgcatt ttcagcactc gactgaatat tagcgcattc attgtctatt 149940
attaccatat ttctaaaccc aaaatgtatg tgttgaacat cagtactatc gttgatgagt 150000
cttatagcat gaattcgctt atcgttatcg ggtttatctt ctgtcacctt agcaattcct 150060
tttttattaa actctacata atcatatcca tttctattgt ttgttctaat ataaacgagt 150120
atagcatcat tgctaaattt ttcaatagta tcgaaaacag aatatcctaa accatataat 150180
atatattcag gaacactcaa actaaatgtc caggattctc ctaaatacgt aaactttaat 150240
agtgcgaaat cattcaaaaa tctaccactt atagatagat agtacataaa tgcgtatagt 150300
agtctaccta tctctttatt atgaaaaccg gcattacgat catatatgtc gtgatatacc 150360
tgtgatccgt ttacgttaaa ccataaatac atgggtgatc ctataaacat gaatttattt 150420
ctaattctca gagctatagt taattgaccg tgtaatattt gcttacatgc atacttgata 150480
cgcttattaa taagattttt atcattgctc gttatctcag aatcgtatat ataaggagta 150540
ccattgtgat tcttaccaga tattatacaa aatactatat ataaaatata ttgacccacg 150600
ttagtaatca tataaatgtt taacgtttta aattttgtat ttaatgatcc attatcatac 150660
gctagcatgg tcttatgata ttcattcttt aaaatataat attgtgttag ccattgcatt 150720
ggggctccta atggagattt tttattctca tccattttag gataggcttt cataaagtcc 150780
ctaataactt cgtgaataat gtttctatgt tttctactga tgcatgtatt tgcttcgatt 150840
tttttatccc atgtttcatc tatcatagat ttaaacgcag taatgctcgc aacattaaca 150900
tcttgaaccg ttggtacaat tccgttccat aaatttataa tgttcgccat ttatataact 150960 catttttga atatactttt aattaacaaa agagttaagt tactcatatg gacgccgtcc 151020
agtctgaaca tcaatctttt tagccagaga tatcatagcc gctcttagag tttcagcgtg 151080
attttccaac ctaaatagaa cttcatcgtt gcgtttacaa cacttttcta tttgttcaaa 151140
ctttgttgtt acattagtaa tcttttttc caaattagtt agccgttgtt tgagagtttc 151200
ctcattgtcg tctccatcgg ctttaacaat tgcttcgcgt ttagcctctg gctttttagc 151260
agcctttgta gaaaaaaatt cagttgctgg aattgcaaga tcgtcatctc cggggaaaag 151320
agttccgtcc atttaaagta cagattttag aaactgacac tctgcgttat ttatatttgg 151380
tacaacacat ggattataaa tatcgatgtt aataacatca gaaaatgtaa agtctataca 151440
ttgttgcatc gtgttaaatt ttctaatgga tctagtatta ttgggtccaa cttctgcctg 151500
aaatccaaat atggaagcgg atacaaaacc gtttcctgga taaaccacac atctccactt 151560
ttgctttaca tcagaaattg tgtcgttgac atcttgaact ctcctatcta atgccggtgt 151620
tccacctata gattttgaat attcgaatgc tgcatgagta gcattaaatt ccttaatatt 151680
gccataattt tcatatattg agtaaccctg gataaaaagt aaacacaccg cagccgtcgc 151740
taccacaata aaaaaaattg atagagagtt catttataat ctattagaag ctgacaaaat 151800
ttttttacac gcatcagaca atgctttaat aaatagttca acatctactt ttgtcatatc 151860
gaaccgatgg tatgattcta acctagaatt acatccgaaa aagttgacta tgttcatagt 151920
cattaagtca ttaacaaaca acattccaga ctctggatta taagacgata ctgtttcgtc 151980
acaattacct accttaatca tgtgattatg aatattggct attagagcac cttctaagaa 152040
atctataata tctttgaaac acgatttaaa atcaaaccac gaatatactt ctacgaagaa 152100
agttagttta cccataggag aaataactat aaatggagat ctaaatacaa aatccggatc 152160
tatgatagtt ttaacattat tatattctct attaaatacc tccacatcta aaaatgttaa 152220
ttttgaaact atgtcttcgt ttattaccgt acctgaacta aacgctataa gctctattgt 152280
ttgagaactc tttaaacgat attcttgaaa tacatgtaac aaagtttcct ttaactcggt 152340
cggtttatct accatagtta cagaatttgt atccttatct ataatataat aatcaaaatc 152400
gtataaagtt atataattat cgcgttcaga ttgggatctt ttcaaataga ctaaaaaccc 152460
catttctcta gtaagtatct tatgtatatg tttgtaaaat atcttcatgg tgggaatatg 152520
ctctaccgca gttagccatt cctcattgac agcggtagat gtattagaca aaactattcc 152580
aatgtttaac aagggccatt ttacgagatt attaaatcct tgtttgataa atgtagccaa 152640
tgagggttcg agttcaacga cgattgaatt ctcttcccgc ggatgctgca tgatgaacga 152700
cgggatgttg ttcgattgat ttggaattct ttttcgactt tttgtttata ttaaatattt 152760
taaaatttat agcggatagc aattcatgta ccacggataa tgtagacgcg tattgcgcat 152820
cgatatcttt attattagat aaatttatca ataaatgtga gaagtttgcc tcgttaaggt 152880
cttccattta aatattatat aaacatttgt gtttgtaact tattcgtctt ttatggaata 152940
gtttttttact agtaaagctg caattacaca ctttgtccgt aaaacataaa tataaacacc 153000
agcttttatc aatcgttcca aaaagtcgac ggcggacatt tttaacatgg catctatttt 153060
aaatacactt aggtttttgg aaaaaacatc attttataat tgtaacgatt caataactaa 153120
agaaaagatt aagattaaac ataagggaat gtcatttgta ttttataagc caaagcattc 153180
taccgttgtt aaatacttgt ctggaggagg tatatatcat gatgatttgg ttgtattggg 153240
gaaggtaaca attaatgatc taaagatgat gctattttac atggatttat catatcatgg 153300
agtgacaagt agtggagcaa tttacaaatt gggatcgtct atcgatagac tttctctaaa 153360
taggactatt gttacaaaag ttaataataa ttataattat gatgatacat tttttgacga 153420
cgatgattga tcgctattgc acaattttgt ttttttactt tctaatatag cgtttagatt 153480
ctttttcatg tgcgaatatt gatttactaa aatatctatg tttaactttt gttctataac 153540
gtccttatcg gcggtatcgg tacatatacg taattcacct tcacaaaata cggagtcttc 153600
gataataata gccaatcgat tattggatct agctgtctgt atcatattca acatgtttaa 153660
tatatccttt cgtttcccct ttacaggcat cgatcgtagc atattttccg cgtctgatat 153720
ggaaatgtta aaactacaaa aatgcgtaat gttagcccgt cctaatattg gtacgtgtct 153780
ataagtttgg catagtagaa taatagacgt gtttaaatgc cttccgaagt ttaagaattc 153840
tattagagta ttgcattttg atagtttatc acctacatca tcaaaaaataa gtaaaaagtg 153900
tgctgatttt ttatgatttt gtgcgacagc aatacatttt tctatgttac ttttagttcg 153960
tatcagatta tattctagag attcctgact actaacgaaa ttaatatgat ttggccaaat 154020
gtatccatca taatctgggt tataaacggg tgtaaacaag aatatatgtt tatattttt 154080 aactagtgta gaaaacagag atagtaaata gatagttttt ccagatccag atcctcccgt 154140
taaaaccatt ctaaacggca tttttaataa attttctctt gaaaattgtt tttcttggaa 154200
acaattcata attatattta cagttactaa attaatttga taataaatca aaatatggaa 154260
aactaaggtt gttagtaggg aggagaacaa agaaggcaca tcgtgatata aataacattt 154320
attatcatga tgacaccaga aaacgacgaa gagcagacat ctgtgttctc cgctactgtt 154380
tacggagaca aaattcaggg aaagaataaa cgcaaacgcg tgattggtct atgtattaga 154440
atatctatgg ttatttcact actatctatg attaccatgt ccgcgtttct catagtgcgc 154500
ctaaatcaat gcatgtctgc taacgaggct gctattactg acgccgctgt tgccgttgct 154560
gctgcatcat ctactcatag aaaggttgcg tctagcacta cgcaatatga tcacaaagaa 154620
agctgtaatg gtttatatta ccagggttct tgttatatat tacattcaga ctaccagtta 154680
ttctcggatg ctaaagcaaa ttgcactgcg gaatcatcaa cactacccaa taaatccgat 154740
gtcttgacta cctggctcat tgattatgtt gaggatacat ggggatctga tggtaatcca 154800
attacaaaaa ctacatccaa ttatcaagat tctgatgtat cacaagaagt tagaaagtat 154860
ttttgtgtta aaacaatgaa ctaatattta tttttgtaca ttaataaatg aaatcgctta 154920
atagacaaac tgtaagtagg tttaagaagt tgtcggtgcc ggccgctata atgatgatac 154980
tctcaaccat tattagtggc ataggaacat ttctgcatta caaagaagaa ctgatgccta 155040
gtgcttgcgc caatggatgg atacaatacg ataaacattg ttatttagat actaacatta 155100
aaatgtctac agataatgcg gtttatcagt gtcgtaaatt acgagctaga ttgcctagac 155160
ctgatactag acatctgaga gtattgttta gtatttttta taaagattat tgggtaagtt 155220
taaaaaagac caataataaa tggttagata ttaataatga taaagatata gatattagta 155280
aattaacaaa ttttaaacaa ctaaacagta cgacggatgc tgaagcgtgt tatatataca 155340
agtctggaaa actggttaaa acagtatgta aaagtactca atctgtacta tgtgttaaaa 155400
aattctacaa gtgacaacaa aaaatgaatt aataataagt cgttaacgta cgccgccatg 155460
gacgccgcgt ttgttattac tccaatgggt gtgttgacta taacagatac attgtatgat 155520
gatctcgata tctcaatcat ggactttata ggaccataca ttataggtaa cataaaaact 155580
gtccaaatag atgtacggga tataaaatat tccgacatgc aaaaatgcta ctttagctat 155640
aagggtaaaa tagttcctca ggattctaat gatttggcta gattcaacat ttatagcatt 155700
tgtgccgcat acagatcaaa aaataccatc atcatagcat gcgactatga tatcatgtta 155760
gatatagaag ataaacatca gccattttat ctattcccat ctattgatgt ttttaacgct 155820
acaatcatag aagcgtataa cctgtataca gctggagatt atcatctaat catcaatcct 155880
tcagataatc tgaaaatgaa attgtcgttt aattcttcat tctgcatatc agacggcaat 155940
ggatggatca taattgatgg gaaatgcaat agtaattttt tatcataaaa gttgtaaagt 156000
aaataataaa acaataaata ttgaactagt agtacgtata ttgagcaatc agaaatgatg 156060
ctggtacctc ttatcacggt gaccgtagtt gcgggaacaa tattagtatg ttatatatta 156120
tatatttgta ggaaaaagat acgtactgtc tataatgaca ataaaattat catgacaaaa 156180
ttaaaaaaga taaagagttc taattccagc aaatctagta aatcaactga tagcgaatca 156240
gactgggagg atcactgtag tgctatggaa caaaaacaatg acgtagataa tatttctagg 156300
aatgagatat tggacgatga tagcttcgct ggtagtttaa tatgggataa cgaatccaat 156360
gttatagcgc ctagcacaga acacatttac gatagtgttg ctggaagcac gctgctaata 156420
aataatgatc gtaatgaaca gactatttat cagaacacta cagtagtaat taatgaaacg 156480

```
gagactgtta aagtacttaa tgaagatacc aaacagaatc ctaactattc atccaatcct 156540
ttcgtaaatt ataataaaac cagtatttgt agcaagtcaa atccgtttat tacagaactt 156600
aacaataaat ttagtgagaa taatccgttt agacgagcac atagcgatga ttatcttaat 156660
aagcaagaac aagatcatga acacgatgat atagaatcat cggtcgtatc attggtgtga 156720
ttagtttcct ttttataaaa ttgaagtaat atttagtatt attgctgccg tcacgttgta 156780
caaatggaga tattccctgt attcggcatt tctaaaatta gcaattttat tgctaataat 156840
gactgtagat attatataga tacagaacat caaaaaatta tatctgatga gatcaataga 156900
cagatggatg aaacggtact tcttaccaac atcttaagcg tagaagttgt aaatgacaat 156960
gagatgtacc atcttattcc tcatagatta tcgacgatta tactctgtat tagttctgtc 157020
ggaggatgtg ttatctctat agataatgac atcaatgaca aaaatattct aacatttccc 157080
attgatcatg ctgtaatcat atccccactg agtaaatgtg tcgtagttag caagggtcct 157140
acaaccatat tggttgttaa agcggatata cctagcaaac gattggtaac atcgtttaca 157200
aacgacatac tatatgtaaa caatctgtca ctgattaatt atttgccgtt gtctgtattc 157260
attattagac gagtcaccga ctatttggat agacgcatat gcgatcagat atttgctaat 157320
aataagtggt attccattat aaccatcgac gataagcaat atcctattcc atcaaactgt 157380
ataggtatgt cctctgccaa gtacataaat tctagcatcg agcaagatac tttaatccat 157440
gtttgtaacc tcgagcatcc gttcgactca gtatacaaaa aaatgcagtc gtacaattct 157500
ctacctatca aggaacaaat attgtacggt agaattgata atataaatat gagcattagt 157560
atttctgtgg attaatagat ttctagtatg ggatcatta atcatctcta atctctaaat 157620
acctcataaa acgaaaaaaa agctattatc aaatactgta cggaatggat tcattctctt 157680
ctctttttat gaaactctgt tgtatatcta ctgataaaac tggaagcaaa aaatctgata 157740
aaaagaataa gaataagatc aaggattata tggaacacga ttattataaa ataacaatag 157800
ttcctggttc ctcttccacg tctactagct cgtggtatta tacacatgcc tagtaatagt 157860
ctctttgcgt tgacggaaag cagactagaa ataacaggct aaaatgttca gacaccataa 157920
tagttcccaa cccagataat aacagagttc catcaacaca ttcctttaaa ctcaatccca 157980
aacccaaaac cgttaaaatg tatccggcca attgatagta gataatgagg tgtacagcgc 158040
atgataattt acacagtaac caaaatgaaa atactttagt aattataaga aatatagatg 158100
gtaacgtcat catcaacaat ccgataatat gcctgagagt aaacattgat ggataaaaca 158160
aaaatgctcc gcataactct atcatggcaa taacacaacc aaacacttgt aaaattccta 158220
aattagtaga aaatacaacg gatatcgatg tataagtgat ctcgagaaat aataagaata 158280
aagtaatgcc cgtaaagata aacatcaaca ttgtttggta atcattaaac caattagtat 158340
gaagttgaac taatttcaca gtagatttta ttccagtgtt atcctcgcat gtataagtac 158400
ctggtaagat atctttatat tccataatca atgagacatc actatccgat aacgaatgaa 158460
gtctagcact agtatgccat ttacttaata ttgtcgtctt ggaagtttta ttataagtta 158520
aaatatcatg gttatccaat ttccatctaa tatactttgt cggattatct atagtacacg 158580
gaataatgat ggtatcatta catgctgtat actctatggt ctttgtagtt gttataacaa 158640
ccaacgtata gaggtatatc aacgatattc taactcttga catttttat ttatttaaaa 158700
tgatacctttt gttatttatt ttattctatt ttgctaacgg tattgaatgg cataagtttg 158760
aaacgagtga agaaataatt tctacttact tattagacga cgtattatac acgggtgtta 158820
```

atggggcggt atacacattt tcaaataata aactaaacaa aactggttta actaataata 158880
attatataac aacatctata aaagtagagg atgcggataa ggatacatta gtatgcggaa 158940
ccaataacgg aaatcccaaa tgttggaaaa tagacggttc agacgaccca aaacatagag 159000
gtagaggata cgctccttat caaaatagca aagtaacgat aatcagtcac aacggatgtg 159060
tactatctga cataaacata tcaaaagaag gaattaaacg atggagaaga tttgacggac 159120
catgtggtta tgatttatac acggcggata acgtaattcc aaaagatggt ttacgaggag 159180
cattcgtcga taaagacggt acttatgaca aagtttacat tcttttcact gatactatcg 159240
gctcaaagag aattgtcaaa attccgtata tagcacaaat gtgcctaaac gacgaaggtg 159300
gtccatcatc attgtctagt catagatggt cgacgtttct caaagtcgaa ttagaatgtg 159360
atatcgacgg aagaagttat agacaaatta ttcattctag aactataaaa acagataatg 159420
atacgatact atatgtattc ttcgatagtc cttattccaa gtccgcatta tgtacctatt 159480
ctatgaatac cattaaacaa tctttttcta cgtcaaaatt ggaaggatat acaaagcaat 159540
tgccgtctcc agctcctggt atatgtttac cagctggaaa agttgttcca cataccacgt 159600
ttgaagtcat agaaaaatat aatgtactag atgatattat aaagccttta tctaaccaac 159660
ctatcttcga aggaccgtct ggtgttaaat ggttcgatat aaaggagaag gaaaatgaac 159720
atcgggaata tagaatatac ttcataaaag aaaattctat atattcgttc gatacaaaat 159780
ctaaacaaac tcgtagctcg caagtcgatg cgcgactatt ttcagtaatg gtaacttcga 159840
aaccgttatt tatagcagat atagggatag gagtaggaat gccacaaatg aaaaaaatac 159900
ttaaaatgta atcttaatcg agtacaccac acgacaatga acaaacataa gacagattat 159960
gctggttatg cttgctgcgt aatatgcggt ctaattgtcg gaattatttt tacagcgaca 160020
ctattaaaag ttgtagaacg taaattagtt catacaccat caatagataa aacgataaaa 160080
gatgcatata ttagagaaga ttgtcctact gactggataa gctataataa taaatgtatc 160140
catttatcta ctgatcgaaa aacctgggag gaaggacgta atgcatgcaa agctctaaat 160200
ccaaattcgg atctaattaa gatagagact ccaaacgagt taagtttttt aagaagcatt 160260
agacgcggat attgggtagg agaatccgaa atattaaacc agacaacccc atataatttt 160320
atagctaaga atgccacgaa gaatggaact aaaaaacgga aatatatttg tagcacaacg 160380
aatactccca aactgcattc gtgttacact atataacaat tacactacat ttttatcata 160440
ccactacttc ggttagatgt tttagaaaaa aataaatatc gccgtaccgt tcttgttttt 160500
ataaaaataa caattaacaa ttatcaaatt ttttctttaa tattttacgt ggttgaccat 160560
tcttggtggt aaaataatct cttagtgttg gaatggaatg ctgtttaatg tttccacact 160620
catcgtatat tttgacgtat gcagtcacat cgtttacgca atagtcagac tgtagttcta 160680
tcatgcttcc tacatcagaa ggaggaacag ttttaaagtc tcttggtttt aatctattac 160740
cgttagtttt catgaaatcc tttgttttat ccacttcaca ttttaaataa atgtccacta 160800
tacattcttt tgttaatttt actagatcgt catgggtcat agaatttata ggttccgtag 160860
tccatggatc caaactagca aacttcgcgt atacggtatc gcgattagtg tatacaccaa 160920
ctgtatgaaa attaagaaaa cagtttaata gatcaacaga aatatttaat cctccgtttg 160980
atacagatgc gccatattta tggatttcgg attcacacgt tgtttgtctg aggtgttcgt 161040
ctagtgttgc ttctacgtaa acttcgattc ccatatattc tttattgtca gaatcgcata 161100
ccgatttatc atcatacact gtttgaaaac taaatggtat acacatcaaa ataacaaata 161160
ctaacgagta cattctgcaa tattgttatc gtaattggaa aaatagtgtt cgagtgagtt 161220
ggattatgtg agtattggat tgtatatttt attttatatt ttgtaataag aataaaatgc 161280
taatgtcaag tttattccaa tagatgtctt attaaaaaca tatataataa ataacaatgg 161340
ctgaatggca taaaattatc gaggatatct caaaaaataa taagttcgag gatgccgcca 161400
tcgttgatta caagactaca aagaatgttc tagctgctat tcctaacaga acatttgcca 161460
agattaatcc gggtgaaatt attcctctca tcactaatcg taatattcta aaacctctta 161520
ttggtcagaa atattgtatt gtatatacta actctctaat ggatgagaac acgtatgcta 161580
tggagttgct tactgggtac gcccctgtat ctccgatcgt tatagcgaga actcataccg 161640
cacttatatt tttgatgggt aagccaacaa catccagacg tgacgtgtat agaacgtgta 161700
gagatcacgc tacccgtgta cgtgcaactg gtaattaaaa taaaaagtaa tattcatatg 161760
tagtgtcaat tttaaatgat gatgatgaaa tgtataaatat ccatattgac gatgtcaata 161820
atgccggtat tggcatacag ttcatcgatt tttagatttc attcagagga tgtggaatta 161880
tgttatgggc atttgtattt tgataggatc tataatgtag taaatataaa atataatccg 161940
catattccat atagatataa ttttattaat cgcacgttaa ccgtagatga actagacgat 162000
aatgtctttt ttacacatgg ttattttttta aaacacaaat atggttcact taatcctagt 162060
ttgattgtct cattatcagg aaacttaaaa tataatgata tacaatgctc agtaaatgta 162120
tcgtgtctca ttaaaaattt ggcaacgagt acatctacta tattaacatc taaacataag 162180
acttattctc tacatcggtc cacgtgtatt actataatag gatacgattc tattatatgg 162240
tataaagata taaatgacaa gtataatgac atctatgatt ttactgcaat atgtatgcta 162300
atagcgtcta cattgatagt gaccatatac gtgtttaaaa aaataaaaat gaactcttaa 162360
ttatgctatg ctattagaaa tggataaaat caaaattacg gttgattcaa aaattggtaa 162420
tgttgttacc atatcgtata acttggaaaa gataactatt gatgtcacac ctaaaaagaa 162480
aaaagaaaag gatgtattat tagcgcaatc agttgctgtc gaagaggcaa aagatgtcaa 162540
ggtagaagaa aaaaatatta tcgatattga agatgacgat gatatggatg tagaaagcgc 162600
gtaatactat ctataaaaat aagtatataa taaatacttt ttatttacgg tactcttgta 162660
gtggtgatac cctactcaat tattttttta aaaaaatact tattctgatt cttctaacca 162720
tttccgtgtt cgttcgaatg ccacatcgac gtcaaagata ggggagtagt tgaaatctag 162780
ttctgcattg ttggtacgca cctcaaatgt agtgttggat atcttcaacg tatagttgtt 162840
gagtagtgat ggttttctaa atagaattct cttcatatca ttcttgcacg cgtacatttt 162900
tagcatccat cttggaattc tagatccttg ttctattccc aatggtttca tcaataaaag 162960
attaaacata tcgtacgaac acgatggaga gtaatcgtag caaaagtaag catttccttt 163020
aatctcagat cccggatact ggatatattt tgcagccaac acgtgcatcc atgcaacatt 163080
tcctacatat acccggctat gcaccgcgtc atcatcgact gtacgataca taatgttacc 163140
gtgttgctta cattgctcgt aaaagacttt cgtcaatttg tctccttctc cgtaaattct 163200
agtgggtctt aggcaacaag tatacaattt tgctccattc atgattacgg aattattggc 163260
tttcataacc agttgctcgg ccatacgttt actttttgcg tatacatgtc ctggtgatat 163320
atcataaagg gtatgctcat ggccgatgaa tggatcaccg tgtttattgg gtcctattgc 163380
ttccatgcta ctagtataga tcaaatactt gattcctagg tccacacaag ctgccaaaat 163440
agtctgtgtt ccataatagt ttactttcat gatttcatta tcggtgtatt ttccaaatac 163500
atccactaga gcagccgtat gaataatcag atttacccca tctagcgctt ctctcacctt 163560

-continued atcaaagtcg tttatatcac attgtatata gtttataacc ttaactttcg aggttattgg 163620
ttgtggatct tctacaatat ctatgactct gatttcttga acatcatctg cactaattaa 163680
cagttttact atatacctgc ctagaaatcc ggcaccacca gtaaccgcgt acacggccat 163740
tgctgccact cataatatca gactacttat tctattttac taaataatgg ctgtttgtat 163800
aatagaccac gataaatatca gaggagttat ttactttgaa ccagtccatg gaaaagataa 163860
agttttagga tcagttattg gattaaaatc cggaacgtat agtttaataa ttcatcgtta 163920
cggagatatt agtcaaggat gtgattccat aggcagtcca gaaatattta tcggtaacat 163980
ctttgtaaac agatatggtg tagcatatgt ttatttagat acagatgtaa atatatctac 164040
aattattgga aaggcgttat ctatttcaaa aaatgatcag agattagcgt gtggagttat 164100
tggtatttct tacataaatg aaaagataat acattttctt acaattaacg agaatggcgt 164160
ttgatatatc agttaatgcg tctaaaacaa taaatgcatt agtttacttt tctactcagc 164220
aaaataaatt agtcatacgt aatgaagtta atgatacaca ctacactgtc gaatttgata 164280
gggacaaagt agttgacacg tttatttcat ataataaaca taatgacacc atagagataa 164340
gaggggtgct tccagaggaa actaatattg gttgcgcggt taatacgccg gttagtatga 164400
cttacttgta taataagtat agttttaaac tgattttagc agaatatata agacacagaa 164460
atactatatc cagcaatatt tattcggcat tgatgacact agatgatttg gctattaaac 164520
agtatggaga cattgatcta ttatttaatg agaaacttaa agtagactcc gattcgggac 164580
tatttgactt tgtcaacttt gtaaaggata tgatatgttg tgattctaga atagtagtag 164640
ctctatctag tctagtatct aaacattggg aattgacaaa taaaaagtat aggtgtatgg 164700
cattagccga acatatatct gatagtattc caatatctga gctatctaga ctacgataca 164760
atctatgtaa gtatctacgc gggcacactg agagcataga ggatgaattt gattattttg 164820
aagacgatga ttcgtctaca tgttctgccg taaccgacag ggaaacggat gtataatttt 164880
ttttatagcg tgaaggatat gataaaaaat ataattgttg tatttatccc attccaatca 164940
ccttatatga ttctgtaaca caataaagga gtctcataga tgtatagagg tcagatactg 165000
gtttgataaa ctgtttattc cacataagta tgtttgactt tatggttaga cccgcatact 165060
ttaacaaatc actgaaaatt ggagttaggt attgacctct cagaatcagt tgccgttctg 165120
gaacattaaa tgtatttttt atgatatact ccaacgcatt tatgtgggca tacaacaagt 165180
cattactaat ggagtattcc aagagtttta gttgtctagt atttaacaag agaagagatt 165240
tcaacagact gtttatgaac tcgaatgccg cctcattgtc gcttatattg atgatgtcga 165300
attctcccaa tatcatcacc gatgagtagc tcatcttgtt atcgggatcc aagttttcta 165360
aagatgtcat taaaccctcg atcatgaatg gatttatcat catcgttttt atgttggaca 165420
tgagcttagt ccgtttgtcc acatctatag acgacgattt ctgaattatt tcatatatcc 165480
ctctctttaa ctccaggaac ttgtcaggat ggtctacttt aatatgttct cgtctaagag 165540
atgaaaatct ttggatggtc gcatgtgact tttctctaaa ggatgacgtt gcccaagatc 165600
ctctcttaaa tgaatccatc ttatccttgg acaagatgga cagtctattt tccttagatg 165660
gtttaatatt tttgttaccc atgatctata aaggtagacc taatcgtctc ggatgaccta 165720
tatatttatt ttcagtttta ttatacgcat aaattgtaaa aaatatgtta ggtttacaaa 165780
aatgtctcgt ggggcattaa tcgtttttga aggattggac aaatctggaa aaacaacaca 165840
atgtatgaac atcatggaat caatactttc aaacacaata aaatacctta actttcctca 165900
gagatccact gtcactggaa agatgataga tgactatcta actcgtaaaa aaacctataa 165960

-continued

```
tgatcatata gttaatctat tattttgtgc aaatagatgg gagtttgcat cttttataca 166020
agaacaacta gaacagggaa ttactttaat agttgataga tacgcatttt ctggagtagc 166080
gtatgccgcc gctaaaggcg cgtcaatgac tctcagtaag agttatgaat ctggattgcc 166140
taaacccgac ttagttatat tcttggaatc tggtagcaaa gaaattaata gaaacgtcgg 166200
cgaggaaatt tatgaagatg ttacattcca acaaaaggta ttacaagaat ataaaaaaat 166260
gattgaagaa ggagatattc attggcaaat tatttcttct gaattcgagg aagatgtaaa 166320
gaaggagttg attaagaata tagttataga ggctatacac acggttactg gaccagtggg 166380
gcaactgtgg atgtaatagt gaaattacat tttttataaa tagatgttag tacagtgtta 166440
taaatggatg aagcatatta ctctggcaac ttggaatcag tactcggata cgtgtccgat 166500
atgcataccg aactcgcatc aatatctcaa ttagttattg ccaagataga aactatagat 166560
aatgatatat taaacaagga cattgtaaat tttatcatgt gtagatcaaa cttggataat 166620
ccatttatct ctttcctaga tactgtatat actattatag atcaagagaa ctatcagact 166680
gagttgatta attcattaga cgacaatgaa attatcgatt gtatagttaa taagtttatg 166740
agcttttata aggataacct agaaaatata gtagatgcta tcattactct aaaatatata 166800
atgaataatc cagattttaa aactacgtat gccgaagtac tcggttccag aatagccgat 166860
atagatatta aacaagtgat acgtaagaat atactacaat tgtctaatga tatccgcgaa 166920
cgatatttgt gaaaaatatt aaaaaaaaat actttttttta ttaaatgacg tcgcttcgcg 166980
aatttagaaa attatgctgt gatatatatc acgcatcagg atataaagaa aaatctaaat 167040
taattagaga ctttataaca gatagggatg ataaatattt gatcattaag ctattgcttc 167100
ccggattaga cgatagaatt tataacatga acgataaaca aattataaaa ttatatagta 167160
taatatttaa acaatctcag gaagatatgc tacaagattt aggatacgga tatataggag 167220
acactattag gactttcttc aaagagaaca cagaaatccg tccacgagat aaaagcattt 167280
taactttaga agaagtggat agtttcttaa ctacgttatc atccgtaact aaagaattgc 167340
atcaaataaa attattgact gatatcgcat ccgtttgtac atgtaatgat ttaaaatgtg 167400
tagtcatgct tattgataaa gatctaaaaa ttaaagcggg tcctcggtac gtacttaacg 167460
ctattagtcc tcatgcctat gatgtgttta gaaaatctaa taacttgaaa gagataatag 167520
aaaattcatc taaacaaaat ctagactcta tatctatttc tgttatgact ccaattaatc 167580
ccatgttagc ggaatcgtgt gattctgtca ataaagcgtt taaaaaattt ccatcaggaa 167640
tgtttgcgga agtcaaatac gatggtgaaa gagtacaagt tcataaaaat aataacgagt 167700
ttgccttctt tagtagaaac atgaaaccag tactctctca taaagtggat tatctcaaag 167760
aatacatacc gaaagcattt aaaaaagcta cgtctatcgt attggattct gaaattgttc 167820
ttgtagacga acataatgta ccgctaccgt ttggaagttt aggaatacac aaaaagaaag 167880
aatataaaaa ctctaacatg tgtttgttcg tgtttgactg tttgtacttt gatggattcg 167940
atatgacgga cattccattg tacgaacgaa gatcttttct caaagatgtt atggttgaaa 168000
tacccaatag aatagtattc tcagagttga cgaatattag taacgagtct cagttaactg 168060
acgtattgga tgatgcacta acgagaaaat tagaaggatt ggtcttaaaa gatattaatg 168120
gagtatacga accgggaaag agaagatggt taaaaataaa gcgagactat ttgaacgagg 168180
gttccatggc agattctgcc gatttagtag tactaggtgc ttactatggt aaaggagcaa 168240
agggtggtat catggcagtc tttctaatgg gttgttacga cgatgaatcc ggtaaatgga 168300
```

agacggttac caagtgttca ggacacgatg ataatacgtt aagggagttg caagaccaat 168360
taaagatgat taaaattaac aaggatccca aaaaaattcc agagtggtta gtagttaata 168420
aaatctatat tcccgatttt gtagtagagg atccgaaaca atctcagata tgggaaattt 168480
caggagcaga gtttacatct tccaagtccc ataccgcaaa tggaatatcc attagatttc 168540
ctagatttac taggataaga gaggataaaa cgtggaaaga atctactcat ctaaacgatt 168600
tagtaaactt gactaaatct taatagttac atacaaacta aaaattaaaa taacactatt 168660
tagttggtgg tcgccatgga tggtgttatt gtatactgtc taaacgcgct agtaaaacat 168720
ggcgaggaaa taaatcatat aaaaaatgat ttcatgatta aaccatgttg tgaaagagtt 168780
tgtgaaaaag tcaagaacgt tcacatcggc ggacaatcta aaaacaatac agtgattgca 168840
gatttgccat atctggataa tgctgtatcc gatgtatgca aatcgatata tatatagtat 168900
caagaatatc cagatttgct aatttgataa agatagatga cgatgacaag actcctactg 168960
gtgtatataa ttattttaaa cttaaagatg ccattcctgt tattatatct ataggaaagg 169020
ataaagatgt ctgtgaacta ttaatctcat cagacatatc gtgtgcatgc gtggagttaa 169080
attcatatca cgtagccatt cttcccatgg atgtttcctt ttttaccaaa ggaaatgcat 169140
cattgattat tctcctgttt gatttctcta tcgatgcggc acctctctta agaagtgtaa 169200
ccgataataa tgttattata tctagacacc agcgtctaca tgacgagctt ccgagttcca 169260
attggttcaa gttttacata agtataaagt ccgactattg ttctatatta tatatggttg 169320
ttgatggatc tgtgatgcat gcgatagctg ataatagaac tcacgcaatt attagcaaaa 169380
atatattaga caatactacg attaacgatg agtgtagatg ctgttatttt gaaccacaga 169440
ttaggattct tgatagagat gagatgctca atggatcatc gtgtgatatg aacagacatt 169500
gtattatgat gaatttacct gatgtaggcg aatttggatc tagtatgttg gggaaatatg 169560
aacctgacat gattaagatt gctctttcgg tggctggtaa tttaataaga aatcgagact 169620
acattcccgg gagacgagga tatagctact acgtttacgg tatagcctct agataatttt 169680
tttaagcacg aaataaaaaa cataatttta aaccaatcta tttcatacta ttttgtgtga 169740
tcaccatgga cataaagata gatattagta tttctggtga taaatttacg gtgactacta 169800
ggagggaaaa tgaagaaaga aaaaaatatc tacctctcca aaaagaaaaa actactgatg 169860
ttatcaaacc tgattatctt gagtacgatg acttgttaga tagagatgag atgtttacta 169920
ttctagagga atattttatg tacagaggtc tattaggcct cagaataaaa tatggacgac 169980
tctttaacga aattaaaaaa ttcgacaatg atgcggaaga acaattcggt actatagaag 170040
aactcaagca gaaacttaga ttaaattctg aagagggagc agataacttt atagattata 170100
taaaggtaca aaaacaggat atcgtcaaac ttactgtata cgattgcata tctatgatag 170160
gattgtgtgc atgcgtggta gatgtttgga gaaatgagaa actgttttct agatggaaat 170220
attgtttacg agcgattaaa ctgtttattg atgatcacat gcttgataag ataaaatcta 170280
tactgcagaa tagactagtg tatgtggaaa tgtcatagaa agttaatgag agcaaaaata 170340
tataaggttg tattccatat ttgttatttt tttctgtaat agttagaaaa atacattcga 170400
tggtctatct atcagattat tatgtgttat aaggtacttt ttctcataat aaactagagt 170460
atgagtaaga tagtgttttt caaaacatat aaatctaaaa ttgatggatg agatatacag 170520
ctattaattt cgaaaatata ttttaatctg ataactttaa acatggattt ttgatggtgg 170580
tttaacgttt taaaaaaaga ttttgttatt gtagtatatg ataatattaa aagatggata 170640
taaagaattt gctgactgta tgtactattt tttacattac tacattggct acggcagata 170700
tacctactcc gccaccaacg gggcatgtga cgagggagaa tatcttgata agaggcataa 170760
tcaatgttgt aatcggtgtc cacctggaga atttgccaag gtcagatgta gtggtagtga 170820
taacacaaaa tgtgaacgct gcccacctca tacatatacc gcaatcccca attactctaa 170880
tggatgtcat caatgtagaa aatgcccaac aggatcattt gataaggtaa agtgtaccgg 170940
aacacagaac agtaaatgtt cgtgtcttcc tggttggtat tgcgctactg attcttcaca 171000
gactgaagat tgtcgagatt gtataccaaa aaggagatgt ccatgcggat actttggtgg 171060
aatagatgaa caaggaaatc ctatttgtaa atcgtgttgt gttggtgaat attgcgacta 171120
cctacgtaat tatagacttg atccatttcc tccatgcaaa ctatctaaat gtaattaatt 171180
atgattttga tgataatgtt accatacatt atatcgctac ttggttagtg tattattcag 171240
tatgaagacc tattaataat tacttatctt ttgacgatct tgttataatt ataatataaa 171300
aacttatggc atagtaactt ataattgctg acgcgataaa ttcgtaataa tctgttttgt 171360
tcaaaggaat ctacaggcat aaaaataaaa atataattta taatatactc ttacagcgcg 171420
ccatcatgaa taacagcagt gaattgattg ctgttattaa tggatttaga aatagtggac 171480
gattttgtga tattagtata gttattaatg atgaaaggat aaacgctcat aaactcatcc 171540
tatctggagc ctccgaatat ttttccattc tgttttccaa taattttatc gattctaatg 171600
aatacgaagt taatctaagt catttagatt atcaaagtgt taacgatttg atcgattata 171660
tttatgggat acctttgagc ctaactaacg ataacgtgaa atatattctt tcaaccgctg 171720
attttttaca aattggatct gccattactg agtgcgaaaa atacatactt aaaaatcttt 171780
gttctagaaa ctgtatcgat ttctacatat acgctgataa atataataac aagaaaatag 171840
aatcagcgtc gtttaacaca atattacaaa atattttgag actcatcaac gatgaaaact 171900
ttaaatactt aacagaggaa tcaatgataa aaattttaag cgatgatatg ttaaatataa 171960
aaaatgagga tttcgcccca ctaattctca ttaaatggtt agagagtact caacaatcat 172020
gcaccgtcga gttacttaga tgcctcagaa tatcattgct ttccccacaa gttataaaat 172080
cactttatag tcatcgactg gttagttcaa tctacgaatg tataacattc ttaaacaata 172140
tagcattctt ggatgaatca tttcctagat accatagcat cgagttgata tctatcggta 172200
taagtaattc gcatgataag atttccataa actgctacaa tcataaaaaa aatacatggg 172260
aaatgatatc ttcacgtaga tataggtgta gtttcgcagt ggccgtcctg gataatatta 172320
tttatatgat gggtggatat gatcagtccc cgtatagaag ttcaaaggtt atagcgtaca 172380
atacatgtac aaattcttgg atatatgata taccagagct aaaatatcct cgttctaatt 172440
gtgggggact ggctgatgac gaatacattt attgtatagg cggcatacgc gatcaggatt 172500
catcgttgac atctagtatt gatagatgga agccatcaaa accatattgg cagaagtatg 172560
ctaaaatgcg cgaaccaaaa tgtgatatgg gggttgcgat gttaaacgga ttaatatatg 172620
tcatgggtgg aatcgttaaa ggtgacacgt gtaccgacgc actagagagt ttatcagaag 172680
atggatggat gaagcatcaa cgtcttccaa taaaaatgtc caatatgtcg acgattgttc 172740
atgatggcaa gatttatata tctggaggtt acaacaatag tagtgtagtt aatgtaatat 172800
cgaatctagt ccttagctat aattcgatat atgatgaatg gaccaaatta tcatcattaa 172860
acattcctag aattaatccc gctctatggt cagcgcataa taaattatat gtaggaggag 172920
gaatatctga tgatgttcga actaatacat ctgagacata cgacaaagaa aaagattgtt 172980
ggacattgga taatggtcac gtgttaccac gcaattatat aatgtataaa tgcgaaccga 173040
ttaaacataa atatccattg gaaaaaacac agtacacgaa tgattttcta aagtatttgg 173100
aaagttttat aggtagttga tagaacaaaa tacataattt tgtaaaaata aatcactttt 173160
tatactaata tgacacgatt accaatactt ttgttactaa tatcattagt atacgctaca 173220
ccttctcctc agacatctaa aaaaataggt gatgatgcaa ctctatcatg taatcgaaat 173280
aatacaaatg actacgttgt tatgagtgct tggtataagg agcccaattc cattattctt 173340
ttagctgcta aaagcgacgt cttgtatttt gataattata ccaaggataa aatatcttac 173400
gactctccat acgatgatct agttacaact atcacaatta aatcattgac tgctagagat 173460
gccggtactt atgtatgtgc attctttatg acatcgccta caaatgacac tgataaagta 173520
gattatgaag aatactccac agagttgatt gtaaatacag atagtgaatc gactatagac 173580
ataatactat ctggatctac acattcaccg gaaactagtt ctgagaaacc tgattatata 173640
gataattcta attgctcgtc ggtattcgaa atcgcgactc cggaaccaat tactgataat 173700
gtagaagatc atacagacac cgtcacatac actagtgata gcattaatac agtaagtgca 173760
tcatctggag aatccacaac agacgagact ccggaaccaa ttactgataa agaagaagat 173820
catacagtca cagacactgt ctcatacact acagtaagta catcatctgg aattgtcact 173880
actaaatcaa ccaccgatga tacgtacaat gataatgata cagtaccacc aactactgta 173940
ggcggtagta caacctctat tagcaattat aaaaccaagg actttgtaga aatatttggt 174000
attaccgcat taattatatt gtcggccgtg gcaatattct gtattacgta ttatatatgt 174060
aataaacgtt cacgtaaata caaaacagag aacaaagtct agatttttga cttacataaa 174120
tgtctgggat agtaaaatct atcatattga gcggaccatc tggtttagga aagacagcca 174180
tagccaaaag actatgggaa tatatttgga tttgtggtgt cccataccac tagatttcct 174240
cgtcctatgg aacgagaagg tgtcgattac cattacgtta acagagaggc catctggaag 174300
ggaatagccg ccggaaactt tctagaacat actgagtttt taggaaatat ttacggaact 174360
tctaaaactg ctgtgaatac agcggctatt aataatcgta tttgtgtgat ggatctaaac 174420
atcgatggcg ttagaagtct taaaaatacg tacctaatgc cttactcggt gtatataaga 174480
cctacctctc ttaaaatggt tgagaccaag cttcgtcgta gaaacactga agcggatgat 174540
gagattcatc gtcgtgtgat gttggcaaaa actgacatgg atgaggcagg tgaagccggt 174600
ctattcgaca ctattattat tgaagatgat gtgaatttag catatagtaa gttaattcag 174660
atactacagg accgtattag aatgtatttt aacactaatt agagacttaa gacttaaaac 174720
ttgataatta ataatataac tcgtttttat atgtgtctat ttcaacgtct aatgtattag 174780
ttaaatatta aaacttacca cgtaaaactt aaaatttaaa atgatatttc attgacagat 174840
agatcacaca ttatgaactt tcaaggactt gtgttaactg acaattgcaa aaatcaatgg 174900
gtcgttggac cattaatagg aaaaggtgga ttcggtagta tttatactac taatgacaat 174960
aattatgtag taaaaataga gcccaaagct aacggatcat tatttaccga acaggcattt 175020
tatactagag tacttaaacc atccgttatc gaagaatgga aaaaatctca caatataaag 175080
cacgtaggtc ttatcacgtg caaggcattt ggtctataca aatccattaa tgtggaatat 175140
cgattcttgg taattaatag attaggtgca gatctagatg cggtgatcag agccaataat 175200
aatagattac caaaaaggtc ggtgatgttg atcggaatcg aaatcttaaa taccatacaa 175260
tttatgcacg agcaaggata ttctcacgga gatattaaag cgagtaatat agtcttggat 175320
caaatagata agaataaatt atatctagtg gattacggat tggtttctaa attcatgtct 175380
aatggcgaac atgttccatt tataagaaat ccaaataaaa tggataacgg tactctagaa 175440
tttacaccta tagattcgca taaaggatac gttgtatcta gacgtggaga tctagaaaca 175500
cttggatatt gtatgattag atggttggga ggtatcttgc catggactaa gatatctgaa 175560
acaaagaatt gtgcattagt aagtgccaca aaacagaaat atgttaacaa tactgcgact 175620
ttgttaatga ccagtttgca atatgaacct agagaattgc tgcaatatat taccatggta 175680
aactctttga catattttga ggaacccaat tacgacaagt ttcggcacat attaatgcag 175740
ggtgtatatt attaagtgtg gtgtttggtc gatgtaaaat ttttgtcgat aaaaattaaa 175800
aaataactta atttattatt gatctcgtgt gtacaaccga aatcatggcg atgttttacg 175860
cacacgctct cggtgggtac gacgagaatc ttcatgcctt tcctggaata tcatcgactg 175920
ttgccaatga tgtcaggaaa tattctgttg tgttagttta taataacaag tatgacattg 175980
taaaagacaa atatatgtgg tgttacagtc aggtgaacaa gagatatatt ggagcactgc 176040
tgcctatgtt tgagtgcaat gaatatctac aaattggaga tccgatccat gatcaagaag 176100
gaaatcaaat ctctatcatc acatatcgcc acaaaaacta ctatgctcta agcggaatcg 176160
ggtacgagag tctagacttg tgtttggaag gagtagggat tcatcatcac gtacttgaaa 176220
caggaaacgc tgtatatgga aaagttcaac atgattattc tactatcaaa gagaaggcca 176280
aagaaatgag tacacttagt ccaggaccta tcatcgatta ccacgtctgg ataggagatt 176340
gtatctgtca agttactgct gtggacgtac atggaaagga aattatgaga atgagattca 176400
aaaagggtgc ggtgcttccg atcccaaatc tggtaaaagt taaacttggg gagaatgata 176460
cagaaaatct ttcttctact atatcggcgg caccatcgag gtaaccacct ctctggaaga 176520
cagcgtgaat aatgtactca tgaaacgttt ggaaactata cgccatatgt ggtctgtcgt 176580
atatgatcat tttgatattg tgaatggtaa agaatgctgt tatgtgcata cgcatttgtc 176640
taatcaaaat cctataccga gtactgtaaa aacaaatttg tacatgaaga ctatgggatc 176700
atgcattcaa atggattcca tggaatctct agagtatctt agcgaactga aggaatcagg 176760
tggatggagt cccagaccag aaatgcagga atttgaatat ccagatggag tggaagacac 176820
tgaatcaatt gagagattgg tagaggagtt cttcaataga tcagaacttc aggctggtga 176880
atcagtcaaa tttggtaatt ctattaattg ttaaacatac atctgtttca gctaagcaac 176940
taagaacacg tatacggcag cagcttcctt tatactctca tcttttacca acacaaaggg 177000
tggatatttg ttcattggag ttgataataa tacacacaaa gtatttggat tcacggtggg 177060
ttacgactac ctcagactga tagagaatga tatagaaaag catatcaaaa gactttgtgt 177120
tgtgtatttc tgtgagaaga aagaggacat caagtacgcg tgtcgattca tcaaggtata 177180
taaacctggg gatgagacta ccttgacata cgtgtgcgct atcaaagtgg aaagatgctg 177240
ttgtgctgtg tttgcagatt ggccagaatc atggtatatg gatactaatg gtatcaagaa 177300
gtattctcca gatgaatggg tgtcacatat aaaattttaa ttaatgtaat agagaacaaa 177360
taataaggtt gtaatatcat atagacaata actaacaatt aattagtaac tgttatctct 177420
tttttaacta accaactaac tatataccta ttaatacatc gtaattatag ttcttaacat 177480
ctattaatca ttaattcgct tctttaattt tttataaact aacattgtta attgaaaagg 177540
gataacatgt tacagaatat aaattatata tggatttttt taaaaaggaa atacttgact 177600
ggagtatata tttatctctt cattatatag cacgcgtgtt ttccaatttt tccacatccc 177660
atataataca ggattataat ctcgttcgaa catacgagaa agtggataaa acaatagttg 177720
attttttatc taggttgcca aatttattcc atattttaga atatggggaa aatattctac 177780
atatttattc tatggatgat gctaatacga atattataat ttttttcta gatagagtat 177840 taaatattaa taagaacggg tcatttatac acaatctcgg gttatcatca tccattaata 177900
taaaagaata tgtatatcaa ttagttaata atgatcatcc agataatagg ataagactaa 177960
tgcttgaaaa tggacgtaga acaagacatt ttttgtccta tatatcagat acagttaata 178020
tctatatatg tattttaata aatcatggat tttatataga tgccgaagac agttacggtt 178080
gtacattatt acatagatgt atatatcact ataagaaatc agaatcagaa tcatacaatg 178140
aattaattaa gatattgtta aataatggat ccgatgtaga taaaaaagat acgtacggaa 178200
acacaccttt tatcctatta tgtaaacacg atatcaacaa cgtggaattg tttgagatat 178260
gtttagagaa tgctaatata gactctgtag actttaatag atatacacct cttcattatg 178320
tctcatgtcg taataaatat gattttgtaa agttattaat ttctaaagga gcaaatgtta 178380
atgcgcgtaa tagattcgga actactccat tttattgtgg aattatacac ggtatctcgc 178440
ttataaaact atatttggaa tcagacacag agttagaaat agataatgaa catatagttc 178500
gtcatttaat aattttgat gctgttgaat ctttagatta tctattatcc agaggagtta 178560
ttgatattaa ctatcgtact atatacaacg aaacatctat ttacgacgct gtcagttata 178620
atgcgtataa tacgttggtc tatctattaa acaaaaatgg tgattttgag acgattacta 178680
ctagtggatg tacatgtatt tcggaagcag tcgcaaacaa caacaaaata ataatggaag 178740
tactattgtc taaacgacca tctttgaaaa ttatgataca gtctatgata gcaattacta 178800
aacataaaca gcataatgca gatttattga aaatgtgtat aaaatatact gcgtgtatga 178860
ccgattatga tactcttata gatgtacagt cgctacagca atataaatgg tatattttaa 178920
gatgtttcga tgaaatagat atcatgaaga gatgttatat aaaaaataaa actgtattcc 178980
aattagtttt ttgtatcaaa gacattaata ctttaatgag atacggtaaa catccttctt 179040
tcgtgaagtg cactagtctc gacgtatacg gaagtcgtgt acgtaatatc atagcatcta 179100
ttagatatcg tcagagatta attagtctat tatccaagaa gctggatgcg ggagataaat 179160
ggtcgtgttt tcctaacgaa ataaaatata aaatattgga aaactttaac gataacgaac 179220
tatccacata tctaaaaatc ttataaacat tattaaaata taaaatctaa gtggataaaa 179280
tcacactaca tcattgtttc cttttagtgc tcgacagtgt atactatttt taacgctcat 179340
aaataaaaat gaaaacgatt tccgttgtta cgttgttatg cgtactacct gctgttgttt 179400
attcaacatg tactgtaccc actatgaata acgctaaatt aacgtctacc gaaacatcgt 179460
ttaatgataa acagaaagtt acatttacat gtgatcaggg atatcattct ttggatccaa 179520
atgctgtctg tgaaacagat aaatggaaat acgaaaatcc atgcaagaaa atgtgcacag 179580
tttctgatta tgtctctgaa ttatatgata agccattata cgaagtgaat tccaccatga 179640
cactaagttg caacggcgaa acaaaatatt ttcgttgcga agaaaaaaat ggaaatactt 179700
cttggaatga tactgttacg tgtcctaatg cggaatgtca acctcttcaa ttagaacacg 179760
gatcgtgtca accagttaaa gaaaaatact catttgggga atatatgact atcaactgtg 179820
atgttggata tgaggttatt ggtgcttcgt acataagttg tacagctaat tcttggaatg 179880
ttattccatc atgtcaacaa aaatgtgata tgccgtctct atctaacgga ttaatttccg 179940
gatctacatt ttctatcggt ggcgttatac atcttagttg taaaagtggt tttacactaa 180000
cggggtctcc atcatccaca tgtatcgacg gtaaatggaa tcccatactc ccaacatgtg 180060
tacgatctaa cgaaaaattt gatccagtgg atgatggtcc cgacgatgag acagatttga 180120
gcaaactctc gaaagacgtt gtacaatatg aacaagaaat agaatcgtta gaagcaactt 180180
atcatataat catagtggcg ttaacaatta tgggcgtcat atttttaatc tccgttatag 180240
tattagtttg ttcctgtgac aaaaataatg accaatataa gttccataaa ttgctaccgt 180300
aaatataaat ccgttaaaat aattaataat taataacgaa caagtatcaa aagattaaag 180360
acttatagct agaatcaatt gagatgtctt cttcagtgga tgttgatatc tacgatgccg 180420
ttagagcatt tttactcagg cactattata acaagagatt tattgtgtat ggaagaagta 180480
acgccatatt acataatata tacaggctat ttacaagatg cgccgttata ccgttcgatg 180540
atatagtacg tactatgcca aatgaatcac gtgttaaaca atgggtgatg gatacactta 180600
atggtataat gatgaatgaa cgcgatgttt ctgtaagcgt tggcaccgga atactattca 180660
tggaaatgtt tttcgattac aataaaaata gtatcaacaa tcaactaatg tatgatataa 180720
ttaatagcgt atctataatt ctagctaatg agagatatag aagcgctttt aacgacgatg 180780
gtatatacat ccgtagaaat atgattaaca agttgtacgg atacgcatct ctaactacta 180840
ttggcacgat cgctggaggt gtttgttatt atctgttgat gcatctagtt agtttgtata 180900
aataattatt tcaatatact agttaaaatt ttaagatttt aaatgtataa aaaactaata 180960
acgtttttat ttgtaatagg tgcattagca tcctattcga ataatgagta cactccgttt 181020
aataaactga gtgtaaaact ctatatagat ggagtagata atatagaaaa ttcatatact 181080
gatgataata atgaattggt gttaaatttt aaagagtaca caatttctat tattacagag 181140
tcatgcgacg tcggatttga ttccatagat ataaatgtta taaacgacta taaaattatt 181200
gatatgtata ccattgactc gtctactatt caacgcagag gtcacacgtg tagaatatct 181260
accaaattat catgccatta tgataagtac ccttatattc acaaatatga tggtgatgag 181320
cgacaatatt ctattactgc agagggaaaa tgctataaag gaataaaata tgaaataagt 181380
atgatcaacg atgatactct attgagaaaa catactctta aaattggatc tacttatata 181440
tttgatcgtc atggacatag taatacatat tattcaaaat atgattttta aaaatttaaa 181500
atatattatc acttcagtga cagtagtcaa ataacaaaca acaccatgag atatattata 181560
attctcgcag ttttgttcat taatagtata catgctaaaa taactagtta taagtttgaa 181620
tccgtcaatt ttgattccaa aattgaatgg actggggatg gtctatacaa tatatccctt 181680
aaaaattatg gcatcaagac gtggcaaaca atgtatacaa atgtaccaga aggaacatac 181740
gacatatccg catttccaaa gaatgatttc gtatctttct gggttaaatt tgaacaaggc 181800
gattataaag tggaagagta ttgtacggga ctatgcgtcg aagtaaaaat tggaccaccg 181860
actgtaacat tgactgaata cgacgaccat atcaatttgt acatcgagca tccgtatgct 181920
actagaggta gcaaaaagat tcctatttac aaacgcggtg acatgtgtga tatctacttg 181980
ttgtatacgg ctaacttcac attcggagat tctaaagaac cagtaccata tgatatcgat 182040
gactacgatt gcacgtctac aggttgcagc atagactttg tcacaacaga aaaagtgtgc 182100
gtgacagcac agggagccac agaagggttt ctcgaaaaaa ttactccatg gagttcgaaa 182160
gtatgtctga cacctaaaaa gagtgtatat acatgcgcaa ttagatccaa agaagatgtt 182220
cccaatttca aggacaaaat ggccagagtt atcaagagaa aatttaatac acagtctcaa 182280
tcttatttaa ctaaatttct cggtagcaca tcaaatgatg ttaccacttt tcttagcatg 182340
cttaacttga ctaaatattc ataactaatt tttattaatg atacaaaaac gaaataaaac 182400
tgcatattat acactggtta acgcccttat aggctctaac cattttcaag atgaggtccc 182460
tgattatagt ccttctgttc ccctctatca tctactccat gtctattaga caatgtgaga 182520

-continued aaactgaaga ggaaacatgg ggattgaaaa tagggttgtg tataattgcc aaagatttct 182580
atcccgaaag aactgattgc agtgttcatc tcccaactgc aagtgaagga ttgataactg 182640
aaggcaatgg attcagggat atacgaaaca ccgataaatt ataaaaaaag caatgtgtcc 182700
gctgtttccg ttaataatac tatttttgta actggcggat tattcataaa taactctaat 182760
agcacgatcg tggttaacaa tatggaaaaa cttgacattt ataaagacaa acaatggtcg 182820
attatagaaa tgcctatggc tagggtatat cacggcatcg actcgacatt tggaatgtta 182880
tattttgccg gaggtctatc cgttaccgaa caatatggta atttagagaa aaacaacgag 182940
atatcttgtt acaatcctag aacgaataag tggtttgata tttcatatac tatttataag 183000
atatccatat catcattgtg taaactaaat aacgtcttct atgtatttag taaggacatt 183060
ggatatgtgg aaaagtatga tggtgcatgg aagttagtac atgatcgtct ccccgctata 183120
aaggcattat caacttctcc ttattgattg aaaatgaaaa tataaatagt ttttatgtat 183180
agcagtatta ccctatagtt ttattgctta ctactaacat ggatacagat gttacaaatg 183240
tagaagatat cataaatgaa atagatagag agaaagaaga aatactaaaa aatgtagaaa 183300
ttgaaaataa taaaaacatt aacaagaatc atccaagtgg atatattaga gaagcactcg 183360
ttattaatac cagtagtaat agtgattcca ttgataaaga agttatagaa tgtatctgtc 183420
acgatgtagg aatatagatc atatctacta atttttataa tcgatacaaa acataaaaaa 183480
caactcgtta ttacatagca ggcatggaat ccttcaagta ttgttttgat aacgatggca 183540
agaaatggat tatcggaaat actttatatt ctggtaattc aatactctat aaggtcagaa 183600
aaaatttcac tagttcgttc tacaattacg taatgaagat agatcacaaa tcacacaagc 183660
cattgttgtc tgaaatacga ttctatatat ctgtattgga tcctttgact atcgacaact 183720
ggacacggga acgtggtata aagtatttgg ctattccaga tctgtatgga attggagaaa 183780
ccgatgatta tatgttcttc gttataaaga attcgggaag agtattcgcc ccaaaggata 183840
ctgaatcagt cttcgaagca tgcgtcacta tgataaacac gttagagttt atacactctc 183900
gaggatttac ccatggaaaa atagaaccga ggaatatact gattagaaat aaacgtcttt 183960
cactaattga ctattctaga actaacaaac tatacaagag tggaaactca catatagatt 184020
acaacgagga catgataact tcaggaaata tcaattatat gtgtgtagac aatcatcttg 184080
gagcaacagt ttcaagacga ggagatttag aaatgttggg atattgcatg atagaatggt 184140
tcggtggcaa acttccatgg aaaaacgaaa gtagtataaa agtaataaaa caaaaaaaag 184200
aatataaaaa atttatagct actttctttg aggactgttt tcctgaagga aatgaacctc 184260
tggaattagt tagatatata gaattagtat acacgttaga ttattctcaa actcctaatt 184320
atgacagact acgtaaactg tttatacaag attgaaatta tattcttttt ttatagagtg 184380
tggtagtgtt acggatattt aatattagac tatctctatc gcgctacacg accaatatcg 184440
attactatgg atatcttcta tgaaaggaga gaatgtattc atttctccag cgtcaatctc 184500
gtcagtattg acaatactgt attatggagc taatggatcc actgctgaac agctatcgaa 184560
atatgtagaa aaggaggaga acacggataa ggttagcgct cagaatatct cattcaaatc 184620
catgaataaa gtatatgggc gatattctgc cgtgtttaaa gattcctttt tgagaaaaat 184680
tggcgataag tttcaaactg ttgacttcac tgattgtcgc actatagatg caatcaacaa 184740
gtgtgtagat atctttactg aggggaaaat caatccacta ttggatgaac cattgtctcc 184800
tagcaattag tgccgtatac tttaaagcaa aatggttgac gccattcgaa aaggaattta 184860
ccagtgatta tccctttttac gtatcaccaa cggaaatggt agacgtaagt atgatgtcta 184920
tgtacggcga gctatttaat cacgcatctg taaaagaatc attcggcaac ttttcaatca 184980
tagaactgcc atatgttgga gatactagta tgatggtcat tcttccagac aagattgatg 185040
gattagaatc catagaacaa aatctaacag atacaaattt taagaaatgg tgtgacttta 185100
tggatgctat gtttatagat gttcacattc ccaagtttaa ggtaacaggt tcgtataatc 185160
tggtggatac tctagtaaag tcaggactga cagaggtgtt cggttcaact ggagattata 185220
gcaatatgtg taattcagat gtgagtgtcg acgctatgat ccacaaaacg tatatagatg 185280
tcaatgaaga gtatacagaa gcagctgcag caacttctgt actagtggca gactgtgcat 185340
caacagttac aaatgagttc tgtgcagatc atccgttcat ctatgtgatt aggcatgttg 185400
atggaaaaat tcttttcgtt ggtagatatt gctctccgac aactaattgt taaccatttt 185460
ttttaaaaaa aatagaaaaa acatgtggta ttagtgcagg tcgttattct tccaattgca 185520
attggtaaga tgacggccaa ctttagtacc cacgtctttt caccacagca ctgtggatgt 185580
gacagactga ccagtattga tgacgtcaaa caatgtttga ctgaatatat ttattggtcg 185640
tcctatgcat accgcaacag gcaatgcgct ggacaattgt attccacact cctctctttt 185700
agagatgatg cggaattagt gttcatcgac attcgcgagc tggtaaaaaa tatgccgtgg 185760
gatgatgtca aagattgtac agaaatcatc cgttgttata taccggatga gcaaaaaacc 185820
atcagagaga tttcggccat catcggactt tgtgcatatg ctgctactta ctggggaggt 185880
gaagaccatc ccactagtaa cagtctgaac gcattgtttg tgatgcttga gatgctaaat 185940
tacgtggatt ataacatcat attccggcgt atgaattgat gagttgtaca tcttgacatt 186000
ttctttcttc tcttctccct ttcttctctt ctcccttcct ccctcttctc cctttcccag 186060
aaacaaactt ttttacccac tataaaataa aatgagtata ctacctatta tatttcttcc 186120
tatatttttt tattcttcat tcgttcagac ttttaacgcg cctgaatgta tcgacaaagg 186180
gcaatatttt gcatcattca tggagttaga aaacgagcca gtaatcttac catgtcctca 186240
aataaatacg ctatcatccg gatataatat attagatatt ttatgggaaa aacgaggagc 186300
ggataatgat agaattatac cgatagataa tggtagcaat atgctaattc tgaacccgac 186360
acaatcagac tctggtattt atatatgcat taccacgaac gaaacctact gtgacatgat 186420
gtcgttaaat ttgacaatcg tgtctgtctc agaatcaaat atagatctta tctcgtatcc 186480
acaaatagta aatgagagat ctactggcga aatggtatgt cccaatatta atgcatttat 186540
tgctagtaac gtaaacgcag atattatatg gagcggacat cgacgcctta gaaataagag 186600
acttaaacaa cggacacctg gaattattac catagaagat gttagaaaaa atgatgctgg 186660
ttattataca tgtgttttag aatatatata cggtggcaaa acatataacg taaccagaat 186720
tgtaaaatta gaggtacggg ataaaataat accttctact atgcaattac cagatggcat 186780
tgtaacttca ataggtagta atttgactat tgcatgcaga gtatcgttga gacctcccac 186840
aacggacacc gacgtctttt ggataagtaa tggtatgtat tacgaagaag atgatgggga 186900
cggaaacggt agaataagtg tagcaaataa aatctatatg accgataaga gacgtgttat 186960
tacatcccgg ttaaacatta atcctgtcaa ggaagaagat gctacaacgt ttacgtgtat 187020
ggcgtttact attcctagca tcagcaaaac agttactgtt agtataacgt gaatgtatgt 187080
tgttacattt ccatgtcaat tgagtttata agaattttta tacattatct tccaacaaac 187140
aattgacgaa cgtattgcta tgattaactc ccacgatact atgcatatta ttaatcatta 187200
acttgcagac tatacctagt gctattttga catactcatg ttcttgtgta attgcggtat 187260
ctatattatt aaagtacgta aatctagcta tagttttatt atttaatttt agataatata 187320
ccgtctcctt atttttaaaa attgccacat cctttattaa atcatgaatg ggaatttcta 187380
tgtcatcgtt agtatattgt gaacaacaag agcagatatc tataggaaag ggtggaatgc 187440
gatacattga tctatgtagt tttaaaacac acgcaaactt tgaagaattt atataaatca 187500
ttccatcgat acatccttct atgttgagat gtatatatcc aggaattcgt ttattaatat 187560
cgggaaatgt ataaactaaa acattgcccg aaagcggtgc ctctatctgc gttatatccg 187620
ttcttaactt acaaaatgta accaatacct ttgcatgact tgttttgttc ggcaacgtta 187680
gtttaaactt gacgaatgga ttaattacaa tagcatgatc cgcgcatcta ttaagttttt 187740
ttactttaac gcccttgtat gtttttacag agactttatc taaatttcta gtgcttgtat 187800
gtgttataaa tataacggga tatagaactg aatcacctac cttagatacc caattacatt 187860
ttatcagatc cagataataa acaaattttg tcgccctaac taattctata ttgttatata 187920
ttttacaatt ggttatgata tcatgtaata acttggagtc taacgcgcat cgtcgtacgt 187980
ttatacaatt gtgatttagt gtagtatatc tacacatgta tttttccgca ctatagtatt 188040
ctggactagt gataaaacta tcgttatatc tatcttcaat gaactcatcg agatattgct 188100
ctctgtcata ttcatacacc tgcataaact ttctagacat cttacaatcc gtgttatttt 188160
aggatcatat ttacatattt acgggtatat caaagatgtt agattagtta atgggaatcg 188220
tctataataa tgaatattaa acaattatat gaggactttt accacaaagc atcataaaaa 188280
tgagtcgtcg tctgatttat gttttaaata tcaaccgcga atcaactcat aaaatacaag 188340
agaatgaaat atatacatat tttagtcatt gcaatataga ccatacttct acagaacttg 188400
attttgtagt taaaaactat gatctaaaca gacgacaaca tgtaactggg tatactgcac 188460
tacactgcta tttgtataat aattacttta caaacgatgt actgaagata ttattaaatc 188520
atggagtgga tgtaacgatg aaaaccagta gcggacgtat gcctgtttat atattgctta 188580
ctagatgttg taatatttca catgatgtag tgatagatat gatagacaaa gataaaaacc 188640
acttattaca tagagactat tccaacctat tactagagta tataaaatct cgttacatgt 188700
tattgaagga agaggatatc gatgagaaca tagtatccac tttattagat aagggaatcg 188760
atcctaactt taaacaagac ggatatacag cgttacatta ttattatttg tgtctcgcac 188820
acgtttataa accaggtgag tgtagaaaac cgataacgat aaaaaaggcc aagcgaatta 188880
tttctttgtt tatacaacat ggagctaatc taaacgcgtt agataattgt ggtaatacac 188940
cattccattt gtatcttagt attgaaatgt gtaataatat tcatatgact aaaatgctgt 189000
tgacttttaa tccgaatttc gaaatatgta ataatcatgg attaacgcct atactatgtt 189060
atataacttc cgactacata caacacgata ttcttgttat gttaatacat cactatgaaa 189120
caaatgttgg agaaatgccg atagatgagc gtcgtatgat cgtattcgag tttatcaaaa 189180
catattctac acgtccggca gattcgataa cttatttgat gaataggttt aaaaatataa 189240
atatttatac ccgctatgaa ggaaagacat tattacacgt agcatgtgaa tataataata 189300
cacaagtaat agattatctt atacgtatca acggagatat aaatgcgtta accgacaata 189360
acaaacacgc tacacaactc attatagata acaaagaaaa ttccccatat accattaatt 189420
gtttactgta tatacttaga tatattgtag ataagaatgt gataagatcg ttggtggatc 189480
aacttccatc tctacctatc tttcgtcgct tatcatacta gtcatatcct aaatgttgat 189540
catattccac caaatgattg tgaaagagat tgagattaaa tcgtctaaca aacaattagt 189600
ttttatgaca ttaacatata ataaataaat taatcattat tgacttaacg atgacgaaag 189660
ttatcatcat cttaggattc ttgattatta atacaaattc attgtctatg aaatgtgaac 189720
aaggtgtctc atattataat tcacaagaat taaagtgttg taaactatgt aagccaggaa 189780
catattcaga tcatcgatgt gataaataca gcgataccat ttgtggacat tgtccgagtg 189840
acacattcac gtcaatatat aatcgttctc cttggtgtca tagttgtaga ggtccatgtg 189900
gtactaatcg agtagaggtc acaccttgta cacctaccac aaatagaatc tgtcattgtg 189960
actcgaatag ttattgtctc cttaaagctt ctgatggtaa ctgtgttaca tgtgctccta 190020
aaacaaaatg tggtcgtggg tatggaaaga aaggagaaga tgaaatgggt aataccattt 190080
gtaagaaatg tcggaagggt acttattcag atattgtatc tgactctgat caatgtaaac 190140
caatgacaag ataagactta ctcgcatcta ctggatagac ataaaatatc ctcctcgtaa 190200
taatgaaata taaatataca ctaattatta atatcaataa caatcgagta ttaatatata 190260
ggtcattttt aaatcccttt tgggttccgt cccaaacggc gtttcggtct gcgtcgccgc 190320
catggccatg ccgagcctct ccgcgtgctc ctccatcgag gacgacttca actatggcag 190380
ctcggtggcg tctgccagcg tgcacatacg aatggcattt ctaagaaaag tctacggtat 190440
cctttgtcta caatttcttt taacaacggc aacaactgca gtatttttat actttgactg 190500
catgcggaca tttatacaag ggagtcctgt tctaatattg gcatcaatgt tcggatctat 190560
aggcttgatt ttcgcattga ctttacacag acataaacat cccctgaatc tgtacctgct 190620
ttgtggattt acactgtcgg aatctctaac gctggcctct gttgttactt tctatgatgt 190680
gcatgtcgtt atgcaagctt tcatgctgac tactgcagcg tttcttgctc tgactacata 190740
tactctacaa tcaaagagag atttcagtaa acttggagca ggattgtttg ctgctttgtg 190800
gattttaatt ttgtcaggac tcttggggat atttgtgcaa aatgagacag tgaagctggt 190860
cctgtctgct tttggggccc ttgtattctg tggattcatt atctatgaca cgcactcact 190920
aatacataag ctctcgcctg aagagtatgt gttagcctct atcaatctct acttggatat 190980
catcaatctg ttcttgcatc tgttgcagct tttggaagta tctaataaga aataaagttt 191040
aaaatagaat taataaaaac atataggtca ttttttaaac atggattgga aaccaaggta 191100
gttagttaat acacacaaga tatatttttt tcacatcatc cacccatggg taacaccaag 191160
gttgttagtt aataaatatac aagatatttt ttctcactct gatccatgta aaccaaggac 191220
gagataagac actctcattc ctcatccaca accccattaa aaaatggaaa ttaaagccct 191280
ctattagcat agacggctac aggtctacca tcaggttaac cttcgtctac cttcacaatg 191340
gcctttcctt gtgcccagtt cagaccctgt cattgccacg ctactaagga ctccctgaat 191400
accgtggccg acgtcagaca ttgtctgact gaatacatcc tgtgggtttc tcatagatgg 191460
acccatagag aaagcgcagg gtctctctac aggcttctca tctctttcag aactgatgca 191520
acggagctct ttggtggtga gttgaaggat tcacttccgt gggacaattg cgtggagatc 191580
attaaatgtt tcatcagaaa tgactccatg aaaaccgccg aagaacttcg tgcaatcatt 191640
ggactttgta ctcaatcagc tatcgtctct ggaagagtct tcaacgataa gtatatcgac 191700
atactactta tgctgcgaaa gattctgaac gagaacgact atctcaccct cttggatcat 191760
atccgcactg ctaaatacta aatctccttc atgctctctc actacacttt ttatcatctt 191820
atgaggaatg attgccttta tcatttttcg tgaaatagga ataattagca ccagaatagc 191880
tatggattat tgtggtagag agtgcactat tctatgtcgt ctactggatg aagatgtgac 191940
gtacaaaaaa ataaaactag aaattgaaac gtgtcacaac ttatcaaaac atatagatag 192000
acgaggaaac aatgcgctac attgttacgt ctccaataaa tgcgatacag acattaagat 192060
tgttcggctg ttactctctc gcggagtcga gagactttgt agaaacaacg aaggattaac 192120
tccgctagga gtatacagta agcatagata cgtaaaatct cagattgtgc atctactgat 192180
atccagctat tcaaattcct ctaacgaact caagtcgaat ataaatgatt tcgatctgta 192240
ttcggataat atcgacttac gtctgctaaa atacctaatt gtggataaac ggatacgtcc 192300
gtccaagaat acgaattatg caatcaatgg tctcggattg gtggatatat acgtaacgac 192360
gcctaatccg agaccagaag tattgctatg gcttcttaaa tcagaatgtt acagcaccgg 192420
ttacgtattt cgtacctgta tgtacgacag tgatatgtgt aagaactctc ttcattacta 192480
tatatcgtct catagagaat ctcaatctct atccaaggat gtaattaaat gtttgatcga 192540
taacaatgtt tccatccatg gcagagacga aggaggatct ttacccatcc aatactactg 192600
gtcttgctca accatagata tagagattgt taaattatta ttaataaagg atgtggacac 192660
gtgtagagta tacgacgtca gccctatatt agaggcgtat tatctaaaca agcgatttag 192720
agtaacccca tataatgtag acatggaaat cgttaatctt cttattgaga gacgtcatac 192780
tcttgtcgac gtaatgcgta gtattacttc gtacgattcc agagaatata accactacat 192840
catcgataac attctaaaga gatttagaca acaggatgta caagccatgt tgataaacta 192900
cttacattac ggcgatatgg taagtatacc tatcattcaa tgcatgttgg ataacggagc 192960
aaccatggat aagacgacgg acaacaacta tcctctacac gactactttg ttaataataa 193020
tctcgtcgat gtaaacgtcg taaggtttat cgtggaaaat atggacacgc ggctgtaaat 193080
cacgtatcga acaatggccg tctatgtatg tacggtctga tattatcgag atttaataat 193140
tgcgggtatc actgttatga aaccatacta atagatgtat ttgatatact aagcaagtac 193200
atggatgata tagatatgat cgataactct actatattac gcggtcgatg tcaataatat 193260
acaatttgca aagcggttat tggaatatgg agcgagtgtt acaacatcac gctcgataat 193320
caatacggcc atccagaaaa gcagttacca aagagaaaac aaaacgagga tagttgattt 193380
attacttagc taccatccca ctctagagac tatgattgac gcatttaata gagatatacg 193440
ctatctatat cctgaaccat tattcgcctg tatcagatac gccttaatca tagatgatga 193500
ttttccttct aaagtaaagt atgatatcgc cggtcgtcat aaggaactaa agcgctatag 193560
agcagacatt aatagaatga agaatgccta catatcaggc gtctccatgt ttgatatatt 193620
atttaaacaa agcaaacgcc acagactgag atacgcaaag aatccgacat caaatggtac 193680
aaaaaagaac taacgtccat cattacagaa actgtaaaga acaatgagag gatcgactcc 193740
atagtggaca acattaatac agacgataac ttgatttcga aattacccat ggagatactt 193800
tattactcca ttaaataatt tatcatggag cgataatgtc ctgtttcatt tgtttccatg 193860
acatattaca aaatcgattc cgtccaagat gataaaaaca tttaccggca tcataaacac 193920
ggagtttatt ttatatgtct cgcataaaca ttactaaaaa aatatattgt tctgtttttc 193980
tttcacatct ttaattatga aaaagtaaat cattatgaga tggacgagat tgtacgcatc 194040
gttcgcgaca gtatgtggta catacctaac gtatttatgg acgacggtaa gaatgaaggt 194100
cacgtttctg tcaacaatgt ctgtcatatg tatttcacgt tctttgatgt gaatacatcg 194160
tctcatctgt ttaagctagt tattaaacac tgcgatctga ataaacgagg taactctcca 194220
ttacattgct atacgatgaa tacacgattt aatccatctg tattaaagat attgttacac 194280
cacggcatgc gtaactttga tagcaaggat gaccactatc aatcgataac aagatctttg 194340
atatactaac ggacaccatt gatgacttta gtaaatcatc cgatctattg ctgtgttatc 194400
ttagatataa attcaatggg agcttaaact attacgttct gtacaaagga tccgacccta 194460
attgcgccga cgaggatgaa ctcacttctc ttcattacta ctgtaaacac atatccacgt 194520
tctacgaaag caattattac aagtcaagtc acactaagat gcgagccgag aagcgattca 194580
tctacgcgat aatagattat ggagcaaaca ttaacgcggt tacacactta ccttcaacag 194640
tataccaaac atagtcctcg tgtggtgtat gctcttttat ctcgaggata cgtaataatc 194700
ttgattgtac acccatcatg gaacgattgt gcaacaggtc atattctcat aatgttactc 194760
aattggcacg aacaaaagga agaaggacaa catctacttt atctattcat aaaacataat 194820
caaggataca ctctcaatat actacggtat ctattagata ggttcgacat tcagaaagac 194880
gaatactata ataccgcctt tcaaaattgt aacaacaatg ttgcctcata catcggatac 194940
gacatcaacc ttccgactaa agacggtatt cgacttggtg tttgaaaaca gaaacatcat 195000
atacaaggcg gatgttgtga atgacatcat ccaccacaga ctgaaagtat ctctacctat 195060
gattaaatcg ttgttctaca agatgtctct ccctacgacg attactacgt aaaaaagata 195120
ctagcctact gcctattaag ggacgagtca ttcgcggaac tacatagtaa attctgttta 195180
aacgaggact ataaaagtgt atttatgaaa aatatatcat tcgataagat agattccatc 195240
atcgtgacat aagtcgcctt aaagagattc gaatctccga caccgacctg tatacggtat 195300
cacagctatc ttaaagccat acattcagac agtcacattt catttcccat gtacgacgat 195360
ctcatagaac agtgccatct atcgatggag cgtaaaagta aactcgtcga caaagcactc 195420
aataaattag agtctaccat cggtcaatct agactatcgt atttgcctcc ggaaattatg 195480
cgcaatatca tctaaacagt atgttgtacg gaaagaacca ttacaaatat tatccatgat 195540
agaaagaaaa tatctatatg attggagaag taggaaacag gaacaagacg acgattacta 195600
cattattaaa tcatgaagtc cgtattatac tcgtatatat tgtttctctc atgtataata 195660
ataaacggaa gagatatagc accgcatgca ccatccgatg gaaagtgtaa agacaacgaa 195720
tacaaacgcc ataatttgtg tccgggaaca tacgcttcca gattatgcga tagcaagact 195780
aacacacaat gtacgccgtg tggttcgggt accttcacat ctcgcaataa tcatttaccc 195840
gcttgtctaa gttgtaacgg aagacgcgat cgtgtaacac gactcacaat agaatctgtg 195900
aatgctctcc cggatattat tgtcttctca aaggatcatc cggatgcaag gcatgtgttt 195960
cccaaacaaa atgtggaata ggatacggag tatccggaga cgtcatctgt tctccgtgtg 196020
gtctcggaac atattctcac accgtctctt ccgcagataa atgcgaaccc gtacccagta 196080 ataccttaa ctatatcgat gtggaaatta atctgtatcc agttaacgac acgtcgtgta 196140
ctcggacgac cactaccggt ctcagcgaat ccatctcaac gtcggaacta actattacta 196200
tgaatcataa agactgcgat cccgtctttc gtgatggata cttctccgtc cttaataagg 196260
tagcgacttc aggtttcttt acaggagaaa ggtgtgcact ctgaatttcg agattaaatg 196320
caataacaaa gattcttcct ccaaacagtt aacgaaagca aagaatgata ctatcatgcc 196380
gcattcggag acagtaactc tagtgggcga catctatata ctatatagta ataccaatac 196440
tcaagactac gaaactgata caatctctta tcatgtgggt aatgttctcg atgtcgatag 196500
ccatatgccc ggtagttgcg atatacataa actgatcact aattccaaac ccacccactt 196560
tttatagtaa gtttttcacc cataaataat aaatacaata attaatttct cgtaaaagta 196620
gaaaatatat tctaatttat tgcacggtaa ggaagtagaa tcataaagaa cagtactcaa 196680
tcaatagcaa ttatgaaaca atatatcgta ctggcatgca tgtgcctggc ggcagctgct 196740
atgcctgcca gtcttcagca atcatcctca tcctcctcct cgtgtacgga agaagaaaac 196800
aaacatcata tgggaatcga tgttattatc aaagtcacaa agcaagacca aacaccgacc 196860
aatgataaga tttgccaatc cgtaacggaa attacagagt ccgagtcaga tccagatccc 196920
gaggtggaat cagaagatga ttccacatca gtcgaggatg tagatcctcc taccacttat 196980
tactccatca tcggtggagg tctgagaatg aactttggat tcaccaaatg tcctcagatt 197040
aaatccatct cagaatccgc tgatggaaac acagtgaatg ctagattgtc cagcgtgtcc 197100
ccaggacaag gtaaggactc tcccgcgatc actcatgaag aagctcttgc tatgatcaaa 197160
gactgtgagg tgtctatcga catcagatgt agcgaagaag agaaagacag cgacatcaag 197220
acccatccag tactcgggtc taacatctct cataagaaag tgagttacga agatatcatc 197280
ggttcaacga tcgtcgatac aaaatgtgtc aagaatctag agtttagcgt tcgtatcgga 197340
gacatgtgca aggaatcatc tgaacttgag gtcaaggatg gattcaagta tgtcgacgga 197400
tcggcatctg aaggtgcaac cgatgatact tcactcatcg attcaacaaa actcaaagcg 197460
tgtgtctgaa tcgataactc tattcatctg aaattggatg agtagggtta atcgaacgat 197520
tcaggcacac cacgaattaa aaaagtgtac cggacactat attccggttt gcaaaacaaa 197580
aatgttctta actacattca caaaaagtta cctctcgcga cttcttcttt ttctgtctca 197640
atagtgtgat acgattatga cactattcct attcctattc ctattcctat ttcctttcag 197700
ggtatcacaa aaatattaaa cctctttctg atggtctcat aaaaaaagtt ttacaaaaat 197760
atttttattc tctttctctc tttgatggtc tcataaaaaa agttttacaa aaatattttt 197820
attctctttc tctctttgat ggtctcataa aaaaagtttt acaaaaatat ttttattctc 197880
tttctctctt tgatggtctc ataaaaaaag ttttacaaaa atatttttat tctctttctc 197940
tctttgatgg tctcataaaa aaagttttac aaaaatattt ttattctctt tctctctttg 198000
atggtctcat aaaaaaagtt ttacaaaaat atttttattc tctttctctc tttgatggtc 198060
tcataaaaaa agttttacaa aaatattttt attctctttc tctctttgat ggtctcataa 198120
aaaaagtttt acaaaaatat ttttattctc tttctctctt tgatggtctc ataaaaaaag 198180
ttttacaaaa atatttttat tctctttctc tctttgatgg tctcataaaa aaagttttac 198240
aaaaatattt ttattctctt tctctctttg atggtctcat aaaaaaagtt ttacaaaaat 198300
atttttattc tctttctctc tttgatggtc tcataaaaaa agttttacaa aaatattttt 198360
attctctttc tctctttgat ggtctcataa aaaaagtttt acaaaaatat ttttattctc 198420
tttctctctt tgatggtctc ataaaaaaag ttttacaaaa atatttttat tctctttctc 198480
tctttgatgg tctcataaaa aaagttttac aaaaatattt ttattctctt tctctctttg 198540
atggtctcat aaaaaaagtt ttacaaaaat atttttattc tctttctctc tttgatggtc 198600
tcataaaaaa agttttacaa aaatattttt attctctttc tctctttgat ggtctcataa 198660
aaaaagtttt acaaaaatat ttttattctc tttctctctt tgatggtctc ataaaaaaag 198720
ttttacaaaa atatttttat tctctttctc tctttgatgg tctcataaaa aaagttttac 198780
aaaaatattt ttattctctt tctctctttg atggtctcat aaaaaaagtt ttacaaaaat 198840
atttttattc tctttctctc tttgatggtc tcataaaaaa agttttacaa aaatattttt 198900
attctctttc tctctttgat ggtctcataa aaaaagtttt acaaaaatat ttttattctc 198960
tttctctctt tgatggtctc ataaaaaaag ttttacaaaa atatttttat tctctttctc 199020
tctttgatgg tctcataaaa aaagttttac aaaaatattt ttattctctt tctctctttg 199080
atggtatcat aaaaaaagtt ttacaaaaat atttttattc tctttctctc tttgatggtc 199140

-continued

```
tcataaaaaa agttttacaa aaatattttt attctctttc tctctttgat ggtctcataa 199200
aaaaagtttt acaaaaatat ttttattctc tttctctctt tgatggtctc ataaaaaaag 199260
ttttacaaaa atatttttat tctctttctc tctttgatgg tctcataaaa aaagttttac 199320
aaaaatattt ttattctctt tctctctttg atggtctcat aaaaaaagtt ttacaaaaat 199380
atttttattc tctttctctc tttgatggtc tcataaaaaa agttttacaa aaatattttt 199440
attctctttc tctctttgat ggtctcataa aaaaagtttt acaaaaatat ttttattctc 199500
tttctctctt tgatggtctc ataaaaaaag ttttacaaaa atatttttat tctctttctc 199560
tctttgatgg tctcataaaa aaagttttac aaaaatattt ttattctctt tctctctttg 199620
atggtctcat aaaaaaagtt ttacaaaaat atttttattc tctttctctc tttgatggtc 199680
tcataaaaaa agttttacaa aaatattttt attctctttc tctctttgat ggtctcataa 199740
aaaaagtttt acaaaaatat ttttattctc tttctctctt tgatggtctc ataaaaaaag 199800
ttttacaaaa atatttttat tctctttctc tctttgatgg tctcataaaa aaagttttac 199860
aaaaatattt ttattctctt tctctctttg atggtctcat aaaaaaagtt ttacaaaaat 199920
atttttattc tctttctctc tttgatggtc tcataaaaaa agttttacaa aaatattttt 199980
attctctttc tctctttgat ggtctcataa aaaaagtttt acaaaaatat ttttattctc 200040
tttctctctt tgatggtctc ataaaaaaag ttttacaaaa atatttttat tctctttctc 200100
tctttgatgg tctcataaaa aaagttttac aaaaatattt ttattctctt tctctctttg 200160
atggtctcat aaaaaaagtt ttacaaaaat atttttattc tctttctctc tttgatggtc 200220
tcataaaaaa agttttacaa aaatattttt attttctttc tctctttgat ggtctcataa 200280
aaaatattaa acctctttct gatggtgtca ctaaaatatt tttattctca ttctcatttt 200340
ctctttctct cttcaatgga gtcataaaat atttttattc tctttctctc ttcgatggtc 200400
tcacaaaaat attaaacctc tttctgatgg tgtcactaaa atatttttat tctcattctc 200460
attttctctt tctctcttca atggagtcat aaaatatttt tattctcttt ctctcttcga 200520
tggtctcaca aaaatattaa acctctttct gatggagtcg taaaaaaagtt ttatctcttt 200580
ctctcttcga tggtctcact aaaatatttt ttattctctt tctgatgcat caactatttc 200640
ttaaacaata acgtccaaca acatatactc gtcgagctta tcaacatccc ctatgcccat 200700
ctaggttacc agacaattgt atatcataaa ataatgttta taatttacac gttaaaatca 200760
tataataaaa cgtagatcgt ataatatttt ttggtatata aatgatctag taaaatccat 200820
gtaggggata ctgctcacat tttttctttg gtacaaaatt tcacacaagt ttttatacag 200880
acaaattctt gtccatatat tttaaaacat tgacttttgt actaagaaaa atatctagac 200940
taactatctc tttctctttc tctcttcgat ggtctcacaa aaatattaaa cctctttctg 201000
atggagtcgt aaaaaagttt tatctctttc tctcttcgat ggtctcacaa aaatattaaa 201060
cctctttctg atggagtcgt aaaaaagttt tatctctttc tctcttcgat ggtctcacaa 201120
aaatattaaa cctctttctg atggagtcgt aaaaaagttt tatctctttc tctcttcgat 201180
ggtctcacaa aaatattaaa cctctttctg atggagtcgt aaaaaagttt tatctctttc 201240
tctcttcgat ggtctcacaa aaatattaaa cctctttctg atggagtcgt aaaaaagttt 201300
tatctctttc tctcttcgat ggtctcacaa aaatattaaa cctctttctg atggagtcgt 201360
aaaaaagttt tatctctttc tctcttcgat ggtctcacaa aaatattaaa cctctttctg 201420
atggagtcgt aaaaaagttt tatctctttc tctcttcgat ggtctcacaa aaatattaaa 201480
```

cctctttctg atggagtcgt aaaaaagttt tatctctttc tctcttcgat ggtctcacaa 201540
aaatattaaa cctctttctg atggagtcgt aaaaaagttt tatctctttc tctcttcgat 201600
ggtctcacaa aaatattaaa cctctttctg atggagtcgt aaaaaagttt tatctctttc 201660
tctcttcgat ggtctcacaa aaatattaaa cctctttctg atggagtcgt aaaaaagttt 201720
tatctctttc tctcttcgat ggtctcacaa aaatattaaa cctctttctg atggagtcgt 201780
aaaaaagttt tatctctttc tctcttcgat ggtctcacaa aaatattaaa cctctttctg 201840
atggagtcgt aaaaaagttt tatctctttc tctcttcgat ggtctcacaa aaatattaaa 201900
cctctttctg atggagtcgt aaaaaagttt tatctctttc tctcttcgat ggtctcacaa 201960
aaatattaaa cctctttctg atggagtcgt aaaaaagttt tatctctttc tctcttcgat 202020
ggtctcacaa aaatattaaa cctctttctg atggagtcgt aaaaaagttt tatctctttc 202080
tctcttcgat ggtctcacaa aaatattaaa cctctttctg atggagtcgt aaaaaagttt 202140
tatctctttc tctcttcgat ggtctcacaa aaatattaaa cctctttctg atggagtcgt 202200
aaaaaagttt tatctctttc tccttcgatg gtctcacaaa aatattaaac ctctttctga 202260
tggagtcgta aaaaagtttt atctctttct ctcttcgatg gtctcacaaa aatattaaac 202320
ctctttctga tggagtcgta aaaaagtttt atctctttct ctcttcgatg gtctcacaaa 202380
aatattaaac ctctttctga tggtctctat aaagcgatcg atctttctta cactctagag 202440
tttcctacag tcatgggtca cacatttttt tctagacact aaataaaat 202489

<210> SEQ ID NO 22
<211> LENGTH: 908
<212> TYPE: DNA
<213> ORGANISM: Artificial Sequence
<220> FEATURE:
<223> OTHER INFORMATION: polynucleotide comprising p7.5k promoter-DsReD

<400> SEQUENCE: 22
cctgcaggtc aattcggtag ttgcgatata cataaactga tcactaattc caaacccacc 60
cactttttat agtaagtttt tcacccataa ataataaata caataattaa tttctcgtaa 120
aagtagaaaa tatattctaa tttattgcac ggtaaggaag tagtcgaaac gaattcgccc 180
ttgcttgcaa gccaccatgg cctcctccga ggacgtcatc aaggagttca tgcgcttcaa 240
ggtgcgcatg gagggctccg tgaacggcca cgagttcgag atcgagggcg agggcgaggg 300
ccgcccctac gagggcaccc agaccgccaa gctgaaggtg accaagggcg gcccccctgcc 360 cttcgcctgg gacatcctgt ccccccagtt ccagtacggc tccaaggtgt acgtgaagca 420
ccccgccgac atccccgact acaagaagct gtccttcccc gagggcttca agtgggagcg 480
cgtgatgaac ttcgaggacg gcggcgtggt gaccgtgacc caggactcct ccctgcagga 540
cggctccttc atctacaagg tgaagttcat cggcgtgaac ttcccctccg acggccccgt 600
aatgcagaag aagactatgg gctgggaggc ctccaccgag cgcctgtacc cccgcgacgg 660
cgtgctgaag ggcgagatcc acaaggccct gaagctgaag gacggcggcc actacctggt 720
ggagttcaag tccatctaca tggccaagaa gcccgtgcag ctgcccggct actactacgt 780
ggactccaag ctggacatca cctcccacaa cgaggactac accatcgtgg agcagtacga 840
gcgcgccgag ggccgccacc acctgttcct gtaggcgcgc ctataagggc gaattcgcgg 900
cctcgacg 908

<210> SEQ ID NO 23
<211> LENGTH: 2349

```
<212> TYPE: DNA
<213> ORGANISM: Artificial Sequence
<220> FEATURE:
<223> OTHER INFORMATION: polynucleotide comprising mouse IL-12

<400> SEQUENCE: 23

accggtcgcc accatgtgcc ctcagaaact gaccatctca tggttcgcca ttgttctgtt      60

ggtcagtccc ctgatggcca tgtgggaact ggagaaagac gtctatgtgg tggaggtcga     120

ttggacccca gatgctcctg gagagactgt gaacctgacc tgtgatacac ctgaggagga     180

cgacattacg tggactagtg accagagaca tggggtgatt ggaagtggta agaccctgac     240

aatcacagtc aaagaattcc tggatgcagg gcagtatacg tgtcacaaag gcggcgaaac     300

gctctcccat tcccacttgc tccttcacaa gaaggagaat ggcatttggt ctacagagat     360

cctcaagaac tttaagaaca agacctttct gaagtgcgaa gcacccaact atagcggtag     420

gtttacttgc agttggctgg tacagcgaaa tatggacctc aaattcaaca tcaaaagctc     480

tagcagctct cccgattctc gtgccgtgac ctgtgggatg gcctctcttt ccgccgagaa     540

agtcaccctg gaccaaagag actacgagaa gtattcagtg agctgtcaag aagatgtgac     600

atgcccaaca gctgaggaaa cccttcccat cgaattggct ctggaagcta gacagcagaa     660

caagtacgaa aactactcca ctagcttctt catacgcgac atcatcaagc cagatcctcc     720

gaagaatctg cagatgaagc ccctgaagaa ctctcaggtc gaagttagct gggagtatcc     780

ggactcctgg tcaactccac actcctactt ttcactgaag ttcttcgtga ggatacagag     840

gaagaaggag aaaatgaaag agactgagga gggatgtaat cagaaaggag cctttctcgt     900

ggaaaagacc agtacagagg ttcaatgcaa aggcggcaat gtatgcgttc aagcgcagga     960

tcggtactac aatagcagct gttccaagtg ggcatgcgtg ccttgtcggg tacgctcatg    1020

atgcatctag ggcggccaat tccgcccctc tccctccccc ccccctaacg ttactggccg    1080

aagccgcttg gaataaggcc ggtgtgcgtt tgtctatatg tgattttcca ccatattgcc    1140

gtcttttggc aatgtgaggg cccggaaacc tggccctgtc ttcttgacga gcattcctag    1200

gggtctttcc cctctcgcca aaggaatgca aggtctgttg aatgtcgtga aggaagcagt    1260

tcctctggaa gcttcttgaa gacaaacaac gtctgtagcg accctttgca ggcagcggaa    1320

ccccccacct ggcgacaggt gcctctgcgg ccaaaagcca cgtgtataag atacacctgc    1380

aaaggcggca caaccccagt gccacgttgt gagttggata gttgtggaaa gagtcaaatg    1440

gctctcctca agcgtattca acaaggggct gaaggatgcc cagaaggtac cccattgtat    1500

gggatctgat ctggggcctc ggtgcacatg ctttacatgt gtttagtcga ggttaaaaaa    1560

acgtctaggc cccccgaacc acggggacgt ggttttcctt tgaaaaacac gatgataagc    1620

ttgccaatgg tgtcagtccc taccgcttct cctagtgcct catccagcag ctctcagtgt    1680

cgtagcagca tgtgccaatc acggtacctg ttgttccttg ctactctcgc tctgctcaac    1740

cacctgtctt tggcacgcgt gattccggtt tccggtcctg cgagatgcct gtcacagtcc    1800

cggaatctgc tgaaaaccac cgatgacatg gtcaagacag ccagagagaa gctgaagcac    1860

tacagttgca ctgcagagga tatagaccac gaagatatca cgcgagatca aaccagcaca    1920

ctgaaaacat gcttgccact cgagttgcat aagaacgagt cttgtcttgc cactagagaa    1980

acctctagca ccacaagggg cagttgtctc ccaccccaga aaacgtccct gatgatgaca    2040

ctgtgtcttg gaagcatcta tgaggacctg aagatgtacc agacagagtt tcaggccata    2100

aatgccgctc tgcagaacca caaccatcag cagattatcc tggacaaagg gatgcttgtc    2160
```

-continued

```
gccattgacg agctgatgca aagcctgaat cacaacggcg aaactctgcg acagaaacca   2220

cccgtaggag aagcagaccc ctatagggtg aagatgaagc tctgcatcct cctccatgca   2280

ttctccacta gggtggtgac catcaatcgc gttatggggt atctgagttc cgcttgagct   2340

agcgaattc                                                           2349
```

GENETICALLY ENGINEERED VACCINIA VIRUSES

CROSS-REFERENCE TO RELATED APPLICATIONS

This application is Continuation of PCT/JP2017/019921, filed May 29, 2017, which claims priority from Japanese application JP 2016-107481, filed May 30, 2016.

The instant application contains a Sequence Listing which has been submitted in ASCII format via EFS-WEB and is hereby incorporated by reference in its entirety. Said ASCII copy, created on Jul. 27, 2017, is named sequence.txt and is 275 KB.

BACKGROUND OF THE INVENTION

Field of the Invention

The present invention relates to a novel genetically engineered vaccinia virus.

Description of the Related Art

Various techniques for using viruses for cancer treatments have been recently developed. Vaccinia virus is one of the viruses used for cancer treatment. Vaccinia virus has been studied for the cancer treatment as a vector for delivering therapeutic genes to cancer cells, as an oncolytic virus that proliferates in cancer cells and destroys the cancer cells, or as a cancer vaccine that expresses tumor antigens or immunomodulatory molecules (Expert Opinion on Biological Therapy, 2011, vol. 11, p. 595-608).

Vaccinia viruses engineered so as to have an N1L gene inactivated by the insertion of a foreign gene encoding interleukin-12 (IL-12) or interleukin-21 (IL-21) and to be deficient in the thymidine kinase (TK) gene by the insertion of the lacZ reporter gene and the firefly luciferase gene have been reported to suppress the tumor growth or improve the survival rate in cancer-bearing mice (Patent Literature 1).

A technique for employing, for cancer treatment, recombinant vaccinia viruses that are deficient in the function of the viral proteins vaccinia virus growth factor (VGF) and O1L and proliferate specifically in cancer cells and destroy the cancer cells has been reported. Although it is stated that a foreign gene such as a marker gene or a therapeutic gene encoding a product having cytotoxicity or the immunopotentiating effect may be introduced into a gene that is not essential to the life cycle of vaccinia virus, the introduction of a gene specifically examined in Examples is that of a marker gene, a luciferase-green fluorescent protein (GFP) fusion gene or an expression cassette of DsRed. No therapeutic gene is examined for the introduction. No suggestion is made for combining plural therapeutic genes (Patent Literature 2).

Meanwhile, it has been reported that, in the examination of effects of recombinant proteins on isolated $CD8^+$T cells, a recombinant human interleukin-7 (IL-7) protein alone does not induce detectable levels of interferon-gamma (IFN-γ) production by $CD8^+$T cells, but a combination of the recombinant human IL-7 protein and a recombinant human IL-12 protein synergistically enhances the production of IFN-γ (The Journal of Immunology, 1995, vol. 154, p. 5093-5102). It has been reported that an oncolytic vaccinia virus that expresses an immune-stimulating molecule may rapidly be cleared by strong immune responses. It is also stated that strong immune response could serve either as a foe or as an ally to the vaccinia virus-mediated cancer therapy (Molecular Therapy, 2005, vol. 11, No. 2, p. 180-195).

CITATION LIST

Patent Literatures

Patent Literature 1: WO2015/150809
Patent Literature 2: WO2015/076422

SUMMARY OF THE INVENTION

Technical Problem

An object of the present invention is to provide a recombinant vaccinia virus (in particular, oncolytic vaccinia virus), a pharmaceutical composition and a combination kit, for treating or preventing cancer.

Solution to Problem

As a result of considerable repetitive thinking and studies in the generation of vaccinia virus, the present inventors have generated vaccinia viruses comprising a polynucleotide encoding IL-7 or vaccinia viruses comprising a polynucleotide encoding IL-12, and vaccinia viruses comprising two polynucleotides, a polynucleotide encoding IL-7 and a polynucleotide encoding IL-12 (Example 2); and found that 1) a vaccinia virus comprising two polynucleotides, a polynucleotide encoding IL-7 and a polynucleotide encoding IL-12 and 2) a mixture of two vaccinia viruses, a vaccinia virus comprising a polynucleotide encoding IL-7 and a vaccinia virus comprising a polynucleotide encoding IL-12 exhibit a cytolytic effect on various human cancer cells (Example 3), thereby completing the present invention: 1) a vaccinia virus comprising two polynucleotides, a polynucleotide encoding IL-7 and a polynucleotide encoding IL-12 could exhibit a tumor regression effect in cancer-bearing humanized mouse models (Example 6), could achieve complete remission (Example 7), and could induce acquired immunity to maintain the antitumor effect (Example 8) in syngeneic cancer-bearing mouse models. Moreover, 2) a mixture of two vaccinia viruses, a vaccinia virus comprising a polynucleotide encoding IL-7 and a vaccinia virus comprising a polynucleotide encoding IL-12 could achieve complete remission (Example 7), and could induce acquired immunity to maintain the antitumor effect (Example 8) in syngeneic cancer-bearing mouse models.

More specifically, the present invention may encompass, as a substance or method useful in medicine or industry, the following inventions:

[1] A vaccinia virus comprising the following (1) and (2):
(1) a polynucleotide encoding interleukin-7 (IL-7); and
(2) a polynucleotide encoding interleukin-12 (IL-12).

[2] A pharmaceutical composition selected from the following (1) or (2):
(1) a pharmaceutical composition comprising a vaccinia virus comprising a polynucleotide encoding IL-12 to be used in combination with a pharmaceutical composition comprising a vaccinia virus comprising a polynucleotide encoding IL-7; or
(2) a pharmaceutical composition comprising a vaccinia virus comprising a polynucleotide encoding IL-7 to be used in combination with a pharmaceutical composition comprising a vaccinia virus comprising a polynucleotide encoding IL-12.

[3] A combination kit comprising the following vaccinia viruses (1) and (2):

(1) a vaccinia virus comprising a polynucleotide encoding IL-7; and (2) a vaccinia virus comprising a polynucleotide encoding IL-12.

[4] The vaccinia virus according to [1], wherein the vaccinia virus is deficient in the function of vaccinia virus growth factor (VGF).

[5] The vaccinia virus according to [1], wherein the vaccinia virus is deficient in the function of O1L.

[6] The vaccinia virus according to [1], wherein the vaccinia virus is deficient in the functions of VGF and O1L.

[7] The vaccinia virus according to [1], wherein the vaccinia virus has a deletion in the short consensus repeat (SCR) domains in the B5R extracellular region.

[8] The vaccinia virus according to [1], wherein the vaccinia virus is deficient in the functions of VGF and O1L and has a deletion in the SCR domains in the B5R extracellular region.

[9] The vaccinia virus according to any one of [1] and [4]-[8], wherein the vaccinia virus is a LC16mO strain.

[10] A pharmaceutical composition comprising a vaccinia virus according to any one of [1] and [4]-[9] and a pharmaceutically acceptable excipient.

[11] The pharmaceutical composition according to [2] or the kit according to [3], wherein the vaccinia virus is deficient in the function of VGF.

[12] The pharmaceutical composition according to [2] or the kit according to [3], wherein the vaccinia virus is deficient in the function of O1L.

[13] The pharmaceutical composition according to [2] or the kit according to [3], wherein the vaccinia virus is deficient in the functions of VGF and O1L.

[14] The pharmaceutical composition according to [2] or the kit according to [3], wherein the vaccinia virus has a deletion in the SCR domains in the B5R extracellular region.

[15] The pharmaceutical composition according to [2] or the kit according to [3], wherein the vaccinia virus is deficient in the functions of VGF and O1L and has a deletion in the SCR domains in the B5R extracellular region.

[16] The pharmaceutical composition according to any one of [2] and [11]-[15] or the kit according to any one of [3] and [11]-[15], wherein the vaccinia virus is a LC16mO strain.

[17] The pharmaceutical composition according to any one of [2] and [11]-[16] or the kit according to any one of [3] and [11]-[16], further comprising a pharmaceutically acceptable excipient.

[18] The pharmaceutical composition or kit according to any one of [10]-[17], for preventing or treating cancer.

[19] The pharmaceutical composition or kit according to [18], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[20] A method for preventing or treating cancer, comprising the step of administering the vaccinia virus according to any one of [1] and [4]-[9] to a subject in need of the prevention or treatment for cancer.

[21] The method according to [20], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[22] The vaccinia virus according to any one of [1] and [4]-[9], for use in preventing or treating cancer.

[23] The vaccinia virus according to [22], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[24] Use of the vaccinia virus according to any one of [1] and [4]-[9] for the manufacture of a pharmaceutical composition for preventing or treating cancer.

[25] The use according to [24], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[26] A method for preventing or treating cancer, comprising the step of administering (1) a vaccinia virus comprising a polynucleotide encoding IL-7; and (2) a vaccinia virus comprising a polynucleotide encoding IL-12 to a subject in need of the prevention or treatment for cancer.

[27] The method according to [26], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[28] A vaccinia virus selected from the following (1) or (2):

(1) a vaccinia virus comprising a polynucleotide encoding IL-7, for preventing or treating cancer in combination with a pharmaceutical composition comprising a vaccinia virus comprising a polynucleotide encoding IL-12; or (2) a vaccinia virus comprising a polynucleotide encoding IL-12, for preventing or treating cancer in combination with a pharmaceutical composition comprising a vaccinia virus comprising a polynucleotide encoding IL-7.

[29] The vaccinia virus according to [28], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[30] Use of a vaccinia virus selected from the following (1) or (2):

(1) use of a vaccinia virus comprising a polynucleotide encoding IL-7 for the manufacture of a pharmaceutical composition for preventing or treating cancer to be used in combination with a pharmaceutical composition comprising a vaccinia virus comprising a polynucleotide encoding IL-12; or (2) use of a vaccinia virus comprising a polynucleotide encoding IL-12 for the manufacture of a pharmaceutical composition for preventing or treating cancer to be used in combination with a pharmaceutical composition comprising a vaccinia virus comprising a polynucleotide encoding IL-7.

[31] The use according to [30], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

[32] Use of (1) a vaccinia virus comprising a polynucleotide encoding IL-7 and (2) a vaccinia virus comprising a polynucleotide encoding IL-12 for the manufacture of a combination kit for preventing or treating cancer.

[33] The use according to [32], wherein the cancer is malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer or gastric cancer.

Advantageous Effects of the Invention

The vaccinia virus according to the present invention and the vaccinia viruses contained in the pharmaceutical composition and combination kit according to the present invention exhibit oncolytic activity, express IL-12 and IL-7 polypeptides encoded by polynucleotides carried by the viruses in cancer cells, and induce complete remission and acquired immunity. The vaccinia virus, pharmaceutical composition, and combination kit according to the present invention can be used for preventing or treating cancer.

DETAILED DESCRIPTION OF THE PREFERRED EMBODIMENTS

Figure 1:
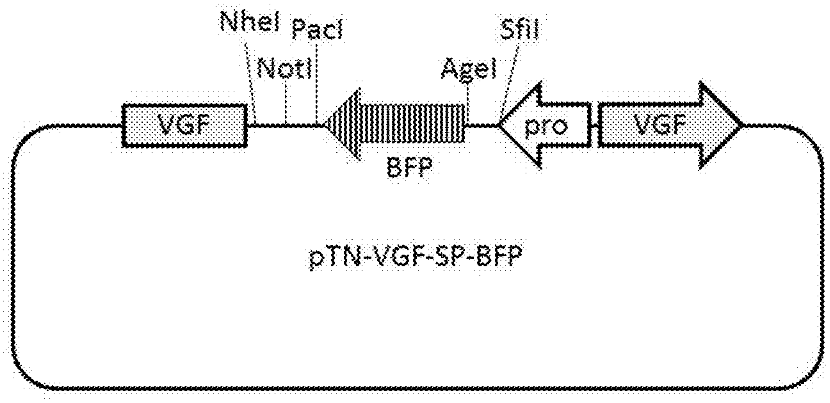
FIG. 1 is a drawing illustrating an example of transfer vector plasmid DNAs used in the present invention, in which the upper map illustrates an example in which the BFP gene operably linked to a promoter is incorporated in the VGF gene and the lower map illustrates an example in which the BFP gene operably linked to a promoter is incorporated in the O1L gene.
Figure 1:
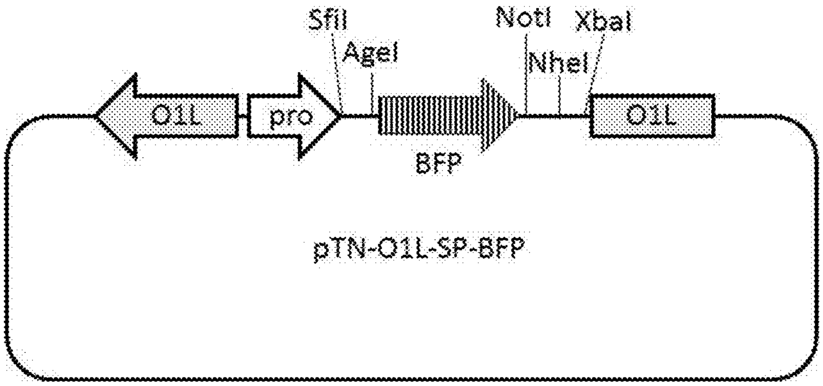

The present invention is described in detail below.

<Vaccinia virus, pharmaceutical composition to be used in combination and combination kit according to the present invention>

The present invention provides a vaccinia virus comprising the following (1) and (2):

(1) a polynucleotide encoding IL-7; and (2) a polynucleotide encoding IL-12.

(As used herein, the vaccinia virus is also referred to as the "vaccinia virus according to the present invention".)

The present invention also provides a pharmaceutical composition selected from the following (1) or (2):

(1) a pharmaceutical composition comprising a vaccinia virus comprising a polynucleotide encoding IL-12 to be used in combination with a pharmaceutical composition comprising a vaccinia virus comprising a polynucleotide encoding IL-7; or (2) a pharmaceutical composition comprising a vaccinia virus comprising a polynucleotide encoding IL-7 to be used in combination with a pharmaceutical composition comprising a vaccinia virus comprising a polynucleotide encoding IL-12.

(As used herein, the pharmaceutical composition is also referred to as the "pharmaceutical composition to be used in combination according to the present invention" and a vaccinia virus comprising a polynucleotide encoding IL-7 or a vaccinia virus comprising a polynucleotide encoding IL-12 contained in the pharmaceutical composition to be used in combination according to the present invention described in (1) or (2) above is also referred to as the "vaccinia virus to be used in combination".)

The present invention also provides a combination kit comprising the following vaccinia viruses (1) and (2):

(1) a vaccinia virus comprising a polynucleotide encoding IL-7; and (2) a vaccinia virus comprising a polynucleotide encoding IL-12.

(As used herein, the combination kit is also referred to as the "combination kit according to the present invention" and the vaccinia viruses contained in the combination kit according to the present invention are also referred to as the "vaccinia viruses for the combination kit".)

The combination kit according to the present invention means one or more pharmaceutical compositions to be used to administer two vaccinia viruses: (1) a vaccinia virus comprising a polynucleotide encoding IL-7 and (2) a vaccinia virus comprising a polynucleotide encoding IL-12. When both vaccinia viruses are administered simultaneously, the combination kit can contain the two vaccinia viruses for the combination kit together in a single pharmaceutical composition such as a powder or separately in plural pharmaceutical compositions. The combination kit according to the present invention encompasses a pharmaceutical composition containing two vaccinia viruses: a vaccinia virus comprising a polynucleotide encoding IL-7 and a vaccinia virus comprising a polynucleotide encoding IL-12. When both vaccinia viruses for the combination kit are not simultaneously administered, the combination kit contains the two vaccinia viruses for the combination kit in separate pharmaceutical compositions. For example, the combination kit comprises the two vaccinia viruses for the combination kit in separate pharmaceutical compositions in a single package or in separate pharmaceutical compositions in separate packages. The combination kit according to the present invention may comprise a pharmaceutically acceptable excipient.

The vaccinia virus used for the vaccinia virus according to the present invention, the vaccinia virus to be used in combination, and the vaccinia viruses for the combination kit is a virus in the genus Orthopoxvirus in the family Poxviridae. Strains of the vaccinia virus used in the present invention include, but not limited to, the strains Lister, New York City Board of Health (NYBH), Wyeth, Copenhagen, Western Reserve (WR), Modified Vaccinia Ankara (MVA), EM63, Ikeda, Dalian, Tian Tan, and the like. The strains Lister and MVA are available from American Type Culture Collection (ATCC VR-1549 and ATCC VR-1508, respectively). Furthermore, vaccinia virus strains established from these strains may be used in the present invention. For example, the strains LC16, LC16m8, and LC16mO established from the strain Lister may be used in the present invention. The strain LC16mO is a strain generated via the strain LC16 by subculturing at low temperature the Lister strain as the parent strain. The LC16m8 strain is a strain generated by further subculturing at low temperature the strain LC16mO, having a frameshift mutation in the B5R gene, a gene encoding a viral membrane protein, and attenuated by losing the expression and the function of this protein (Tanpakushitsu kakusan koso (Protein, Nucleic acid, Enzyme), 2003, vol. 48, p. 1693-1700). The whole genome sequences of the strains Lister, LC16m8, and LC16mO are known as, for example, Accession No.AY678276.1, Accession No.AY678275.1, and Accession No.AY678277.1, respectively. Therefore, the strains LC16m8 and LC16mO can be made from the strain Lister by a known technique, such as homologous recombination or site-directed mutagenesis.

In one embodiment, the vaccinia virus used in the present invention is the strain LC16mO.

The vaccinia virus used in the present invention can include attenuated and/or tumor-selective vaccinia viruses. As used herein, "attenuated" means low toxicity (for example, cytolytic property) to normal cells (for example, non-tumor cells). As used herein, "tumor selective" means toxicity to tumor cells (for example, oncolytic) higher than that to normal cells (for example, non-tumor cell). Vaccinia viruses genetically modified to be deficient in the function of a specific protein or to suppress the expression of a specific gene or protein (Expert Opinion on Biological Therapy, 2011, vol. 11, p. 595-608) may be used in the present invention. For example, in order to increase tumor selectivity of vaccinia virus, vaccinia virus deficient in the function of TK (Cancer Gene Therapy, 1999, vol. 6, p. 409-422), vaccinia virus deficient in the function of VGF (Cancer Research, 2001, vol. 61, p. 8751-8757), vaccinia virus having a modified TK gene, a modified hemagglutinin (HA) gene, and a modified F3 gene or an interrupted F3 locus (WO 2005/047458), vaccinia virus deficient in the function of VGF and O1L (WO 2015/076422), vaccinia virus in which a target sequence of a microRNA whose expression is decreased in cancer cells is inserted into the 3' noncoding region of the B5R gene (WO 2011/125469), vaccinia virus deficient in the function of VGF and TK (Cancer Research, 2001, vol. 61, p. 8751-8757), vaccinia virus deficient in the function of TK, HA, and F14.5L (Cancer Research, 2007, vol. 67, p. 10038-10046), vaccinia virus deficient in the function of TK and B18R (PLoS Medicine, 2007, vol. 4, p. e353), vaccinia virus deficient in the function of TK and ribonucleotide reductase (PLoS Pathogens, 2010, vol. 6, p. e1000984), vaccinia virus deficient in the function of SPI-1 and SPI-2 (Cancer Research, 2005, vol. 65, p. 9991-9998), vaccinia virus deficient in the function of SPI-1, SPI-2, and TK (Gene Therapy, 2007, vol. 14, p. 638-647), or vaccinia virus having mutations in the E3L and K3L regions (WO 2005/007824) may be used. Moreover, vaccinia virus deficient in the function of O1L may be used (Journal of Virology, 2012, vol. 86, p. 2323-2336). Moreover, in hope that the clearance of virus by the neutralization effect of anti-vaccinia virus antibodies is reduced in the living body, vaccinia virus deficient in the extracellular region of B5R (Virology, 2004, vol. 325, p. 425-431) or vaccinia virus deficient in the A34R region (Molecular Therapy, 2013, vol. 21, p. 1024-1033) may be used. Moreover, in hope of the activation of immune cells by vaccinia virus, vaccinia virus deficient in interleukin-1b (IL-1b) receptor (WO 2005/030971) may be used. Such insertion of a foreign gene or deletion or mutation of a gene can be made, for example, by a known homologous recombination or site-directed mutagenesis. Moreover, vaccinia virus having a combination of such genetic modifications may be used in the present invention. As used herein, "being deficient" means that the gene region specified by this term has no function and used in a meaning including deletion of the gene region specified by this term. For example, "being deficient" may be a result of the deletion in a region consisting of the specified gene region or the deletion in a neighboring gene region comprising the specified gene region.

In one embodiment, the vaccinia virus according to the present invention, the vaccinia virus to be used in combination, or the vaccinia viruses for the combination kit is (are) deficient in the function of VGF. In one embodiment, the vaccinia virus according to the present invention, the vaccinia virus to be used in combination, or the vaccinia viruses for the combination kit is (are) deficient in the function of O1L. In one embodiment, the vaccinia virus according to the present invention, the vaccinia virus to be used in combination or the vaccinia viruses for the combination kit is (are) deficient in the functions of VGF and O1L. The function of VGF and/or O1L may be made deficient in vaccinia virus based on the method described in WO 2015/076422.

VGF is a protein having a high amino acid sequence homology with epidermal growth factor (EGF), binds to the epidermal growth factor receptor like EGF, and activates the signal cascade from Ras, Raf, Mitogen-activated protein kinase (MAPK)/the extracellular signal-regulated kinase (ERK) kinase (MAPK/ERK kinase, MEK), and to following ERK to promote the cell division.

O1L maintains the activation of ERK and contributes to the cell division along with VGF.

Being deficient in the function of VGF and/or O1L of vaccinia virus refers to loss of the expression of the gene encoding VGF and/or the gene encoding O1L or the normal function of VGF and/or O1L when expressed. The deficiency in the function of VGF and/or O1L of vaccinia virus may be caused by the deletion of all or a part of the gene encoding VGF and/or the gene encoding O1L. Moreover, the genes may be mutated by nucleotide substitution, deletion, insertion, or addition to prevent the expression of normal VGF and/or O1L. Moreover, a foreign gene may be inserted in the gene encoding VGF and/or the gene encoding O1L. In the present invention, a gene is stated to be deficient when the normal product of the gene is not expressed by mutation such as genetic substitution, deletion, insertion, or addition.

Whether or not the vaccinia virus according to the present invention, the vaccinia virus to be used in combination, or the vaccinia viruses for the combination kit is (are) deficient in the function of VGF and/or O1L may be determined with a known method, for example, by evaluating the function of VGF and/or O1L, testing for the presence of VGF or O1L by an immunochemical technique using an antibody against VGF or an antibody against O1L, or determining the presence of the gene encoding VGF or the gene encoding O1L by the polymerase chain reaction (PCR).

B5R (Accession No.AAA48316.1) is a type 1 membrane protein resides in the envelope of vaccinia virus, and serves to increase the infection efficiency when the virus infects and is transmitted to neighboring cells or other sites in the host. The extracellular region of B5R contains 4 structural domains called SCR domains (Journal of Virology, 1998, vol. 72, p. 294-302). In one embodiment, the vaccinia virus according to the present invention, the vaccinia virus to be used in combination, or the vaccinia viruses for the combination kit has (have) a deletion in the SCR domains in the extracellular region of B5R.

The deletion in the SCR domains in the B5R extracellular region of vaccinia virus encompasses the deletion of a part or all of the 4 SCR domains in the B5R extracellular region and refers to the lack of expression of a gene region encoding a part or all of the 4 SCR domains in the B5R extracellular region or the lack of a part or all of the 4 SCR domains in the extracellular region in the expressed B5R protein. In one embodiment, the vaccinia virus according to the present invention, the vaccinia virus to be used in combination, or the vaccinia viruses for the combination kit has (have) the deletion of all 4 SCR domains. In one embodiment, the 4 SCR domains deleted in the vaccinia virus according to the present invention, the vaccinia virus to be used in combination, and the vaccinia viruses for the combination kit correspond to the region from amino acid 22 to amino acid 237 in the amino acid sequence of Accession No.AAA48316.1 described above.

Whether or not the vaccinia virus according to the present invention, the vaccinia virus to be used in combination, or the vaccinia viruses for the combination kit has (have) a deletion in the SCR domains in the B5R extracellular region can be determined with a known method, for example, by testing for the presence of the SCR domains by an immunochemical technique using an antibody against the SCR domains or determining the presence or the size of the gene encoding the SCR domains by PCR.

In one embodiment, the vaccinia virus according to the present invention, the vaccinia virus to be used in combination, or the vaccinia viruses for the combination kit is (are) vaccinia virus deficient in the functions of VGF and O1L and having a deletion in the SCR domains in the B5R extracellular region.

In one embodiment, the vaccinia virus according to the present invention, the vaccinia virus to be used in combination, or the vaccinia viruses for the combination kit is (are) vaccinia virus of the strain LC16mO deficient in the functions of VGF and O1L and having a deletion in the SCR domains in the B5R extracellular region.

In one embodiment, the vaccinia virus according to the present invention is vaccinia virus comprising a polynucleotide encoding IL-7 and a polynucleotide encoding IL-12 and being deficient in the functions of VGF and O1L.

In one embodiment, the vaccinia virus according to the present invention is vaccinia virus of the strain LC16mO comprising a polynucleotide encoding IL-7 and a polynucleotide encoding IL-12 and being deficient in the functions of VGF and O1L.

In one embodiment, the vaccinia virus according to the present invention is vaccinia virus comprising a polynucleotide encoding IL-7 and a polynucleotide encoding IL-12, being deficient in the functions of VGF and O1L, and having a deletion in the SCR domains in the B5R extracellular region.

In one embodiment, the vaccinia virus according to the present invention is vaccinia virus of the strain LC16mO comprising a polynucleotide encoding IL-7 and a polynucleotide encoding IL-12, being deficient in the functions of VGF and O1L, and having a deletion in the SCR domains in the B5R extracellular region.

In one embodiment, the vaccinia virus to be used in combination or the vaccinia viruses for the combination kit is (are) vaccinia virus comprising a polynucleotide encoding IL-7 and being deficient in the functions of VGF and O1L or vaccinia virus comprising a polynucleotide encoding IL-12 and being deficient in the functions of VGF and O1L.

In one embodiment, the vaccinia virus to be used in combination or the vaccinia viruses for the combination kit is (are) vaccinia virus of the strain LC16mO comprising a polynucleotide encoding IL-7 and being deficient in the functions of VGF and O1L or vaccinia virus of the strain LC16mO comprising a polynucleotide encoding IL-12 and being deficient in the functions of VGF and O1L.

In one embodiment, the vaccinia virus to be used in combination or the vaccinia viruses for the combination kit is (are) vaccinia virus comprising a polynucleotide encoding IL-7, being deficient in the functions of VGF and O1L, and having a deletion in the SCR domains in the B5R extracellular region or vaccinia virus comprising a polynucleotide encoding IL-12, being deficient in the functions of VGF and O1L, and having a deletion in the SCR domains in the B5R extracellular region.

In one embodiment, the vaccinia virus to be used in combination or the vaccinia viruses for the combination kit is (are) vaccinia virus of the strain LC16mO comprising a polynucleotide encoding IL-7, being deficient in the functions of VGF and O1L and having a deletion in the SCR domain in the B5R extracellular region or vaccinia virus of the strain LC16mO comprising a polynucleotide encoding IL-12, being deficient in the functions of VGF and O1L, and having a deletion in the SCR domains in the B5R extracellular region.

IL-7 is a secretory protein functioning as an agonist for the IL-7 receptor. It is reported that IL-7 contributes to the survival, proliferation, and differentiation of T cells, B cells, or the like (Current Drug Targets, 2006, vol. 7, p. 1571-1582). In the present invention, IL-7 encompasses IL-7 occurring naturally and modified forms having the function thereof. In one embodiment, IL-7 is human IL-7. In the present invention, human IL-7 encompasses human IL-7 occurring naturally and modified forms having the function thereof. In one embodiment, human IL-7 is selected from the group consisting of the following (1) to (3):

(1) a polypeptide comprising the amino acid sequence set forth in Accession No. NP_000871.1 and having the function of human IL-7;

(2) a polypeptide consisting of an amino acid sequence in which 1 to 10 amino acids are deleted from, substituted in, inserted into, and/or added to the amino acid sequence set forth in Accession No. NP_000871.1 and having the function of human IL-7; and (3) a polypeptide comprising an amino acid sequence having a 90% or more identity with the amino acid sequence set forth in Accession No. NP_000871.1 and having the function of human IL-7.

In relation with this, the function of human IL-7 refers to the effect on the survival, proliferation, and differentiation of human immune cells.

Human IL-7 used in the present invention is preferably a polypeptide consisting of the amino acid sequence set forth in Accession No. NP_000871.1.

IL-12 is a heterodimer of the IL-12 subunit p40 and the IL-12 subunit α. IL-12 has been reported to have the function of activating and inducing the differentiation of T cells and NK cells (Cancer Immunology Immunotherapy, 2014, vol. 63, p. 419-435). In the present invention, IL-12 encompasses IL-12 occurring naturally and modified forms having the function thereof. In one embodiment, IL-12 is human IL-12. In the present invention, human IL-12 encompasses human IL-12 occurring naturally and modified forms having the function thereof. In one embodiment, human IL-12 is selected, as a combination of the human IL-12 subunit p40 and the human IL-12 subunit α, from the group consisting of the following (1) to (3):

(1) polypeptides comprising (1-a) a polypeptide comprising the amino acid sequence set forth in Accession No. NP_002178.2, (1-b) a polypeptide consisting of an amino acid sequence in which 1 to 10 amino acids are deleted from, substituted in, inserted into, and/or added to the amino acid sequence set forth in Accession No. NP_002178.2, or (1-c) a polypeptide comprising an amino acid sequence having a 90% or more identity with the amino acid sequence set forth in Accession No. NP_002178.2; and (2-a) a polypeptide comprising the amino acid sequence set forth in Accession No. NP_ 13000873.2, (2-b) a polypeptide consisting of an amino acid sequence in which 1 to 10 amino acids are deleted from, substituted in, inserted into, and/or added to the amino acid sequence set forth in Accession No. NP_000873.2, or (2-c) a polypeptide comprising an amino acid sequence having a 90% or more identity with the amino acid sequence set forth in Accession No. NP_000873.2, and having the function of human IL-12;

(2) polypeptides comprising (1-a) a polypeptide consisting of the amino acid sequence set forth in Accession No. NP_002178.2, and (2-a) a polypeptide comprising the amino acid sequence set forth in Accession No. NP_000873.2, (2-b) a polypeptide consisting of an amino acid sequence in which 1 to 10 amino acids are deleted from, substituted in, inserted into, and/or added to the amino acid sequence set forth in Accession No. NP_000873.2, or (2-c) a polypeptide comprising an amino acid sequence having a 90% or more identity with the amino acid sequence set forth in Accession No. NP_000873.2, and having the function of human IL-12; and (3) a polypeptide comprising (1-a) a polypeptide comprising the amino acid sequence set forth in Accession No. NP_002178.2, (1-b) a polypeptide consisting of an amino acid sequence in which 1 to 10 amino acids are deleted from, substituted in, inserted into, and/or added to the amino acid sequence set forth in Accession No. NP_002178.2, or (1-c) a polypeptide comprising an amino acid sequence having a 90% or more identity with the amino acid sequence set forth in Accession No. NP_002178.2, and (2-a) a polypeptide consisting of the amino acid sequence set forth in Accession No. NP_000873.2, and having the function of human IL-12.

In relation with this, the function of human IL-12 refers to activating and/or differentiating effects on T cells or NK cells. The IL-12 subunit p40 and the IL-12 subunit α can form IL-12 by direct binding. Moreover, the IL-12 subunit p40 and the IL-12 subunit α can be conjugated via a linker.

Human IL-12 used in the present invention is preferably a polypeptide comprising a polypeptide consisting of the amino acid sequence set forth in Accession No. NP_002178.2 and a polypeptide consisting of the amino acid sequence set forth in Accession No. NP_000873.2.

As used herein, "identity" means the value Identity obtained by a search using the NEEDLE program (Journal of Molecular Biology, 1970, vol. 48, p. 443-453) with the default parameters. The parameters are as follows.

Gap penalty=10
Extend penalty=0.5
Matrix=EBLOSUM62

The vaccinia virus according to the present invention, the vaccinia virus to be used in combination, or the vaccinia viruses for the combination kit has (have) the oncolytic activity. Examples of methods for evaluating whether or not a test virus has the oncolytic activity include a method for evaluating decrease of the survival rate of cancer cells by the addition of the virus. Examples of cancer cells to be used for the evaluation include the malignant melanoma cell RPMI-7951 (for example, ATCC HTB-66), the lung adenocarcinoma HCC4006 (for example, ATCC CRL-2871), the lung carcinoma A549 (for example, ATCC CCL-185), the small cell lung cancer cell DMS 53 (for example, ATCC CRL-2062), the lung squamous cell carcinoma NCI-H226 (for example, ATCC CRL-5826), the kidney cancer cell Caki-1 (for example, ATCC HTB-46), the bladder cancer cell 647-V (for example, DSMZ ACC 414), the head and neck cancer cell Detroit 562 (for example, ATCC CCL-138), the breast cancer cell JIMT-1 (for example, DSMZ ACC 589), the breast cancer cell MDA-MB-231 (for example, ATCC HTB-26), the esophageal cancer cell OE33 (for example, ECACC 96070808), the glioblastoma U-87MG (for example, ECACC 89081402), the neuroblastoma GOTO (for example, JCRB JCRB0612), the myeloma RPMI 8226 (for example, ATCC CCL-155), the ovarian cancer cell SK-OV-3 (for example, ATCC HTB-77), the ovarian cancer cell OVMANA (for example, JCRB JCRB1045), the colon cancer cell RKO (for example, ATCC CRL-2577), the colorectal carcinoma HCT 116 (for example, ATCC CCL-247), the pancreatic cancer cell BxPC-3 (for example, ATCC CRL-1687), the prostate cancer cell LNCaP clone FGC (for example, ATCC CRL-1740), the hepatocellular carcinoma JHH-4 (for example, JCRB JCRB0435), the mesothelioma NCI-H28 (for example, ATCC CRL-5820), the cervical cancer cell SiHa (for example, ATCC HTB-35), and the gastric cancer cell Kato III (for example, RIKEN BRC RCB2088). Specific examples of methods for the evaluation that can be used include the method described in Example 3 below.

The vaccinia virus according to the present invention, the vaccinia virus to be used in combination, or the vaccinia viruses for the combination kit produce(s) the IL-7 and/or IL-12 polypeptide(s). Use of the vaccinia virus according to the present invention, the vaccinia virus to be used in combination, or the vaccinia viruses for the combination kit markedly increases the antitumor effect by producing the IL-7 and IL-12 polypeptides. The production of IL-7 and IL-12 can be confirmed using a method known in the field, for example, after culturing, with cancer cells, vaccinia virus in which polynucleotides encoding the IL-7 and IL-12 polypeptides are introduced followed by measuring the IL-7 and IL-12 concentrations in the culture supernatant, by immunostaining of cells, by conducting Western blot analysis of the cell lysate, or by measuring the concentrations of IL-7 and IL-12 in the cell lysate. The concentrations of IL-7 and IL-12 can be measured using, for example, Human IL-7 ELISA kit (RayBiotech, Inc.) and Human IL-12 p70 DuoSet ELISA (R&D Systems, Inc.), respectively. Specific examples of methods for evaluating polypeptide concentrations in the culture supernatant or cell lysate that can be used include the method described in Example 4 below. The immunostaining of cells or the Western blot analysis of the cell lysate can be conducted using commercially available antibodies against IL-7 and IL-12.

The polynucleotides encoding IL-7 and IL-12 can be synthesized based on publicly available sequence information using a method of polynucleotide synthesis known in the field. Moreover, once the polynucleotides are obtained; then modified forms having the function of each polypeptide can be generated by introducing mutation into a predetermined site using a method known by those skilled in the art, such as site-directed mutagenesis (Current Protocols in Molecular Biology edition, 1987, John Wiley & Sons Sections 8.1-8.5).

The polynucleotides each encoding IL-7 and IL-12 can be introduced into vaccinia virus by a known technique, such as homologous recombination or site-directed mutagenesis. For example, a plasmid (also referred to as transfer vector plasmid DNA) in which the polynucleotide(s) is (are) introduced into the nucleotide sequence at the site desired to be introduced can be made and introduced into cells infected with vaccinia virus. The region in which the polynucleotides each encoding IL-7 and IL-12, foreign genes, are introduced is preferably a gene region that is inessential for the life cycle of vaccinia virus. For example, in a certain aspect, the region in which IL-7 and/or IL-12 is (are) introduced may be a region within the VGF gene in vaccinia virus deficient in the VGF function, a region within the O1L gene in vaccinia virus deficient in the 01 function, or a region or regions within either or both of the VGF and O1L genes in vaccinia virus deficient in both VGF and 01 functions. In the above, the foreign gene(s) can be introduced so as to be transcribed in the direction same as or opposite to that of the VGF and O1L genes.

Methods for introducing transfer vector plasmid DNA into cells are not particularly limited, but examples of methods that can be used include the calcium phosphate method and electroporation.

When introducing the polynucleotides each encoding IL-7 and IL-12, which are foreign genes, a suitable promoter(s) can be operably linked in the upstream of the foreign gene(s). In this way, the foreign gene(s) in the vaccinia virus according to the present invention, the vaccinia virus to be used in combination, or the vaccinia viruses for the combination kit can be linked to a promoter that can promote expression in tumor cells. Examples of such a promoter include PSFJ1-10, PSFJ2-16, the p7.5K promoter, the p11K promoter, the T7.10 promoter, the CPX promoter, the HF promoter, the H6 promoter, and the T7 hybrid promoter.

In one embodiment, the vaccinia virus according to the present invention, the vaccinia virus to be used in combination, or the vaccinia viruses for the combination kit has (have) no drug-selection marker gene.

The vaccinia virus according to the present invention, the vaccinia virus to be used in combination, or the vaccinia viruses for the combination kit may be expressed and/or proliferated by infecting host cells with the vaccinia virus(es) and culturing the infected host cells. Vaccinia virus may be expressed and/or proliferated by a method known in the field. Host cells to be used to express or proliferate the vaccinia virus according to the present invention, the vaccinia virus to be used in combination, or the vaccinia viruses for the combination kit are not particularly limited, as long as the vaccinia virus according to the present invention, the vaccinia virus to be used in combination, or the vaccinia viruses for the combination kit can be expressed and proliferated. Examples of such host cells include animal cells such as BS-C-1, A549, RK13, HTK-143, Hep-2, MDCK, Vero, HeLa, CV-1, COS, BHK-21, and primary rabbit kidney cells. BS-C-1 (ATCC CCL-26), A549 (ATCC CCL-185), CV-1 (ATCC CCL-70), or RK13 (ATCC CCL-37) may be preferably used. Culture conditions for the host cells, for example, temperature, pH of the medium, and culture time, are selected as appropriate.

Methods for producing the vaccinia virus according to the present invention, the vaccinia virus to be used in combination, and the vaccinia viruses for the combination kit may comprise the steps of: infecting host cells with the vaccinia virus according to the present invention, the vaccinia virus to be used in combination, or the vaccinia viruses for the combination kit; culturing the infected host cells; and expressing the vaccinia virus according to the present invention, the vaccinia virus to be used in combination, or the vaccinia viruses for the combination kit; and optionally collecting and preferably purifying the vaccinia virus according to the present invention, the vaccinia virus to be used in combination, or the vaccinia viruses for the combination kit. Methods that can be used for the purification include DNA digestion with Benzonase, sucrose gradient centrifugation, Iodixanol density gradient centrifugation, ultrafiltration, and diafiltration.

<Pharmaceutical composition according to the present invention>

The pharmaceutical compositions according to the present invention include a pharmaceutical composition comprising the vaccinia virus according to the present invention and a pharmaceutically acceptable excipient. The pharmaceutical compositions according to the present invention also include the pharmaceutical composition to be used in combination according to the present invention. In one embodiment, the pharmaceutical composition to be used in combination according to the present invention comprises a pharmaceutically acceptable excipient.

The pharmaceutical compositions according to the present invention may be prepared by a method usually used in the field, using an excipient usually used in the field, that is, a pharmaceutical excipient, a pharmaceutical carrier, or the like. Examples of the dosage form of such pharmaceutical compositions include parenteral formulations such as injections and infusions and these can be administered by intravenous administration, subcutaneous administration, intratumoral administration, or the like. In the formulation, excipients, carriers, or additives suitable for these dosages form may be used as long as these are pharmaceutically acceptable.

The effective dose varies according to the severity of the symptom or the age of the patient, the dosage form of the formulation to be used, or the titer of the virus, but, for example, approximately $10^2$-$10^{10}$ plaque-forming units (PFU) may be used as an effective dose of a single virus, as a combined effective dose of 2 viruses in a combination kit, or as a combined effective dose of 2 viruses administered in combination. Two viruses in a combination kit may be used, for example, at a dosage ratio of approximately 1:10 to 10:1, approximately 1:5 to 5:1, approximately 1:3 to 3:1, approximately 1:2 to 2:1, or about 1:1.

<Application for preventing or treating cancer>

The pharmaceutical compositions according to the present invention can be used as a prophylactic or therapeutic agent for cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer.

The present invention includes a pharmaceutical composition for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer, the composition comprising the vaccinia virus according to the present invention or the vaccinia virus to be used in combination.

The present invention includes a combination kit for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer, the combination kit comprising each of the vaccinia viruses for the combination kit.

Moreover, the present invention includes a method for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer, the method comprising the step of administering the vaccinia virus according to the present invention to a subject (for example, a patient) in need of the prevention or treatment of cancer.

Moreover, the present invention includes a method for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer, the method comprising the step of administering the following (1) and (2) to a subject (for example, a patient) in need of the prevention or treatment of cancer:

(1) a vaccinia virus comprising a polynucleotide encoding IL-7; and (2) a vaccinia virus comprising a polynucleotide encoding IL-12.

The two vaccinia viruses may be administered to a subject simultaneously, separately, continuously, or at intervals.

Moreover, the present invention includes the vaccinia virus according to the present invention, for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer.

The present invention includes the vaccinia virus selected from the following (1) or (2), for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer:

(1) a vaccinia virus comprising a polynucleotide encoding IL-7, for preventing or treating cancer in combination with a pharmaceutical composition comprising a vaccinia virus comprising a polynucleotide encoding IL-12; or (2) a vaccinia virus comprising a polynucleotide encoding IL-12, for preventing or treating cancer in combination with a pharmaceutical composition comprising a vaccinia virus comprising a polynucleotide encoding IL-7.

Furthermore, the present invention includes use of the vaccinia virus according to the present invention, for the manufacture of a pharmaceutical composition for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer.

The present invention includes use of a vaccinia virus selected from the following (1) or (2), for the manufacture of a pharmaceutical composition for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer:

(1) use of a vaccinia virus comprising a polynucleotide encoding IL-7, for the manufacture of a pharmaceutical composition for preventing or treating cancer to be used in combination with a pharmaceutical composition comprising a vaccinia virus comprising a polynucleotide encoding IL-12; or (2) use of a vaccinia virus comprising a polynucleotide encoding IL-12, for the manufacture of a pharmaceutical composition for preventing or treating cancer to be used in combination with a pharmaceutical composition comprising a vaccinia virus comprising a polynucleotide encoding IL-7.

Furthermore, the present invention includes use of a vaccinia virus comprising a polynucleotide encoding IL-7 and a vaccinia virus comprising a polynucleotide encoding IL-12, for the manufacture of a combination kit for preventing or treating cancer, for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer.

As used herein, "for preventing" is used synonymously with "for use in preventing" and "for treating" is used synonymously with "for use in treating".

The pharmaceutical compositions or the combination kit according to the present invention may be used in combination with various therapeutic agents having efficacy for cancer for example, a cancer selected from the group consisting of malignant melanoma, lung adenocarcinoma, lung cancer, small cell lung cancer, lung squamous carcinoma, kidney cancer, bladder cancer, head and neck cancer, breast cancer, esophageal cancer, glioblastoma, neuroblastoma, myeloma, ovarian cancer, colorectal cancer, pancreatic cancer, prostate cancer, hepatocellular carcinoma, mesothelioma, cervical cancer and gastric cancer. The combination use may be performed by simultaneous administration, or separate administration continuously or at the desired interval. When administered simultaneously, the pharmaceutical compositions according to the present invention may be administered as a combined drug or as formulations formulated separately.

Cancers that the vaccinia virus according to the present invention, the pharmaceutical compositions according to the present invention, the combination kit according to the present invention, the method for preventing or treating cancer according to the present invention, or use according to the present invention is (are) applied to include metastatic cancers to an organ, for example, a lymph node, liver, or the like, besides the primary lesion.

The present invention has been generally described, but specific Examples for reference to get further understanding of the present invention are provided below. These Examples are for the illustration purpose, but not intended to limit the present invention.

EXAMPLES

Experiments with a commercially available kit or a reagent were conducted according to attached protocols unless otherwise specified.

Example 1

Construction of Transfer Vector Plasmid DNA

Transfer vector plasmid DNAs to be used for generating recombinant vaccinia viruses by homologous recombination were prepared as follows.

(1) Construction of pTN-VGF-P-DsRed transfer vector plasmid DNA

The pUC19-VGF vector was prepared according to WO 2015/076422. More specifically, genomic DNA (Accession No.AY678277.1) of the strain LC16mO was used as template and the pUC19 vector (product cord: 54357) from Invitrogen was used for the preparation of the pUC19-VGF vector. The prepared pUC19-VGF vector was digested with the restriction enzyme AccI and then the ends were blunted. The transfer vector plasmid DNA was constructed by inserting a DNA fragment (SEQ ID NO: 22) containing the p7.5k promoter and a DsRed fragment in this cleavage site. The constructed plasmid DNA was named pTN-VGF-P-DsRed.

(2) Construction of pTN-VGF-SP-IL12 and pTN-VGF-SP-IL7 transfer vector plasmid DNAs A BFP gene region was amplified with two primers (SEQ ID NO: 1 and SEQ ID NO: 2) using DNA of the pTagBFP-N vector (FP172, Evrogen) as template. The PCR product was digested with the restriction enzymes SfiI and EcoRI and cloned into the same restriction enzyme sites in the pTK-SP-LG vector (WO 2015/076422 with the proviso that genomic DNA (Accession No.AY678277.1) of the strain LC16mO was used as template and the pUC19 vector (product cord: 54357) from Invitrogen was used; and, for the pVNC110-Luc/IRES/EGFP plasmid, pVNC110-Luc/IRES/EGFP described in WO 2011/125469 was used.) to construct pTK-SP-BFP in which BFP is linked to a synthetic vaccinia virus promoter (Journal of Virological Methods, 1997, vol. 66, p. 135-138). Next, pTK-SP-BFP was digested with the restriction enzymes SphI and EcoRI and the ends were blunted. The resulting DNA fragment was cloned into the pUC19-VGF vector at a site generated by digesting the plasmid with the restriction enzyme AccI and blunting the ends to construct pTN-VGF-SP-BFP (FIG. 1). Next, a polynucleotide encoding human IL-12 (a polynucleotide containing the human IL-12 subunit p40, an internal ribosomal entry site, and the human IL-12 subunit α; SEQ ID NO: 7) and a polynucleotide (SEQ ID NO: 8) encoding human IL-7 (each polynucleotide contains the restriction enzyme site accggtcgccacc (SEQ ID NO: 16) at the 5' side and the restriction enzyme site gctagcgaattc (SEQ ID NO: 17) at the 3' side.) were digested with the restriction enzymes AgeI and NheI. Each of the polynucleotide fragments was cloned into the same restriction enzyme site in pTN-VGF-SP-BFP to construct the transfer vector plasmid DNA. The constructed plasmid DNAs were named pTN-VGF-SP-IL12 and pTN-VGF-SP-IL7, respectively.

(3) Construction of pTN-O1L-SP-BFP, pTN-O1L-SP-LacZ, pTN-O1L-SP-IL12, and pTN-O1L-SP-IL7 transfer vector plasmid DNAs In the same way as (2) above, pTK-SP-BFP was digested with the restriction enzymes SphI and EcoRI and the DNA fragment obtained by blunting the ends was cloned into the pUC19-O1L vector (WO 2015/076422 with the proviso that, like the preparation of the pUC19-VGF vector, genomic DNA (Accession No.AY678277.1) of the strain LC16mO was used as template and the pUC19 vector (product cord: 54357) from Invitrogen was used; and the O1L gene region was inserted into the XbaI site in the pUC19 vector.) at a site generated by digesting the plasmid with the restriction enzyme XbaI and blunting the ends to construct the transfer vector plasmid DNA (FIG. 1). The prepared plasmid DNA was named pTN-O1L-SP-BFP. Next, a polynucleotide (SEQ ID NO: 9) containing the Escherichia coli LacZ gene with codons optimized for human, a polynucleotide (SEQ ID NO: 7) encoding human IL-12, and a polynucleotide (SEQ ID NO: 8) encoding human IL-7 were digested with the restriction enzymes AgeI and NheI. Each of the polynucleotide fragments encoding LacZ, IL-12, or IL-7 was cloned into the same restriction enzyme sites (the AgeI and NheI sites) in the pTN-O1L-SP-BFP vector to construct the transfer vector plasmid DNA. The constructed plasmid DNAs were named pTN-O1L-SP-LacZ, pTN-O1L-SP-IL12, and pTN-O1L-SP-IL7, respectively.

(4) Construction of pTN-DsRed (B5R-) and pTN-B5RΔ1-4 transfer vector plasmid DNAs The B4R gene region was amplified with two primers (SEQ ID NO: 3 and SEQ ID NO: 4) using DNA of pB5R (WO 2011/125469, with the proviso that genomic DNA (Accession No.AY678277.1) of the strain LC16mO was used as template) as template. Moreover, the DsRed gene region was amplified with two primers (SEQ ID NO: 5 and SEQ ID NO: 6) using DNA of pDsRed-Express-N1 (Clontech Laboratories, Inc.) as template. The former PCR product was digested with the restriction enzymes NotI and FspI and the latter PCR product was digested with the restriction enzymes FspI and MfeI. These two DNA fragments were cloned into pB5R digested with the restriction enzymes NotI and MfeI to construct the transfer vector plasmid DNA. The prepared plasmid DNA was named pTN-DsRed (B5R-). Meanwhile, pB5R was digested with the restriction enzymes NotI and NspI or the restriction enzymes NspI and SacI. These two DNA fragments were cloned into pB5R digested with the restriction enzymes NotI and SacI to construct the transfer vector plasmid DNA. The prepared plasmid DNA was named pTN-B5RΔ1-4. pTN-B5RΔ1-4 encodes the B5R protein with the deletion of four SCR domains. The amino acid sequence thereof is the sequence set forth in SEQ ID NO: 18.

Example 2

Construction of Genetically Engineered Vaccinia Virus

A recombinant vaccinia virus (referred to as LC16mO VGF-SP-LucGFP/O1L-p7.5-DsRed) deficient in the functions of VGF and O1L was prepared from the vaccinia virus strain LC16mO. This recombinant vaccinia virus was sequenced with a next-generation sequencer PacBio RSII (Pacific Biosciences of California, Inc.) and the virus genome was reconstituted from the obtained sequence information using the Sprai [BMC GENOMICS. 2014 AUG. 21, 15:699.] software to determine the nucleotide sequence, which is the nucleotide sequence set forth in SEQ ID NO: 21. Moreover, loop sequences were added to both ends of the nucleotide sequence and the loop sequences at both ends were the nucleotide sequences set forth in SEQ ID NOs: 19 or 20.

Figure 2:
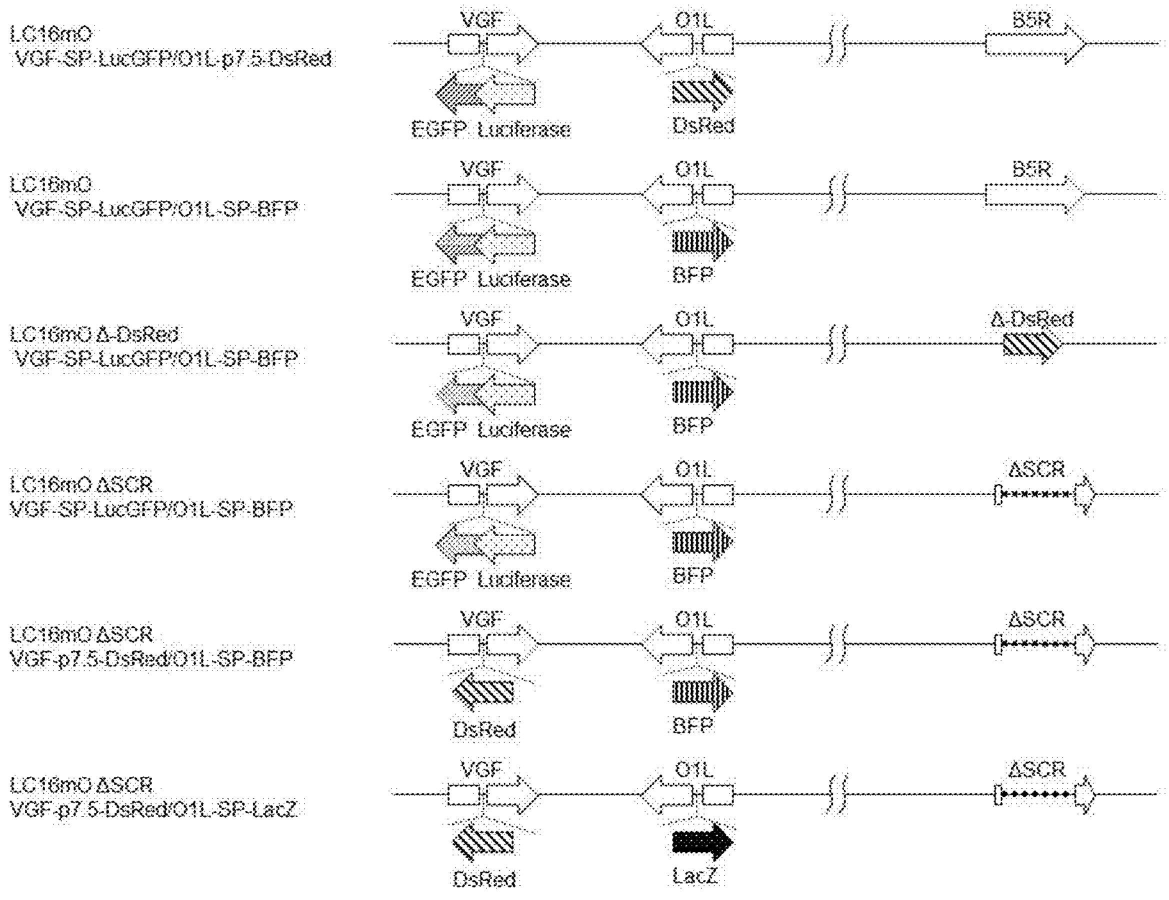
FIG. 2 is a schematic view of the genome structure of recombinant vaccinia viruses (LC16mO ΔSCR VGF-p7.5-DsRed/O1L-SP-LacZ and viruses constructed in the process of generating the virus vector)

(1) The recombinant vaccinia viruses having the virus genome illustrated in FIG. 2 were collected. The virus collecting procedure is specifically described below. CV1 cells (ATCC CCL-70) or RK13 cells (ATCC CCL-37) cultured to 80% confluent in 6 well dishes were infected with LC16mO VGF-SP-LucGFP/O1L-p7.5-DsRed at a Multiplicity of infection (MOI)=0.02-0.1 and the virus was allowed to be adsorbed at room temperature for 1 hour. pTN-O1L-SP-BFP constructed in Example 1 (3) was mixed with FuGENE® HD Transfection Reagent (Roche), added to cells according to the manual to be incorporated into the cells and the cells were cultured at 5% $CO_2$ and 37° C. for 2-5 days. The cells were freeze-thawed, sonicated, and diluted with Opti-MEM (Invitrogen) so as to obtain single plaques by the following operation. 100 μL of the resulting diluted fluid was added to inoculate BS-C-1 cells (ATCC CCL-26) or RK13 cells cultured to sub-confluent in 6 well dishes. 2 mL of the Eagle MEM medium (NISSUI, 05900) containing 0.8% methylcellulose (Wako Pure Chemical Industries, Ltd., 136-02155), 5% fetal bovine serum, 0.225% sodium bicarbonate (Wako Pure Chemical Industries, Ltd., 195-16411), and GlutaMAX (™) Supplement I (GIBCO, 35050-061) was added and the cells were cultured at 5% $CO_2$ and 37° C. for 2-5 days. The medium was removed and plaques, as indicated by the BFP expression, were scraped off with the pointing end of a tip to be suspended into Opti-MEM. This operation was repeated three times or more with BS-C-1 or RK13 cells to purify plaques and collect the virus plaques (In this Example, the procedure up to this point is hereinafter referred to as the "collecting".). The plaques were suspended into Opti-MEM and sonicated. Genomic DNA was extracted from 200 μL of the sonicated solution using High Pure Viral Nucleic Acid Kit (Roche) according to the manual and screened by PCR. PCR was performed for VGF with the two primers (SEQ ID NO: 10 and SEQ ID NO; 11), for O1L with the two primers (SEQ ID NO: 12 and SEQ ID NO: 13), and for B5R with the two primers (SEQ ID NO: 14 and SEQ ID: NO 15). Among the clones from which an expected size of PCR product was detected, a virus clone for which the correct nucleotide sequence of the PCR product was confirmed by direct sequencing (referred to as LC16mO VGF-SP-LucGFP/O1L-SP-BFP. FIG. 2) was selected and proliferated with A549 (ATCC CCL-185) or RK13 cells and then the virus titer was measured with RK13 cells. Using LC16mO VGF-SP-LucGFP/O1L-SP-BFP and pTN-DsRed (B5R-) prepared in Example 1 (4), the recombinant virus, as indicated by the DsRed expression instead of the BFP expression, was collected in a way same as that described above. The virus was named LC16mO Δ-DsRed VGF-SP-LucGFP/O1L-SP-BFP (FIG. 2).

(2) A recombinant virus having the deletion of the 4 SCR domains in the B5R protein was collected. Specifically, using LC16mO Δ-DsRed VGF-SP-LucGFP/O1L-SP-BFP prepared in Example 2 (1) and pTN-B5RΔ1-4 constructed in Example 1 (4), the recombinant virus, as indicated by the disappearance of DsRed expression instead of the BFP expression, was collected in a way same as that in Example 2 (1). The virus was named LC16mO ΔSCR VGF-SP-LucGFP/O1L-SP-BFP (FIG. 2). Moreover, using the prepared LC16mO ΔSCR VGF-SP-LucGFP/O1L-SP-BFP and pTN-VGF-P-DsRed constructed in Example 1 (1), the recombinant virus, as indicated by the DsRed expression instead of the BFP expression, was collected in a way same as that in Example 2 (1). The virus is named LC16mO ΔSCR VGF-p7.5-DsRed/O1L-SP-BFP (FIG. 2). Next, using the obtained LC16mO ΔSCR VGF-p7.5-DsRed/O1L-SP-BFP and pTN-O1L-SP-LacZ constructed in Example 1 (3), the recombinant virus, as indicated by the disappearance of BFP expression instead of the BFP expression, was collected in a way same as that in Example 2 (1). The virus was named LC16mO ΔSCR VGF-p7.5-DsRed/O1L-SP-LacZ (FIG. 2).

Figure 3:
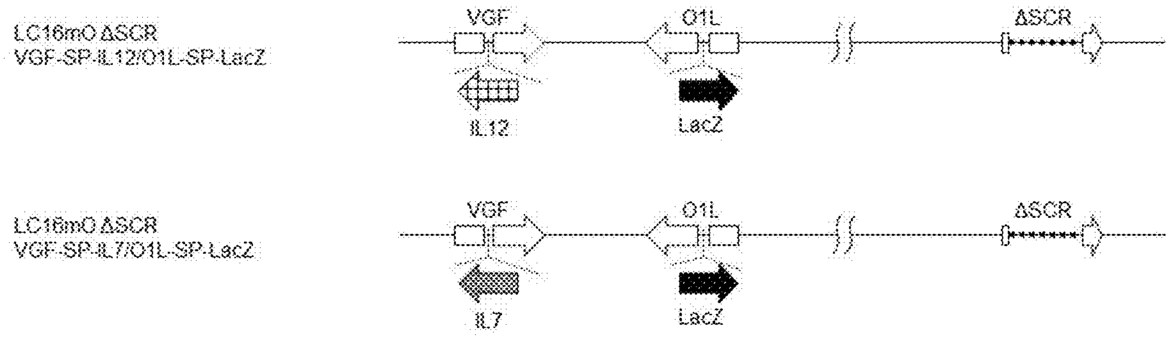
FIG. 3 is a schematic view of the genome structure of recombinant vaccinia viruses (LC16mO ΔSCR VGF-SP-IL12/O1L-SP-LacZ, LC16mO ΔSCR VGF-SP-IL7/O1L-SP-LacZ)

(3) The SCR region-deleted recombinant vaccinia viruses having the virus genome illustrated in FIG. 3 and expressing a therapeutic gene and a marker gene were collected. Specifically, using each of LC16mO ΔSCR VGF-p7.5-DsRed/O1L-SP-LacZ prepared in Example 2 (2) and the transfer vector plasmid DNAs (pTN-VGF-SP-IL12 and pTN-VGF-SP-IL7) constructed in Example 1 (2), each of the recombinant viruses, as indicated by the disappearance of DsRed expression instead of the BFP expression, was collected in a way same as that in Example 2 (1). The viruses were named LC16mO ΔSCR VGF-SP-IL12/O1L-SP-LacZ (hereinafter, referred to as the "hIL12-carrying vaccinia virus".) and LC16mO ΔSCR VGF-SP-IL7/O1L-SP-LacZ (hereinafter, referred to as the "hIL7-carrying vaccinia virus".) (FIG. 3). For purification, A549 or RK13 cells were infected with each of the recombinant viruses. The cells were cultured at 5% $CO_2$ and 37° C. for 2-5 days and then the infected cells were harvested. The cells were freeze-thawed and sonicated. The viruses were purified by density gradient centrifugation using OptiPrep (Axis-Shield Diagnostics Ltd.). The virus titer of each virus was measured with RK13 cells.

Figure 4:
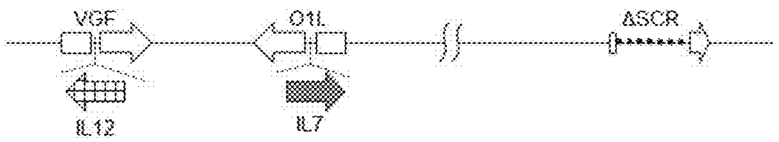
FIG. 4 is a schematic view of the genome structure of a recombinant vaccinia virus (LC16mO ΔSCR VGF-SP-IL12/O1L-SP-IL7)
Figure 5A:
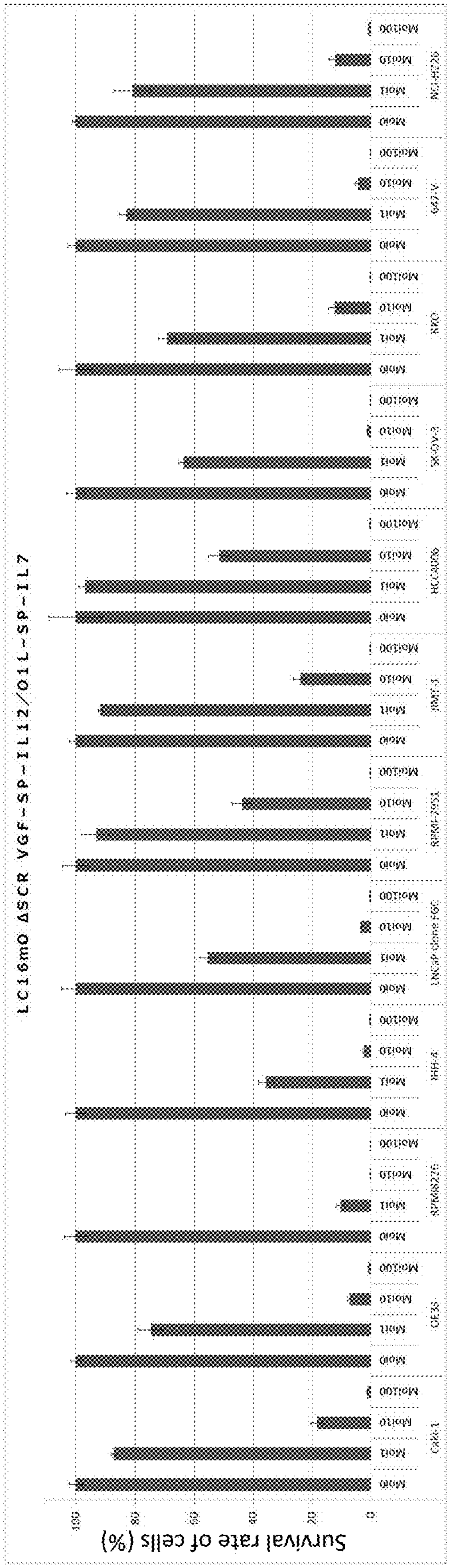
FIG. 5A is a graph illustrating oncolytic properties of a recombinant vaccinia virus (LC16mO ΔSCR VGF-SP-IL12/O1L-SP-IL7), in which the ordinate represents the cancer cell survival rate (%) and the error bars represent standard deviation.
Figure 5B:
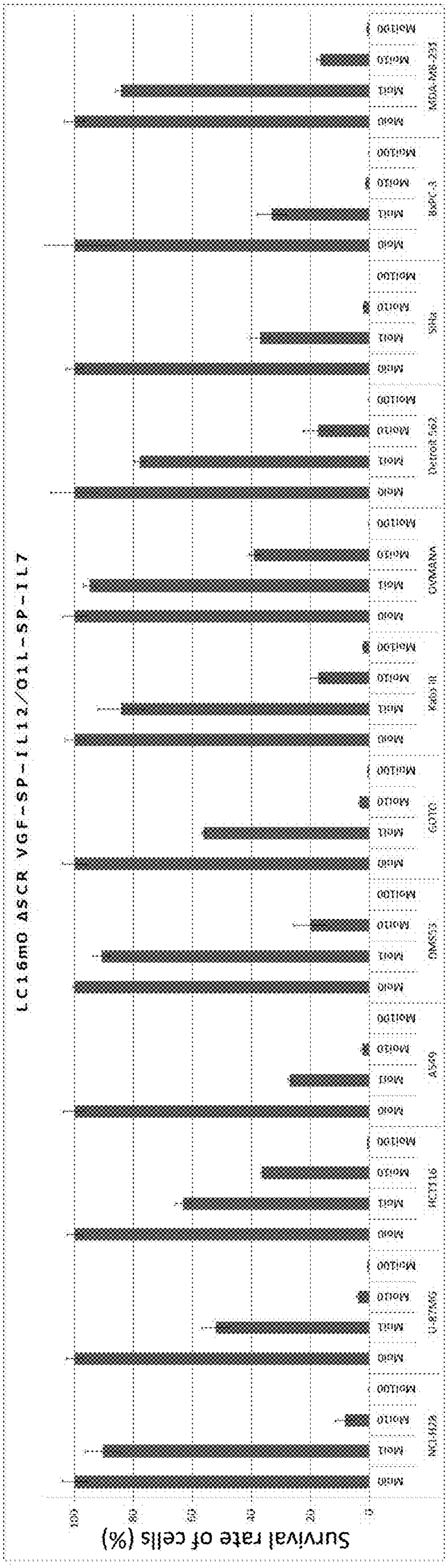
FIG. 5B is a graph illustrating oncolytic properties of a recombinant vaccinia virus (LC16mO ΔSCR VGF-SP-IL12/O1L-SP-IL7), in which the ordinate represents cancer cell survival rate (%) and the error bars represents standard deviation, FIG. 5A and FIG. 5B being graphs obtained under the same experimental conditions except that the cell types measured were different.
Figure 5C:
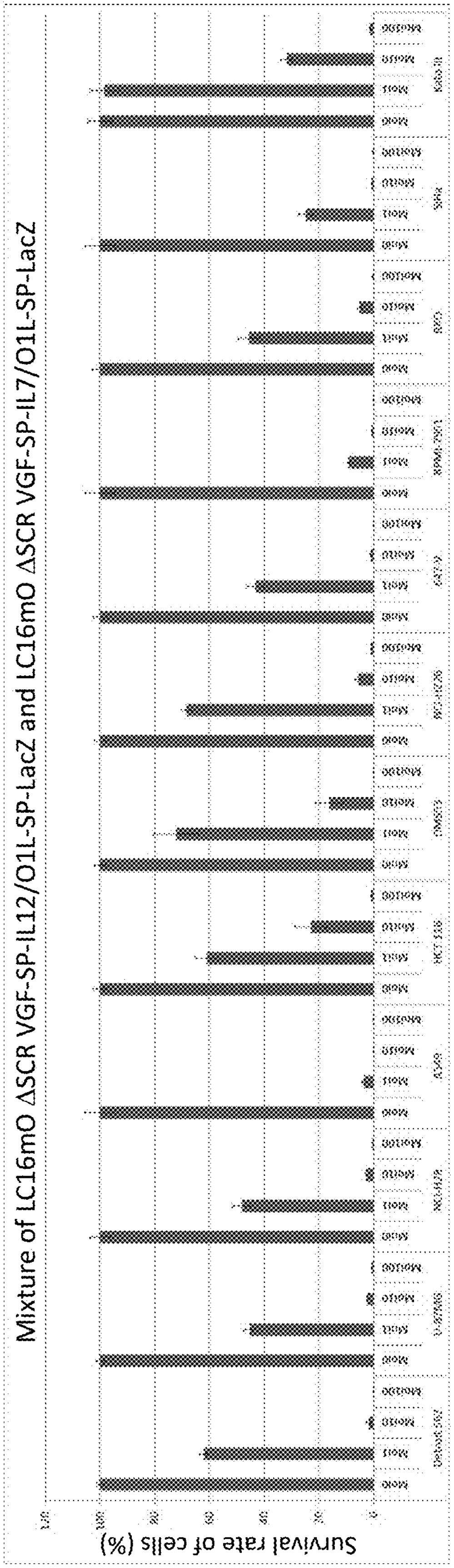
FIG. 5C is a graph illustrating oncolytic properties of a mixture of 2 recombinant vaccinia viruses (a mixture of LC16mO ΔSCR VGF-SP-IL12/O1L-SP-LacZ and LC16mO ΔSCR VGF-SP-IL7/O1L-SP-LacZ), in which the ordinate represents cancer cell survival rate (%) and the error bars represent standard deviation.
Figure 5D:
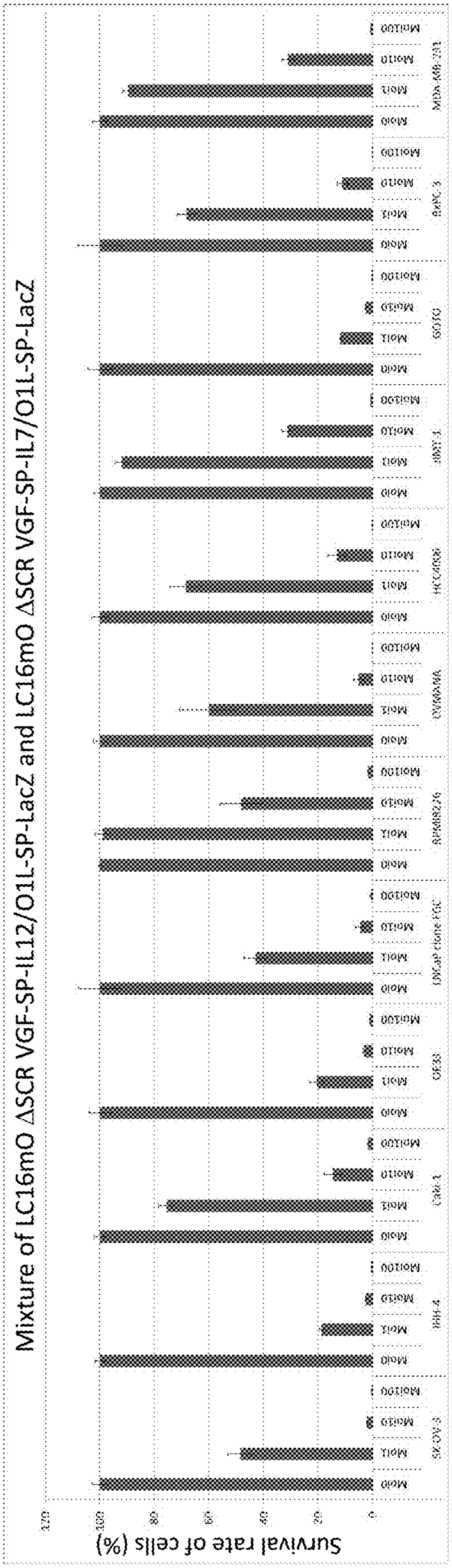
FIG. 5D is a graph illustrating oncolytic properties of a mixture of 2 recombinant vaccinia viruses (a mixture of LC16mO ΔSCR VGF-SP-IL12/O1L-SP-LacZ and LC16mO ΔSCR VGF-SP-IL7/O1L-SP-LacZ), in which the ordinate represents cancer cell survival rate (%) and the error bars represent standard deviation, FIG. 5C and FIG. 5D being graphs obtained under the same experimental conditions except that the cell types measured were different.

(4) The SCR domain-deleted recombinant vaccinia virus having the virus genome illustrated in FIG. 4 and expressing a polynucleotide encoding human IL-7 and a polynucleotide encoding human IL-12 was collected.

(4-1) Specifically, using LC16mO ΔSCR VGF-p7.5-DsRed/O1L-SP-BFP prepared in Example 2 (2) and the transfer vector plasmid DNA pTN-VGF-SP-IL12 constructed in Example 1 (2), each of the recombinant viruses, as indicated by the disappearance of DsRed expression instead of the BFP expression, was collected in a way same as that in Example 2 (1). The virus was named LC16mO ΔSCR VGF-SP-IL12/O1L-SP-BFP.

(4-2) Next, using LC16mO ΔSCR VGF-SP-IL12/O1L-SP-BFP prepared in Example 2 (4-1) and the transfer vector plasmid DNA pTN-O1L-SP-IL7 constructed in Example 1 (3), each of the recombinant viruses, as indicated by the disappearance of BFP expression instead of the BFP expression, was collected in a way same as that in Example 2 (1). The virus was named LC16mO ΔSCR VGF-SP-IL12/O1L-SP-IL7 (hereinafter, in Examples below, also referred to as the "hIL12 and hIL7-carrying vaccinia virus".) (FIG. 4). Each recombinant virus was purified by the method in Example 2 (3) and then the virus titer of each virus was measured with RK13 cells.

Example 3

Oncolytic Property of Genetically Engineered Vaccinia Virus

The ability of the hIL12 and hIL7-carrying vaccinia virus prepared in Example 2 to lyse various human cancer cells (ability to kill cells) was evaluated. Moreover, the ability of a combined mixture of 2 viruses, the hIL12-carrying vaccinia virus and the hIL7-carrying vaccinia virus prepared in Example 2, to lyse various human cancer cells was similarly evaluated.

Specifically, 100 μL each of the cells suspended at $1\times10^4$ cells/mL in a medium (a medium described below containing 10% fetal bovine serum (GE Healthcare) and 1% penicillin-streptomycin (Life Technologies)) was first added into 96 well plates (AGC TECHNO GLASS CO., LTD.). After culturing overnight, 1) the hIL12 and hIL7-carrying vaccinia virus and 2) a mixture combining 1:1 concentrations of the hIL12-carrying vaccinia virus and the hIL7-carrying vaccinia virus (hereinafter, referred to as the "mixture of hIL12-carrying vaccinia virus and hIL7-carrying vaccinia virus") were each diluted with Opti-MEM (Life Technologies) at $5\times10^4$ PFU/mL, $5\times10^5$ PFU/mL, and $5\times10^6$ PFU/mL, respectively. 20 μL each of the virus solutions was added to each well to infect cells at MOI=1.0, 10, or 100. As control, wells with no cells and wells to which Opti-MEM was added instead of virus (MOI=0) were prepared. The cells were then cultured for 5 days in a $CO_2$ incubator set to a $CO_2$ concentration of 5% and at 37° C. The cell survival rate on Day 5 was measured with CellTiter-Glo Luminescent Cell Viability Assay (Promega KK.). Specifically, according to the protocol of the assay kit, 100 μL each of CellTiter-Glo Reagent was added to each well and left to stand for 30 minute, the total amount was then transferred into 96 well black plates (Corning Incorporated), and the strength of luminescence in each well was measured with EnSpire (PerkinElmer Inc.). For the calculation of the cell survival rate in each well, the value of wells in which no cells have seeded was defined as 0% survival and the value of wells in which cells have seeded and no virus was added was defined as100% survival.

The evaluated cells were the malignant melanoma cell RPMI-7951 (ATCC HTB-66), the lung adenocarcinoma HCC4006 (ATCC CRL-2871), the lung carcinoma A549 (ATCC CCL-185), the small cell lung cancer cell DMS 53, the lung squamous cell carcinoma NCI-H226 (ATCC CRL-5826), the kidney cancer cell Caki-1 (ATCC HTB-46), the bladder cancer cell 647-V (DSMZ ACC 414), the head and neck cancer cell Detroit 562 (ATCC CCL-138), the breast cancer cell JIMT-1 (DSMZ ACC 589), the breast cancer cell MDA-MB-231 (ATCC HTB-26), the esophageal cancer cell OE33 (ECACC 96070808), the glioblastoma U-87MG (ECACC 89081402), the neuroblastoma GOTO (JCRB JCRB0612), the myeloma RPMI 8226 (ATCC CCL-155), the ovarian cancer cell SK-OV-3 (ATCC HTB-77), the ovarian cancer cell OVMANA (JCRB JCRB1045), the colon cancer cell RKO (ATCC CRL-2577), the colorectal carcinoma HCT 116, the pancreatic cancer cell BxPC-3 (ATCC CRL-1687), the prostate cancer cell LNCaP clone FGC (ATCC CRL-1740), the hepatocellular carcinoma JHH-4 (JCRB JCRB0435), the mesothelioma NCI-H28 (ATCC CRL-5820), the cervical cancer cell SiHa (ATCC HTB-35) and the gastric cancer cell Kato III (RIKEN BRC RCB2088).

The media used were RPMI1640 medium (Sigma-Aldrich Co. LLC., R8758) for RPMI-7951, HCC4006, DMS 53, NCI-H226, Caki-1, 647-V, Detroit 562, JIMT-1, OE33, U-87MG, GOTO, RPMI8226, SK-OV-3, OVMANA, RKO, HCT 116, BxPC-3, LNCaP clone FGC, JHH-4, NCI-H28, and Kato III, DMEM medium (Sigma-Aldrich Co. LLC., D6429) for A549 and MDA-MB-231, and EMEM medium (ATCC 30-2003) for SiHa. The results were as illustrated in FIGS. 5-1 to 5-4. In relation with this, the effects of the hIL12 and hIL7-carrying vaccinia virus were illustrated separately in FIGS. 5-1 and 5-2 and the effects of the mixture of hIL12-carrying vaccinia virus and hIL7-carrying vaccinia virus were illustrated separately in FIGS. 5-3 and 5-4.

As a result, the hIL12 and hIL7-carrying vaccinia virus was shown to have the ability to kill cells in all examined human cancer cells (FIGS. 5-1 and 5-2). Moreover, the mixture of hIL12-carrying vaccinia virus and hIL7-carrying vaccinia virus was also shown to have the ability to kill cells in all examined human cancer cells (FIGS. 5-3 and 5-4). In FIGS. 5-1 to 5-4, the oncolytic properties at MOI=0, 1, 10, and 100 are shown from the left in this order for each cell line.

Example 4

Protein Production from Cancer Cells Infected with Genetically Engineered Vaccinia Virus When cancer cells were infected with the hIL12 and hIL7-carrying vaccinia virus, the concentrations of the human IL-7 protein and the human IL-12 protein produced by cancer cells were measured. Furthermore, the concentrations of the human IL-7 protein and the human IL-12 protein produced by cancer cells when cancer cells were infected with the mixture of hIL12-carrying vaccinia virus and hIL7-carrying vaccinia virus were similarly measured.

The measurement of the human IL-7 protein was conducted as follows. Specifically, first, 100 μL of SK-OV-3 ovarian cancer cells suspended at $1\times10^4$ cells/mL in RPMI1640 medium containing 10% fetal bovine serum and the 1% penicillin-streptomycin was seeded into 96 well plates. After culturing overnight, 1) the hIL12 and hIL7-carrying vaccinia virus or 2) the mixture of hIL12-carrying vaccinia virus and hIL7-carrying vaccinia virus was prepared in Opti-MEM and 20 μL each was added to infect the cells at MOI=1.0. The cells were then cultured for 24 hours in a $CO_2$ incubator set at a $CO_2$ concentration of 5% and 37° C. and the culture supernatant was collected. The concentration of the protein contained in the culture supernatant was measured with the ELISA kit listed in Table 1 and EnSpire.

The measurement of the human IL-12 protein was conducted as follows. Specifically, first, 100 μL of SK-OV-3 ovarian cancer cells suspended at $1\times10^5$ cells/mL in RPMI1640 medium containing 10% fetal bovine serum and the 1% penicillin-streptomycin was seeded into 96 well plates. After culturing overnight, 1) the hIL12 and hIL7-carrying vaccinia virus or 2) the mixture of hIL12-carrying vaccinia virus and hIL7-carrying vaccinia virus was prepared in Opti-MEM and 20 μL each was added to infect the cells at MOI=1.0. The cells were then cultured for 48 hours in a $CO_2$ incubator set at a $CO_2$ concentration of 5% and 37° C. and the culture supernatant was collected. The concentration of the protein contained in the culture supernatant was measured with the ELISA kit listed in Table 1 and EnSpire.

TABLE 1

ELISA kit used in Example 4

| Protein | ELISA kit | Provider |
|---|---|---|
| Human IL-7 | Human IL-7 ELISA kit | RayBiotech, Inc. |
| Human IL-12 | Human IL-12 p70 DuoSet ELISA | R&D Systems, Inc. |

As a result, it was shown that the human IL-12 protein and the human IL-7 protein were produced from the cells to which the hIL12 and hIL7-carrying vaccinia virus was added and the cells to which the mixture of hIL12-carrying vaccinia virus and hIL7-carrying vaccinia virus was added (Tables 2-1 and 2-2).

TABLE 2-1

Concentration of human IL-12 protein in culture supernatant

| Genetically engineered vaccinia virus | Human IL-12 protein concentration (ng/mL) |
|---|---|
| hIL12 and hIL7-carrying vaccinia virus | 31.45 |
| Mixture of hIL12-carrying vaccinia virus and hIL7-carrying vaccinia virus | 17.74 |

TABLE 2-2

Concentration of human IL-7 protein in culture supernatant

| Genetically engineered vaccinia virus | Human IL-7 protein concentration (ng/mL) |
|---|---|
| hIL12 and hIL7-carrying vaccinia virus | 0.86 |
| Mixture of hIL12-carrying vaccinia virus and hIL7-carrying vaccinia virus | 0.60 |

Example 5

Construction of Transfer Vector Plasmid DNA Carrying Polynucleotide Encoding Murine IL-12 and Construction of Recombinant Vaccinia Virus Carrying Polynucleotide Encoding Murine IL-12

(1) The transfer vector plasmid DNA pTN-VGF-SP-mIL12 was constructed according to the method described in Example 1 (2). Instead of the polynucleotide (SEQ ID NO: 7) encoding human IL-12 in the method described in Example 1 (2), a polynucleotide encoding murine IL-12 (a polynucleotide containing the murine IL-12 subunit p40, an internal ribosomal entry site, and the murine IL-12 subunit α. SEQ ID NO: 23) was used and this polynucleotide fragment was cloned into pTN-VGF-SP-BFP.

(2) The transfer vector plasmid DNA pTN-O1L-SP-Luc2 was constructed according to the method described in Example 1 (3). Instead of the polynucleotide (SEQ ID NO: 9) containing the Escherichia coli LacZ gene in the method described in Example 1 (3), a polynucleotide (100-1752 in Accession No.DQ188840) encoding the luciferase Luc2 gene was used and this polynucleotide fragment was cloned into pTN-O1L-SP-BFP.

(3) The recombinant virus was collected according to the method in Example 2 (2). In the method in Example 2 (2), LC16mO ΔSCR VGF-p7.5-DsRed/O1L-SP-BFP and pTN-O1L-SP-Luc2 prepared in Example 5 (2) instead of pTN-O1L-SP-LacZ were used. The virus was named LC16mO ΔSCR VGF-p7.5-DsRed/O1L-SP-Luc2 (hereinafter, this virus is also referred to as the "control vaccinia virus".).

(4) The recombinant virus was collected according to the method in Example 2 (3). Instead of LC16mO ΔSCR VGF-p7.5-DsRed/O1L-SP-LacZ and pTN-VGF-SP-IL12 in the method in Example 2 (3), respectively, LC16mO ΔSCR VGF-p7.5DsRed/O1L-SP-Luc2 prepared in Example 5 (3) and pTN-VGF-SP-mIL12 prepared in Example 5 (1) were used. The virus was named LC16mO ΔSCR VGF-SP-mIL12/O1L-SP-Luc2 (hereinafter, also referred to as the "mIL12-carrying vaccinia virus".).

(5) The recombinant virus was collected according to the method in Example 2 (4-1). LC16mO ΔSCR VGF-p7.5-DsRed/O1L-SP-BFP and pTN-VGF-SP-mIL12 prepared in Example 5 (1) instead of pTN-VGF-SP-IL12 in the method in Example 2 (4-1) were used. The virus was named LC16mO ΔSCR VGF-SP-mIL12/O1L-SP-BFP.

Furthermore, the recombinant virus was collected according to the method in Example 2 (4-2). Instead of LC16mO ΔSCR VGF-SP-IL12/O1L-SP-BFP in the method in Example 2 (4-2), LC16mO ΔSCR VGF-SP-mIL12/O1L-SP-BFP prepared as described above and pTN-O1L-SP-IL7 were used. The virus was named LC16mO ΔSCR VGF-SP-mIL12/O1L-SP-IL7 (hereinafter, also referred to as the "mIL12 and hIL7-carrying vaccinia virus".).

Example 6

Antitumor Effect of Genetically Engineered Vaccinia Virus in Cancer-bearing Humanized Mouse The in vivo antitumor effect of the hIL12 and hIL7-carrying vaccinia virus was evaluated using humanized mice (mice in which the immune system is replaced with human immune cells by introducing human hematopoietic stem cells into a severely immunodeficient mouse) into which human cancer cells are transplanted.

Specifically, in order to generate humanized mice, $3\times10^4$ hematopoietic stem cells (Lonza) derived from human umbilical cord blood were first introduced by injecting via a tail vein into NOG mice (NOD/Shi-scidIL-2RγKO Jic, female, 6 week-old, CLEA Japan, Inc.) irradiated with X-ray at a strength of 2.0 grays using an X-ray irradiation apparatus. 13 weeks after the introduction, 100 μL of the human lung cancer cell NCI-H1373 (ATCC CRL-5866) suspended at $3\times10^7$ cells/mL in PBS was transplanted by injecting the cells subcutaneously in the right back side of the mice. The tumor diameter was measured with a caliper after cancer cell transplantation and the mice were assigned to groups so that the mean tumor volumes of the groups (minor axis mm ×minor axis mm×major axis mm×0.52) will become 37 $mm^3$ to 47 $mm^3$. On the same day, 20 μL of the hIL12 and hIL7-carrying vaccinia virus diluted to a concentration of $1.0\times10^8$ PFU/mL in PBS was injected into tumor (referred to as the "hIL12 and hIL7-carrying VV treated group" in the Table). 20 μL of PBS was administered into tumor in a group, which was referred to as the vehicle (PBS) treated group. The tumor diameter of each mouse was measured with a caliper every 2-4 days, the tumor volume was calculated based on the formula above, and the percent (%) change in tumor volume on the 14th day after the virus administration was calculated by the following formula for each individual (n=7-8):

Percent (%) change in tumor volume on 14th day after virus administration=100 (%)×tumor volume ($mm^3$) on 14th day after virus administration/tumor volume ($mm^3$) on day of virus administration.

The tumor regression effect was determined to be positive when the mean percent (%) change in tumor volume on the 14th day after the virus administration of each group was less than 100 and a significant difference was observed (the significant difference was defined when p value<0.05) between the tumor volume on the 14th day after the virus administration and the tumor volume on the day of the virus administration in each group when tested by the paired t-test.

In this Example, the control vaccinia virus ($2\times10^6$ PFU/individual), the hIL12-carrying vaccinia virus ($2\times10^6$ PFU/individual), or the hIL7-carrying vaccinia virus ($2\times10^6$ PFU/individual) (referred to as the "control VV treated group", the "hIL12-carrying VV treated group", and the "hIL7-carrying VV treated group" in the Table.) were used with the same injection volume (20 μL) and the same dilution solution (PBS) as a virus compared with the hIL12 and hIL7-carrying vaccinia virus ($2\times10^6$ PFU/individual).

As a result, the hIL12 and hIL7-carrying vaccinia virus treated group exhibited a mean percent change in tumor volume on the 14th day after the virus administration of less than 100%. Furthermore, there was a significant difference observed between the tumor volume on the 14 days after the virus administration and the tumor volume on the day of virus administration examined by the paired t-test and therefore the tumor regression effect was determined to be positive (Table 3). Thus, the administration of the hIL12 and hIL7-carrying vaccinia virus was shown to have the tumor regression effect. On the other hand, the tumor regression effect was not confirmed in the group receiving either of the hIL12-carrying vaccinia virus or the hIL7-carrying vaccinia virus (Table 3).

TABLE 3

Percent (%) change in tumor volume in cancer-bearing humanized mouse with the hIL12 and hIL7-carrying vaccinia virus

| Experimental group | n | Percent (%) change in tumor volume on 14th day after administration Mean +/− standard error | p value (tumor volume on 14th day after virus administration and tumor volume on day of virus administration were examined by the paired t-test) |
|---|---|---|---|
| Vehicle (PBS) treated group | 7 | 653 ± 43 | <0.05 |
| Control VV treated group | 7 | 187 ± 39 | 0.09 |
| hIL7-carrying VV treated group | 8 | 199 ± 33 | <0.05 |
| hIL12-carrying VV treated group | 8 | 140 ± 29 | 0.40 |
| hIL12 and hIL7-carrying VV treated group | 8 | 61 ± 6 | <0.05 |

Example 7

Complete Remission-inducing Effect of Genetically Engineered Vaccinia Virus In Syngeneic Cancer-bearing Mouse Models (1) Effect of mIL12 and hIL7-carrying vaccinia virus The complete remission-inducing effect of the mIL12 and hIL7-carrying vaccinia virus in vivo was evaluated using mice subcutaneously transplanted with syngeneic murine cancer cell line (syngeneic cancer-bearing mice). Since human IL-12 is known to have no effect on murine immune cells, a genetically engineered vaccinia virus carrying a polynucleotide encoding murine IL-12 instead of the polynucleotide encoding human IL-12 (prepared in Example 5) was used.

Specifically, 50 μL of the murine lung cancer cell LL/2 (LLC1) (ATCC CRL-1642) (hereinafter referred to as LLC1) prepared at $4\times10^6$ cells/mL in PBS was first subcutaneously transplanted in the right flank of C57BL/6J mice (male, 5-7 week-old, CHARLES RIVER LABORATORIES JAPAN, INC.). The tumor volume was calculated in a way same as that in Example 6 and mice were assigned to groups so that the mean tumor volume of each group will become 50 $mm^3$ to 60 $mm^3$. On the next day, 30 μL of the mIL12 and hIL7-carrying vaccinia virus diluted to a concentration of $6.7\times10^8$ PFU/mL in PBS was intratumorally injected in 12 mice ($2\times10^7$ PFU, referred to as the "mIL12 and hIL7-carrying VV treated group" in the Table.). Similar intratumoral injection of the virus was conducted 2 days and 4 days after the first administration. 30 μL of PBS instead of the virus was intratumorally administered in a group, which was referred to as the vehicle (PBS) treated group.

The tumor diameter was measured with a caliper twice a week and the tumor volume was calculated. Absence of tumor observed by palpation on 27th day after the first administration of the virus was defined as complete remission and the number of individuals achieved complete remission was counted. Groups reached a mean tumor volume above 1,700 $mm^3$ during the test period were euthanized from the viewpoint of animal ethic. In this example, the control vaccinia virus, the mIL12-carrying vaccinia virus, or the hIL7-carrying vaccinia virus (each $2\times10^7$ PFU/dose, three doses) (respectively referred to as the “control VV treated group”, the “mIL12-carrying VV treated group”, and the “hIL7-carrying VV treated group” in the Table.) was used with the same injection volume (30 μL per dose) and the same dilution solution (PBS) as a virus compared with the mIL12 and hIL7-carrying vaccinia virus ($2\times10^7$ PFU/dose, three doses).

As a result, three individuals finally achieved complete remission in the mIL12 and hIL7-carrying vaccinia virus treated group. On the other hand, no individual achieved complete remission in the group receiving the comparison virus (Table 4-1). Thus, the administration of the mIL12 and hIL7-carrying vaccinia virus was shown to have a higher complete remission-inducing effect in comparison with the hIL7-carrying vaccinia virus or the mIL12-carrying vaccinia virus in syngeneic cancer-bearing mouse models.

TABLE 4-1

The number of mice individual that achieved complete remission by administration of mIL12 and hIL7-carrying vaccinia virus

| Experimental group | Number of mouse individual achieved complete remission/Number of mouse individual examined |
|---|---|
| Vehicle (PBS) treated group | 0/12 |
| Control VV treated group | 0/12 |
| hIL7-carrying VV treated group | 0/12 |
| mIL12-carrying VV treated group | 0/12 |
| mIL12 and hIL7-carrying VV treated group | 3/12 |

(2) a mixture of mIL12-carrying vaccinia virus and hIL7-carrying vaccinia virus

The complete remission-inducing effect of a 1:1 mixture of the mIL12-carrying vaccinia virus and the hIL7-carrying vaccinia virus (hereinafter, referred to as the “mixture of mIL12-carrying vaccinia virus and hIL7-carrying vaccinia virus”) in vivo was evaluated using syngeneic cancer-bearing mice.

Experiment was conducted in the same way as (1), with the proviso that the murine lung cancer cell LLC1 suspended at $8\times10^6$ cells/mL was transplanted. Furthermore, instead of 30 μL ($2\times10^7$ PFU) of the mIL12 and hIL7-carrying vaccinia virus diluted to a concentration of $6.7\times10^8$ PFU/mL, 30 μL (each $2\times10^7$ PFU/dose, three doses) of the mixture of mIL12-carrying vaccinia virus and hIL7-carrying vaccinia virus (each virus was diluted to $6.7\times10^8$ PFU/mL in PBS) (referred to as the “treatment group of mixture of mIL12-carrying VV and hIL7-carrying VV” in the Table.) was used. Seven mice (n=7) were used. The control vaccinia virus ($4\times10^7$ PFU/dose, three doses), the 1:1 mixture of the mIL12-carrying vaccinia virus and the control vaccinia virus (each $2\times10^7$ PFU/dose, three doses), or the 1:1 mixture of the hIL7-carrying vaccinia virus and the control vaccinia virus (each $2\times10^7$ PFU/dose, three doses) (respectively, referred to as the “control VV treated group”, the “treatment group of mixture of mIL12-carrying VV and control VV”, and the “treatment group of mixture of hIL7-carrying VV and control VV” in the Table.) was used with an injection volume of 30 μL each as a comparison virus.

As a result, four individuals in the group receiving the mixture of mIL12-carrying vaccinia virus and hIL7-carrying vaccinia virus achieved complete remission. Only one individual achieved complete remission in the group receiving the mixture of mIL12-carrying vaccinia virus and the control vaccinia virus, while no individual achieved complete remission in the groups receiving other comparison viruses (Table 4-2). Thus, the mixture of mIL12-carrying vaccinia virus and hIL7-carrying vaccinia virus was shown to have higher complete remission-inducing effect in comparison with mixtures containing either of the hIL7-carrying vaccinia virus or the mIL12-carrying vaccinia virus in a syngeneic cancer-bearing mouse model.

TABLE 4-2

The number of mice individual that achieved complete remission by administration of the mixture of mIL12-carrying vaccinia virus and hIL7-carrying vaccinia virus

| Experimental group | Number of mouse individual achieved complete remission/Number of mouse individual examined |
|---|---|
| Vehicle (PBS) treated group | 0/7 |
| Control VV treated group | 0/7 |
| Treatment group of mixture of hIL7-carrying VV and control VV | 0/7 |
| Treatment group of mixture of mIL12-carrying VV and control VV | 1/7 |
| Treatment group of mixture of mIL12-carrying VV and hIL7-carrying VV | 4/7 |

Example 8

Acquired Immunity Effect of Genetically Engineered Vaccinia Virus in Syngeneic Cancer-Bearing Mouse Models (Tumor-Rejecting Effect by Acquired Immunity)

(1) mIL12 and hIL7-carrying vaccinia virus:

To the mice achieved complete remission as a result of treating with the mIL12 and hIL7-carrying vaccinia virus, the rechallenge experiment of the same cancer cells was conducted to evaluate acquired immunity effect of the virus.

Specifically, LLC1 cancer-bearing mice were first generated according to Example 7, and the mIL12 and hIL7-carrying vaccinia virus was intratumorally administered in the mice (with the proviso that the intratumoral injection of the virus was also conducted on 1st and 3rd days after the first administration in addition to 2nd and 4th days (total 5 times); referred to as the “mIL12 and hIL7-carrying VV treated group” in the Table.). The complete remission was confirmed on 23th day after the last administration of the virus. Into the individuals that still maintain the complete remission state on 51th day after the last administration and age-matched mice not inoculated with virus (control group), 50 μL of LLC1 cancer cells suspended at $8\times10^6$/mL in PBS was subcutaneously transplanted. The tumor volume was calculated according to Example 6 and the number of individuals that were recognized to have tumor formation by visual observation and palpation on 14th day after the LLC1 transplantation was counted to determine the ratio of the number of mouse individuals having engrafted tumor/the number of mouse individuals in which cancer cells were transplanted. In this Example, the control group and the virus treated group were tested by the Fisher's exact test and the acquired immunity effect was evaluated to be positive when there was a significant difference (less than 5%).

As a result, subcutaneous tumor was formed in the all cases of 10 individuals in the total 10 individuals in the control group, but 6 individuals in the total 10 individuals in the mIL12 and hIL7-carrying virus treated group had no tumor formation of rechallenged LLC1 cancer cells found in the visual observation and palpation (Table 5-1) ($P<0.05$, Fisher's exact test). Thus, the acquired immunity effect of the administration of the mIL12 and hIL7-carrying vaccinia virus was confirmed in this Example.

TABLE 5-1

Result of cancer cell rechallenge test in mice achieved complete remission

| Experimental group | Number of mouse individual having engrafted tumor/ Number of mouse individual in which cancer cells were transplanted |
|---|---|
| Control group | 10/10 |
| mIL12 and hIL7-carrying VV treated group | 4/10 |

(2) Mixture of mIL12-carrying vaccinia virus and hIL7-carrying vaccinia virus:

To the mice achieved complete remission as a result of treating with the mixture of mIL12-carrying vaccinia virus and hIL7-carrying vaccinia virus, the rechallenge experiment of the same cancer cells was conducted to evaluate acquired immunity effect of the virus.

Specifically, the experiment was conducted in the same way as in (1). However, instead of the mice achieved complete remission by the administration of the mIL12 and hIL7-carrying vaccinia virus, the mice achieved complete remission by the administration of the mixture of mIL12-carrying vaccinia virus and hIL7-carrying vaccinia virus according to Example 7 (2) (1st, 3rd, and 5th day after the group assignment, total 3 times) were used (referred to as the "treatment group of mixture of mIL12-carrying VV and hIL7-carrying VV" in the Table.). The further transplantation of the cancer cells was conducted on 74th day after the last administration of the viruses (determination of complete remission was made on 24th day after the last administration).

As a result, subcutaneous tumor was formed in the all individuals in the total eight individuals in the control group on 14th day after further transplantation of the cancer cells, but eight individuals in the total 10 individuals in the treatment group of mixture of mIL12-carrying vaccinia virus and hIL7-carrying vaccinia virus had no tumor formation of rechallenged LLC1 cancer cells found in the visual observation and palpation (Table 5-2) ($P<0.05$, Fisher's exact test).

Thus, the acquired immunity effect of the administration of the mixture of mIL12-carrying vaccinia virus and hIL7-carrying vaccinia virus was confirmed in this Example.

TABLE 5-2

Result of cancer cell rechallenge test in mice achieved complete remission

| Experimental group | Number of mouse individual having engrafted tumor/Number of mouse individual in which cancer cells were transplanted |
|---|---|
| Control group | 8/8 |
| Treatment group of mixture of mIL12-carrying VV and hIL7-carrying VV | 2/10 |

Industrial Availability

The vaccinia virus, the pharmaceutical composition, and the combination kit according to the present invention are useful for preventing or treating various cancers.

Free text of sequence listing

The description of "Artificial Sequence" is stated in the numeric identifier <223> of the sequence listing.

The nucleotide sequences set forth in SEQ ID NOs: 1-6 and 10-15 are primers.

The nucleotide sequences set forth in SEQ ID NOs: 7, 8, and 9 are a polynucleotide containing the human IL-12 gene, a polynucleotide containing the human IL-7 gene, and a polynucleotide containing the Escherichia coli LacZ gene, respectively. In SEQ ID NO: 7, the nucleotide sequence of 14-1000 corresponds to the region encoding the p40 subunit of IL-12 and the nucleotide sequence of 1606-2367 corresponds to the region encoding the subunit $\alpha$ of IL-12.

The nucleotide sequences set forth in SEQ ID NOs: 16 and 17 are the restriction enzyme sites linked to each of the gene coding regions of SEQ ID NOs: 7-9.

The amino acid sequence set forth in SEQ ID NO: 18 is a B5R protein having the deletion of the 4 SCR domains.

The nucleotide sequences set forth in SEQ ID NOs: 19 and 20 are the sequences of loop sequences at both ends in LC16mO VGF-SP-LucGFP/O1L-p7.5-DsRed.

The nucleotide sequence set forth in SEQ ID NO: 21 is the sequence except the loop sequences at both ends in LC16mO VGF-SP-LucGFP/O1L-p7.5-DsRed.

The nucleotide sequence set forth in SEQ ID NO: 22 is a DNA fragment containing the p7.5k promoter and the DsRed fragment.

The nucleotide sequence set forth in SEQ ID NO: 23 is a polynucleotide containing the murine IL-12 gene.

What is claimed is:

1. A vaccinia virus comprising a polynucleotide encoding interleukin-7(IL-7); and a polynucleotide encoding interleukin-12(IL-12), wherein the vaccinia virus is deficient in the function of vaccinia virus growth factor (VGF) or deficient in the function of O1L, and wherein the vaccinia virus is oncolytic against human cancer cells.

2. The vaccinia virus according to claim 1, wherein the vaccinia virus is deficient in the function of VGF.

3. The vaccinia virus according to claim 1, wherein the vaccinia virus is deficient in the function of O1L.

4. The vaccinia virus according to claim 1, wherein the vaccinia virus is deficient in the functions of VGF and O1L.

5. The vaccinia virus according to claim 1, wherein the vaccinia virus has a deletion in the short consensus repeat (SCR) domains in the B5R extracellular region.

6. The vaccinia virus according to claim 1, wherein the vaccinia virus is deficient in the functions of VGF and O1L and has a deletion in the SCR domains in the B5R extracellular region.

7. The vaccinia virus according to claim 1, wherein the vaccinia virus is a LC16mO strain.

8. The vaccinia virus according to claim 1, wherein the vaccinia virus is deficient in the functions of VGF and O1L and has a deletion in the SCR domains in the B5R extracellular region and is a LC16mO strain.

9. A pharmaceutical composition comprising a vaccinia virus according to claim 1 and a pharmaceutically acceptable excipient.

10. The pharmaceutical composition according to claim 9, wherein the vaccinia virus is deficient in the function of VGF.

11. The pharmaceutical composition according to claim 9, wherein the vaccinia virus is deficient in the function of O1L.

12. The pharmaceutical composition according to claim 9, wherein the vaccinia virus is deficient in the functions of VGF and O1L.

13. The pharmaceutical composition according to claim 9, wherein the vaccinia virus has a deletion in the SCR domains in the B5R extracellular region.

14. The pharmaceutical composition according to claim 9, wherein the vaccinia virus is deficient in the functions of VGF and O1L and has a deletion in the SCR domains in the B5R extracellular region.

15. The pharmaceutical composition according to claim 9, wherein the vaccinia virus is a LC16mO strain.

16. The pharmaceutical composition according to claim 9, wherein the vaccinia virus is deficient in the functions of VGF and O1L and has a deletion in the SCR domains in the B5R extracellular region and is a LC16mO strain.

17. A combination kit comprising: a vaccinia virus comprising a polynucleotide encoding IL-7 and a vaccinia virus comprising a polynucleotide encoding IL-12, wherein the vaccinia viruses are deficient in the function of VGF or deficient in the function of O1L, and wherein the vaccinia viruses in combination are oncolytic against human cancer cells.

18. The kit according to claim 17, wherein the vaccinia viruses are deficient in the function of VGF.

19. The kit according to claim 17, wherein the vaccinia viruses are deficient in the function of O1L.

20. The kit according to claim 17, wherein the vaccinia viruses are deficient in the functions of VGF and O1L.

21. The kit according to claim 17, wherein the vaccinia viruses have a deletion in the SCR domains in the B5R extracellular region.

22. The kit according to claim 17, wherein the vaccinia viruses are deficient in the functions of VGF and O1L and has a deletion in the SCR domains in the B5R extracellular region.

23. The kit according to claim 17, wherein the vaccinia viruses are a LC16mO strain.

24. The kit according to claim 17, wherein the vaccinia viruses are deficient in the functions of VGF and O1L and has a deletion in the SCR domains in the B5R extracellular region and is a LC16mO strain.

25. The kit according to claim 17, further comprising a pharmaceutically acceptable excipient.

* * * * *